US010544192B2

(12) United States Patent
Colloca et al.

(10) Patent No.: US 10,544,192 B2
(45) Date of Patent: Jan. 28, 2020

(54) CHIMPANZEE CLADE E ADENOVIRUS NUCLEIC ACID-AND AMINO ACID-SEQUENCES, VECTORS CONTAINING SAME, AND USES THEREOF

(71) Applicant: GLAXOSMITHKLINE BIOLOGICALS SA, Rixensart (BE)

(72) Inventors: Stefano Colloca, Rome (IT); Alfredo Nicosia, Rome (IT); Riccardo Cortese, Sr., Rome (IT); Virginia Ammendola, S. Guisepe Vesuviano (IT); Maria Ambrosio, Terzigno (IT)

(73) Assignee: GLAXOSMITHKLINE BIOLOGICALS SA, Rixensart (BE)

( * ) Notice: Subject to any disclaimer, the term of this patent is extended or adjusted under 35 U.S.C. 154(b) by 0 days.

(21) Appl. No.: 15/623,723

(22) Filed: Jun. 15, 2017

(65) Prior Publication Data

US 2018/0057540 A1 Mar. 1, 2018

Related U.S. Application Data

(62) Division of application No. 13/147,193, filed as application No. PCT/EP2010/000616 on Feb. 2, 2010.

(60) Provisional application No. 61/266,342, filed on Dec. 3, 2009, provisional application No. 61/174,852, filed on May 1, 2009, provisional application No. 61/172,624, filed on Apr. 24, 2009.

(30) Foreign Application Priority Data

Feb. 2, 2009 (WO) ................. PCT/EP2009/000672

(51) Int. Cl.
| | | |
|---|---|---|
| C07K 14/005 | (2006.01) | |
| A61K 39/12 | (2006.01) | |
| A61K 39/235 | (2006.01) | |
| C12N 7/00 | (2006.01) | |
| C12N 15/86 | (2006.01) | |
| A61K 39/00 | (2006.01) | |
| A61K 48/00 | (2006.01) | |

(52) U.S. Cl.
CPC ............ *C07K 14/005* (2013.01); *A61K 39/12* (2013.01); *A61K 39/235* (2013.01); *C12N 7/00* (2013.01); *C12N 15/86* (2013.01); *A61K 39/0011* (2013.01); *A61K 48/00* (2013.01); *A61K 2039/525* (2013.01); *A61K 2039/5256* (2013.01); *A61K 2039/545* (2013.01); *C12N 2710/10321* (2013.01); *C12N 2710/10322* (2013.01); *C12N 2710/10334* (2013.01); *C12N 2710/10343* (2013.01); *C12N 2710/16634* (2013.01); *C12N 2740/16134* (2013.01); *C12N 2770/24234* (2013.01)

(58) Field of Classification Search
None
See application file for complete search history.

(56) References Cited

U.S. PATENT DOCUMENTS

| 5,922,315 A | 7/1999 | Roy |
| 8,470,310 B2 | 6/2013 | Roy et al. |

FOREIGN PATENT DOCUMENTS

| WO | 1996013597 A2 | 5/1996 |
| WO | 2003000851 A2 | 1/2003 |
| WO | 2003031588 A2 | 4/2003 |
| WO | 2003046124 A3 | 11/2003 |
| WO | 2003102236 A1 | 12/2003 |
| WO | 2005071093 A2 | 8/2005 |
| WO | 2006086284 A2 | 8/2006 |
| WO | 2006133911 A2 | 12/2006 |
| WO | 2009073104 A2 | 6/2009 |
| WO | 2009105084 A2 | 8/2009 |
| WO | 2009146902 A1 | 12/2009 |
| WO | 2009136977 A3 | 3/2010 |

OTHER PUBLICATIONS

Altschul et al. (1990) J. Mol. Biol. 215: 403-410.
Andrew J. Davison, et al., (2003) Journal of General Virology, 84: 2895-2908.
Bangari DS and Mittal SK (2006) Vaccine, 24(7): 849-862.
Barnes, et al. (2012) Sci Transl Med, 4(115):115ra1.
Birgitt Tauber and Thomas Dobner, (2001) Oncogene, 20:7847-7854.
Brody et al, (1994) Ann NY Acad Sci., 716: 90-101.
Capone, et al. (2010) Vaccine, 29(2):256-65.
Colloca, et al. (2012) Sci Transl Med, 4(115):115ra2.
Dambrosio, E. (1982) J. Hyg. (London) 89: 209-219.
Database EMBL Accession No. FJ025899, Jul. 9, 2009.
Database EMBL Accession No. FJ025903, Jul. 9, 2009.
Database EMBL Accession No. FJ025907, Jul. 9, 2009.
Database EMBL Accession No. FJ025926, Jul. 9, 2009.
Deposit Reference 08110601; Virus ChAd83; The European Collection of Cell Cultures; Nov. 6, 2008.
Deposit Reference 08110602; Virus ChAd73; The European Collection of Cell Cultures; Nov. 6, 2008.
Deposit Reference 08110603; Virus ChAd55; The European Collection of Cell Cultures; Nov. 6, 2008.

(Continued)

*Primary Examiner* — Nicole Kinsey White
(74) *Attorney, Agent, or Firm* — Lisa M. Maatovcik

(57) ABSTRACT

The present invention relates to novel adenovirus strains with an improved seroprevalence. In one aspect, the present invention relates to isolated polypeptides of adenoviral capsid proteins such as hexon, penton and fiber protein and fragments thereof and polynucleotides encoding the same. Also provided is a vector comprising the isolated polynucleotide according to the invention and adenoviruses comprising the isolated polynucleotides or polypeptides according to the invention and a pharmaceutical composition comprising said vector, adenovirus, polypeptide and/or polynucleotide. The invention also relates to the use of the isolated polypeptides, the isolated polynucleotides, the vector, the adenoviruses and/or the pharmaceutical composition for the therapy or prophylaxis of a disease.

3 Claims, 17 Drawing Sheets

Specification includes a Sequence Listing.

(56) References Cited

OTHER PUBLICATIONS

Deposit Reference 08110604; Virus ChAd147; The European Collection of Cell Cultures; Nov. 6, 2008.
Deposit Reference 08110605; Virus ChAd146; The European Collection of Cell Cultures; Nov. 6, 2008.
Draper SJ, et al. (2008) Nat Med., 14(8):819-21.
Draper, et al. (2010) J Immunol, 185(12):7583-95.
Farina, Steven F., et al. "Replication-defective vector based on a chimpanzee adenovirus." Journal of virology 75.23 (2001): 11603-11613.
Fattori (2006) Gene Ther., 13(14):1088-96.
Folgori A, et al. (2006) Nat Med., 12(2): 190-7.
Graham & Prevec, (1991) In Methods in Molecular Biology: Gene Transfer and Expression Protocols, (Ed. Murray, EJ.), p. 109.
Hierholzer, et al. (1988) J. Infect. Dis.,158: 804-813.
Hitt et al., (1997) Advances in Pharmacology 40:137-206.
Jong et al. (1999) J Clin. Microbiol., 37: 3940-3945.
K. J. Fisher and J. M. Wilson (1994) Biochem. J., 299: 49.
Karlin and Altschul (1993) Proc. Natl. Acad. Sci. USA 90: 5873-5877.
Krieg, J. Clin. Invest., 2007, 117(5):1184-1194.
Lauer, Kim P., et al. "Natural variation among human adenoviruses: genome sequence and annotation of human adenovirus serotype 1." Journal of general virology 85.9 (2004): 2615-2625.
Madisch, et al (2005) J. Virol, 79(24): 15265-76.
Madisch, et al (2007) J Virol, 81(15):8270-81.
Mastrangeli, et al (1996) Human Gene Therapy, 7: 79-87.
McCoy, Kimberly, et al; "Effect of Preexisting Immunity to Adenovirus Human Serotype 5 Antigens on the Immune Responses of Nonhuman Primates to Vaccine Regimens Based on Human- or Chimpanzee-Derived Adenovirus Vectors"; Journal of Virology; vol. 81, No. 12; Jun. 2007; pp. 6594-6604.
Moore, et al. (2008) Science, 320(5877):753-5.
NCBI GenBank Locus No. AAS10364 published on Aug. 19, 2004.
NCBI GenBank Locus No. AAS10369 published on Aug. 19, 2004.
NCBI GenBank Locus No. AP.sub.-000330 published on Dec. 8, 2008.
Notice of Preliminary Rejection issued in Korean Application No. 10-2016-7024396 dated Dec. 9, 2016.
O'Hara, et al. (2012) J Infect Dis., 205(5):772-81.
Peruzzi, Daniela, et al; "A novel Chimpanzee serotype-based adenoviral vector as delivery tool for cancer vaccines": Vaccine; vol. 27, No. 9; Jan. 20, 2009; pp. 1293-1300.
Pichla-Gollon, et al (2007) J. Virol., 81 (4): 1680-9.
Plenus Press, and Horwitz (1990); in Virology, eds. B. N. Fields and D. M. Knipe, pp. 1679-1721.
Rosario, et al. (2010) Eur J Immunol, 40(7):1973-84.
Rosario, et al. (2012) AIDS, 26(3):275-84.
Roy et al., Virology, 2004, 324(2):361-372.
Russel (2000) J. Gen.Virol., 81: 2573-2604.
Rux et al, (2003) J. of Virology, 77(17):9553-66.
Schnurr and Dondero, (1993) Intervirology., 36: 79-83.

FIG. 1A

Adenovirus Hexon Protein

CLUSTAL W (1.83) multiple sequence alignment

```
PanAd1     MATPSMMPQWSYMHISGQDASEYLSPGLVQFARATDSYFSLSNKFRNPTVAPTHDVTTDR
PanAd2     MATPSMMPQWSYMHISGQDASEYLSPGLVQFARATDSYFSLSNKFRNPTVAPTHDVTTDR
PanAd3     MATPSMMPQWSYMHISGQDASEYLSPGLVQFARATDSYFSLSNKFRNPTVAPTHDVTTDR
ChAd55     MATPSMLPQWAYMHIAGQDASEYLSPGLVQFARATDTYFSLGNKFRNPTVAPTHDVTTDR
ChAd73     MATPSMLPQWAYMHIAGQDASEYLSPGLVQFARATDTYFSLGNKFRNPTVAPTHDVTTDR
ChAd83     MATPSMLPQWAYMHIAGQDASEYLSPGLVQFARATDTYFSLGNKFRNPTVAPTHDVTTDR
ChAd146    MATPSMLPQWAYMHIAGQDASEYLSPGLVQFARATDTYFSLGNKFRNPTVAPTHDVTTDR
ChAd147    MATPSMLPQWAYMHIAGQDASEYLSPGLVQFARATDTYFSLGNKFRNPTVAPTHDVTTDR
           ******:*****:****************:****:*************************

PanAd1     SQRLTLRFIPVDREDTAYSYKARFTLAVGDNRVLDMASTYFDIRGVLDRGPTFKPYSGTA
PanAd2     SQRLTLRFIPVDREDTAYSYKARFTLAVGDNRVLDMASTYFDIRGVLDRGPTFKPYSGTA
PanAd3     SQRLTLRFIPVDREDTAYSYKARFTLAVGDNRVLDMASTYFDIRGVLDRGPTFKPYSGTA
ChAd55     SQRLTLRFVPVDREDNTYSYKVRYTLAVGDNRVLDMASTYFDIRGVLDRGPSFKPYSGTA
ChAd73     SQRLTLRFVPVDREDNTYSYKVRYTLAVGDNRVLDMASTYFDIRGVLDRGPSFKPYSGTA
ChAd83     SQRLTLRFVPVDREDNTYSYKVRYTLAVGDNRVLDMASTYFDIRGVLDRGPSFKPYSGTA
ChAd146    SQRLTLRFVPVDREDNTYSYKVRYTLAVGDNRVLDMASTYFDIRGVLDRGPSFKPYSGTA
ChAd147    SQRLTLRFVPVDREDNTYSYKVRYTLAVGDNRVLDMASTYFDIRGVLDRGPSFKPYSGTA
           ********:******:*:***.*:****************:*******:*********

----------- HVR 1-6 -----------
PanAd1     YNSLAPKGAPNSCEWEQVEP--AEEAAENE-DEEEEEDVVDPQEQPTTNTHVYAQAPLS
PanAd2     YNSLAPKGAPNPCEWDEAVT--AVDINLDELGEDEODAEGEAEQQ------KSRVFGQAPYG
PanAd3     YNSLAPKGAPRSCEWEQESTQTAEPAQDESEDEAEAEEEMPQEEQAPVKPTHVYAQAPLS
ChAd55     YNSLAPKGAPNTSQWITKDN-----------------------------GTDKTYSFGNAPVR
ChAd73     YNSLAPKGAPNTSQWITKDN-----------------------------GTDKTYSFGNAPVR
ChAd83     YNSLAPKGAPNTSQWITKDN-----------------------------GTDKTYSFGNAPVR
ChAd146    YNSLAPKGAPNTSQWITKDN-----------------------------GTDKTYSFGNAPVR
ChAd147    YNSLAPKGAPNTSQWVTKDN-----------------------------GTDKTYSFGNAPVR
           ***********. :.*                                   : ::.**

----------- HVR 1-6 -----------
PanAd1     GEKITKDGLQIGTEATAACGTKDLFADPTFQFEPQVGESQWNEAD--ATAAGGRVLKKTT
PanAd2     GQNITKEGTQIGVDTTSQA-QTPLYADNTFQFEPQVGESQWNETE--INYGAGRVLKKTT
PanAd3     GEKITKDGLQTGTDATATE-QKPIYADPTFQFEPQIGESQWNEAD--ASVAGGRVLKKTT
ChAd55     GLDITEEGLQIGPDESGGE-SKKIFADKTYQPEPQLGDEEWHDTIGAEDKYGGRALKPAT
ChAd73     GLDITEEGLQIRTDESGGE-SKKIFADKTYQPEPQLGDEEWHDTIGAEDKYGGRALKPAT
ChAd83     GLDITEEGLQIGTDESGGE-SKKIFADKTYQPEPQLGDEEWHDTIGAEDKYGGRALKPAT
ChAd146    GLDITEEGLQIGTDESGGK-SKKIFADKTYQPEPQLGDEEWHDTIGAEDKYGGRALKPAT
ChAd147    GLDITEEGLQIGTDDSSTE-SKKIFADKTYQPEPQVGDEEWHDTIGAEDKYGGRALKPAT
           * ::*::*: :  :          :** *:*.***:*.. *::.    . . **.**.:*

----------- HVR 1-6 -----------
PanAd1     PMKPCYGSYARPTNANGGQQVLKANAQGVLESQVERQFFSTSTSATN-RQWNIQFKLVLY
```

FIG. 1B

```
PanAd2    LMKPCYGSYARPTNENGQGILLEKEGGKFSQVEMQFFSTTQAAAGNSDNLTPKVVLY
PanAd3    PMKPCYGSYARPTNANGGQCVLVEKDGGKMESQVDMQFFSTSENARN-EANNIQFSLVLY
ChAd55    NMKPCYGSFAKPTNAKGGQAKSRTKDDGTTEPDIDMAFFDDRSQQAS------FSPELVLY
ChAd73    NMKPCYGSFAKPTNAKGGQAKSRTKDDGTTEPDIDMAFFDDRSQQAS------FSPELVLY
ChAd83    NMKPCYGSFAKPTNAKGGQAKSRTKDDGTTEPDIDMAFFDDRSQQAS------FSPELVLY
ChAd146   NMKPCYGSFAKPTNAKGGQAKSRTKDDGTTEPDIDMAFFDDRSQQAS------FSPELVLY
ChAd147   NMKPCYGSFAKPTNAKGGQAKTREKDGGTTEPDIDMAFFDDRSQQAS------FSPELVLY
          ***:*****:****:.:**.(***.    : * *.::(:* **:            * *:;***

<--- HVR 1-6 --------------------->
PanAd1    SEDVHNETPDTHISYKPTKSDDNSKVMLGQQSMPNRPNYIAFRDNFIGLMYYRSTGNMGV
PanAd2    SEDVHLETPDTHISYMPTSNEAMSRELLGQQAMPNRPNYIAFRDNFIGLMYYNSTGNMGV
PanAd3    SEDVHNETPDTHISYKPAKSDDRSKVMLGQQSMPNRPNYIGFRDNFIGLMYYRSTGNMGV
ChAd55    TENVDLDTPDTHIIYKPGTDETSSSFNLGQQSMPNRPNYIGFRDNFIGLMYYNSTGNMGV
ChAd73    TENVDLDTPDTHIIYKPGTDETSSSFNLGQQSMPNRPNYIGFRDNFIGLMYYNSTGNMGV
ChAd83    TENVDLDTPDTKIIYKPGTDETSSSFNLGQQSMPNRPNYIGFRDNFIGLMYYNSTGNMGV
ChAd146   TENVDLDTPDTRIIYKPGTDETSSGFNXGQQSMPNRPNYIGFRDNFIGLMYYNSTGNMGV
ChAd147   TENVDLETPDTHIIYKPGTDETSSSFNLGQQSMPNRPNYIGFRDNFIGLMYYNSTGNMGV
          :*.:. ::(****** * *  ..: :*   ****;*******.**************

PanAd1    LAGQASQLNAVVDLQDRNTELSYQLLLDSMGDRTKYFSMWNQAVDSYDPDVRIIENHGTE
PanAd2    LAGQASQLNAVVDLQDRRTELSYQLLLDSMGDRTRYFSMWNQAVDSYDPDVRIIENHGTE
PanAd3    LAGQASQLNAVVDLQDRNTELSYQLLLDSMGDRTRYFSMWNQAVDSYDPDVRIIENHGTE
ChAd55    LAGQASQLNAVVDLQDRNTELSYQLLLDSLGDRTRYFSMWNQAVDSYDPDVRIIENHGVE
ChAd73    LAGQASQLNAVVDLQDRNTELSYQLLLDSLGDRTRYFSMWNQAVDSYDPDVRIIENHGVE
ChAd83    LAGQASQLNAVVDLQDRNTELSYQLLLDSLGDRTRYFSMWNQAVDSYDPDVRIIENHGVE
ChAd146   LAGQASQLNAVVDLQDRNTELSYQLLLDSLGDRTRYFSMWNQAVDSYDPDVRIIENHGVE
ChAd147   LAGQASQLNAVVDLQDRNTELSYQLLLDSLGDRTRYFSMWNQAVDSYDPDVRIIENHGVE
          ****************:**********: ****:*******************  *

<--------------- HVR 7 --------------->
PanAd1    DELPNYCFPLGGIGITDTYQAIKTNG-NGAGDQATTWQKDSQFADRNEIGVGNEFAMEIN
PanAd2    DELPNYCFPLGGTINTETLTKVKF--------KTGQDAQWEKDTKFSEKNETRVGNNFAMEIN
PanAd3    DELPNYCFPLGGIGVTDFQAIKTNG-NGNGQRTTWTKDSTFADKNSIGVGNEFAMEIN
ChAd55    DELPNYCFPLNGVGFTDTEQGIKVKTTNNGTANATEWESDTSVNNAHEIAKGNPFAMEIN
ChAd73    DELPNYCFPLNGVGFTDTFQGIKVKTTNNGTANATEWESDTSVNNAHEIAKGNPFAMEIN
ChAd83    DELPNYCFPLNGVGFTDTFQGIKVKTTNNGTANATEWESDTSVNNANEIAKGNPFAMEIN
ChAd146   DELPNYCFFLNGVGFTDTFQGIKVKTTNNGTANATEWESDTSVNNAHEIAKGNPFAMEIN
ChAd147   DELPNYCFFLRGVGFTDTFQGIKVKTTNNGTANATEWESDTSVNNAHEIAKGNPFAMEIN
          *******:*: .;   *:*     :*          * :*   : *** ** ******

PanAd1    LSANLWRNFLYSNVALYLPDKLKYNPSNVETSDNPNTYDYMNKRVVAPGLVDCYINLGAR
PanAd2    LSANLWRNFLYSNVALYLPDKLKYTPANVQISSNSHSYDYMRKRVVAPGLVDCYINLGAR
PanAd3    LSANLWRNFLYSNVALYLPDKLKYNPSNVETSDNPNTYDYMNKRVVAPGLVDCYINLGAR
ChAd55    IQANLWRNFLYANVALYLPDSYKYTPANITLPTNTNTYDYMNGRVVAPSLVDAYINIGAR
ChAd73    IQANLWRNFLYANVALYLPDSYKYTPANITLPTNTNTYDYMNGRVVAPSLVDAYINIGAR
ChAd83    IQANLWRNFLYANVALYLPDSYKYTPANITLPTNTNTYDYMNGRVVAPSLVDAYINIGAR
ChAd146   IQANLWRNFLYANVALYLPDSYKYTPANITLPTNTNTYDYMNGRVVAPSLVDAYINIGAR
ChAd147   IQANLWRNFLYANVALYLPDSYKYTPANVTLPTNTNTYEYMNGRVVAPSLVDSYINIGAR
          :**********:*****  **.:.::  :: ..  *:*****.*****.*** ***

PanAd1    WSLDYMDNVNPFNHHRNAGLRYRSMLLGNGRYVPFHIQVPQKFFAIKNLLLLPGSYTYEW
PanAd2    WSLDYMDNVNPFNHHRNAGLRYRSMLLGNGRYVPFHIQVPQKFFAIKNLLLLPGSYTYEW
PanAd3    WSLDYMDNVNPFNHHRNAGLRYRSMLLGNGRYVPFHIQVPQKFFAIKNLLLLPGSYTYEW
```

FIG. 1C

```
ChAd55    WSLDPMDNVNPFNHHRNAGLRYRSMLLGNGRYVPFHIQVPQKFFAIKSLLLLPGSYTYEW
ChAd73    WSLDPMDKVNPFNHRRNAGLRYRSMLLGNGRYVPFHIQVPQKFFAIKSLLLLPGSYTYEW
ChAd83    WSLDPMDNVNPFNHHRNAGLRYRSMLLGNGRYVPFHIQVPQKFFAIKSLLLLPGSYTYEW
ChAd146   WSLDPMDNVNPFNHHRNAGLRYRSMLLGNGRYVPFHIQVPQKFFAIKNLLLLPGSYTYEW
ChAd147   WSLDPMDKVNPFNGHRNAGLRYRSMLLGNXRPVFFHIQVPQKFFAIKSLLLLPGSYTYEW
          ****  *  *  *** ***************  * *  ***************  ****

PanAd1    NFRKDVNMVLQSSLGNDLRVDGASIKFESICLYATFFPMAHNTASTLEAMLRNDTNDQSF
PanAd2    NFRKDVNMVLQSSLGNDLRVDGASIKFESICLYATFFPMAHNTASTLEAMLRNDTNDQSF
PanAd3    NFRKDVNMVLQSSLGNDLRVDGASIKFESICLYATFFPMAHNTASTLEAMLRNDTNDQSF
ChAd55    NFRKDVNMILQSSLGNDLRTDGASIAFTSINLYATFFPMAHNTASTLEAMLRNDTNDQSF
ChAd73    NFRKDVNMILQSSLGNDLRTDGASIAFTSINLYATFFPMAHNTASTLEAMLRNDTNDQSF
ChAd83    NFRKDVNMILQSSLGNDLRTDGASIAFTSINLYATFFPMAHNTASTLEAMLRNDTNDQSF
ChAd146   NFRKDVNMILQSSLGNDLRTDGASIAFTSINLYATFFPMAHNTASTLEAMLRNDTNDQSF
ChAd147   NFRKDVNMILQSSLGNDLRTDGASISFTSINLYATFFPMAHNTAGTLEAMLRNDTNDQSF
          ******** *********** **** ** * ******************  ********

PanAd1    NDYLSAANMLYPIPANATNVPISIPSRNWAAFRGWAFTRLKTKETPSLGSGFDPYYTYSG
PanAd2    NDYLSAANMLYPIPANATNVPISIPSRNWAAFRGWAFTRLKTKETPSLGSGFDPYYTYSG
PanAd3    NDYLSAANMLYPIPANATNVPISIPSRNWAAFRGWAFTRLKTKETPSLGSGFDPYYTYSG
ChAd55    NDYLSAANMLYPIPANATNVPISIPSRNWAAFRGWSFTRLKTRETPSLGSGFDPYFVYSG
ChAd73    NDYLSAANMLYPIPANATNVPISIPSRNWAAFRGWSFTRLKTRETPSLCSGFDPYFVYSG
ChAd83    NDYLSAANMLYPIPANATNVPISIPSRNWAAFRGWSFTRLKTKETPSLGSGFDPYFVYSG
ChAd146   NDYLSAANMLYPIPANATNVPISIPSRNWAAFRGWSFTRLKTRETPSLGSGFDPYFVYSG
ChAd147   NDYLSAANMLYPIPANATNVPISIPSRNWAAFRGWSFTRLKTKETPSLGSGFDPYFVYSG
          *********************************** *****  ****  ****** ***

PanAd1    SIPYLDGTFYLNHTFKKVSVTFDSSVSWPGNDRLLTPNEFEIKRSVDGEGYNVAQCNMTK
PanAd2    SIPYLDGTFYLNHTFKKVSVTFDSSVSWPGNDRLLTPNEFEIKRSVDGEGYNVAQCNMTK
PanAd3    SIPYLDGTFYLNHTFKKVSVTFDSSVSWPGNDRLLTPNEFEIKRSVDGEGYNVAQCNMTK
ChAd55    SIPYLDGTFYLNHTFKKVSITFDSSVSWPGNDRLLTPNEFEIKRTVDGEGYNVAQCNMTK
ChAd73    SIPYLDGTFYLNHTFKKVSITFDSSVSWPGNDRLLTPNEFEIKRTVDGEGYNVAQCNMTK
ChAd83    SIPYLDGTFYLNHTFKKVSITFDSSVSWPGNDRLLTPNEFEIKRTVDGEGYNVAQCNMTK
ChAd146   SIPYLDGTFYLNHTFKKVSITFDSSVSWPGNDRLLTPNEFEIKRTVDGEGYNVAQCNMTK
ChAd147   SIPYLDGTFYLNHTFKKVSTTFDSSVSWPGNDRLLTPNEFEIKRTVDGEGYNVAQCNMTK
          ******************* ***********************  ***************

PanAd1    DWFLIQMLANYNIGYQGFYIPESYKDRMYSFFRNFQPMSRQVVDETKYKDYQQVGIIHQH
PanAd2    DWFLIQMLANYNIGYQGFYIPESYKDRMYSFFRNFQPMSRQVVDETKYKDYQQVGIIHQH
PanAd3    DWFLIQMLANYNIGYQGFYIPESYKDRMYSFFRNFQPMSRQVVDETKYKDYQQVGIIHQH
ChAd55    DWFLVQMLANYNIGYQGFYVPEGYKDRMYSFFRNFQPMSRQVVDEVNYKDYQAVTLAYQH
ChAd73    DWFLVQMLANYNIGYQGFYVPEGYKDRMYSFFRNFQPMSRQVVDEVNYKDYQAVTLAYQH
ChAd83    DWFLVQMLANYNIGYQGFYVPEGYKDRMYSFFRNFQPMSRQVVDEVNYKDYQAVTLAYQH
ChAd146   DWFLVQMLANYNIGYQGFYVPEGYKDRMYSFFRNFQPMSRQVVDEVNYKDYQAVTLAYQH
ChAd147   DWFLVQMLANYNIGYQGFYVPEGYKDRMYSFFRNFQPMSRQVVDEVNYKDYQAVTLAYQH
          **** ************** ** *****************  * ****  *  * ***

PanAd1    NNSGFVGYLAPTMREGQAYPANFPYPLIGKTAVDSITQKKFLCDRTLWRIPFSSNFMSMG
PanAd2    NNSGFVGYLAPTMREGQAYPANFPYPLIGKTAVDSITQKKFLCDRTLWRIPFSSNFMSMG
PanAd3    NNSGFVGYLAPTMREGQAYPANFPYPLIGKTAVDSVTQKKFLCDRTLWRIPFSSNFMSMG
ChAd55    NNSGFVGYLAPTMRQGQPYPANYPYPLIGKSAVASVTQKKFLCDRVMWRIPFSSNFMSMG
ChAd73    NNSGFVGYLAPTMRQGQPYPANYPYPLIGKSAVASVTQKKFLCDRVMWRIPFSSNFMSMG
ChAd83    NNSGFVGYLAPTMRQGQPYPANYPYPLIGKSAVASVTQKKFLCDRVMWRIPFSSNFMSMG
ChAd146   NNSGFVGYLAPTMRQGQPYPANYPYPLIGKSAVASVTQKKFLCDRVMWRIPFSSNFMSMG
```

FIG. 1D

```
ChAd147    NNSGFVGYLAPTHRQGQPYPANYPYPLIGKSAVTSVTQKKFLCDRVMWRIPFSSNFMSMG
           * * * * * * * * * * * * , * * , * * * * ; * * * * * * * , * * * ; * * * * * * * * * * , ; * * * * * * * * * * *

PanAd1     ALTDLGQNLLYANSAHALDMTFEVDPMDEPTLLYVLFEVFDVVRVHQPHRGVIETVYLRT
PanAd2     ALTDLGQNLLYANSAHALDMTFEVDPMDEPTLLYVLFEVFDVVRVHQPHRGVIETVYLRT
PanAd3     ALTDLGQNMLYANSAHALDMTFEVDPMDEPTLLYVLFEVFDVVRVHQPHRGVIETVYLRT
ChAd55     ALTDLGQNMLYANSAHALDMNFEVDPMDESTLLYVVFEVFDVVRVHQPHRGVIEAVYLRT
ChAd73     ChAd83     ALTDLGQNMLYANSAHALDMNFEVDPMDESTLLYVVFEVFDVVRVHQPHRGVIKAVYLRT
ChAd83     ALTDLGQNMLYANSAHALDMNFEVDPMDESTLLYVVFEVFDVVRVHQPHRGVIEAVYLRT
ChAd146    ALTDLGQNMLYANSAHALDMNFEVDPMDESTLLYVVFEVFDVVRVHQPHRGVIEAVYLRT
ChAd147    ALTDLGQNMLYANSAHALDMNFEVDPMDESTLLYVVFEVFDVVRVHQPHRGVIEAVYLRT

PanAd1     PFSAGNATT (SEQ ID NO: 25)
PanAd2     PFSAGNATT (SEQ ID NO: 53)
PanAd3     PFSAGNATT (SEQ ID NO: 54)
ChAd55     PFSAGNATT (SEQ ID NO: 20)
ChAd73     PFSAGNATT (SEQ ID NO: 21)
ChAd83     PFSAGNATT (SEQ ID NO: 22)
ChAd146    PFSAGNATT (SEQ ID NO: 23)
ChAd147    PFSAGNATT (SEQ ID NO: 24)
```

FIG. 2A

Adenovirus Fiber Protein

CLUSTAL W (1.83) multiple sequence alignment

PanAd1    -MKRAKTSDETFNPVYPYDTENGPPSVFPLTPPFVSPDGFQESPPGVLSLRLSEPLVTSN
PanAd2    -MKRAKTSDETFNPVYPYDTENGPPSVFPLTPPFVSPDGFQESPPGVLSLRLSEPLVTSN
PanAd3    -MKRAKTSDETFNPVYPYDTENGPPSVFPLTPPFVSPDGFQESPPGVLSLRLSEPLVTSN
ChAd55    MSKRRVRVDDDFDPVYPYDADN-APTVFFINPPFVSSDGFQEKPLGVLSLRLADPVTTKN
ChAd73    MSKRRVRVDDDFDPVYPYDADN-APTVFFINPPFVSSDGFQEKPLGVLSLRLADPVTTKN
ChAd83    MSKRRVRVDDDFDPVYPYDADN-APTVFFINPPFVSSDGFQEKPLGVLSLRLADPVTTKN
ChAd146   MSKRRVRVDDDFDPVYPYDADN-APTVFFINPPFVSSDGFQEKPLGVLSLRLADPVTTKN
ChAd147   MSKKRARVDDGFDPVYPYDADN-APTVFFINPPFVSSDGFQEKPLGVLSLRLADPVTTKN
            *:   *: *:****:*   *:**.**** * *********:*:*:. *

PanAd1    GNLALKMGNGLSLDDAGNLTSQDVTTVTPPLKKTKTNLSLQTSAPLTVSSGSLTVAAAAP
PanAd2    GNLALKMGNGLSLDDAGNLTSQDVTTVTPPLKKTKTNLSLQTSAPLTVSSGSLTVAAAAP
PanAd3    GNLALKMGNGLSLDDAGNLTSQDVTTVTPPLKKTKTNLSLQTSAPLTVSSGSLTVAAAAP
ChAd55    GEITLKLGEGVDLDDSGKLISKNAT-----------------------------------
ChAd73    GEITLKLGEGVDLDDSGKLISKNAT-----------------------------------
ChAd83    GEITLKLGEGVDLDDSGKLISNTAT-----------------------------------
ChAd146   GEITLKLGEGLDLDSSGKLISNTAT-----------------------------------
ChAd147   GAVPLKLGEGVDLDDSGKLISKKST-----------------------------------
           * :.*:**:*:.**.:*:.  *:

PanAd1    LAVAGTSLTMQSQAPLTVQDAKLGLATQGPLTVSEGKLTLQTSAPLTAADSSTLTVSATP
PanAd2    LAVAGTSLTMQSQAPLTVQDAKLGLATQGPLTVSEGKLTLQTSAPLTAADSSTLTVSATP
PanAd3    LAVAGTSLTMQSQAPLTVQDAKLGLATQGPLTVSEGKLTLQTSAPLTAADSSTLTVGTTP
ChAd55    -----------------------------------------------------KATA
ChAd73    -----------------------------------------------------KATA
ChAd83    -----------------------------------------------------KAAA
ChAd146   -----------------------------------------------------KAAA
ChAd147   -----------------------------------------------------KANS
                                                                 *

PanAd1    PLSTSNGSLSIDMQAPIYTTNGKLALNIGAPLHVVD--TLNALTVVTGQGLPINGRALQT
PanAd2    PLSTSNGSLSIDMQAPIYTTNGKLALNIGAPLHVVD--TLNALFVVTGQGLTINGRALQT
PanAd3    PISVSSGSLGLSNEDFMYTRDCKLGIEIGGPLOVVD--SLRTLTVVTGNGITVANNALQT
ChAd55    PLSTSNGTISLMMDKPLYNNGKLGTRIGAPLKVVD--LLNFLAVAYGSGLGLKNNALTV
ChAd73    PLSISNSTISLSMAAPFYRNNGTISLNVSTPLAVFP--TPRTLGISLGSGLQTSNKILAV
ChAd83    PLSFSNNTISLNMDHPFYTKDGKLALQVSPPLRILRTSILNTIALGPGSGLGLRGSALAV
ChAd146   PLSFSNNTISLNMDHPFYTKDGKLSLQVSPPLNILRTSILNTIALGPGSGLGLRGSALAV
ChAd147   PLSTSNNTISLNMDTPFYTKDGKLTNQVTAPLKLANTAILNTLAMAYGNGLGLNNNALTV
           *:*.*.:.*:  : *:*  .*:   ::  *:  :   :::*:  *:. .    * *

PanAd1    RVTGALSYDTEGNIQLQAGGG--------NRIDHNGQLILNVAYPFDAQNNLSLRLGQGP
PanAd2    RVTGALSYDTEGNIQLQAGGG--------NRIDHNGQLILNVAYPFDAQNNLSLRLGQGP

FIG. 2B

```
PanAd3    KVAGALGYDSSGNLELRAAGG---------MKINTGSQLILDVAYPFDQNNLSLRLGQGP
ChAd55    QLVSPLTFDNKGFVKINLGNSPLTVAANRLSVTCKRGLYVTTG-DALESNISWAKG---I
ChAd73    QLTHPLTFSS-NSITYKTD-------------RGLYIDSSGRNGLEANTSLKRG---L
ChAd83    QLVSPLTFDTDGNIKLTLD-------------RGLRVTTG--DAIESNISWAKG---L
ChAd146   QLVSPLTFDTDGNIKLTLD-------------RGLHVTTG--DAIESNISWAKG---L
ChAd147   QVTSPLTFDN-SKVKIRLGNSPLWVSANKLSINCLRGLYVAPNN-TGLETNISNANA--N
                                            *          *  *

PanAd1    LIVNSAHNLDLNLNRGLYLFTSGNTKKLEVNIKTAKGLFYDGTAIAINAGDGLQPGSGSD
PanAd2    LIVNSAHNLDLRLNRGLYLFTSGNTKKLEVNIKTAKGLPYDGTAIAINAGDGLQPGSGSD
PanAd3    LYVNTNHNLDLNQNRGLTTTTSSHTTKLETKIDS---------------------------
ChAd55    RFEGNAIAANIG--KGLEFGTTSSES----------------------------------
ChAd73    IPDGNAIATYLG--SGLDYGSYDSDGKTRFIITK----------------------------
ChAd83    KFEDGAIATKIG--NGLRFGSSSTET-----------------------------------
ChAd146   KFEDGAIATNIG--NGLEFGSSSTET-----------------------------------
ChAd147   RFEGNAMVYIDTNKGLQPGTTSTES-----------------------------------
                  *   **     *

PanAd1    TNPLQTKLGLGLEYDSNKAIITKLGTGLSFDNTGAITVGNKDDKLTLWTTPDPSPNCRI
PanAd2    TNPLQTKLGLGLEYDSNKAIITKLGTGLSFDNTGAITVGNKDDKLTLNTTPDPSPNCRI
PanAd3    ------------GLDYNANGAIIAKLGTGLTFDNTGAITVGNTGDKLTLWTTPDPSPNCRT
ChAd55    -----------DVSNAYPIQVKLGTGLTFDSTGAIVAWNKEDDKLTLWTTADPSPNCHI
ChAd73    ----------IGAGLNPDSNNAMAVKLGTGLSPDSAGALTAGNKEDDKLTLWTTPDPSPNCQL
ChAd83    -----------GVDDAYPIQVKLGSGLSFDSTGAIMAGNKEDDKLTLWTTPDPSPNCQI
ChAd146   -----------GVDDAYPIQVKLGSGLSFDSTGAINAGNKEDDKLTLWTTPDPSPNCQI
ChAd147   -----------GVTNAYPIQVKLGAGLAFDSTGAIVAWNKERDSLTLWTTPDPSPNCKI
                         *   ** ***  ***     *    * **********    *

PanAd1    NSEKDAKLTLVLTKCGSQVLASVDLSVKG--SLAPISGTVTSAQIVLRFDENGVLLSNS
PanAd2    NSEKDAKLTLVLTKCGSQVLASVSLSVKG--SLAPISGTVTSAQIVLRFDENGVLLSNS
PanAd3    HAQKDCKFTLVLTKCGSQLLASVAALAVSG--NLSSMTQTVESVTIFLRFDQNGVLMEHS
ChAd55    YSDKDAKLTLCLTKCGSQILGTVSLIAVPT-GSENFITGQVTTALVSLRFDANGVLQTSS
ChAd73    LSDRDAKFTLCLTKCGSQILGTVAVAAVTVSSALNPINDTVKSAIYFLRFDSDGVLMSNG
ChAd83    LAENDAKLTLCLTKCGSQILATVSVLVVGS-QNLNFITGFVSSAQVFLRFDANGVLLTEH
ChAd146   LAENDAKLTLCLTKCGSQILKTVSVLFVGS-GNLRFITGVSSAQVPLRFDANGVLLTEH
ChAd147   ASEKDAKLTLCLTKCGSQILGTVSLLAVS--GSLAPITGAVSTALVSLKFRANGALLDKS
               *  *****   *                       *     *       *

PanAd1    SLDPQYWNYRKGDSTEGTAYTNAVGFMSNLTAYPKTQSQTAKSNIVSQVYLNGDKTKPMT
PanAd2    SLDPQYWNYRKGDSTEGTAYTNAVGFMPNLTAYPKTQSQTAKSNIVSQVYLNGDKTKPMT
PanAd3    SLDKEYWNFRNGNSTNAPYTNAVGFMPNLSAYPKTQSQTAKNNIVSEVYLNGDKSKPMI
ChAd55    TLDKEYWNFRKGDVTPAEPYTNAIGFMPNIRAYPKNTNSAAKSRIVGKVYLNGEVSMPLD
ChAd73    SMVGSYWNFRKGQTTGSVAYTNAVGFMPNLQAYPKTGSKTPKNSIVSQVYLNGEYTMPMT
ChAd83    STLKKYWGYRQGDSTDGTPYVEAVGFNPWLKAYPKSQSSTTKNNIVGQVYMNGDVSKPML
ChAd146   STLKKYWGYRQGDSIDGTPYTNAVGFNPNLKAYPKSQSSTTKNNIVGQVYMNGDVSKPML
ChAd147   TLNKEYWNYRQGDLIPGTPYTHAVGFMPNKRAYPKNTAASKSNIVGDVYLDGDASKPLS
                 *       *  *  ****       *       *   ** *

PanAd1    LTITLNGTNETG-DATVSTYSMSFSWNWNGS-NYINDTFQTNSFTFSYIAQE (SEQ ID NO: 19)
PanAd2    LTITLNGTNETG-DATVSTYSMSFSWNWNGS-NYINDTFQTNSFTFSYIAQE (SEQ ID NO: 50)
```

FIG. 2C

```
PanAd3    LTITLNGTNESSETSQVSHYSMSFTWSNDSG-KYATSTFATNSFTFSYIAEQ (SEQ ID NO: 53)
ChAd55    LIITFNETSNE-----FCTYCINFQWQWGTD-KYKNETLAVSSFTFSYIAQE (SEQ ID NO: 14)
ChAd73    LTITFNGTDEKD-TTPVSTYSMTFTNQWTGDYKDKNITEATNSFTFSYNAGE (SEQ ID NO: 15)
ChAd83    LTITLNGTDDS------NSTYSNSFSYTWTNG-SYVGATFGANSYTFSYIAQE (SEQ ID NO: 16)
ChAd146   LTITLNGTDDS------NSTYSNSFSYTWTNG-SYVGATFGANSYTFSYIAQE (SEQ ID NO: 17)
ChAd147   LIITFNETDDE------FCDYCINFQWKWGAD-QYKDKTLATSSFTFSYIAQE (SEQ ID NO: 18)
          * **:* *:;         *.:.* :  *  : ,  *: .,*;****;*;;
```

FIG. 3A

Adenovirus Penton Protein

CLUSTAL W (1.83) multiple sequence alignment

```
PanAd1     -MRRAAMYHEGPPPSYESVVGA--AAASPFASQLEPPYVPPRYLRPTGGRNSIRYSELAP
PanAd2     -MRRAAMYHEGPPPSYESVVGA--AAASPFASQLEPPYVPPRYLRPTGGRNSIRYSELAP
PanAd3     -MRRAAMYHEGPPPSYESVVGA--AAASPFASQLEPPYVPPRYLRPTGGRNSIRYSELAP
ChAd55     MMRR---VYPEGPPPSYESVMQQ--AVAAAMQPPLEAPYVPPRYLAPTEGRNSIRYSELAP
ChAd73     MMRR---VYPEGPPPSYESVMQQ--AVAVAMQPPLEAPYVPPRYLAPTEGRNSIRYSELAP
ChAd83     MMRR---VYPEGPPPSYESVMQQ--AVAAAMQPPLEAPYVPPRYLAPTEGRNSIRYSELAP
ChAd146    MMRR---VYPEGPPPSYESVMQQ--AVAAAMQPPLEAPYVPPRYLAPTEGRNSIRYSELAP
ChAd147    MMRR---AYPEGPPPSYESVMQQAMAAAAMQPPLEAPYVPPRYLAPTEGRNSIRYSELAP
              **   * ********;       *.*.(*. **,********* ** ************

PanAd1     LYDTTRVYLVDNKSADVASLNYQNDHSNFLTTVIQNNDYTPSEASTQTIRLDDPSRWGGD
PanAd2     LYDTTRVYLVDNKSADVASLNYQNDHSNFLTTVIQNNDYTPSEASTQTIRLDDRSRWGGD
PanAd3     LYDTTRVYLVDNKSADVASLNYQMDRSNFLTTVIQNEDYTPSEASTQTINLSURSRWGGD
ChAd55     LYDTTRLYLVDNKSADIASLNYQNDHSNFLTTVVQNNDFTPTEASTQTINFDERSRWGCQ
ChAd73     LYDTTRLYLVDNKSADIASLNYQNDHSNFLTTVVQNNDFTPTEASTQTINFDERSRWGCQ
ChAd83     LYDTTRLYLVDNKSADIASLNYQNDHSNELTTVVQNNDFTPTEASTQTIRFDERSRWGCQ
ChAd146    LYDTTRLYLVDNKSADIASLNYQNDHSNFLTTVVQNNDFTPTEASTQTINFDERSRWGCQ
ChAd147    LYDTTRLYLVDNKSADIASLNYQNDHSNFLTTVVQNNDFTPTEASTQTINFDERSRWGCQ
           ****;******** *;***************;****(** ***********;;***;

PanAd1     LKTILHTNMPVNEFMFTNKFKARVMVSRSHTK--------DDRVELKYEWVEFELPEG
PanAd2     LKTILHTNMPVNEFMFTNKFKARVMVSRSHTK--------DDRVELKYEWVEFELPEG
PanAd3     LKTILHTNMPVNEFMFTNKFKARVMVSRSHTK--------DDRVELKYEWVEFELPEG
ChAd55     LKTIMHTNMPVNEFMYSNKFKARVMVSRKTPNSVAVGDDYDGSQDELTYEWVEFELPEG
ChAd73     LKTIMHTNMPVNEFMYSNKFKARVMVSRKTPNGVTVGDDYDGSQDELTYEWVEFELPEG
ChAd83     LKTIMHTNMPVNEFMYSNKFKARVMVSRKTPNGVTVTD---GSQDELTYEWVEFELPEG
ChAd146    LKTIMHTNMPVNEFLYSNKFKARVMVSRKTPNGVTVTD---GSQDELTYEWVEFELPEG
ChAd147    LKTIMHTNMPVNEFMYSNKFKARVMVSRKTPNGVTVTEDYDGSQDELKYEWVEFELPEG
           ****;********;;;********.****,.)       ...;**,************

PanAd1     NYSETMTIDLMNNAIVEHYLKVGRQNGVLESDIGVKFDTRRFPLGLDPVTGLVMPGVYTN
PanAd2     NYSETMTIDLMNNAIVEHYLKVGRQNGVLESDIGVKFDTRRFPLGLDPVTGLVMPGVYTN
PanAd3     NYSETMTIDLMNNAIVEHYLKVGRQNGVLESDIGVKFDTRRFRLGLDPVTGLVMPGVYTN
ChAd55     NFSVTMTIDLMNNAIIDNYLAVGRQNGVLESDIGVKFDTRRFRLGWDPVTELVMPGVYTN
ChAd73     NFSVTMTIDLMNNAIIDNYLAVGRQNGVLESDIGVKFDTRRFRLGWDPVTELVMPGVYTN
ChAd83     NFSVTMTIDLMNNAIIDNYLAVGRQNGVLESDIGVKFDTRRFRLGWDPVTELVMPGVYTN
ChAd146    NFSVTMTIDLMNNAIIDNYLAVGRQNGVLESDIGVKFDTRRFRLGWDPVTELVMPGVYTN
ChAd147    NFSVTMTIDLMNNAIIDNYLAVGRQNGVLESDIGVKFDTRRFRLGWDPVTELVMPGVYTN
           *;* ***********;;;*** ****************************   *******

PanAd1     EAFHPDIILLPGCGVDFTYSRLSMLLGIRKRQPFQEGFRITYEDLEGGHIPALLDVEAYQ
PanAd2     EAFHPDIILLPGCGVDFTYSRLSMLLGIRKRQPFQEGFRITYEDLKGGHIPALLDVEAYQ
```

FIG. 3B

```
PanAd3    EAFHPDIILLPGCGVDFTYSRLSNLLGIKKRQPFQEGFRITYEDLEGGNIPALLDVEAYQ
ChAd55    EAFHPDIVLLPGCGVDFTESRLSNLLGIRKRQPFQEGFQILYEDLEGGNIPALLDVEAYE
ChAd73    EAFHPDIVLLPGCGVDFTESRLSNLLGIRKRQPFQEGFQILYEDLEGGNIPALLDVEAYE
ChAd83    EAFHPDIVLLPGCGVDFTESRLSNLLGIRKRQPFQEGFQILYEDLEGGNIPALLDVEAYE
ChAd146   EAFHPDIVLLPGCGVDFTESRLSNLLGIRKRQPFQEGFQIMYEDLEGGNIPALLDVEAYE
ChAd147   EAFHPDIVLLPGCGVDFTESRLSNLLGIRKRQPFQEGFQIMYEDLEGGNIPALLDVDAYE
          ******:*****************:******:**:****:*:***********:.***

PanAd1    DSLKEEEAGEGEGGG--AGQEEGGASSEASADPAAAAEAEAADPAMVVEEEKDMNDEAVR
PanAd2    NSLKEEEAGEGSGGGG-AGQEEGGASSEASADAAAAAEAEEAKDPAMVVEEEKDMNDEAVR
PanAd3    DSLKEEEAGEGSGGGGGGAGQEEGGASSEASADAAAAAEAEAADPAMVVEEEKDMNDEAVR
ChAd55    KSKEE---------------------SAAAATAAVA------------------TASTEVR
ChAd73    KSKEDS----------------AAATTAAVATAATTD-------------------ADATTTR
ChAd83    KSKED-----------------STAVATAATV-----------------------ADATVTR
ChAd146   KSKED--------------------SAAAATAAVA--------------------TASTEVR
ChAd147   KSKEE--------------------SAAAATAAVA--------------------TASTEVR
          .*  ::  ..                ;  *  *  .*.                   *

PanAd1    GDTFATRGEEKKAEACAAAEAAAAAA-VEAAAEAEKPPKEPVIKPLTEDSKKKSYNVL
PanAd2    GDTFATRGEEKKAEAEAAAEBAAAAAAA-VEAAAEAEKPPKEPVIKPLTEDSKKRSYNVL
PanAd3    GDTFATRGEEKKAEAEAAAEAAAAAAAVEAAAEAEKPPREPVIKALTEDSKKRSYNVL
ChAd55    GDNFASAAAVA-----EAAETESKIVIQP------------------VEKDSKDRSYNVL
ChAd73    GDTFATQAEEAAALAATDDSESKIYIKP-------------------VEKDSKDRSYNVL
ChAd83    GDTFATQAEEAALAATDSESKIVIKP--------------------VEKDSKDRSYNVL
ChAd146   GDNFASAAAVA-----EAAETESKIVIQP------------------VEKDSKDRSYNVL
ChAd147   GDNFASAAAVAA---AEAAETESKIVIQP------------------VEKDSKDRSYNVL
          **.**:..  .       *  *   *                     : : **.*****

PanAd1    KDSTNTEYRSWYLAYNYGDEADGVRSWTLLCTPDVTCGSEQVYWSLPDMMQDPVTFRSTR
PanAd2    KDSTNTEYRSWYLAYNYGDPATGVRSWTLLCTPDVTCGSEQVYWSLPDMMQDPVTFRSTR
PanAd3    KDSTNTAYRSWYLAYNYGDPATGVRSWTLLCTPDVTGGSEQVYWSLPDMMQDPVTFRSTR
ChAd55    ADKNTAYRSWYLAYNYGDPEKGVRSWTLLTTSDVTCGVEQVYWSLPDMMQDPVTFRSTR
ChAd73    ADKKNTAYRSWYLAYNYGDPEKGVRSWTLLTTSDVTCGVEQVYWSLPDMMQDPVTFRSTR
ChAd83    SDGKNTAYRSWYLAYNYGDPEKGVRSWTLLTTSDVTCGVDQVYWSLPDMMQDPVTFRSTR
ChAd146   ADKKNTAYRSWYLAYNYGDPEKGVRSWTLLTTSDVTCGVEQVYWSLPDMMQDPVTERSTR
ChAd147   PDKINTAYRSWYLAYNYGDPEKGVRSWTLLTTSDVTCGVEQVYWSLPDMMQDPVTFRSTR
          .  :* ********************:***:**:****.:**********:*:*****

PanAd1    QVSNFPVVGAELLPVHSKSFYNDQAVYSQLIRQFTSLTHVFNRFPENQILARPPAPTITT
PanAd2    QVSNFPVVGAELLPVHSKSFYNDQAVYSQLIRQFTSLTHVFNRFPENQILARPPAPTITT
PanAd3    QVSNFPVVGAELLPVHSKSFYNDQAVYSQLIRQFTSLTHVFNRFPENQILARPPAPTITT
ChAd55    QVSNFPVVGAELLPVYSKSFFNEQAVYSQQLRAFTSLTHVFNRFPENQILVRPFAPTITT
ChAd73    QVSNYPVVGAELLPVYSKSFFNEQAVYSQQLRAFTSLTHVFNRFPENQILVRPFAPTITT
ChAd83    QVSNYPVVGAELLPVYSKSFFNEQAVYSQQLRAFTSLTHVFNRFPENQILVRPFAPTITT
ChAd146   QVSNYPVVGAELLPVYSKSFFNEQAVYSQQLRAFTSLTHVFNRFPENQILVRPFAPTITT
ChAd147   QVSNYPVVGAELLPVYSKSFFNEQAVYSQQLRAFTSLTHVFNRFPENQILVRPFAPTITT
          ****:**********:****:*:*******  * ***************:**.*****

PanAd1    VSENVPALTDHGTLPLRNSIGGVQRVTVTDARRRTCPYVYKALGIVSPRVLSSRTF (SEQ ID NO:31)
PanAd2    VSENVPALTDHGTLPLRNSIGGVQRVTVTDARRRTCPYVYKALGIVSPRVLSSRTF (SEQ ID NO:52)
PanAd3    VSENVPALTDHGTLPLRNSIGGVQRVTVTDARRRTCPYVYKALGIVSPRVLSSRTF (SEQ ID NO:55)
ChAd55    VSENVPALTDHGTLPLRSSIRGVQRVTVTDARRRTCPYVYKALGVVAPRVLSSRTF (SEQ ID NO:26)
```

FIG. 3C

```
ChAd73    VSENVPALTDHGTLPLRSSIRGVQRVTVTDARRRTCPYVYKALGVVAPRVLSSRTF  (SEQ ID NO: 27)
ChAd83    VSENVPALTDHGTLPLRSSIRGVQRVTVTDARRRTCPYVYKALGVVAPRVLSSRTF  (SEQ ID NO: 28)
ChAd146   VSENVPALTDHGTLPLRSSIRGVQRVTVTDARRRTCPYVYKALGVVAPRVLSSRTF  (SEQ ID NO: 29)
ChAd147   VSENVPALTDHGTLPLRSSIRGVQRVTVTDARRRTCPYVYKALGIVAPRVLSSRTF  (SEQ ID NO: 30)
          ***************.:* *********************:***********
```

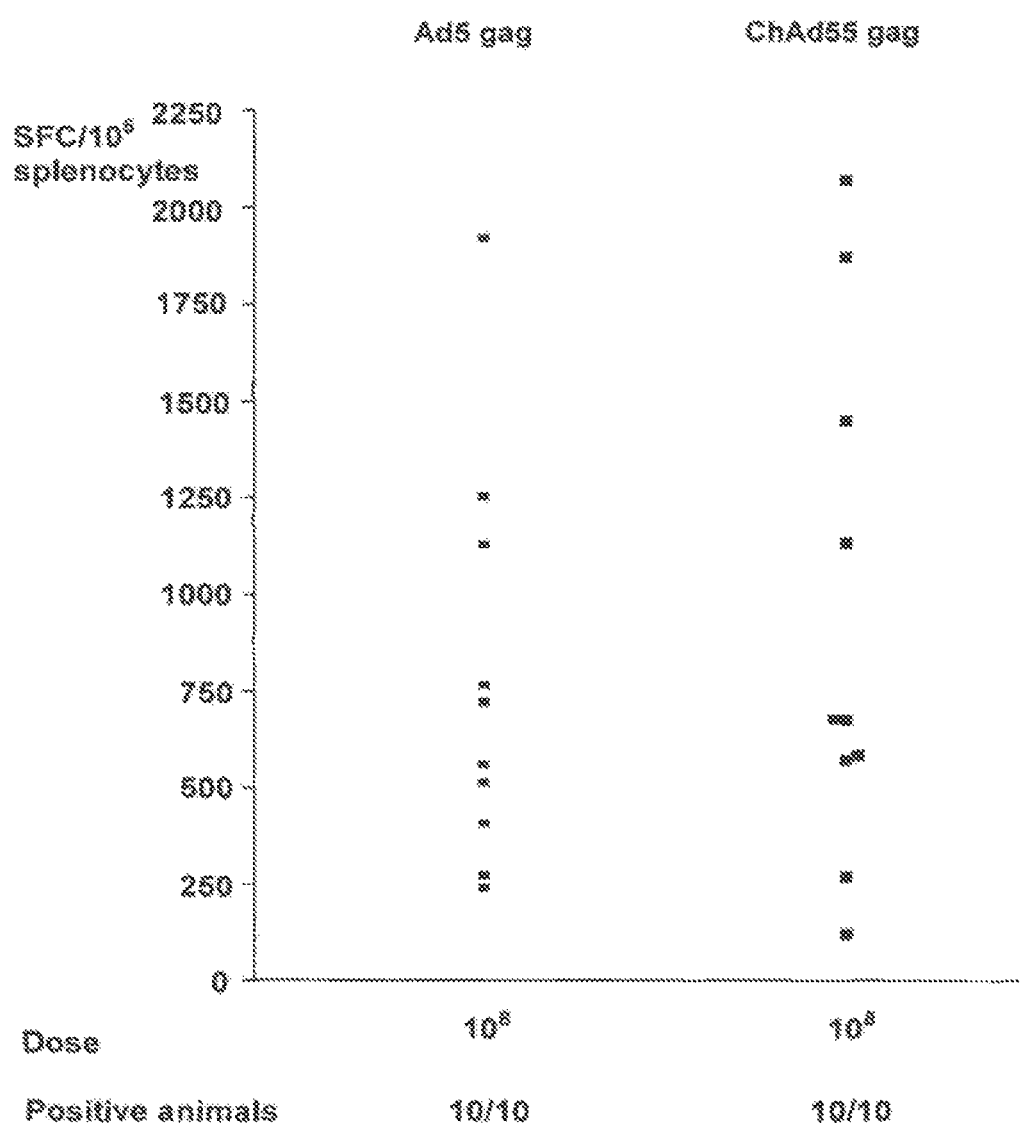

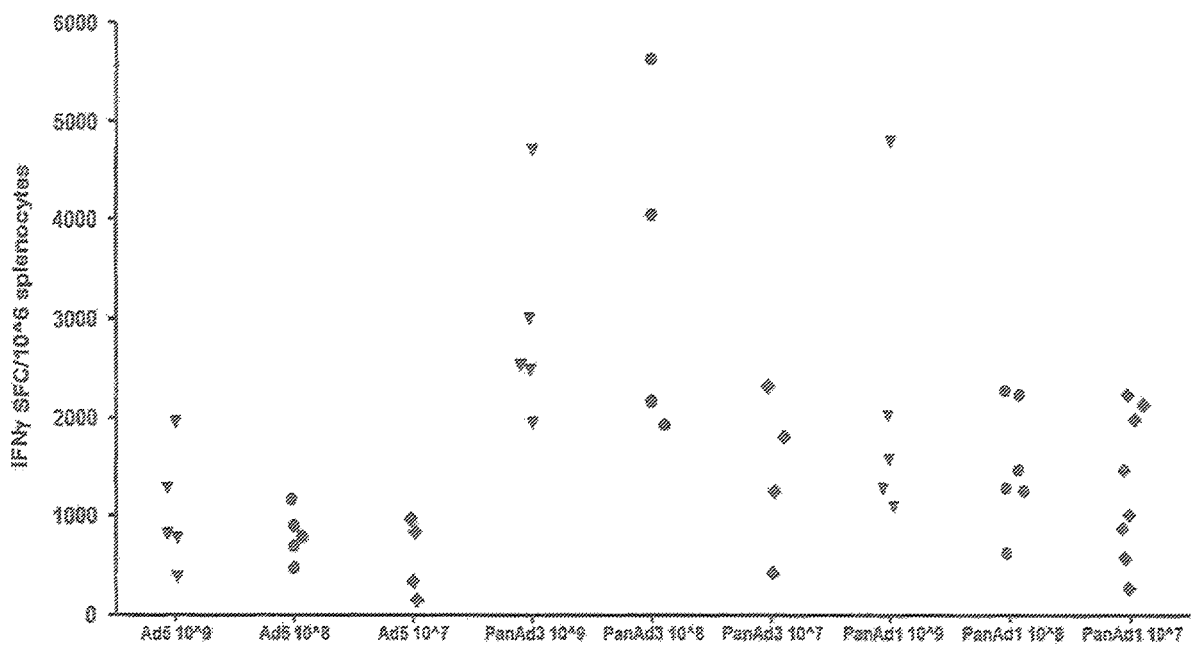

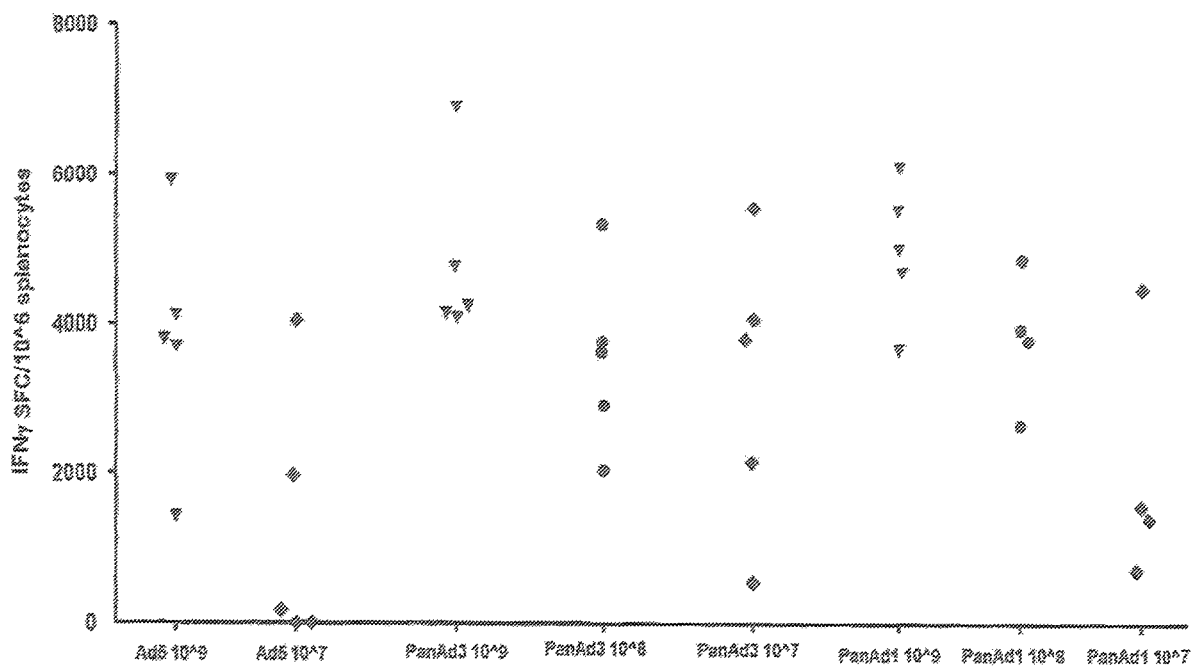

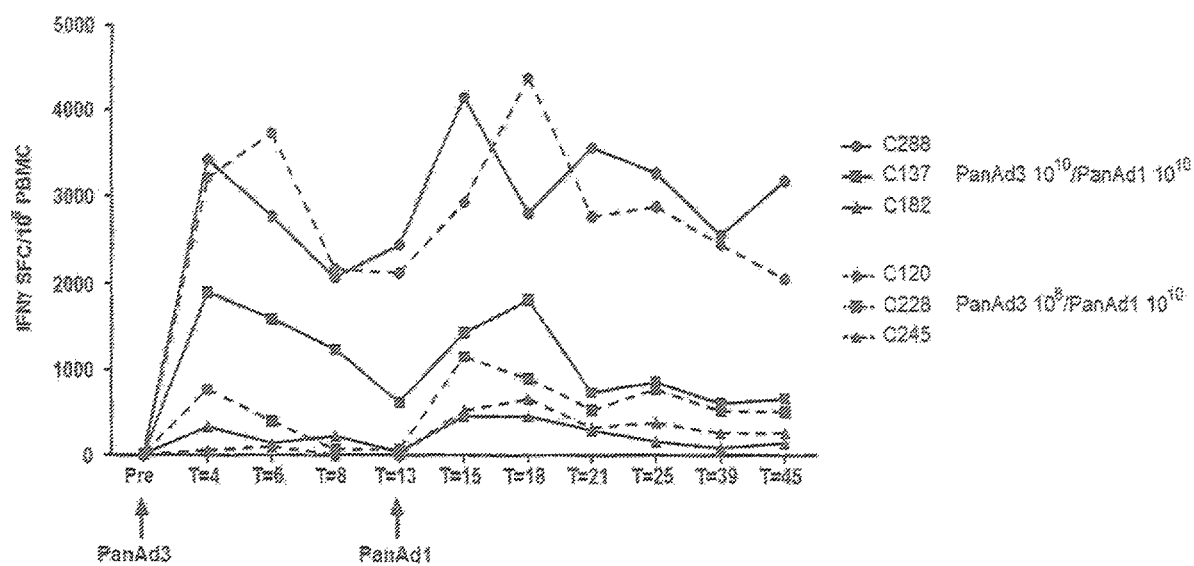

SEQUENCE LISTING

```
<160> NUMBER OF SEQ ID NOS: 65

<210> SEQ ID NO 1
<211> LENGTH: 1503
<212> TYPE: DNA
<213> ORGANISM: Human immunodeficiency virus

<400> SEQUENCE: 1
atgggtgcta gggcttctgt gctgtctggt ggtgagctgg acaagtggga gaagatcagg      60
ctgaggcctg gtggcaagaa gaagtacaag ctaaagcaca ttgtgtgggc ctccagggag     120
ctggagaggt ttgctgtgaa ccctggcctg ctggagacct ctgaggggtg caggcagatc     180
ctgggccagc tccagccctc cctgcaaaca ggctctgagg agctgaggtc cctgtacaac     240
acagtggcta ccctgtactg tgtgcaccag aagattgatg tgaaggacac caaggaggcc     300
ctggagaaga ttgaggagga gcagaacaag tccaagaaga aggcccagca ggctgctgct     360
ggcacaggca actccagcca ggtgtcccag aactacccca ttgtgcagaa cctccagggc     420
cagatggtgc accaggccat ctccccccgg accctgaatg cctgggtgaa ggtggtggag     480
gagaaggcct tctcccctga ggtgatcccc atgttctctg ccctgtctga gggtgccacc     540
ccccaggacc tgaacaccat gctgaacaca gtgggggggcc atcaggctgc catgcagatg     600
ctgaaggaga ccatcaatga ggaggctgct gagtgggaca ggctgcatcc tgtgcacgct     660
ggccccattg cccccggcca gatgagggag cccaggggct ctgacattgc tggcaccacc     720
tccaccctcc aggagcagat tggctggatg accaacaacc ccccatccc tgtgggggaa     780 atctacaaga ggtggatcat cctgggcctg aacaagattg tgaggatgta ctcccccacc     840
tccatcctgg acatcaggca gggccccaag gagcccttca gggactatgt ggacaggttc     900
tacaagaccc tgagggctga gcaggcctcc caggaggtga agaactggat gacagagacc     960
ctgctggtgc agaatgccaa ccctgactgc aagaccatcc tgaaggccct gggccctgct    1020
gccaccctgg aggagatgat gacagcctgc aggggggtgg ggggccctgg tcacaaggcc    1080
agggtgctgg ctgaggccat gtcccaggtg accaactccg ccaccatcat gatgcagagg    1140
ggcaacttca ggaaccagag gaagacagtg aagtgcttca ctgtggcaa ggtgggccac    1200 attgccaaga actgtaggggc ccccaggaag aagggctgct ggaagtgtgg caaggagggc    1260
caccagatga aggactgcaa tgagaggcag gccaacttcc tgggcaaaat ctggcccctcc    1320 cacaagggca ggcctggcaa cttcctccag tccaggcctg agcccacagc ccctcccgag    1380
gagtccttca ggttttggga ggagaagacc accccccagcc agaagcagga gcccattgac    1440
aaggagctgt accccctgc ctccctgagg tccctgtttg gcaacgaccc ctcctcccag    1500
```

```
taa                                                        1503

<210> SEQ ID NO 2
<211> LENGTH: 20
<212> TYPE: DNA
<213> ORGANISM: artificial
<220> FEATURE:
<223> OTHER INFORMATION: TLR9 agonist

<400> SEQUENCE: 2
tccatgacgt tcctgacgtt                                        20

<210> SEQ ID NO 3
<211> LENGTH: 22
<212> TYPE: DNA
<213> ORGANISM: artificial
<220> FEATURE:
<223> OTHER INFORMATION: Primer: HVR7 primer1

<400> SEQUENCE: 3
tgtcctacca rctcttgctt ga                                     22

<210> SEQ ID NO 4
<211> LENGTH: 18
<212> TYPE: DNA
<213> ORGANISM: artificial
<220> FEATURE:
<223> OTHER INFORMATION: primer: HVR7 primer2

<400> SEQUENCE: 4
gtggaarggc acgtagcg                                          18

<210> SEQ ID NO 5
<211> LENGTH: 20
<212> TYPE: DNA
<213> ORGANISM: artificial
<220> FEATURE:
<223> OTHER INFORMATION: primer: HVR1-6fd

<400> SEQUENCE: 5
caygatgtga ccaccgaccg                                        20

<210> SEQ ID NO 6
<211> LENGTH: 20
<212> TYPE: DNA
<213> ORGANISM: artificial
<220> FEATURE:
<223> OTHER INFORMATION: primer: HVR1-6rev

<400> SEQUENCE: 6
gtgttyctgt cytgcaagtc                                        20

<210> SEQ ID NO 7
<211> LENGTH: 45
<212> TYPE: DNA
<213> ORGANISM: artificial
<220> FEATURE:
<223> OTHER INFORMATION: primer: PanAd1 left end P1

<400> SEQUENCE: 7
atctggaatt cgtttaaacc atcatcaata atataccttta ttttg           45

<210> SEQ ID NO 8
<211> LENGTH: 46
<212> TYPE: DNA
```

```
<213> ORGANISM: artificial
<220> FEATURE:
<223> OTHER INFORMATION: primer: PanAd1 left end P2

<400> SEQUENCE: 8
tcaggaacta gttccgtata cctataataa taaaacggag actttg               46

<210> SEQ ID NO 9
<211> LENGTH: 34
<212> TYPE: DNA
<213> ORGANISM: artificial
<220> FEATURE:
<223> OTHER INFORMATION: primer: PanAd1 right end P1

<400> SEQUENCE: 9
tccagcggcg cgccagaccc gagtcttacc agga                            34

<210> SEQ ID NO 10
<211> LENGTH: 51
<212> TYPE: DNA
<213> ORGANISM: artificial
<220> FEATURE:
<223> OTHER INFORMATION: primer: PanAd1 right end P2

<400> SEQUENCE: 10
attcaggatc cgaattcgtt taaaccatca tcaataatat accttatttt g         51

<210> SEQ ID NO 11
<211> LENGTH: 33
<212> TYPE: DNA
<213> ORGANISM: artificial
<220> FEATURE:
<223> OTHER INFORMATION: primer: pIX P1

<400> SEQUENCE: 11
tattctgcga tcgctgaggt gggtgagtgg gcg                             33

<210> SEQ ID NO 12
<211> LENGTH: 44
<212> TYPE: DNA
<213> ORGANISM: artificial
<220> FEATURE:
<223> OTHER INFORMATION: primer: pIX P2

<400> SEQUENCE: 12
ttactggcgc gcctgcctcg agtaaacggc atttgcagga gaag                 44

<210> SEQ ID NO 13
<211> LENGTH: 37772
<212> TYPE: DNA
<213> ORGANISM: Adenoviridae - Mastadenovirus

<400> SEQUENCE: 13
catcatcaat aatataccct attttggatt gaagccaata tgataatgag gtgggcggag     60
cggggcgggg cggggaggag cggcggcgcg gggcgggccg ggaggtgtgg cggaagttga    120
gtttgtaagt gtggcggatg tgacttgcta gcgccggatg tggtaaaagt gacgtttttt    180
ggagtgcgac aacgcccacg ggaagtgaca ttttttcccgc ggttttttacc ggatgtcgta    240 gtgaatttgg gcgttaccaa gtaagatttg gccattttcg cgggaaaact gaaatgggga    300
agtgaaatct gattaatttc gcgttagtca taccgcgtaa tatttgccga gggccgaggg    360
actttgaccg attacgtgga ggaatcgccc aggtgttttt tgaggtgaat tccgcgttc    420 cgggtcaaag tctccgtttt attattatag tcagctgacg cggagtgtat ttatacccgc    480
```

```
tgatctcgtc aagaggccac tcttgagtgc cagcgagtag agttttctcc tctgccgctc    540
cgctctgaca ccgggggaaa aatgagacat ttcacctacg atggcggtgt cctcaccggc    600
cagctggctg cctcggtcct ggacgccctg atcgaggagg tattggccga caattatcct    660
cctccagctc attttgagcc acctactctt cacgaactgt atgatttgga cgtggtggca    720
cctagcgacc cgaacgagca ggcggtttcc agttttttc ctgactctat gctgttggcc    780
agccaggagg gggtcgagct cgagacccct cctccaatcg ccgtttctcc tgagcctccg    840
accctgacca ggcagcccga tcgccgtgtt ggacctgcga ctatgcccca tctgctgccc    900
gaggtgatcg atctcacctg taacgagtct ggttttccac ccagcgagga tgaggacgaa    960
gagggtgagc agtttgtgtt agattctgtg gaggaacccg ggcgcggttg cagatcttgt   1020
caataccatc ggaaaaatac aggagacccc caaattatgt gttccctgtg ttatatgaag   1080
acgacctgta tgtttattta cagtaagttt gtgattggtg ggtcggtggg ctgtagtgtg   1140
ggtaggtggt ctgtggtttt ttttttttta atatcagctt gggctaaaaa actgctatgg   1200
taattttttt aaggtccggt gtctgaacct gagcaggaag ctgaaccgga gcctgagagt   1260
cgccccagga gaaggcctgc aattctaact agaccgagtg cacctgtagc gagggacctc   1320
agcagtgcag agaccaccga ttccggtcct tcctcatccc ctccagagat tcatcccgtg   1380
gtgcctttgt gtcccctcaa gcccgttgcc gtgagagtta gtgggcggag ggccgccgtg   1440
gagagcattg aggacttgct taatgagaca caggaacctt tggacttgag ctgtaaacgc   1500
cctaggcaat aaacctgctt acctggactg aatgagttga cgcctatgtt tgcttttgaa   1560
tgacttaatg tgtatataat aaagagtgag ataatgttta attgcatggt gtgtttgatt   1620
ggggcgggt tgttgggta tataagcttc cctgggctaa acttggttac acttgacctc   1680
atggaggcct gggagtgttt agagagcttt gccgaagtgc gtgccttgct ggaagagagc   1740
tctaataata cctctgggtg gtggaggtat ttttggggct ctccccaggc taagttagtt   1800
tgtagaatca aggaggatta caagtgggaa tttgaacagc ttttgaaatc ctgtggtgag   1860
ctcttggatt ctttgaatct gggccaccag gctcttttcc aggacaagat catcaggact   1920
ttggattttt ccacaccggg gcgcattgct gccggggttg cttttctagc tttttttgaag  1980
gataaatgga gcgaagagac ccacttgagt tcgggatacg tcctggattt tctggccata   2040
caactgtgga gagcatggat caggcacaag aacagaatgc aactgttgtc ttccgtccgt   2100
ccgttgctga ttcagccgga ggagcagcag accgggccgg aggaccgggc tcgtctggaa   2160
ccagaagaga gggcaccgga gaggagcgcg tggaacctgg gagccggcct gaacggccat   2220
ccacatcggg agtgaatgtt ggacaggtgg cggatctctt tccagaactg cgacgaatct   2280
taactatcag ggaggatgga caatttgtta aggggcttaa gagggagcgg ggggcttctg   2340
aacataacga ggaggccagt aatttagctt ttagtctgat gaccagacac cgtcccgagt   2400
gcattacttt tcagcagatt aaggataatt gtgccaatga gttagatctg ctgggtcaga   2460
agtacagcat agagcagttg accacttact ggctgcagcc gggtgatgat ctggaggaag   2520
ctattagggt gtatgccaag gtggcccctga ggcccgattg caagtacaag ctcaaggggc   2580
tggtgaatat caggaattgt tgctacattt ctggaacgg ggcggaggtg gagatagaga   2640
ccgatgacag ggtggccttt aggtgtagca tgatgaatat gtggcctggg gtgctgggca   2700
tggacggggt ggtgattatg aatgtgaggt tcacggggcc caattttaat ggcacggtgt   2760
tcctgggcaa caccaacttg gtgctgcacg gggtgagctt ctatggcttt aacaacaccct  2820
```

-continued

```
gtgtggaggc ctggaccgat gtgaaggtcc gtggctgtgc cttctacgga tgttggaagg    2880
cggtagtgtg tcgccccaag agcaggagtt ccattaaaaa atgcttgttt gagaggtgca    2940
ccctgggggt gctggcggag ggcaactgtc gggtgcgcca caatgtggcc tcagaatgcg    3000
gttgcttcat gctagtcaag agcgtggcgg tcatcaagca taacatggtg tgcggcaaca    3060
gcgaggacaa ggcctcgcag atgctgacct gctcggatgg caactgccac ttactgaaga    3120
ccgtacatat aaccagccac agccgcaagg cctggcccgt gttcgagcac aacgtgttga    3180
cccgctgctc tttgcatctg ggcaacagga ggggtgtgtt cctgccctat caatgcaact    3240
tgagccacac caagatcttg ctagagcccg aaagcatgtc caaggtgaac ctgaacgggg    3300
tgtttgacat gaccctgaag atatggaagg tgctgaggta cgacgagacc aggtctcgat    3360
gcaggccctg cgagtgcggg ggcaagcata tgaggaacca gcctgtgatg ctggatgtga    3420
ccgaggagct gaggcctgac cacttggttc tggcctgcac cagggccgag tttggttcta    3480
gcgatgaaga cacagactga ggtgggtgag tgggcgtggt ctgggggtgg gaagcaatat    3540
ataagttggg ggtcttaggg tctctgtgtc tgttttgcag agggaccgcc ggcgccatga    3600 gcggagcag tagcagcaac gccttggatg gcagcatcgt gagcccttat ttgacgacgc    3660
gcatgcccca ctgggccggg gtgcgtcaga atgtgatggg ctccagcatc gacggacgac    3720
ccgtgctgcc cgcaaattcc gccacgctga cctacgcgac cgtcgcgggg accccgttgg    3780
acgccaccgc cgccgccgcc gccaccgcgc ccgcctcggc cgtgcgcagc ctggccacgg    3840
actttgcatt cttgggaccc ttggccaccg gggcggccgc ccgtgccgcc gttcgcgatg    3900
acaagctgac cgccctgctg gcgcagttgg atgcgcttac ccgggaactg ggtgaccttt    3960
cgcagcaggt cgtggccctg cgccagcagg tctccgccct gcaggctagc gggaatgctt    4020
ctcctgcaaa tgccgtttaa gataaataaa accagactct gtttggatta agaaaagta    4080 gcaagtgcat tgctctcttt atttcataat tttccgcgcg cgataggccc gagtccagcg    4140
ttctcggtcg ttgagggtgc ggtgtatctt ctccaggacg tggtagaggt ggctctggac    4200
gttgagatac atgggcatga gcccgtcccg ggggtggagg tagcaccact gcagagcttc    4260
atgctccggg gtggtgttgt agatgatcca gtcgtagcag gagcgctggg catggtgcct    4320
aaaaatgtcc ttaagcagca ggccgatggc caggggagg cccttggtgt aagtgtttac    4380
aaaacggttg agtgggaag ggtgcatgcg gggtgagatg atgtgcatct tagattgtat    4440
ttttagattg gcgatgtttc ctcccagatc ccttctggga ttcatgttgt ggaggaccac    4500
cagcacagta tatccggtgc acttgggaaa tttgtcatgc agcttagagg gaaatgcgtg    4560
gaagaacttg gagacgccct tgtggcctcc cagattctcc atgcattcgt ccatgatgat    4620
ggcaatgggc ccgcgggagg cggcctgggc aaagatgttt ctgggtcac tgacatcgta    4680 gttgtgttcc agggtgagat cgtcataggc cattttata aagcgcgggc ggagggtgcc    4740
cgactggggg atgatggttc cctcgggccc cggggcgtag ttgccttcgc agatctgcat    4800
ttcccaggcc ttaatctctg aggggggaat catatccact tgcggggcga tgaagaaaac    4860
ggtttccgga gccggggaga ttaactggga tgagagcagg tttctcagca gctgtgactt    4920
tccacagccg gtgggtccat aaataacacc tataaccggc tgcagctggt agttgagcga    4980
gctgcagctg ccgtcgtccc ggaggagggg ggccacctca ttgagcatgt cccggacgcg    5040
cttgttctcc tcgaccaggt ccgcagaag gcgctcgccg cccagggaca gcagctcttg    5100
caaggaagca aagtttttca gcggtttgag gccgtccgcc gtgggcatgt ttttcagggt    5160
ctggccgagc agctccaggc ggtcccagag ctcggtgacg tgctctacgg catctctatc    5220
```

```
cagcatatct cctcgtttcg cgggttgggg cggctttcgc tgtagggcac caggcgatgg    5280
tcgtccagcg cggccagagt catgtccttc catgggcgca gggtcctcgt cagggtggtc    5340
tgggtcacgg tgaaggggtg cgccccgggc tgggcgctgg ccagggtgcg cttgagactg    5400
gtcctgctgg tgctgaagcg ctgccggtct tcgccctgcg cgtcggccag gtagcatttg    5460
accatggtgt cgtagtccag cccctccgcg gcgtgtccct tggcgcgcag cttgcccttg    5520
gaggtggcgc gcacgcggg gcactgcagg ctcttgagcg cgtagagctt ggggcgagg    5580 aagaccgatt cggggagta ggcgtccgcg ccgcaggccc cgcacacggt ctcgcactcc    5640
accagccagg tgagctcggg gcgctcgggg tcaaaaacca ggtttccccc atgctttttg    5700
atgcgtttct tacctcgggt ctccatgagg cggtgtcccc gttcggtgac gaagaggctg    5760
tccgtgtctc cgtagaccga cttgaggggt ctgtcctcca ggggggtccc tcggtcctct    5820
tcgtagagaa actcggacca ctctgagaca aaggcccgcg tccaggccag gacgaaggag    5880
gccaggtggg aggggtaccg gtcgttgtcc actaggggt ccaccttctc caaggtgtga    5940
agacacatgt cgccctcctc ggcgtccagg aaggtgattg gcttgtaggt gtaggccacg    6000
tgacccgggg ttccggacgg gggggtataa aaggggtgg gggcgcgctc gtcctcactc    6060
tcttccgcat cgctgtctgc gagggccagc tgctggggtg agtattccct ctcgaaggcg    6120
ggcatgacct cagcgctgag gctgtcagtt tctaaaaacg aggaggattt gatgttcacc    6180
tgtcccgagc tgatgccttt gagggtgccc gcgtccatct ggtcagaaaa cacgatcttt    6240
ttattgtcca gcttggtggc gaacgacccg tagagggcgt tggagagcag cttggcgatg    6300
gagcgcaggg tctgattctt gtcccggtcg gcgcgctcct tggccgcgat gttgagctgc    6360
acgtactcgc gcgcgacgca gcgccactcg gggaagacgg tggtgcgctc gtcgggcacc    6420
aggcgcacgc gccagccgcg gttgtgcagg gtgacgaggt ccacgctggt ggcgacctcg    6480
ccgcgcaggc gctcgttggt ccagcagagg cgcccgccct tgcgcgagca aaggggggc    6540 aggggtcga gttgggtttc gtccgggggg tccgcgtcca ccgtgaagac cccggggcgc    6600
aggcgcgcgt cgaagtagtc gatcttgcat ccttgcaagt ccagcgcccg ctgccagtcg    6660
cgggcggcga gcgcgcgctc gtaggggttg agcggcgggc cccagggcat ggggtgggtg    6720
agcgcggagg cgtacatgcc gcagatgtca tagacgtaga ggggctcccg gaggatgccc    6780
aggtaggtgg ggtagcagcg gccgccgcg atgctggcgc gcacgtagtc gtagagctcg    6840 tgcgagggg cgaggaggtc ggggcccagg ttggtgcggg cggggcgctc cgcgcggaag    6900
acgatctgcc tgaagatggc atgcgagttg aagagatgg tggggcgctg gaagacgttg    6960
aagctggcgt cctgcaggcc gacggcgtcg cgcacgaagg aggcgtagga ctcgcgcagc    7020
ttgtgcacca gctcggcggt gacctgcacg tcgagcgcgc agtagtcgag ggtctcgcgg    7080
atgatgtcat acttagcctg ccccttcttt ttccacagct cgcggttgag gacgaactct    7140
tcgcggtctt tccagtactc ttggatcggg aaaccgtccg gctccgaacg gtaagagccc    7200
agcatgtaga actggttgac ggcctggtag gcgcagcagc ccttctccac gggcagggcg    7260
taggcctgcg cggccttgcg gagcgaggtg tgggtcaggg cgaaggtgtc cctgaccatg    7320
accttgaggt actggtgttt gaagtcggag tcgtcgcagc cgccccgctc ccagagcgag    7380
aagtcggtgc gcttttttga gcgggggttg ggcagcgcga aggtgacatc gttgtagagg    7440
atcttgcccg cgcgaggcat gaagttgcgg gtgatgcgga agggcccggg cacttccgag    7500
cggttgttga tgacctgggc ggcgagcacg atctcgtcga agccgttgat gttgtggccc    7560
```

```
acgatgtaga gttccaggaa gcggggccgg cccttgacgc tgggcagctt ctttagctct    7620
tcgtaggtga gctcctcggg cgaggcgagg ccgtgctcgg ccagggccca gtccgccagg    7680
tgcgggttgt ccgcgaggaa ggaccgccag aggtcgcggg ccaggagggt ctgcaggcgg    7740
tccctgaagg tcctgaactg gcggcctacg gccatctttt cggggggtgac gcagtagaag   7800
gtgaggggt cttgctgcca ggggtcccag tcgagctcca gggcgaggtc gcgcgcggcg     7860
gcgaccaggc gctcgtcgcc cccgaatttc atgaccagca tgaagggcac gagctgcttt    7920
ccgaaggcgc ccatccaagt gtaggtctct acatcgtagg tgacaaagag acgttccgtg    7980
cgaggatgcg agccgatcgg gaagaactgg atctcccgcc accagttgga ggagtggctg    8040
ttgatgtggt gaaagtagaa gtcccgtcgg cgggccgagc actcgtgctg cttttgtaa     8100
aagcgagcgc agtactggca cgcgctgcacg ggctgtacct cttgcacgag atgcacctgc    8160
cgaccgcgga cgaggaagct gagtgggaat ctgagccccc cgcatggctc gcggcctggc   8220
tggtgctctt ctactttgga tgcgtggccg tcaccgtctg gctcctcgag gggtgttacg    8280
gtggagcgga tcaccacgcc gcgcgagccg caggtccaga tatcggcgcg cggcggtcgg    8340
agtttgatga cgacatcgcg cagctgggag ctgtccatgg tctggagctc ccgcggcggc    8400
ggcaggtcag ccgggagttc ttgcaggttt acctcgcaga gacgggccag ggcgcggggc    8460
aggtccaggt ggtacttgaa ttcgagaggc gtgttggtgg cggcgtcgat ggcttgcagt    8520
atgccgcagc cccggggcgc gacgacggtg ccccgcgggg cggtgaagct cccgccgccg    8580
ctcctgctgt cgccgccggt ggcggggctt agaagcggtg ccgcggtcgg gcccccggag    8640
gtaggggggg ctccggtccc gcgggcaggg gcggcagcgg cacgtcggcg ccgcgcgcgg    8700
gcaggagctg gtgctgcgcc cggaggttgc tggcgaaggc gacgacgcgg cggttgatct    8760
cctggatctg gcgcctctgc gtgaagacga cgggtccggt gagcttgaac ctgaaagaga    8820
gttcgacaga atcaatctcg gtgtcattga ccgcgacctg gcgcaggatc tcctgcacgt    8880
cgcccgagtt gtcttggtag gcgatctcgg ccatgaactg ttcaatctct tcctcctgga    8940
ggtctccgcg tccggcgcgc tccacggtgg ccgccaggtc gttggagatg cgcgccatga    9000
gctgcgagaa ggcgttgagt ccgccctcgt tccacactcg gctgtagacc acgccgccct    9060
ggtcgtcgcg ggcgcgcatg accacctgcg cgaggttgag ttccacgtgg cgcgcaaaga    9120
cggcgtagtt gcgcaggcgc tggaagaggt agttgagggt ggtggcggtg tgctcggcca    9180
caaagaagta catgacccag cggcgcaacg tggattcgtt gatgtccccc aaggcctcca    9240
gtcgctccat ggcctcgtag aagtccacgg cgaagttgaa aaactgggag ttgcgcgccg    9300
acacggtcaa ctcctcctcc agaagacgga tgagctcggc gacggtgtcg cgcacctcgc    9360
gctcgaaggc tatgggaatc tcttcctccg ccagcatcac cacctcttcc tcttcttcct    9420
cctctggcac ttccatgatg gcttcctcct cttcgggggg tggcggcggg ggaggggcg     9480
ctcggcgccg gcggcggcgc accgggaggc ggtccacgaa gcgctcgatc atctccccgc    9540
ggcggcgacg catggtctcg gtgacggcgc ggccgttctc tcggggacgc agctggaaga    9600
cgccgccggt catctggtgc tgggggcgggt ggccgtgggg cagcgagacc gcgctgacga   9660
tgcatcttaa caattgctgc gtaggtacgc gccgaggga cctgagggag tccagatcca    9720
ccggatccga aaccctttcg aggaaggcat ctaaccagtc gcagtcgcaa ggtaggctga    9780
gcaccgtggc gggcggcggg gggtgggggg agtgtctggc ggaggtgctg ctgatgatgt    9840
aattgaagta ggcggtcttg acacggcgga tggtcgacag gagcaccata tctttgggcc    9900
cggcctgctg gatgcggagg cggtcggcca tgccccaggc ttcgttctgg catctgcgca   9960
```

```
ggtctttgta gtagtcttgc atgagccttt ccaccggcac ctcttctcct tcttcttctg    10020
acatctctgc tgcatctgcg gccctggggc gacggcgcgc gccctgccc cccatgcgcg     10080 tcaccccgaa cccctgagc ggctggagca gggccaggtc ggcgacgacg cgctcggcca     10140
ggatggcctg ctggacctgc gtgagggtgg tttggaagtc atccaagtcc acgaagcggt    10200
ggtaggcgcc cgtgttgatg gtgtaggtgc agttggccat gacggaccag ttgacggtct    10260
ggtggcccgg ttgcgtcatc tcggtgtacc tgaggcgcga gtaggcgcgc gagtcgaaga    10320
tgtagtcgtt gcaagtccgc accaggtact ggtagcccac caggaagtgc ggcggcggct    10380
ggcggtagag gggccagcgg agggtggcgg gggctccggg ggccaggtct tccagcatga    10440
ggcggtggta ttcgtagatg tacctggaca tccaggtgat gcccgcggcg gtggtggagg    10500
cgcgcgggaa gtcgcgcacc cggttccaga tgttgcgcag cggcagaaag tgctccatgg    10560
taggcgtgct ctggccggtc aggcgcgcgc agtcgttgat actctagacc agggaaaacg    10620
aaagccggtc agcgggcact cttccgtggt ctggtggata aattcgcaag ggtatcatgg    10680
cggagggcct cggttcgagc cccgggcccg ggccggacgg tccgccatga tccacgcggt    10740
taccgcccgc gtgtcgaacc caggtggcga cgtcagacaa cggtggagtg ttccttttgg    10800 gtttttttc caaattttc tggccgggcg ccgacgccgc cgcgtaagag actagagtgc      10860
aaaagcgaaa gcagtaagtg gctcgctccc tgtagcccgg aggatccttg ctaagggttg    10920
cgttgcggcg aaccccggtt cgagtctggc tctcgcgggc cgctcgggtc ggccggaacc    10980
gcggctaagg cgggattggc ctccccctca ttaaagaccc cgcttgcgga ttcctccgga    11040
cacaggggac gagccccttt ttactttgc ttttctcaga tgcatccggt gctgcggcag     11100
atgcgccccc cgcccagca gcagcagcaa catcagcaag agcggcacca gcagcagcgg    11160
gagtcatgca gggcccctc gcccacgctc ggcggtccgg cgacctcggc gtccgcggcc    11220
gtgtctggag ccggcggcgg ggggctggcg gacgacccgg aggagccccc gcggcgcagg    11280
gccagacagt acctggacct ggaggagggc gagggcctgg cgcgactggg ggcgccgtcc    11340
cccgagcgcc acccgcgggt gcagctgaag cgcgactcgc gcgaggcgta cgtgcctcgg    11400
cagaacctgt tcagagaccg cgcgggcgag gagcccgagg agatgcggga ccgcaggttc    11460
gccgcggggc gggagctgcg gcaggggctg aaccgggagc ggctgctgcg cgaggaggac    11520
tttgagcccg acgcgcggac ggggatcagc cccgcgcgcg cgcacgtggc ggccgccgac    11580
ctggtgacgg catacgagca gacggtgaac caggagatca acttccaaaa aagcttcaac    11640
aaccacgtgc gcacgctggt ggcgcgcgag gaggtgacca tcggcctgat gcacctgtgg    11700
gactttgtga gcgcgctgga gcagaacccc aacagcaagc ctctgacggc gcagctgttc    11760
ctgatagtgc agcacagcag ggacaacgag gcgttcaggg acgcgctgct gaacatcacc    11820
gagcccgagg gtcggtggct cctggacctg attaacatct gcagagcat agtggtgcag     11880 gagcgcagcc tgagcctggc cgacaaggtg cggccatca attactcgat gctcagtctg     11940
ggcaagtttt acgcgcgcaa aatctaccag acgccgtacg tgcccataga caaggaggtg    12000
aagatcgacg gcttctacat gcgcatggcg ctgaaggtgc tgaccctgag cgacgacctg    12060
ggcgtgtacc gcaacgagcg catccacaag gccgtgagcg tgagcggcg gcgcgagctg     12120 agcgaccgcg agctgatgca cagcctgcag cgggcgctgg cggggccgg cagcggcgac    12180 agggaggcca gtcctactt cgaggcgggg cggacctgc gctgggtgcc cagcggagg       12240 gccctggagg ccgcggggc ccgccgcgag gactatgcag acgaggagga ggaggatgac    12300
```

```
gaggagtacg agctagagga gggcgagtac ctggactaaa ccgcaggtgg tgttttggt    12360
agatgcaaga cccgaacgtg gtggacccgg cgctgcgggc ggctctgcag agccagccgt   12420
ccggccttaa ctctacagac gactggcgac aggtcatgga ccgcatcatg tcgctgacgg   12480
cgcgcaatcc ggacgcgttc cggcagcagc cgcaggccaa caggctctcc gccatcttgg   12540
aggcggtggt gcctgcgcgc gcgaacccca cgcacgagaa ggtgctggcc atagtgaacg   12600
cgctggccga gaacagggcc atccgcccgg acgaggccgg gctggtgtac gacgcgctgc   12660
tgcagcgcgt ggcccgctac aacagcggca acgtgcagac caacctggac cggctggtgg   12720
gggacgtgcg cgaggcggtg gcgcagcggg agcgcgcgga gcggcagggc aacctgggct   12780
ccatggtggc gctgaacgcc ttcctgagca cgcagccggc caacgtgccg cggggcagg   12840
aggactacac caactttgta agcgcgctgc ggctgatggt gaccgagacc ccccagagcg   12900
aggtgtacca gtcggggccg gactacttct tccagaccag cagacagggc ctgcagacgg   12960
tgaacctgag ccaggctttc aagaacctgc ggggctgtg gggggtgaag cgcccaccg    13020
gggaccgggc gacggtgtcc agcctgctga cgcccaactc gcgcctgctg ctgctgctga   13080
tcgcgccgtt cacggacagc ggcagcgtgt cccgggagac ctacctcggg cacctgctga   13140
cgctgtaccg cgaggccatc gggcagaccc aggtggacga gcacaccttc caggagatca   13200
ccagcgtgag ccgcgcgctg gggcaggagg acacgggcag cctggaggcg accctgaact   13260
acctgctgac caaccggcgg cagaagatcc cctcgctgca tagtttgacc accgaggagg   13320
agcgcatcct gcgctacgtg cagcagagcg tgagcctgaa cctgatgcgc gacggggtga   13380
cgcccagcgt ggcgctggac atgaccgcgc gcaacatgga accgggcatg tacgccgcgc   13440
accggcctta catcaaccgc ctgatggact acttgcatcg cgcggcggcc gtgaaccccg   13500
agtacttcac caacgccatc ctgaaccgc actggctccc gccgcccggg ttctacagcg   13560
ggggcttcga ggtccccgag gccaacgacg gcttcctgtg ggacgacatg gacgacagcg   13620
tgttctcccc gcgccgcag gcgctggcgg aggcgtcgct gctccgcctc cccaagaagg   13680
aagagagccg ccggcccagc agcgcggcgg cctctctgtc cgagctgggg cggcggccg    13740
cgcggcccgg gtcccggggg ggcagcccct ttcccagcct ggtgggtgt ctgcagagcg    13800
ggcgcaccac ccggccccgg ctgctgggcg aggacgagta cctgaacaac tccctgatgc   13860
agccggtgcg ggagaaaaac ctgccccccg ccttccccaa caacgggata gagagcctgg   13920
tagacaagat gagcagatgg aagacctatg cgcaggagca cagggactcg cccgtgctcc   13980
gtccgcccac gcggcgccag cgccacgacc ggcagcgggg gctggtgtgg gatgacgagg   14040
actccgcgga cgatagcagc gtgctggacc tgggggggag cggcggcaac ccgttcgcgc   14100
acctgcgccc ccgcctgggg aggatgtttc aataaaaaa aaaaaaaatc aagcatgatg   14160
caaggttttt taagcggata aataaaaac tcaccaaggc catggcgacc gagcgttgtt   14220
ggtttcttgt tgtgttccct tagtatgcgg cgcgcggcga tgtaccacga gggacctcct   14280
ccctcttatg agagcgtggt gggcgcggcg gcggcctctc cctttgcgtc gcagctggag   14340
ccgccgtacg tgcctccgcg gtacctgcgg cctacggggg aagaaacag catccgttac    14400
tcggagctgg cgcccctgta cgacaccacc ggggtgtacc tggtggacaa caagtcggcg   14460
gacgtggcct ccctgaacta ccagaacgac cacagcaatt ttttgaccac ggtcatccag   14520
aacaatgact acacccccga gcgaggccagc acccagacca tcaatctgga tgaccggtcg   14580
cactggggcg cgacctgaa aaccatcctg cacaccaaca tgcccaacgt gaacgagttc   14640
atgttcacca ataagttcaa ggcgcgggtg atggtgtcgc gctcgcacac caaggacgac   14700
```

```
cgggtggagc tgaagtacga gtgggtagag ttcgagctgc ccgagggcaa ctactcggag   14760
accatgacca tagacctgat gaacaacgcg atcgtggagc actatctgaa agtgggcagg   14820
cagaacgggg tcctggagag cgacatcggg gtcaagttcg acaccaggaa cttccgcctg   14880
gggctggacc cggtcaccgg gctggttatg cccggggtct acaccaacga ggccttccac   14940
cccgacatca tcctgctgcc cggctgcggg gtggacttca cctacagccg cctgagcaac   15000
ctgctgggca tccgcaagcg gcagcccttc caggagggct tcaggatcac ctacgaggac   15060
ctggaggggg gcaacatccc cgcgctcctg gatgtggagg cctaccagga tagcttgaag   15120
gaagaagagg cgggagaggg cagcggcggt ggcgccggtc aggaggaggg cggggcctcc   15180
tctgaggcct ctgcggaccc agccgctgcc gccgaggcgg aggcggccga ccccgcgatg   15240
gtggtagagg aagagaagga tatgaacgac gaggcggtgc gcggcgacac ctttgccact   15300 cgggggagg agaagaaagc ggaggccgag gccgcggcag aggaggcggc agcagcggcg   15360
gcggcagtag aggcggcggc cgaggcggag aagccccca aggagcccgt gattaagccc   15420
ctgaccgaag atagcaagaa gcgcagttac aacgtgctca aggacagcac caacaccgag   15480
taccgcagct ggtacctggc ctacaactac ggcgacccgg cgacggggt gcgctcctgg   15540 accctgctgt gtacgccgga cgtgacctgc ggctcggagc aggtgtactg gtcgctgccc   15600
gacatgatgc aagaccccgt gaccttccgc tccacgcggc aggtcagcaa cttcccggtg   15660
gtgggcgccg agctgctgcc cgtgcactcc aagagcttct acaacgacca ggccgtctac   15720
tcccagctca tccgccagtt cacctctctg acccacgtgt tcaatcgctt tcctgagaac   15780
cagattctgg cgcgcccgcc cgccccacc atcaccaccg tcagtgaaaa cgttcctgct   15840
ctcacagatc acgggacgct accgctgcgc aacagcatcg gaggagtcca gcagtgacc   15900 gtaactgacg ccagacgccg cacctgcccc tacgtttaca aggccctggg catagtctcg   15960
ccgcgcgtcc tttccagccg cacttttaa gcatgtccat cctcatctcg cccagcaata   16020
acaccggctg gggcctgctg cgcgcgccca gcaagatgtt cggaggggcg aggaagcgct   16080
ccgaccagca ccccgtgcgc gtgcgcgggc actaccgcgc tccctggggc gcgcacaaac   16140
gcgggcgcac cggcaccgcg gggcgcacca ccgtggacga agccatcgac tcggtggtgg   16200
agcaggcgcg caactacacg cccgcggtct ccaccgtgga cgcggctatc gagagcgtgg   16260
tgcgaggcgc gcggcggtac gccaaggcga agagccgccg gaggcgcgtg gcccgccgcc   16320
accgccgccg acccgggagc gccgccaagc gcgccgccgc cgccttgctc cgtcgggcca   16380
gacgcacggg ccgccgtgcc gccatgaggg ccgcgcgccg cctggccgcc ggcatccaca   16440
ccgtggcccc ccgcgccaga agacgcgcgg ccgccgccgc cgccgcggcc atcagcgacc   16500
tggccaccag gcgccgggc aacgtgtact gggtgcgcga ctcggtgagc ggcacgcgcg   16560
tgcccgtgcg cttccgcccc ccgcggactt gagaggagag gacaggaaaa agcaacaaca   16620
tcaacaacac caccactgag tctcctgctg ttgtgtgtat cccagcggcg cgcgcgcaca   16680
cggcgacatg tccaagcgca aaatcaaaga agagatgctc caggtcgtcg cgccggagat   16740
ctatgggccc ccgaagaagg aagagcagga tttcaagccc cgcaagataa agcgggtcaa   16800
aaagaaaaag aaagatgacg atgatggcga ggtggagttt ctgcgcgcca cggcgcccag   16860
gcgcccgctg cagtggaagg gtcggcgcgt aaagcgcgtt ctgcgccccg gcaccgcggt   16920
ggtcttcacg cccggcgagc gctccacccg cactttcaag cgcgtctatg acaggtgta   16980 cggcgacgaa gacctgctgg agcaggccaa cgatcgctcc ggagagtttg cttacgggaa   17040
```

-continued

```
gcggcaccgg gcgatggaga aggacgaggt gctggcgctg ccgctggacc ggggcaaccc      17100
cacccccagc ctgaagcccg tgaccctgca gcaggtgcta ccggccagcg cgccctccga      17160
gatgaagcgg ggcctgaagc gcgagggcgg cgacctggcg cccaccgtgc agctaatggt      17220
gcccaagcgc cagaggctgg aggacgtgct ggagaaaatg aaagtagacc ccggcctgca      17280
gccggacatc agggtccgcc ccatcaagca ggtggcgccg ggcctcggcg tgcagaccgt      17340
ggacgtggtc atccccaccg gcgcctcctc ttccagcgcc gccgccgccg ccactagcac      17400
cgcggacatg gagacgcaga ctagccccgc cgccacctcc tcggcggagg tacagacgga      17460
cccctggttg ccgccgccgg cgaccgcccc ctcgcgcgca cgccgcgggc gcaggaagta      17520
cggcgccgcc agcgcgctca tgcccgagta cgccttgcat ccttccatcg cgcccacccc      17580
cggctaccga ggctacagtt accgcccgcg aagagccaag ggctccaccc gccgcagccg      17640
ccgcgccgcc acctctaccc gccgccgcag tcgccgccgc cgccggcagc ccgcgctggc      17700
tccgatctcc gtgaaaagag tggcgcgcaa cgggaacacc ttggtgctgc ccagggcgcg      17760
ctaccacccc agcatcgttt aaaaagcctg ttgtggttct tgcagatatg gccctcactt      17820
gccgcctccg tttccggtg ccgggatacc gaggaagatc gcgccgcagg aggggtatgg       17880
ccggacgcgc cctgagcgga ggcagtcgcc gtgcgcaccg gcggcgacgc gccaccagcc      17940
gacgcatgcg cggcggagtg ctgcctctgc tgatcccccct gatcgccgcg gcgatcggcg     18000
ccgtgcccgg gatcgcctcc gtggccttgc aggcgtccca gaggcgttga cacagacttc      18060
ttgcaagctt gcaaaaatat ggaaaaatcc cccaataaa aaagtctaga ctctcacgct       18120
cgcttggtcc tgtgactatt ttgtagaaaa aagatgaaag acatcaactt tgcgtcgctg      18180
gccccgcgtc acggctcgcg cccgttcctg ggacactgga acgatatcgg caccagcaac     18240
atgagcggtg gcgccttcag ttggggctct ctgtggagcg gcattaaaaa tatcggttct     18300
gccgttaaga attacggcac caaggcctgg aacagcagca cgggccagat gttgagagac     18360
aagttgaaag agcagaactt ccagcagaag gtggtggagg tctggcctc cggcatcaac      18420 ggggtggtgg acctggccaa tcaggccgtg caaaataaga tcaacagcag actggacccc     18480
cggccgccgg tggaggagct gccgccggcg ctggagacgt tgtccccga tgggcggggc     18540 gaaaagcgcc cgcggcccga cagggaagag accactctgg tcacgcacac cgatgagccg    18600 ccccctacg aggaagccct gaagcaaggc ttgcccacca ctcggcccat cgcgcccatg      18660
gccaccgggg tggtgggccg ccacacccccc gccacgctgg acctgcctcc tcctcctgtt    18720
tcttcttcgg ccgccgatgc gcagcagcag aaggcggcgc tgcccggtcc gcccgcggcc     18780
gccccccgtc ccaccgccag tcgagcgccc ctgcgtcgcg cggccagcgg cccccgcggg    18840
gtcgcgaggc acagcagcgg caactggcag aacacgctga acagcatcgt gggtctgggg    18900
gtgcagtccg tgaagcgccg ccgatgctac tgaatagctt agctaacggt gttgtatgtg    18960
tgtatgcgtc ctatgtcacc gccagaggag ctgctgagtc gccgccgttc gcgcgcccac     19020
cgccactacc accgccggta ccactccagc gcccctcaag atggcgaccc catcgatgat     19080
gccgcagtgg tcgtacatgc acatctcggg ccaggacgcc tcggagtacc tgagccccgg     19140
gctggtgcag ttcgcccgcg ccaccgacag ctacttcagc ctgagtaaca agtttaggaa      19200
ccccacggtg gcgcccacgc acgatgtgac caccgaccgg tcccagcgcc tgacgctgcg     19260
gttcatcccc gtggaccgcg aggacaccgc gtactcttac aaggcgcggt tcaccctggc     19320
cgtgggcgac aaccgcgtgc tggacatggc ctccacctac tttgacatcc gcggcgtgct    19380
ggacaggggc cccaccttca gccctactc cggcaccgcc tacaactccc tggccccccaa    19440
```

```
gggcgccccc aactcctgcg agtgggagca agtggagcca gctgaagagg cagcagaaaa   19500
tgaagatgaa gaagaagaag aggatgttgt tgatcctcag gaacaggagc ccactactaa   19560
aacacatgta tatgctcaag ctccccttc tggcgagaaa attaccaaag atggtctgca    19620
aataggaact gaggctacgg cagcaggagg cactaaagac ttatttgcag ccctacatt    19680 ccagccagaa ccccaagttg gcgaatctca gtggaatgag gcggatgcta cagcagctgg   19740
aggtagagtg ctcaaaaaga ccactcccat gaaaccttgc tatggctcat atgcccgccc   19800
cacaaatgcc aatgggggcc aaggtgtgct aaaggcaaat gcccagggag tgctcgagtc   19860
tcaggttgag atgcagttct tttccacttc tacaaatgcc acaaacgagc aaaacaacat   19920
ccagcccaaa ttggtgctgt acagcgagga tgtgcatatg gagacccag acacacacat    19980 ctcctacaag cctacaaaaa gcgatgataa ttcaaaagtc atgctgggtc agcagtccat   20040
gcccaacagg ccaaattaca tcgccttcag agacaacttt atcgggctca tgtattataa   20100
cagcactggc aacatggggg tgctggcagg tcaggcctca cagttgaatg cagtggtgga   20160
cctgcaagac agaaacacag aactgtccta ccagctcttg cttgattcca tgggagacag   20220
aaccagatac ttttccatgt ggaatcaggc cgtggacagt tatgacccag atgtcagaat   20280
tattgaaaat catggaaccg aagatgagct gcccaactat tgtttccctc tgggaggcat   20340
agggataact gacacttacc aggccattaa gactaatggc aatggggcag agatcaagc    20400 caccacgtgg cagaaagact cacaatttgc agaccgcaac gaaataggg tgggaaacaa    20460 cttcgccatg gagatcaacc tcagtgccaa cctgtggagg aacttcctct actccaacgt   20520
ggccctgtac ctgccagaca gcttaagta caaccctcc aacgtggaaa tctctgacaa     20580
ccccaacacc tacgactaca tgaacaagcg agtggtggcc ccggggctgg tggactgcta   20640
catcaacctg ggcgcgcgct ggtccctgga ctacatggac aacgtcaacc ccttcaacca   20700
ccaccgcaat gcgggcctgc gctaccgctc catgcttctg ggcaacgggc gctacgtgcc   20760
cttccacatc caggtgcccc agaagttctt tgccatcaag aacctcctcc tcctgccggg   20820
ctcctacacc tacgagtgga acttcaggaa ggatgtcaac atggtcctgc agagctctct   20880
gggcaacgac ctcagggtcg acggggccag catcaagttc gagagcatct gcctctacgc   20940
caccttcttc cccatggccc acaacacggc ctccacgctc gaggccatgc tcaggaacga   21000
caccaacgac cagtccttca cgactacct ctccgccgcc aacatgctct accccatccc    21060
cgccaacgcc accaacgtcc ccatctccat ccctcgcgc aactgggcgg ccttccgcgg    21120
ctgggccttc acccgcctta agaccaagga gaccccctcc ctgggctcgg tttcgaccc    21180 ctactacacc tactcgggct ccatacccta cctggacgga accttctacc tcaaccacac   21240
tttcaagaag gtctcggtca ccttcgactc ctcggtcagc tggccgggca acgaccgcct   21300
gctcaccccc aacgagttcg agatcaagcg ctcggtcgac ggggagggct acaacgtagc   21360
ccagtgcaac atgaccaagg actggttcct catccagatg ctggccaact acaacatcgg   21420
ctatcagggc ttctacatcc cagagagcta caaggacagg atgtactcct tctttaggaa   21480
cttccagccc atgagccggc aggtggtgga cgaaaccaag tacaaggact accagcaggt   21540
gggcatcatc caccagcaca acaactcggg cttcgtgggc tacctcgccc ccaccatgcg   21600
cgagggacag gcctaccccg ccaacttccc ctacccgctc attggcaaga ccgcggtcga   21660
cagcatcacc cagaaaaagt tcctctgcga ccgcaccctc tggcgcatcc ccttctccag   21720
caacttcatg tccatgggtg cgctcacgga cctgggccag aacctgctct atgccaactc   21780
```

```
cgcccacgcg ctcgacatga ccttcgaggt cgaccccatg gacgagccca cccttctcta    21840
tgttctgttc gaagtctttg acgtggttcg ggtccaccag ccgcaccgcg gcgtcatcga    21900
gaccgtgtac ctgcgcacgc ccttctcggc cggcaacgcc accacctaaa gaagcaagcc    21960
gccaccgcca ccacctgcat gtcgtcgggt tccaccgagc aggagctcaa ggccatcgtc    22020
agagacctgg gatgcgggcc ctattttttg ggcaccttcg acaaacgctt cccgggcttc    22080
gtcgccccgc acaagctggc ctgcgccatc gtcaacacgg ccggccgcga ccgggggc     22140 gtgcactggc tggccttcgc ctggaacccg cgctccaaaa catgctacct ctttgacccc    22200
ttcggattct cggaccagcg gctcaagcag atctaccagt tcgagtacga gggcctgctg    22260
cgccgcagcg ccatcgcctc ctcgcccgac cgctgcgtca ccctcgagaa gtccacccag    22320
accgtgcagg ggcccgactc ggccgcctgc ggtctcttct gctgcatgtt cctgcatgcc    22380
tttgtgcact ggccccagag tcccatggac cgcaaccccca ccatgaactt gctgacgggg    22440
atccccaact ccatgctcca gagccccag gccgcgccca ccctgcgccg caaccaggag    22500
cggctctaca gcttcctgga gcgccactcg ccctacttcc gccgccacag cgcgcagatc    22560
aggggggcca cctctttctg ccgcatgcaa gagatgcaag ggaaaatgca atgatgtaca    22620
cagacacttt cttttttctca ataaatggca actttattta tacatgctct ctctcgggta    22680
ttcatttccc caccacccac cacccgccgc cgtaaccatc tgctgctggc tttttaaaaa    22740
tcgaaagggt tctgccggga atcgccgtgc gccacgggca gggacacgtt gcggaactgg    22800
tagcgggtgc cccacttgaa ctcgggcacc accatgcggg gcaagtcggg gaagttgtcg    22860
gcccacaggc cgcgggtcag caccagccgc ttcatcaggt cgggcgccga gatcttgaag    22920
tcgcagttgg ggccgccgcc ctgcgcgcgc gagttgcggt acaccgggtt gcaacactgg    22980
aacaccagca gcgccggata attcacgctg ccagcacgc tccggtcgga gatcagctcg    23040
gcgtccaggt cctccgcgtt gctcagcgcg aacggggtca gcttgggcac ctgccgcccc    23100
aggaagggag cgtgccccgg cttcgagttg cagtcgcagc gcagcgggat cagcaggtgc    23160
ccgcggccgg actcggcgtt ggggtacagc gcgcgcatga aggcctccat ctggcggaag    23220
gccatctggg ccttggcgcc ctccgagaag aacatgccgc aggacttgcc cgagaactgg    23280
ttcgcggggc agctagcgtc gtgcaggcag cagcgcgcgt cggtgttggc aatctgcacc    23340
acgttgcgcc cccaccggtt cttcacgatc ttggccttgg aagcctgctc cttcagcgcg    23400
cgctgcccgt tctcgctggt cacatccatc tcgatcacgt gctccttgtt caccatgctg    23460
ctgccgtgca gacacttcag ctcgcccctcc acctcggtgc agcggtgctg ccacagcgcg    23520
cagcccgtgg gctcgaaatg cttgtaggtc acctccgcgt aggactgcag gtaggcctgc    23580
aggaagcgcc ccatcatggt cacgaaggtc ttgttgctgc tgaaggtcag ctgcagcccg    23640
cggtgctcct cgttcagcca ggccttgcac acggccgcca gcgcctccac ctggtcgggc    23700
agcatcttga agttcagctt cagctcattc tccacatggt acttgtccat cagcgcgcgc    23760
gcagcctcca tgcccttctc ccaggccgac accagcggca ggctcaaggg gttcaccacc    23820
gtcgcagtcg ccgccgcgct ttcgcttttcc gctccgctgt tctcttcttc ctcctcctct    23880
tcttcctcgc cgcccgcgcg cagccccgc accacggggt cgtcttcctg caggcgcgc    23940 accgagcgct tgccgctcct gccctgcttg atgcgcacgg gcgggttgct gaagcctacc    24000
atcaccagcg cggcctcttc ttgctcgtcc tcgctgtcca ctatgacctc gggggagggc    24060
gacctcagaa ccgtggcgcg ctgcctcttc tttttcctgg ggggcgtttgc aagctccgcg    24120 gccgcggccg ccgccgaggt cgaaggccga gggctgggcg tgcgcggcac cagcgcgtcc    24180
```

```
tgcgagccgt cctcgtcctc ggactcgagg cggcagcgag cccgcttctt tgggggcgcg    24240
cggggcggcg gcggcggggg cggcggcgac ggagacgggg acgagacatc gtccaggtg     24300 ggaggacggc gggccgcgcc gcgtccgcgc tcggggtgg tttcgcgctg gtcctcttcc     24360
cgactggcca tctcccactg ctccttctcc tataggcaga aagagatcat ggagtctctc    24420
atgcaagtcg agaaggagga ggacagccta accaccgccc cctctgagcc ctccgccgcc    24480
accgccgcgg acgacgcgcc taccaccgcc gccaccacca ccaccattac caccctaccc    24540
ggcgacgcag ccccgatcga aaggaagtg ttgatcgagc aggacccggg ttttgtgagc     24600
gaagaggagg atgaggagga tgaaaaggag aaggataccg ccgcctcagt gccaaaagag    24660
gataaaaagc aagaccagga cgacgcagag acagatgagg cagcaatcgg gcgggggac    24720 gagaggcatg atgatgatga tgatgacggc tacctagacg tgggagacga cgtgctgctt    24780
aagcacctgc accgccagtg cgtcatcgtc tgcgacgcgc tgcaggagcg ctgcgaagtg    24840
cccctggacg tggcggaggt cagccgcgcc tacgagcggc acctcttcgc gccacacgtg    24900
ccccccaagc gccgggagaa cggcacctgc gagcccaacc cgcgcctcaa cttctacccg    24960
gtcttcgcgg tacccgaggt gctggccacc taccacatct tcttccaaaa ctgcaagatc    25020
cccctctcct gccgcgccaa ccgcaccccgc gccgacaagg cgctggccct gcggcagggc    25080
gcccacatac ctgatatcgc ctctctggag gaggtgccca agatcttcga gggtctcggt    25140
cgcgacgaga acgggcggc gaacgctctg caaggagaca gcgaaaacga gagtcactcg    25200
ggggtgctgg tggagctcga gggcgacaac gcgcgcctgg ccgtgctcaa gcgcagcatc    25260
gaagtcaccc acttcgccta cccggcgctc aacctgcccc caaggtcat gagtgtggtc     25320 atgagcgagc tcatcatgcg ccgcgcccag cccctggacg cggatgcaaa cttgcaagag    25380
ccctccgagg aaggcctgcc cgcggtcagc gacgagcagc tggcgcgctg gctggagacc    25440
cgcgaccccg cccagctgga ggagcggcgc aagctcatga tggccgcggt gctcgtcacc    25500
gtggagctcg agtgtctgca gcgcttcttc ggggaccccg agatgcagcg caagctcgag    25560
gagaccctgc actacacctt ccgccagggc tacgtgcgcc aggcctgcaa gatctccaac    25620
gtggagctct gcaacctggt ctcctacctg ggcatcctgc acgagaaccg cctcgggcag    25680
aacgtcctgc actccaccct caaaggggag gcgcgccgcg actacgtccg cgactgcgtc    25740
tacctcttcc tctgctacac gtggcagaca gccatggggg tctggcagca gtgcctggag    25800
gagcgcaacc tcaaggagct ggagaagctc ctcaggcgcg ccctcaggga cctctggagg    25860
ggcttcaacg agcgctcggt ggccgccgcg ctggcggaca tcatcttccc cgagcgcctg    25920
ctcaaaaccc tgcagcaggg cctgcccgac ttcaccagcc agagcatgct gcagaacttc    25980
aggaccttca tcctggagcg ctcgggcatc ctgccggcca cctgctgcgc gctgccagc     26040 gacttcgtgc ccatcaggta cagggagtgc ccgccgccgc tctggggcca ctgctacctc    26100
ttccagctgg ccaactacct cgcctaccac tcggatctca tggaagacgt gagcggcgag    26160
ggcctgctcg agtgccactg ccgctgcaac ctgtgcacgc cccaccgctc tctagtctgc    26220
aacccgcagc tgctcagcga gagtcagatt atcggtacct tcgagctgca gggtccctcg    26280
cccgacgaaa agtccgcggc tccggggttg aaactcactc cggggctgtg gacttccgcc    26340
tacctacgca aatttgtacc tgaagactac cacgcccacg agatcaggtt ttacgaagac    26400
caatcccgcc cgcccaaggc ggagctcacc gcctgcgtca ttacccaggg ccacatcctg    26460
ggccaattgc aagccatcaa caaagcccgc caagagttct tgctgaaaaa gggtcggggg    26520
```

```
gtgtacctgg accccccagtc cggcgaggag ctaaacccgc taccccgcc gccgcccag   26580 cagcgggacc ttgcttccca ggatggcacc cagaaagaag cagccgccgc cgccgccagc   26640
atacatgctt ctggaggaag aggaggactg ggacagtcag gcagaggagg tttcggacga   26700
ggacgaggag gaggagatga tggaagactg ggaggaggac agcctagacg aggaagcttc   26760
agaggccgaa gaggtggcag acgcaacacc atcaccctcg gccgcagccc cctcgccggc   26820 gccccgaaa tcctccgacc ccagcagcag cgctataacc tccgctcctc cggcgccggc   26880
gcccacccgc agcagaccca accgtagatg ggacactaca ggaaccgggg tcggtaagtc   26940
caagtgcccc ccagcgccgc ccccgcaaca ggagcaacag cagcagcagc ggcgacaggg   27000
ctaccgctcg tggcgcggac acaagaacgc catagtcgcc tgcttgcaag actgcggggg   27060
caacatctcc ttcgcccgcc gcttcctgct cttccaccac ggggtggctt ttccccgcaa   27120
tgtcctgcat tactaccgtc atctctacag cccctactgc ggcggcagcg gcgacccaga   27180
gggagcggcg gcagcagcag cgccagccac agcggcgacc acctaggaag acctccgcgg   27240
gcaagacggc gggagccggg agacccgcgg cggcggcggt agcggcggcg gcgggcgcac   27300
tgcgcctctc gcccaacgaa cccctctcga cccgggagct cagacacagg atcttcccca   27360
ctctgtatgc tatcttccag cagagcagag gccaggaaca ggagctgaaa ataaaaaaca   27420
gatctctgcg ctccctcacc cgcagctgtc tgtatcacaa aagcgaagat cagcttcggc   27480
gcacgctgga ggacgcggag gcactcttca gcaaatactg cgcgctgact cttaaggact   27540
agccgcgcgc ccttctcgaa tttaggcggg agaaagacta cgtcatcgcc gaccgccgcc   27600
cagcccaccc agccgacatg agcaaagaga ttcccacgcc ctacatgtgg agctaccagc   27660
cgcagatggg actcgcggcg ggagcggccc aagactactc cacccgcatg aactacatga   27720
gcgcggggcc ccacatgatc tcacgggtta atgggatccg cgcccagcga aaccaaatac   27780
tgctggaaca ggcggccata accgccacac cccgtcatga cctcaatccc cgaaattggc   27840
ccgccgccct cgtgtaccag gaaaccccct ctgccaccac cgtggtactt ccgcgtgaca   27900
cccaggccga agtccagatg actaactcag gggcgcagct cgcgggcggc tttcgtcacg   27960
gggtgcggcc gcaccggccg ggtatattac acctggcgat cagaggccga ggtattcagc   28020
tcaacgacga gtcggtgagc tcttcgctcg gtctccgtcc ggacggaacc ttccagatcg   28080
ccggatcagg tcgctcctca ttcacgcctc gccaggcgta cctgactctg cagacctcct   28140
cctcggagcc tcgctccggc ggcatcggca ccctccagtt cgtggaggag ttcgtgccct   28200
cggtctactt caacccctcc tcgggacctc ccggacgcta ccccgaccag ttcatcccga   28260
actttgacgc ggtgaaggac tcggcggacg gctacgactg aatgtcaagt gctgaggcag   28320
agagcgttcg cctgaaacac ctccagcact gccgccgctt cgcctgcttt gcccgcagct   28380
ccggtgagtt ctgctacttt cagctgcccg aggagcatac cgaggggccg gcgcacggcg   28440
tccgcctaac cacccaggcc gaggttacct gtacccttat ccgggagttt accctccgtc   28500
ccctgctagt ggagcgggag cggggttctt gtgtcataac tatcgcctgc aactgcccta   28560
accctggatt acatcaagat ctttgttgtc acctgtgcgc tgagtataat aaacgctgag   28620
atcagactct actggggctc ctgtcgccat cctgtgaacg ccaccgtctt cacccacccc   28680
gagcagcccc aggcgaacct cacctgcggc ctgcgtcgga gggccaagaa gtacctcacc   28740
tggtacttca acggcacccc ctttgtggtt tacaacagct cgaccagga cggagttgcc   28800 ttgagagacg acctttccgg tctcagctac tccattcaca agaacaccac cctccacctc   28860
ttccctccct acctgccggg aacctacgag tgcgtcaccg gccgctgcac ccacctcctc   28920
```

```
cgcctgatcg taaaccagac ctttccggga acacacctct tccccagaac aggaggtgag    28980
ctcaggaaac cccctggggc cagggcgga  gacttacctt cgaccttgt  ggggttagga    29040 ttttttatcg ccgggttgct ggctctcctg atcaaagctt ccttgagatt tgttctctcc    29100 ctttacttt  atgaacagct caacttctaa taacgctacc ttttctcagg aatcgggtag    29160
taacttctct tctgaaatcg ggctgggtgt gctgcttact ctgttgattt ttttccttat    29220
catacttagc cttctgtgcc tcaggctcgc cgcctgctgc gcacatatct acatctacag    29280
ccggttgctt aactgctggg gtcgccatcc aagatgaacg gggctcaggt gctatgtctg    29340
ctggccctgg tggcctgcag tgccgccgtc aattttgagg aacccgcttg caatgtgact    29400
ttcaagcctg aaggcgcaca ttgcaccact ctggttaaat gtgtgacctc tcatgagaaa    29460
ctgctcatcg cctacaaaaa caaaacaggc gagttcgcgg tctatagcgt gtggcaaccc    29520
ggagaccata ataactactc agtcaccgtc ttcgagggtg cggagtctaa gaaattcgat    29580
tacacctttc ccttcgagga gatgtgtgaa gcggtcatgt acctgtccaa acagtacaag    29640
ctgtggcccc ccacccccga ggcgtgtgtg aaaacactg  ggtctttctg ctgtctctct    29700
ctgacaatca ctgtgcttgc tctaatctgc acgctgctgt acatgaaatt caggcagagg    29760
cgaatcttta tcgatgagaa aaaaatgcct tgatcgctaa caccggcttt ctgtctgcag    29820
aatgaaagca atcacctccc tactaatcag caccaccctc cttgcgattg cccatgggtt    29880
gacacgaatc gaagtgccag tggggtccaa tgtcaccatg gtgggccccg ccggcaattc    29940
ctccctgatg tgggaaaaat atgtccgtaa tcaatgggat cattactgct ctaatcgaat    30000
ctgtatcaag cccagagcca tctgcgacgg gcaaaatcta actttgattg atgtgcaaat    30060
gacggatgct gggtactatt acgggcagcg gggagaaatg attaattact ggcgaccca    30120 caaggactac atgctgcatg tagtcaaggc agtccccact actaccaccc ccaccactac    30180
cactcccacc actcccacta ctaccacccc caccactact actagcactg ctactaccgc    30240
tgcccgcaaa gctattaccc gcaaaagcac catgcttagc accaagcccc attctcactc    30300
ccacgccggc gggcccaccg gtgcggcctc agaaaccacc gagctttgct tctgccaatg    30360
cactaacgcc agcgcccacg aactgttcga cctggagaat gaggatgatg accagctgag    30420
ctccgcttgc ccggtcccgc tgcccgcaga gccggtcgcc ctgaagcagc tcggtgatcc    30480
atttaatgac tctcctgttt atccctctcc cgaatacccg cccgactcta ccttccacat    30540
cacgggcacc aacgacccca acctctcctt ctacctgatg ctgctgcttt gtatctctgt    30600
ggtatcttcc gcgctcatgt tactgggcat gttctgctgc ctcatctgcc gcagaaagag    30660
aaagtctcgc tctcagggcc aaccactgat gcccttcccc taccccccag attttgcaga    30720
taacaagata tgagcacgct gctgacacta accgctttac tcgcctgcgc tctaaccctt    30780
gtcgcttgcg aatccagata ccacaatgtc acagttgtga caggagaaaa tgttacattc    30840
aactccacgg ccgacaccca gtggtcgtgg agcggccacg gtagctatgt atacatctgc    30900
aatagctcca cctcccctag catgtcctct cccaagtacc actgcaatgc cagcctgttc    30960
accctcatca acgcctccac ctcggacaat ggactctatg taggctatgt gacacccggt    31020
gggcggggaa agaccacgc  ctacaacctg caagttcgcc acccctccac caccgccacc    31080
acctctgccg cccctacccg cagcagcagc agcatcagca gcagcagcag cagcagcaga    31140
ttcctgactt taatcctagc cagctcaaca accaccgcca ccgctgagac cacccacagc    31200
tccgcgcccg aaaccaccca cacccaccac ccagagacga ccgcggcctc cagtgaccag    31260
```

```
atgtcggcca acatcaccgc ctcgggtctt gaacttgctt caaccccac cccaaaacca    31320
gtggatgcag ccgacgtctc cgccctcgtc aatgactggg cggggctggg aatgtggtgg   31380
ttcgccatag gcatgatggc gctctgcctg cttctgctct ggctcatctg ctgcctcaac   31440
cgcaggcggg ccagacccat ctatagaccc atcattgttc tcaaccccgc tgatgatggg   31500
atccatagat tggatggtct gaaaaaccta cttttctctt ttacagtatg ataaattgag   31560
acatgcctcg cattttcatg tacttgacac ttctcccact ttttctgggg tgttctacgc   31620
tggccgccgt ctctcacctc gaggtagact gcctcacacc cttcactgtc tacctgattt   31680
acggattggt caccctcact ctcatctgca gcctaatcac agtagtcatc gccttcatcc   31740
agtgcattga ctacatctgt gtgcgcctcg catacctgag acaccacccg cagtaccgag   31800
acaggaacat tgcccaactc ctaagactgc tctaatcatg cataagactg tgatctgcct   31860
cctcatcctc ctctccctgc ccgctctcgt ctcatgccag cccgccacaa aacctccacg   31920
aaaaagacat gcctcctgtc gcttgagcca actgtggaat attcccaaat gctacaatga   31980
aaagagcgag ctttccgaag cctggctata tgcggtcatg tgtgtccttg tcttctgcag   32040
cacaatcttt gccctcatga tctaccccca ctttgatttg ggatggaatg cggtcgatgc   32100
catgaattac cctaccttc ccgcgcccga tatgattcca ctccgacagg ttgtggtgcc    32160
cgtcgccctc aatcaacgcc ccccatcccc tacacccact gaggtcagct actttaatct   32220
aacaggcgga gatgactgac actctagatc tagaaatgga cggcatcggc accgagcagc   32280
gtctcctaca gaggcgcaag caggcggctg aacaagagcg cctcaatcag gagctccgag   32340
atctcattaa cctgcaccag tgcaaaaaag gcatcttttg cctggtcaag caggccgatg   32400
tcacctacga gaaaaccggt aacagccacc gcctcagcta caagctgccc acccaacgcc   32460
agaagttggt gctcatggtg ggtcagaatc ccatcaccgt cacccagcac tcggtggaga   32520
ccgaggggtg tctgcactcc ccctgtcagg gtccggaaga cctctgcacc ctggtaaaga   32580
ccctgtgtgg tcttagagat ttaatcccct ttaactaatc aaacactgga atcaataaaa   32640
agaatcactt actttaaatc agtcagcagg tctctgtcca ctttattcag cagcacctcc   32700
ttcccctcct cccaactctg gtactccaaa cgcctcctgg cggcaaactt cctccacacc   32760
ctgaagggaa tgtcagattc ttgctcctgt ccctccgcac ccactatctt catgttgttg   32820
cagatgaagc gcgccaaaac gtctgacgag accttcaacc ccgtgtaccc ctatgacacg   32880
gaaaacgggc ctcccctccgt cccttcctc accctccct tcgtgtcccc cgacggattt    32940
caagaaagcc ccccagggt cctgtctctg cgcctgtcag agcccctggt cacttcccac    33000
ggcatgcttg ccctgaaaat gggaaatggc ctctccctgg atgacgccgg caacctcacc   33060
tctcaagatg tcaccaccgt caccccctccc ctcaaaaaaa ccaagaccaa cctcagcctc   33120
cagacctcag cccccctgac cgttagctct gggtccctca ccgtcgcggc cgccgctcca   33180
ctggcggtgg ccggcacctc tctcaccatg caatctcagg ccccccttgac agtgcaagat   33240
gcaaaactcg gcctggccac ccagggaccc ctgaccgtgt ctgaaggcaa actcaccttg   33300
cagacatcgg ctccactgac ggccgctgac agcagcactc tcactgttag tgccacacct   33360
cccctcagca caagcaatgg tagtttgagc attgacatgc aggccccgat ttataccacc   33420
aatggaaaac tggcacttaa cattggtgct cccctgcatg tggtagacac cctaaatgca   33480
ctaactgtag taactggcca gggtcttacc ataaatggaa gagccctgca aactagagtc   33540
acgggtgccc tcagttatga cacagaaggc aacatccaac tgcaagccgg agggggtatg   33600
cgcattgaca ataatggcca acttatcctt aatgtagctt atccatttga tgctcaaaac   33660
```

```
aacctcagcc ttagacttgg ccaaggtccc ctaattgtta actctgccca caacttggat   33720 cttaaccttta acagaggcct ttacttattt acatctggaa acacgaaaaa actggaagtt   33780
aacataaaaa cagccaaagg tctattttac gatggcaccg ctatagcaat caatgcaggt   33840
gacgggctac agtttgggtc tggttcagat acaaatccat tgcaaactaa acttggattg   33900
gggctggaat atgactccaa caaagctata atcactaaac ttggaactgg cctaagcttt   33960
gacaacacag gtgccatcac agtaggcaac aaaaatgatg acaagcttac cttgtggacc   34020
acaccagacc cctccccaaa ctgcagaatt aattcagaaa agatgctaa actcacacta    34080 gttttgacta aatgcggcag ccaggtgtta gccagcgttt ctgttttatc tgtaaaaggc   34140
agccttgccc ccatcagcgg cacagtaact agcgcccaga ttgttttaag atttgatgaa   34200
aacggagttt tattgagcaa ttcttctctt gaccccccaat actggaacta tagaaaaggc  34260
gattctacag aaggcactgc atatactaat gctgtgggat ttatgcccaa cctcacagca   34320
taccctaaaa cacagagcca gactgctaaa agcaacattg taagtcaagt ttacttgaat   34380
ggggacaaaa caaaacccat gaccctaacc atcaccctca atggaactaa tgaaacaggg   34440
gatgctacag taagcacata ctccatgtca ttttcatgga actggaatgg aagtaattac   34500
attaatgaca ccttccaaac caactccttt accttctcct acatcgccca agaataaaaa   34560
agcatgacgc tttgttctct gattcagtgt gtttctttta ttttttttca attacaacag   34620
aatcattcaa gtcattctcc atttagctta atagacccag tagtgcaaag ccccatacta   34680
gcttatttca gacagtataa attaaaccat acctttgat ttcaatatta aaaaatcat    34740 cacaggatcc tagtcgtcag gccgcccct ccctgccaag acacagaata cacaatcctc   34800
tccccccggc tggctttaaa caacaccatc tggttggtga cagacaggtt cttcggggtt   34860
atattccaca cggtctcctg gcgggccagg cgctcgtcgg tgatgctgat aaactctccc   34920
ggcagctcgc tcaagttcac gtcgctgtcc agcggctgaa cctcatgctg acgcggtaac   34980
tgcgcgaccg gctgctgaac aaacggaggc cgcgcctaca agggggtaga gtcataatcc   35040
tccgtcagga tagggcggtt atgcagcagc agcgagcgaa tcatctgctg ccgccgccgc   35100
tccgtccggc aggaaaacaa catcccggtg gtctcctccg ctataatccg caccgcccgc   35160
agcataagcc tcctcgttct ccgcgcgcag caccgcaccc tgatctcact caggttggcg   35220
cagtaggtac agcacatcac cacgatgtta ttcatgatcc cacagtgcaa ggcgctgtat   35280
ccaaagctca tgcccgggac caccgccccc acgtgaccgt cgtaccagaa gcgcaggtaa   35340
atcaagtgcc gaccctcat gaacgtgctg gacataaaca tcacctcctt gggcatgttg    35400
taattcacca cctcccggta ccagatgaat ctctgattga acacggcccc ttccaccacc   35460
atcctgaacc aagaggctag gacctgccca ccggctatgc actgcaggga acccgggtta   35520
gaacaatgac aatgcagact ccagggctcg taaccgtgga tcatccggct gctgaagaca   35580
tcgatgttgg cgcaacacag acacacgtgc atacacttcc tcatgattag cagctcctcc   35640
ctcgtcagga tcatatccca agggataacc cattcttgaa tcaacgtaaa gcccacagag   35700
cagggaaggc ctcgcacata actcacgttg tgcatggtta gcgtgttgca ttccggaaac   35760
agcggatgat cctccagtat cgaggcgcgg gtctcgttct cacagggagg taagggggcc   35820
ctgctgtacg gactgtggcg ggacgaccga gatcgtgttg agcgtaacgt catggaaaag   35880
ggaacgccgg acgtggtcat acttcttgaa gcagaaccag gctcgcgcgt gacagacctc   35940
cttgcgtcta cggtctcgcc gcttagctcg ctccgtgtga tagttgtagt acagccactc   36000
```

-continued

```
tctcaaagcg tcgaggcgac acctggcgtc aggatgtatg tagactccgt cttgcaccgc    36060
ggccctgata atatccacca ccgtagaata agccacacca agccaagcaa tacactcgct    36120
ttgcgagcgg cagacaggag gagcggggag agacggaagg accatcataa aattttaaag    36180
aatattttcc aatacttcga aatcaagatc taccaaatgg caacgctccc ctccactggc    36240
gcggtcaaac tctacggcca agaacagat aacggcattt ttaagatgtt cccggacggc     36300
gtctaaaaga caaaccgctc tcaagtcgac ataaattata agccaaaagc catcgggatc    36360
catatccact atggacgcgc cggcggcgtc caccaaaccc aaataatttt cttctctcca    36420
gcgcagcaaa atcccagtaa gcaactccct gatattaaga tgaaccatgc caaaaatctg    36480
ttcaagagcg ccctccacct tcattctcaa gcagcgcatc atgattgcaa aaattcaggt    36540
tcctcagaca cctgtatgag attcaaaacg ggaatattaa caaaaattcc tctgtcgcgc    36600
agatcccttc gcagggcaag ctgaacataa tcagacaggt ctgaacgaac cagcgaggcc    36660
aaatccccgc caggaaccag atccagagac cctatgctga ttatgacgcg catactcggg    36720
gctatgctaa ccagcgtagc gccgatgtag gcgtgctgca tgggcggcga aataaaatgc    36780
aaggtgctgg ttaaaaaatc aggcaaagcc tcgcgcaaaa aagctaagac atcataatca    36840
tgctcatgca ggtagttgca ggtaagctca ggaaccaaaa cggaataaca cacgattttc    36900
ctctcaaaca tgacttccag gtgactgcat aagaaaaaaa ttataaataa taaatattaa    36960
ttaaataaat taaacattgg aagcctgtct cacaacagga aaaaccactc tgatcaacat    37020
aagacgggcc acgggcatgc ccgcgtgacc ataaaaaaat cggtctccgt gattacaaag    37080
caccacagat agctccccgg tcatgtcggg ggtcatcatg tgagactgtg tatacacgtc    37140
cgggctgttg acatcggtca agaaagaaa tcgagctaca tagcccggag gaatcaacac     37200
ccgcacgcgc aggtacagca aaacggtccc cataggagga atcacaaaat tagtaggaga    37260
aaaaaaaaca taaacaccag aaaaaccctc ttgccgaggc aaaacagcgc cctcccgttc    37320
caaaacaaca taaagcgctt ccacaggagc agccatgaca aagacccgag tcttaccagg    37380 aaaatttaa aaaagattcc tcaacgcagc accagcacca acacctgtca gtgtaaaatg     37440
ccaagcgccg agcgagtata tataggaata aaaagtgacg taaacggtta agtccagaa     37500 aacgcccaga aaaccgcac gcgaacctac gccccgaaac gaaagccaaa aacagtgaa      37560 cacgcccttt cggcgtcaac ttccgctttc cacggtacg tcacttccgc atatagtaaa     37620
actacgctac ccaacatgca agaagccacg ccccaaaaca cgtcacacct cccggcccgc    37680
cccgcgccgc cgctcctccc cgccccgccc cgctccgccc acctcattat catattggct    37740
tcaatccaaa ataaggtata ttattgatga tg                                  37772
```

<210> SEQ ID NO 14
<211> LENGTH: 440
<212> TYPE: PRT
<213> ORGANISM: Adenoviridae - Mastadenovirus

<400> SEQUENCE: 14

```
Met Ser Lys Lys Arg Val Arg Val Asp Asp Asp Phe Asp Pro Val Tyr
1               5                   10                  15

Pro Tyr Asp Ala Asp Asn Ala Pro Thr Val Pro Phe Ile Asn Pro Pro
            20                  25                  30

Phe Val Ser Ser Asp Gly Phe Gln Glu Lys Pro Leu Gly Val Leu Ser
        35                  40                  45

Leu Arg Leu Ala Asp Pro Val Thr Thr Lys Asn Gly Glu Ile Thr Leu
    50                  55                  60
```

```
Lys Leu Gly Glu Gly Val Asp Leu Asp Asp Ser Gly Lys Leu Ile Ser
 65                  70                  75                  80

Lys Asn Ala Thr Lys Ala Thr Ala Pro Leu Ser Ile Ser Asn Ser Thr
             85                  90                  95

Ile Ser Leu Asn Met Asp Ala Pro Leu Tyr Asn Asn Asn Gly Lys Leu
        100                 105                 110

Gly Ile Arg Ile Gly Ala Pro Leu Lys Val Val Asp Leu Leu Asn Thr
        115                 120                 125

Leu Ala Val Ala Tyr Gly Ser Gly Leu Gly Leu Lys Asn Asn Ala Leu
130                 135                 140

Thr Val Gln Leu Val Ser Pro Leu Thr Phe Asp Asn Lys Gly Asn Val
145                 150                 155                 160

Lys Ile Asn Leu Gly Asn Gly Pro Leu Thr Val Ala Ala Asn Arg Leu
                165                 170                 175

Ser Val Thr Cys Lys Arg Gly Leu Tyr Val Thr Thr Thr Gly Asp Ala
            180                 185                 190

Leu Glu Ser Asn Ile Ser Trp Ala Lys Gly Ile Arg Phe Glu Gly Asn
        195                 200                 205

Ala Ile Ala Ala Asn Ile Gly Lys Gly Leu Glu Phe Gly Thr Thr Ser
210                 215                 220

Ser Glu Ser Asp Val Ser Asn Ala Tyr Pro Ile Gln Val Lys Leu Gly
225                 230                 235                 240

Thr Gly Leu Thr Phe Asp Ser Thr Gly Ala Ile Val Ala Trp Asn Lys
                245                 250                 255

Glu Asp Asp Lys Leu Thr Leu Trp Thr Thr Ala Asp Pro Ser Pro Asn
            260                 265                 270

Cys His Ile Tyr Ser Asp Lys Asp Ala Lys Leu Thr Leu Cys Leu Thr
        275                 280                 285

Lys Cys Gly Ser Gln Ile Leu Gly Thr Val Ser Leu Ile Ala Val Asp
        290                 295                 300

Thr Gly Ser Leu Asn Pro Ile Thr Gly Gln Val Thr Thr Ala Leu Val
305                 310                 315                 320

Ser Leu Lys Phe Asp Ala Asn Gly Val Leu Gln Thr Ser Thr Thr Leu
                325                 330                 335

Asp Lys Glu Tyr Trp Asn Phe Arg Lys Gly Asp Val Thr Pro Ala Glu
            340                 345                 350

Pro Tyr Thr Asn Ala Ile Gly Phe Met Pro Asn Ile Lys Ala Tyr Pro
        355                 360                 365

Lys Asn Thr Asn Ser Ala Ala Lys Ser His Ile Val Gly Lys Val Tyr
370                 375                 380

Leu His Gly Glu Val Ser Lys Pro Leu Asp Leu Ile Ile Thr Phe Asn
385                 390                 395                 400

Glu Thr Ser Asn Glu Thr Cys Thr Tyr Cys Ile Asn Phe Gln Trp Gln
                405                 410                 415

Trp Gly Thr Asp Lys Tyr Lys Asn Glu Thr Leu Ala Val Ser Ser Phe
            420                 425                 430

Thr Phe Ser Tyr Ile Ala Gln Glu
        435                 440

<210> SEQ ID NO 15
<211> LENGTH: 443
<212> TYPE: PRT
<213> ORGANISM: Adenoviridae - Mastadenovirus
```

<400> SEQUENCE: 15

```
Met Ser Lys Lys Arg Val Arg Val Asp Asp Phe Asp Pro Val Tyr
1               5                   10                  15

Pro Tyr Asp Ala Asp Asn Ala Pro Thr Val Pro Phe Ile Asn Pro Pro
                20                  25                  30

Phe Val Ser Ser Asp Gly Phe Gln Glu Lys Pro Leu Gly Val Leu Ser
            35                  40                  45

Leu Arg Leu Ala Asp Pro Val Thr Thr Lys Asn Gly Glu Ile Thr Leu
    50                  55                  60

Lys Leu Gly Glu Gly Val Asp Leu Asp Asp Ser Gly Lys Leu Ile Ser
65              70                  75                  80

Lys Asn Ala Thr Lys Ala Thr Ala Pro Leu Ser Ile Ser Asn Ser Thr
                85                  90                  95

Ile Ser Leu Asn Met Ala Ala Pro Phe Tyr Asn Asn Gly Thr Leu
            100                 105                 110

Ser Leu Asn Val Ser Thr Pro Leu Ala Val Phe Pro Thr Phe Asn Thr
            115                 120                 125

Leu Gly Ile Ser Leu Gly Asn Gly Leu Gln Thr Ser Asn Lys Leu Leu
    130                 135                 140

Ala Val Gln Leu Thr His Pro Leu Thr Phe Ser Ser Asn Ser Ile Thr
145                 150                 155                 160

Val Lys Thr Asp Lys Gly Leu Tyr Ile Asn Ser Ser Gly Asn Arg Gly
                165                 170                 175

Leu Glu Ala Asn Ile Ser Leu Lys Arg Gly Leu Ile Phe Asp Gly Asn
            180                 185                 190

Ala Ile Ala Thr Tyr Leu Gly Ser Gly Leu Asp Tyr Gly Ser Tyr Asp
        195                 200                 205

Ser Asp Gly Lys Thr Arg Pro Ile Ile Thr Lys Ile Gly Ala Gly Leu
    210                 215                 220

Asn Phe Asp Ser Asn Asn Ala Met Ala Val Lys Leu Gly Thr Gly Leu
225                 230                 235                 240

Ser Phe Asp Ser Ala Gly Ala Leu Thr Ala Gly Asn Lys Glu Asp Asp
                245                 250                 255

Lys Leu Thr Leu Trp Thr Thr Pro Asp Pro Ser Pro Asn Cys Gln Leu
            260                 265                 270

Leu Ser Asp Arg Asp Ala Lys Phe Thr Leu Cys Leu Thr Lys Cys Gly
        275                 280                 285

Ser Gln Ile Leu Gly Thr Val Ala Val Ala Val Thr Val Ser Ser
    290                 295                 300

Ala Leu Asn Pro Ile Asn Asp Thr Val Lys Ser Ala Ile Val Phe Leu
305                 310                 315                 320

Arg Phe Asp Ser Asp Gly Val Leu Met Ser Asn Ser Ser Met Val Gly
                325                 330                 335

Asp Tyr Trp Asn Phe Arg Glu Gly Gln Thr Thr Gln Ser Val Ala Tyr
            340                 345                 350

Thr Asn Ala Val Gly Phe Met Pro Asn Leu Gly Ala Tyr Pro Lys Thr
        355                 360                 365

Gln Ser Lys Thr Pro Lys Asn Ser Ile Val Ser Gln Val Tyr Leu Asn
    370                 375                 380

Gly Glu Thr Thr Met Pro Met Thr Leu Thr Ile Thr Phe Asn Gly Thr
385                 390                 395                 400

Asp Glu Lys Asp Thr Thr Pro Val Ser Thr Tyr Ser Met Thr Phe Thr
                405                 410                 415
```

Trp Gln Trp Thr Gly Asp Tyr Lys Asp Lys Asn Ile Thr Phe Ala Thr
          420                 425                 430

Asn Ser Phe Thr Phe Ser Tyr Met Ala Gln Glu
          435                 440

<210> SEQ ID NO 16
<211> LENGTH: 425
<212> TYPE: PRT
<213> ORGANISM: Adenoviridae - Mastadenovirus

<400> SEQUENCE: 16

Met Ser Lys Lys Arg Val Arg Val Asp Asp Phe Asp Pro Val Tyr
1               5                   10                  15

Pro Tyr Asp Ala Asp Asn Ala Pro Thr Val Pro Phe Ile Asn Pro Pro
            20                  25                  30

Phe Val Ser Ser Asp Gly Phe Gln Glu Lys Pro Leu Gly Val Leu Ser
            35                  40                  45

Leu Arg Leu Ala Asp Pro Val Thr Thr Lys Asn Gly Glu Ile Thr Leu
    50                  55                  60

Lys Leu Gly Glu Gly Val Asp Leu Asp Ser Ser Gly Lys Leu Ile Ser
65                  70                  75                  80

Asn Thr Ala Thr Lys Ala Ala Pro Leu Ser Phe Ser Asn Asn Thr
                85                  90                  95

Ile Ser Leu Asn Met Asp His Pro Phe Tyr Thr Lys Asp Gly Lys Leu
                100                 105                 110

Ala Leu Gln Val Ser Pro Pro Leu Asn Ile Leu Arg Thr Ser Ile Leu
            115                 120                 125

Asn Thr Leu Ala Leu Gly Phe Gly Ser Gly Leu Gly Leu Arg Gly Ser
    130                 135                 140

Ala Leu Ala Val Gln Leu Val Ser Pro Leu Thr Phe Asp Thr Asp Gly
145                 150                 155                 160

Asn Ile Lys Leu Thr Leu Asp Arg Gly Leu His Val Thr Thr Gly Asp
                165                 170                 175

Ala Ile Glu Ser Asn Ile Ser Trp Ala Lys Gly Leu Lys Phe Glu Asp
                180                 185                 190

Gly Ala Ile Ala Thr Asn Ile Gly Asn Gly Leu Glu Phe Gly Ser Ser
            195                 200                 205

Ser Thr Glu Thr Gly Val Asp Asp Ala Tyr Pro Ile Gln Val Lys Leu
    210                 215                 220

Gly Ser Gly Leu Ser Phe Asp Ser Thr Gly Ala Ile Met Ala Gly Asn
225                 230                 235                 240

Lys Glu Asp Asp Lys Leu Thr Leu Trp Thr Thr Pro Asp Pro Ser Pro
                245                 250                 255

Asn Cys Gln Ile Leu Ala Glu Asn Asp Ala Lys Leu Thr Leu Cys Leu
                260                 265                 270

Thr Lys Cys Gly Ser Gln Ile Leu Ala Thr Val Ser Val Leu Val Val
            275                 280                 285

Gly Ser Gly Asn Leu Asn Pro Ile Thr Gly Thr Val Ser Ser Ala Gln
    290                 295                 300

Val Phe Leu Arg Phe Asp Ala Asn Gly Val Leu Leu Thr Glu His Ser
305                 310                 315                 320

Thr Leu Lys Lys Tyr Trp Gly Tyr Arg Gln Gly Asp Ser Ile Asp Gly
                325                 330                 335

Thr Pro Tyr Val Asn Ala Val Gly Phe Met Pro Asn Leu Lys Ala Tyr

```
                340               345               350
Pro Lys Ser Gln Ser Ser Thr Thr Lys Asn Asn Ile Val Gly Gln Val
            355               360               365
Tyr Met Asn Gly Asp Val Ser Lys Pro Met Leu Leu Thr Ile Thr Leu
370             375             380
Asn Gly Thr Asp Asp Ser Asn Ser Thr Tyr Ser Met Ser Phe Ser Tyr
385             390             395             400
Thr Trp Thr Asn Gly Ser Tyr Val Gly Ala Thr Phe Gly Ala Asn Ser
            405             410             415
Tyr Thr Phe Ser Tyr Ile Ala Gln Glu
            420             425

<210> SEQ ID NO 17
<211> LENGTH: 425
<212> TYPE: PRT
<213> ORGANISM: Adenoviridae - Mastadenovirus

<400> SEQUENCE: 17

Met Ser Lys Lys Arg Val Arg Val Asp Asp Phe Asp Pro Val Tyr
1               5               10              15
Pro Tyr Asp Ala Asp Asn Ala Pro Thr Val Pro Phe Ile Asn Pro Pro
            20              25              30
Phe Val Ser Ser Asp Gly Phe Gln Glu Lys Pro Leu Gly Val Leu Ser
            35              40              45
Leu Arg Leu Ala Asp Pro Val Thr Thr Lys Asn Gly Glu Ile Thr Leu
    50              55              60
Lys Leu Gly Glu Gly Leu Asp Leu Asp Ser Ser Gly Lys Leu Ile Ser
65              70              75              80
Asn Thr Ala Thr Lys Ala Ala Pro Leu Ser Phe Ser Asn Asn Thr
            85              90              95
Ile Ser Leu Asn Met Asp His Pro Phe Tyr Thr Lys Asp Gly Lys Leu
            100             105             110
Ser Leu Gln Val Ser Pro Pro Leu Asn Ile Leu Arg Thr Ser Ile Leu
            115             120             125
Asn Thr Leu Ala Leu Gly Phe Gly Ser Gly Leu Gly Leu Arg Gly Ser
            130             135             140
Ala Leu Ala Val Gln Leu Val Ser Pro Leu Thr Phe Asp Thr Asp Gly
145             150             155             160
Asn Ile Lys Leu Thr Leu Asp Arg Gly Leu His Val Thr Thr Gly Asp
            165             170             175
Ala Ile Glu Ser Asn Ile Ser Trp Ala Lys Gly Leu Lys Phe Glu Asp
            180             185             190
Gly Ala Ile Ala Thr Asn Ile Gly Asn Gly Leu Glu Phe Gly Ser Ser
            195             200             205
Ser Thr Glu Thr Gly Val Asp Asp Ala Tyr Pro Ile Gln Val Lys Leu
            210             215             220
Gly Ser Gly Leu Ser Phe Asp Ser Thr Gly Ala Ile Met Ala Gly Asn
225             230             235             240
Lys Glu Asp Asp Lys Leu Thr Leu Trp Thr Thr Pro Asp Pro Ser Pro
            245             250             255
Asn Cys Gln Ile Leu Ala Glu Asn Asp Ala Lys Leu Thr Leu Cys Leu
            260             265             270
Thr Lys Cys Gly Ser Gln Ile Leu Ala Thr Val Ser Val Leu Val Val
            275             280             285
```

Gly Ser Gly Asn Leu Asn Pro Ile Thr Gly Thr Val Ser Ser Ala Gln
            290                 295                 300

Val Phe Leu Arg Phe Asp Ala Asn Gly Val Leu Leu Thr Glu His Ser
305                 310                 315                 320

Thr Leu Lys Lys Tyr Trp Gly Tyr Arg Gln Gly Asp Ser Ile Asp Gly
                325                 330                 335

Thr Pro Tyr Thr Asn Ala Val Gly Phe Met Pro Asn Leu Lys Ala Tyr
                340                 345                 350

Pro Lys Ser Gln Ser Ser Thr Thr Lys Asn Asn Ile Val Gly Gln Val
                355                 360                 365

Tyr Met Asn Gly Asp Val Ser Lys Pro Met Leu Leu Thr Ile Thr Leu
370                 375                 380

Asn Gly Thr Asp Asp Ser Asn Ser Thr Tyr Ser Met Ser Phe Ser Tyr
385                 390                 395                 400

Thr Trp Thr Asn Gly Ser Tyr Val Gly Ala Thr Phe Gly Ala Asn Ser
                405                 410                 415

Tyr Thr Phe Ser Tyr Ile Ala Gln Glu
                420                 425

<210> SEQ ID NO 18
<211> LENGTH: 442
<212> TYPE: PRT
<213> ORGANISM: Adenoviridae - Mastadenovirus

<400> SEQUENCE: 18

Met Ser Lys Lys Arg Ala Arg Val Asp Asp Gly Phe Asp Pro Val Tyr
1               5                   10                  15

Pro Tyr Asp Ala Asp Asn Ala Pro Thr Val Pro Phe Ile Asn Pro Pro
                20                  25                  30

Phe Val Ser Ser Asp Gly Phe Gln Glu Lys Pro Leu Gly Val Leu Ser
            35                  40                  45

Leu Arg Leu Ala Asp Pro Val Thr Thr Lys Asn Gly Ala Val Pro Leu
50                  55                  60

Lys Leu Gly Glu Gly Val Asp Leu Asp Asp Ser Gly Lys Leu Ile Ser
65                  70                  75                  80

Lys Lys Ser Thr Lys Ala Asn Ser Pro Leu Ser Ile Ser Asn Asn Thr
                85                  90                  95

Ile Ser Leu Asn Met Asp Thr Pro Phe Tyr Thr Lys Asp Gly Lys Leu
                100                 105                 110

Thr Met Gln Val Thr Ala Pro Leu Lys Leu Ala Asn Thr Ala Ile Leu
            115                 120                 125

Asn Thr Leu Ala Met Ala Tyr Gly Asn Gly Leu Gly Leu Asn Asn Asn
130                 135                 140

Ala Leu Thr Val Gln Val Thr Ser Pro Leu Thr Phe Asp Asn Ser Lys
145                 150                 155                 160

Val Lys Ile Asn Leu Gly Asn Gly Pro Leu Met Val Ser Ala Asn Lys
                165                 170                 175

Leu Ser Ile Asn Cys Leu Arg Gly Leu Tyr Val Ala Pro Asn Asn Thr
                180                 185                 190

Gly Leu Glu Thr Asn Ile Ser Trp Ala Asn Ala Met Arg Phe Glu Gly
            195                 200                 205

Asn Ala Met Ala Val Tyr Ile Asp Thr Asn Lys Gly Leu Gln Phe Gly
210                 215                 220

Thr Thr Ser Thr Glu Thr Gly Val Thr Asn Ala Tyr Pro Ile Gln Val
225                 230                 235                 240

Lys Leu Gly Ala Gly Leu Ala Phe Asp Ser Thr Gly Ala Ile Val Ala
                245                 250                 255

Trp Asn Lys Glu Asn Asp Ser Leu Thr Leu Trp Thr Thr Pro Asp Pro
            260                 265                 270

Ser Pro Asn Cys Lys Ile Ala Ser Glu Lys Asp Ala Lys Leu Thr Leu
            275                 280                 285

Cys Leu Thr Lys Cys Gly Ser Gln Ile Leu Gly Thr Val Ser Leu Leu
            290                 295                 300

Ala Val Ser Gly Ser Leu Ala Pro Ile Thr Gly Ala Val Ser Thr Ala
305                 310                 315                 320

Leu Val Ser Leu Lys Phe Asn Ala Asn Gly Ala Leu Leu Asp Lys Ser
                325                 330                 335

Thr Leu Asn Lys Glu Tyr Trp Asn Tyr Arg Gln Gly Asp Leu Ile Pro
            340                 345                 350

Gly Thr Pro Tyr Thr His Ala Val Gly Phe Met Pro Asn Lys Lys Ala
            355                 360                 365

Tyr Pro Lys Asn Thr Thr Ala Ala Ser Lys Ser His Ile Val Gly Asp
            370                 375                 380

Val Tyr Leu Asp Gly Asp Ala Asp Lys Pro Leu Ser Leu Ile Ile Thr
385                 390                 395                 400

Phe Asn Glu Thr Asp Asp Glu Thr Cys Asp Tyr Cys Ile Asn Phe Gln
                405                 410                 415

Trp Lys Trp Gly Ala Asp Gln Tyr Lys Asp Lys Thr Leu Ala Thr Ser
            420                 425                 430

Ser Phe Thr Phe Ser Tyr Ile Ala Gln Glu
            435                 440

<210> SEQ ID NO 19
<211> LENGTH: 577
<212> TYPE: PRT
<213> ORGANISM: Adenoviridae - Mastadenovirus

<400> SEQUENCE: 19

Met Lys Arg Ala Lys Thr Ser Asp Glu Thr Phe Asn Pro Val Tyr Pro
1               5                   10                  15

Tyr Asp Thr Glu Asn Gly Pro Pro Ser Val Pro Phe Leu Thr Pro Pro
            20                  25                  30

Phe Val Ser Pro Asp Gly Phe Gln Glu Ser Pro Pro Gly Val Leu Ser
            35                  40                  45

Leu Arg Leu Ser Glu Pro Leu Val Thr Ser His Gly Met Leu Ala Leu
        50                  55                  60

Lys Met Gly Asn Gly Leu Ser Leu Asp Asp Ala Gly Asn Leu Thr Ser
65                  70                  75                  80

Gln Asp Val Thr Thr Val Thr Pro Pro Leu Lys Lys Thr Lys Thr Asn
                85                  90                  95

Leu Ser Leu Gln Thr Ser Ala Pro Leu Thr Val Ser Ser Gly Ser Leu
            100                 105                 110

Thr Val Ala Ala Ala Pro Leu Ala Val Ala Gly Thr Ser Leu Thr
            115                 120                 125

Met Gln Ser Gln Ala Pro Leu Thr Val Gln Asp Ala Lys Leu Gly Leu
            130                 135                 140

Ala Thr Gln Gly Pro Leu Thr Val Ser Glu Gly Lys Leu Thr Leu Gln
145                 150                 155                 160

Thr Ser Ala Pro Leu Thr Ala Ala Asp Ser Ser Thr Leu Thr Val Ser

-continued

```
            165                 170                 175
Ala Thr Pro Pro Leu Ser Thr Ser Asn Gly Ser Leu Ser Ile Asp Met
            180                 185                 190
Gln Ala Pro Ile Tyr Thr Thr Asn Gly Lys Leu Ala Leu Asn Ile Gly
            195                 200                 205
Ala Pro Leu His Val Val Asp Thr Leu Asn Ala Leu Thr Val Val Thr
            210                 215                 220
Gly Gln Gly Leu Thr Ile Asn Gly Arg Ala Leu Gln Thr Arg Val Thr
225                 230                 235                 240
Gly Ala Leu Ser Tyr Asp Thr Glu Gly Asn Ile Gln Leu Gln Ala Gly
            245                 250                 255
Gly Gly Met Arg Ile Asp Asn Asn Gly Gln Leu Ile Leu Asn Val Ala
            260                 265                 270
Tyr Pro Phe Asp Ala Gln Asn Asn Leu Ser Leu Arg Leu Gly Gln Gly
            275                 280                 285
Pro Leu Ile Val Asn Ser Ala His Asn Leu Asp Leu Asn Leu Asn Arg
            290                 295                 300
Gly Leu Tyr Leu Phe Thr Ser Gly Asn Thr Lys Lys Leu Glu Val Asn
305                 310                 315                 320
Ile Lys Thr Ala Lys Gly Leu Phe Tyr Asp Gly Thr Ala Ile Ala Ile
            325                 330                 335
Asn Ala Gly Asp Gly Leu Gln Phe Gly Ser Gly Ser Asp Thr Asn Pro
            340                 345                 350
Leu Gln Thr Lys Leu Gly Leu Gly Leu Glu Tyr Asp Ser Asn Lys Ala
            355                 360                 365
Ile Ile Thr Lys Leu Gly Thr Gly Leu Ser Phe Asp Asn Thr Gly Ala
            370                 375                 380
Ile Thr Val Gly Asn Lys Asn Asp Asp Lys Leu Thr Leu Trp Thr Thr
385                 390                 395                 400
Pro Asp Pro Ser Pro Asn Cys Arg Ile Asn Ser Glu Lys Asp Ala Lys
            405                 410                 415
Leu Thr Leu Val Leu Thr Lys Cys Gly Ser Gln Val Leu Ala Ser Val
            420                 425                 430
Ser Val Leu Ser Val Lys Gly Ser Leu Ala Pro Ile Ser Gly Thr Val
            435                 440                 445
Thr Ser Ala Gln Ile Val Leu Arg Phe Asp Glu Asn Gly Val Leu Leu
            450                 455                 460
Ser Asn Ser Ser Leu Asp Pro Gln Tyr Trp Asn Tyr Arg Lys Gly Asp
465                 470                 475                 480
Ser Thr Glu Gly Thr Ala Tyr Thr Asn Ala Val Gly Phe Met Pro Asn
            485                 490                 495
Leu Thr Ala Tyr Pro Lys Thr Gln Ser Gln Thr Ala Lys Ser Asn Ile
            500                 505                 510
Val Ser Gln Val Tyr Leu Asn Gly Asp Lys Lys Pro Met Thr Leu
            515                 520                 525
Thr Ile Thr Leu Asn Gly Thr Asn Glu Thr Gly Asp Ala Thr Val Ser
            530                 535                 540
Thr Tyr Ser Met Ser Phe Ser Trp Asn Trp Asn Gly Ser Asn Tyr Ile
545                 550                 555                 560
Asn Asp Thr Phe Gln Thr Asn Ser Phe Thr Phe Ser Tyr Ile Ala Gln
            565                 570                 575
Glu
```

```
<210> SEQ ID NO 20
<211> LENGTH: 937
<212> TYPE: PRT
<213> ORGANISM: Adenoviridae - Mastadenovirus

<400> SEQUENCE: 20

Met Ala Thr Pro Ser Met Leu Pro Gln Trp Ala Tyr Met His Ile Ala
1               5                   10                  15

Gly Gln Asp Ala Ser Glu Tyr Leu Ser Pro Gly Leu Val Gln Phe Ala
                20                  25                  30

Arg Ala Thr Asp Thr Tyr Phe Ser Leu Gly Asn Lys Phe Arg Asn Pro
            35                  40                  45

Thr Val Ala Pro Thr His Asp Val Thr Thr Asp Arg Ser Gln Arg Leu
    50                  55                  60

Thr Leu Arg Phe Val Pro Val Asp Arg Glu Asp Asn Thr Tyr Ser Tyr
65                  70                  75                  80

Lys Val Arg Tyr Thr Leu Ala Val Gly Asp Asn Arg Val Leu Asp Met
                85                  90                  95

Ala Ser Thr Tyr Phe Asp Ile Arg Gly Val Leu Asp Arg Gly Pro Ser
            100                 105                 110

Phe Lys Pro Tyr Ser Gly Thr Ala Tyr Asn Ser Leu Ala Pro Lys Gly
        115                 120                 125

Ala Pro Asn Thr Ser Gln Trp Ile Thr Lys Asp Asn Gly Thr Asp Lys
    130                 135                 140

Thr Tyr Ser Phe Gly Asn Ala Pro Val Arg Gly Leu Asp Ile Thr Glu
145                 150                 155                 160

Glu Gly Leu Gln Ile Gly Pro Asp Glu Ser Gly Gly Glu Ser Lys Lys
                165                 170                 175

Ile Phe Ala Asp Lys Thr Tyr Gln Pro Glu Pro Gln Leu Gly Asp Glu
            180                 185                 190

Glu Trp His Asp Thr Ile Gly Ala Glu Asp Lys Tyr Gly Gly Arg Ala
        195                 200                 205

Leu Lys Pro Ala Thr Asn Met Lys Pro Cys Tyr Gly Ser Phe Ala Lys
    210                 215                 220

Pro Thr Asn Ala Lys Gly Gly Gln Ala Lys Ser Arg Thr Lys Asp Asp
225                 230                 235                 240

Gly Thr Thr Glu Pro Asp Ile Asp Met Ala Phe Phe Asp Asp Arg Ser
                245                 250                 255

Gln Gln Ala Ser Phe Ser Pro Glu Leu Val Leu Tyr Thr Glu Asn Val
            260                 265                 270

Asp Leu Asp Thr Pro Asp Thr His Ile Ile Tyr Lys Pro Gly Thr Asp
        275                 280                 285

Glu Thr Ser Ser Ser Phe Asn Leu Gly Gln Gln Ser Met Pro Asn Arg
    290                 295                 300

Pro Asn Tyr Ile Gly Phe Arg Asp Asn Phe Ile Gly Leu Met Tyr Tyr
305                 310                 315                 320

Asn Ser Thr Gly Asn Met Gly Val Leu Ala Gly Gln Ala Ser Gln Leu
                325                 330                 335

Asn Ala Val Val Asp Leu Gln Asp Arg Asn Thr Glu Leu Ser Tyr Gln
            340                 345                 350

Leu Leu Leu Asp Ser Leu Gly Asp Arg Thr Arg Tyr Phe Ser Met Trp
        355                 360                 365

Asn Gln Ala Val Asp Ser Tyr Asp Pro Asp Val Arg Ile Ile Glu Asn
    370                 375                 380
```

```
His Gly Val Glu Asp Glu Leu Pro Asn Tyr Cys Phe Pro Leu Asn Gly
385                 390                 395                 400

Val Gly Phe Thr Asp Thr Phe Gln Gly Ile Lys Val Lys Thr Thr Asn
                405                 410                 415

Asn Gly Thr Ala Asn Ala Thr Glu Trp Glu Ser Asp Thr Ser Val Asn
            420                 425                 430

Asn Ala Asn Glu Ile Ala Lys Gly Asn Pro Phe Ala Met Glu Ile Asn
        435                 440                 445

Ile Gln Ala Asn Leu Trp Arg Asn Phe Leu Tyr Ala Asn Val Ala Leu
    450                 455                 460

Tyr Leu Pro Asp Ser Tyr Lys Tyr Thr Pro Ala Asn Ile Thr Leu Pro
465                 470                 475                 480

Thr Asn Thr Asn Thr Tyr Asp Tyr Met Asn Gly Arg Val Val Ala Pro
                485                 490                 495

Ser Leu Val Asp Ala Tyr Ile Asn Ile Gly Ala Arg Trp Ser Leu Asp
            500                 505                 510

Pro Met Asp Asn Val Asn Pro Phe Asn His His Arg Asn Ala Gly Leu
        515                 520                 525

Arg Tyr Arg Ser Met Leu Leu Gly Asn Gly Arg Tyr Val Pro Phe His
    530                 535                 540

Ile Gln Val Pro Gln Lys Phe Phe Ala Ile Lys Ser Leu Leu Leu Leu
545                 550                 555                 560

Pro Gly Ser Tyr Thr Tyr Glu Trp Asn Phe Arg Lys Asp Val Asn Met
                565                 570                 575

Ile Leu Gln Ser Ser Leu Gly Asn Asp Leu Arg Thr Asp Gly Ala Ser
            580                 585                 590

Ile Ala Phe Thr Ser Ile Asn Leu Tyr Ala Thr Phe Phe Pro Met Ala
        595                 600                 605

His Asn Thr Ala Ser Thr Leu Glu Ala Met Leu Arg Asn Asp Thr Asn
    610                 615                 620

Asp Gln Ser Phe Asn Asp Tyr Leu Ser Ala Ala Asn Met Leu Tyr Pro
625                 630                 635                 640

Ile Pro Ala Asn Ala Thr Asn Val Pro Ile Ser Ile Pro Ser Arg Asn
                645                 650                 655

Trp Ala Ala Phe Arg Gly Trp Ser Phe Thr Arg Leu Lys Thr Arg Glu
            660                 665                 670

Thr Pro Ser Leu Gly Ser Gly Phe Asp Pro Tyr Phe Val Tyr Ser Gly
        675                 680                 685

Ser Ile Pro Tyr Leu Asp Gly Thr Phe Tyr Leu Asn His Thr Phe Lys
    690                 695                 700

Lys Val Ser Ile Thr Phe Asp Ser Ser Val Ser Trp Pro Gly Asn Asp
705                 710                 715                 720

Arg Leu Leu Thr Pro Asn Glu Phe Glu Ile Lys Arg Thr Val Asp Gly
                725                 730                 735

Glu Gly Tyr Asn Val Ala Gln Cys Asn Met Thr Lys Asp Trp Phe Leu
            740                 745                 750

Val Gln Met Leu Ala His Tyr Asn Ile Gly Tyr Gln Gly Phe Tyr Val
        755                 760                 765

Pro Glu Gly Tyr Lys Asp Arg Met Tyr Ser Phe Phe Arg Asn Phe Gln
    770                 775                 780

Pro Met Ser Arg Gln Val Val Asp Glu Val Asn Tyr Lys Asp Tyr Gln
785                 790                 795                 800
```

```
Ala Val Thr Leu Ala Tyr Gln His Asn Asn Ser Gly Phe Val Gly Tyr
            805                 810                 815

Leu Ala Pro Thr Met Arg Gln Gly Gln Pro Tyr Pro Ala Asn Tyr Pro
            820                 825                 830

Tyr Pro Leu Ile Gly Lys Ser Ala Val Ala Ser Val Thr Gln Lys Lys
            835                 840                 845

Phe Leu Cys Asp Arg Val Met Trp Arg Ile Pro Phe Ser Ser Asn Phe
            850                 855                 860

Met Ser Met Gly Ala Leu Thr Asp Leu Gly Gln Asn Met Leu Tyr Ala
865                 870                 875                 880

Asn Ser Ala His Ala Leu Asp Met Asn Phe Glu Val Asp Pro Met Asp
                    885                 890                 895

Glu Ser Thr Leu Leu Tyr Val Val Phe Glu Val Phe Asp Val Val Arg
            900                 905                 910

Val His Gln Pro His Arg Gly Val Ile Glu Ala Val Tyr Leu Arg Thr
            915                 920                 925

Pro Phe Ser Ala Gly Asn Ala Thr Thr
            930                 935

<210> SEQ ID NO 21
<211> LENGTH: 937
<212> TYPE: PRT
<213> ORGANISM: Adenoviridae - Mastadenovirus

<400> SEQUENCE: 21

Met Ala Thr Pro Ser Met Leu Pro Gln Trp Ala Tyr Met His Ile Ala
1               5                   10                  15

Gly Gln Asp Ala Ser Glu Tyr Leu Ser Pro Gly Leu Val Gln Phe Ala
                20                  25                  30

Arg Ala Thr Asp Thr Tyr Phe Ser Leu Gly Asn Lys Phe Arg Asn Pro
            35                  40                  45

Thr Val Ala Pro Thr His Asp Val Thr Thr Asp Arg Ser Gln Arg Leu
        50                  55                  60

Thr Leu Arg Phe Val Pro Val Asp Gly Glu Asp Asn Thr Tyr Ser Tyr
65                  70                  75                  80

Lys Val Arg Tyr Thr Leu Ala Val Gly Asp Asn Arg Val Leu Asp Met
                85                  90                  95

Ala Ser Thr Tyr Phe Asp Ile Arg Gly Val Leu Asp Arg Gly Pro Ser
            100                 105                 110

Phe Lys Pro Tyr Ser Gly Thr Ala Tyr Asn Ala Leu Ala Pro Lys Gly
        115                 120                 125

Ala Pro Asn Thr Ser Gln Trp Ile Thr Lys Asp Asn Gly Thr Asp Lys
    130                 135                 140

Thr Tyr Ser Phe Gly Asn Ala Pro Val Arg Gly Leu Asp Ile Thr Glu
145                 150                 155                 160

Glu Gly Leu Gln Ile Arg Thr Asp Glu Ser Gly Gly Glu Ser Lys Lys
                165                 170                 175

Ile Phe Ala Asp Lys Thr Tyr Gln Pro Glu Pro Gln Leu Gly Asp Glu
            180                 185                 190

Glu Trp His Asp Thr Ile Gly Ala Glu Asp Lys Tyr Gly Gly Arg Ala
        195                 200                 205

Leu Lys Pro Ala Thr Asn Met Lys Pro Cys Tyr Gly Ser Phe Ala Lys
    210                 215                 220

Pro Thr Asn Ala Lys Gly Gly Gln Ala Lys Ser Arg Thr Lys Asp Asp
225                 230                 235                 240
```

```
Gly Thr Thr Glu Pro Asp Ile Asp Met Ala Phe Phe Asp Asp Arg Ser
                245                 250                 255

Gln Gln Ala Ser Phe Ser Pro Glu Leu Val Leu Tyr Thr Glu Asn Val
            260                 265                 270

Asp Leu Asp Thr Pro Asp Thr His Ile Ile Tyr Lys Pro Gly Thr Asp
        275                 280                 285

Glu Thr Ser Ser Ser Phe Asn Leu Gly Gln Gln Ser Met Pro Asn Arg
    290                 295                 300

Pro Asn Tyr Ile Gly Phe Arg Asp Asn Phe Ile Gly Leu Met Tyr Tyr
305                 310                 315                 320

Asn Ser Thr Gly Asn Met Gly Val Leu Ala Gly Gln Ala Ser Gln Leu
                325                 330                 335

Asn Ala Val Val Asp Leu Gln Asp Arg Asn Thr Glu Leu Ser Tyr Gln
            340                 345                 350

Leu Leu Leu Asp Ser Leu Gly Asp Arg Thr Arg Tyr Phe Ser Met Trp
        355                 360                 365

Asn Gln Ala Val Asp Ser Tyr Asp Pro Asp Val Arg Ile Ile Glu Asn
    370                 375                 380

His Gly Val Glu Asp Glu Leu Pro Asn Tyr Cys Phe Pro Leu Asn Gly
385                 390                 395                 400

Val Gly Phe Thr Asp Thr Phe Gln Gly Ile Lys Val Lys Thr Thr Asn
                405                 410                 415

Asn Gly Thr Ala Asn Ala Thr Glu Trp Glu Ser Asp Thr Ser Val Asn
            420                 425                 430

Asn Ala Asn Glu Ile Ala Lys Gly Asn Pro Phe Ala Met Glu Ile Asn
        435                 440                 445

Ile Gln Ala Asn Leu Trp Arg Asn Phe Leu Tyr Ala Asn Val Ala Leu
    450                 455                 460

Tyr Leu Pro Asp Ser Tyr Lys Tyr Thr Pro Ala Asn Ile Thr Leu Pro
465                 470                 475                 480

Thr Asn Thr Asn Thr Tyr Asp Tyr Met Asn Gly Arg Val Val Ala Pro
                485                 490                 495

Ser Leu Val Asp Ala Tyr Ile Asn Ile Gly Ala Arg Trp Ser Leu Asp
            500                 505                 510

Pro Met Asp Asn Val Asn Pro Phe Asn His His Arg Asn Ala Gly Leu
        515                 520                 525

Arg Tyr Arg Ser Met Leu Leu Gly Asn Gly Arg Tyr Val Pro Phe His
    530                 535                 540

Ile Gln Val Pro Gln Lys Phe Phe Ala Ile Lys Ser Leu Leu Leu Leu
545                 550                 555                 560

Pro Gly Ser Tyr Thr Tyr Glu Trp Asn Phe Arg Lys Asp Val Asn Met
                565                 570                 575

Ile Leu Gln Ser Ser Leu Gly Asn Asp Leu Arg Thr Asp Gly Ala Ser
            580                 585                 590

Ile Ala Phe Thr Ser Ile Asn Leu Tyr Ala Thr Phe Phe Pro Met Ala
        595                 600                 605

His Asn Thr Ala Ser Thr Leu Glu Ala Met Leu Arg Asn Asp Thr Asn
    610                 615                 620

Asp Gln Ser Phe Asn Asp Tyr Leu Ser Ala Ala Asn Met Leu Tyr Pro
625                 630                 635                 640

Ile Pro Ala Asn Ala Thr Asn Val Pro Ile Ser Ile Pro Ser Arg Asn
                645                 650                 655
```

-continued

```
Trp Ala Ala Phe Arg Gly Trp Ser Phe Thr Arg Leu Lys Thr Arg Glu
            660                 665                 670

Thr Pro Ser Leu Gly Ser Gly Phe Asp Pro Tyr Phe Val Tyr Ser Gly
        675                 680                 685

Ser Ile Pro Tyr Leu Asp Gly Thr Phe Tyr Leu Asn His Thr Phe Lys
    690                 695                 700

Lys Val Ser Ile Thr Phe Asp Ser Ser Val Ser Trp Pro Gly Asn Asp
705                 710                 715                 720

Arg Leu Leu Thr Pro Asn Glu Phe Glu Ile Lys Arg Thr Val Asp Gly
                725                 730                 735

Glu Gly Tyr Asn Val Ala Gln Cys Asn Met Thr Lys Asp Trp Phe Leu
            740                 745                 750

Val Gln Met Leu Ala His Tyr Asn Ile Gly Tyr Gln Gly Phe Tyr Val
        755                 760                 765

Pro Glu Gly Tyr Lys Asp Arg Met Tyr Ser Phe Phe Arg Asn Phe Gln
    770                 775                 780

Pro Met Ser Arg Gln Val Val Asp Glu Val Asn Tyr Lys Asp Tyr Gln
785                 790                 795                 800

Ala Val Thr Leu Ala Tyr Gln His Asn Asn Ser Gly Phe Val Gly Tyr
                805                 810                 815

Leu Ala Pro Thr Met Arg Gln Gly Gln Pro Tyr Pro Ala Asn Tyr Pro
            820                 825                 830

Tyr Pro Leu Ile Gly Lys Ser Ala Val Ala Ser Val Thr Gln Lys Lys
        835                 840                 845

Phe Leu Cys Asp Arg Val Met Trp Arg Ile Pro Phe Ser Ser Asn Phe
    850                 855                 860

Met Ser Met Gly Ala Leu Thr Asp Leu Gly Gln Asn Met Leu Tyr Ala
865                 870                 875                 880

Asn Ser Ala His Ala Leu Asp Met Asn Phe Glu Val Asp Pro Met Asp
                885                 890                 895

Glu Ser Thr Leu Leu Tyr Val Val Phe Glu Val Phe Asp Val Val Arg
            900                 905                 910

Val His Gln Pro His Arg Gly Val Ile Lys Ala Val Tyr Leu Arg Thr
        915                 920                 925

Pro Phe Ser Ala Gly Asn Ala Thr Thr
    930                 935
```

<210> SEQ ID NO 22
<211> LENGTH: 937
<212> TYPE: PRT
<213> ORGANISM: Adenoviridae - Mastadenovirus

<400> SEQUENCE: 22

```
Met Ala Thr Pro Ser Met Leu Pro Gln Trp Ala Tyr Met His Ile Ala
1               5                   10                  15

Gly Gln Asp Ala Ser Glu Tyr Leu Ser Pro Gly Leu Val Gln Phe Ala
            20                  25                  30

Arg Ala Thr Asp Thr Tyr Phe Ser Leu Gly Asn Lys Phe Arg Asn Pro
        35                  40                  45

Thr Val Ala Pro Thr His Asp Val Thr Thr Asp Arg Ser Gln Arg Leu
    50                  55                  60

Thr Leu Arg Phe Val Pro Val Asp Arg Glu Asp Asn Thr Tyr Ser Tyr
65                  70                  75                  80

Lys Val Arg Tyr Thr Leu Ala Val Gly Asp Asn Arg Val Leu Asp Met
                85                  90                  95
```

-continued

```
Ala Ser Thr Tyr Phe Asp Ile Arg Gly Val Leu Asp Arg Gly Pro Ser
            100                 105                 110

Phe Lys Pro Tyr Ser Gly Thr Ala Tyr Asn Ser Leu Ala Pro Lys Gly
            115                 120                 125

Ala Pro Asn Thr Ser Gln Trp Ile Thr Lys Asp Asn Gly Thr Asp Lys
            130                 135                 140

Thr Tyr Ser Phe Gly Asn Ala Pro Val Arg Gly Leu Asp Ile Thr Glu
145                 150                 155                 160

Glu Gly Leu Gln Ile Gly Thr Asp Glu Ser Gly Gly Glu Ser Lys Lys
                165                 170                 175

Ile Phe Ala Asp Lys Thr Tyr Gln Pro Glu Pro Gln Leu Gly Asp Glu
            180                 185                 190

Glu Trp His Asp Thr Ile Gly Ala Glu Asp Lys Tyr Gly Gly Arg Ala
            195                 200                 205

Leu Lys Pro Ala Thr Asn Met Lys Pro Cys Tyr Gly Ser Phe Ala Lys
            210                 215                 220

Pro Thr Asn Ala Lys Gly Gly Gln Ala Lys Ser Arg Thr Lys Asp Asp
225                 230                 235                 240

Gly Thr Thr Glu Pro Asp Ile Asp Met Ala Phe Phe Asp Asp Arg Ser
            245                 250                 255

Gln Gln Ala Ser Phe Ser Pro Glu Leu Val Leu Tyr Thr Glu Asn Val
            260                 265                 270

Asp Leu Asp Thr Pro Asp Thr His Ile Ile Tyr Lys Pro Gly Thr Asp
            275                 280                 285

Glu Thr Ser Ser Ser Phe Asn Leu Gly Gln Gln Ser Met Pro Asn Arg
            290                 295                 300

Pro Asn Tyr Ile Gly Phe Arg Asp Asn Phe Ile Gly Leu Met Tyr Tyr
305                 310                 315                 320

Asn Ser Thr Gly Asn Met Gly Val Leu Ala Gly Gln Ala Ser Gln Leu
            325                 330                 335

Asn Ala Val Val Asp Leu Gln Asp Arg Asn Thr Glu Leu Ser Tyr Gln
            340                 345                 350

Leu Leu Leu Asp Ser Leu Gly Asp Arg Thr Arg Tyr Phe Ser Met Trp
            355                 360                 365

Asn Gln Ala Val Asp Ser Tyr Asp Pro Asp Val Arg Ile Ile Glu Asn
            370                 375                 380

His Gly Val Glu Asp Glu Leu Pro Asn Tyr Cys Phe Pro Leu Asn Gly
385                 390                 395                 400

Val Gly Phe Thr Asp Thr Phe Gln Gly Ile Lys Val Lys Thr Thr Asn
            405                 410                 415

Asn Gly Thr Ala Asn Ala Thr Glu Trp Glu Ser Asp Thr Ser Val Asn
            420                 425                 430

Asn Ala Asn Glu Ile Ala Lys Gly Asn Pro Phe Ala Met Glu Ile Asn
            435                 440                 445

Ile Gln Ala Asn Leu Trp Arg Asn Phe Leu Tyr Ala Asn Val Ala Leu
            450                 455                 460

Tyr Leu Pro Asp Ser Tyr Lys Tyr Thr Pro Ala Asn Ile Thr Leu Pro
465                 470                 475                 480

Thr Asn Thr Asn Thr Tyr Asp Tyr Met Asn Gly Arg Val Val Ala Pro
            485                 490                 495

Ser Leu Val Asp Ala Tyr Ile Asn Ile Gly Ala Arg Trp Ser Leu Asp
            500                 505                 510
```

-continued

Pro Met Asp Asn Val Asn Pro Phe Asn His His Arg Asn Ala Gly Leu
    515                 520                 525

Arg Tyr Arg Ser Met Leu Leu Gly Asn Gly Arg Tyr Val Pro Phe His
530                 535                 540

Ile Gln Val Pro Gln Lys Phe Phe Ala Ile Lys Ser Leu Leu Leu Leu
545                 550                 555                 560

Pro Gly Ser Tyr Thr Tyr Glu Trp Asn Phe Arg Lys Asp Val Asn Met
                565                 570                 575

Ile Leu Gln Ser Ser Leu Gly Asn Asp Leu Arg Thr Asp Gly Ala Ser
            580                 585                 590

Ile Ala Phe Thr Ser Ile Asn Leu Tyr Ala Thr Phe Phe Pro Met Ala
        595                 600                 605

His Asn Thr Ala Ser Thr Leu Glu Ala Met Leu Arg Asn Asp Thr Asn
    610                 615                 620

Asp Gln Ser Phe Asn Asp Tyr Leu Ser Ala Ala Asn Met Leu Tyr Pro
625                 630                 635                 640

Ile Pro Ala Asn Ala Thr Asn Val Pro Ile Ser Ile Pro Ser Arg Asn
                645                 650                 655

Trp Ala Ala Phe Arg Gly Trp Ser Phe Thr Arg Leu Lys Thr Arg Glu
            660                 665                 670

Thr Pro Ser Leu Gly Ser Gly Phe Asp Pro Tyr Phe Val Tyr Ser Gly
        675                 680                 685

Ser Ile Pro Tyr Leu Asp Gly Thr Phe Tyr Leu Asn His Thr Phe Lys
    690                 695                 700

Lys Val Ser Ile Thr Phe Asp Ser Ser Val Ser Trp Pro Gly Asn Asp
705                 710                 715                 720

Arg Leu Leu Thr Pro Asn Glu Phe Glu Ile Lys Arg Thr Val Asp Gly
                725                 730                 735

Glu Gly Tyr Asn Val Ala Gln Cys Asn Met Thr Lys Asp Trp Phe Leu
            740                 745                 750

Val Gln Met Leu Ala His Tyr Asn Ile Gly Tyr Gln Gly Phe Tyr Val
        755                 760                 765

Pro Glu Gly Tyr Lys Asp Arg Met Tyr Ser Phe Phe Arg Asn Phe Gln
    770                 775                 780

Pro Met Ser Arg Gln Val Val Asp Glu Val Asn Tyr Lys Asp Tyr Gln
785                 790                 795                 800

Ala Val Thr Leu Ala Tyr Gln His Asn Asn Ser Gly Phe Val Gly Tyr
                805                 810                 815

Leu Ala Pro Thr Met Arg Gln Gly Gln Pro Tyr Pro Ala Asn Tyr Pro
            820                 825                 830

Tyr Pro Leu Ile Gly Lys Ser Ala Val Ala Ser Val Thr Gln Lys Lys
        835                 840                 845

Phe Leu Cys Asp Arg Val Met Trp Arg Ile Pro Phe Ser Ser Asn Phe
850                 855                 860

Met Ser Met Gly Ala Leu Thr Asp Leu Gly Gln Asn Met Leu Tyr Ala
865                 870                 875                 880

Asn Ser Ala His Ala Leu Asp Met Asn Phe Glu Val Asp Pro Met Asp
                885                 890                 895

Glu Ser Thr Leu Leu Tyr Val Val Phe Glu Val Phe Asp Val Val Arg
            900                 905                 910

Val His Gln Pro His Arg Gly Val Ile Glu Ala Val Tyr Leu Arg Thr
        915                 920                 925

Pro Phe Ser Ala Gly Asn Ala Thr Thr

<210> SEQ ID NO 23
<211> LENGTH: 937
<212> TYPE: PRT
<213> ORGANISM: Adenoviridae - Mastadenovirus
<220> FEATURE:
<221> NAME/KEY: misc_feature
<222> LOCATION: (296)..(296)
<223> OTHER INFORMATION: Xaa can be any naturally occurring amino acid

<400> SEQUENCE: 23

```
Met Ala Thr Pro Ser Met Leu Pro Gln Trp Ala Tyr Met His Ile Ala
1               5                   10                  15

Gly Gln Asp Ala Ser Glu Tyr Leu Ser Pro Gly Leu Val Gln Phe Ala
                20                  25                  30

Arg Ala Thr Asp Thr Tyr Phe Ser Leu Gly Asn Lys Phe Arg Asn Pro
            35                  40                  45

Thr Val Ala Pro Thr His Asp Val Thr Thr Asp Arg Ser Gln Arg Leu
        50                  55                  60

Thr Leu Arg Phe Val Pro Val Asp Arg Glu Asp Asn Thr Tyr Ser Tyr
65                  70                  75                  80

Lys Val Arg Tyr Thr Leu Ala Val Gly Asp Asn Arg Val Leu Asp Met
                85                  90                  95

Ala Ser Thr Tyr Phe Asp Ile Arg Gly Val Leu Asp Arg Gly Pro Ser
                100                 105                 110

Phe Lys Pro Tyr Ser Gly Thr Ala Tyr Asn Ser Leu Ala Pro Lys Gly
            115                 120                 125

Ala Pro Asn Thr Ser Gln Trp Ile Thr Lys Asp Asn Gly Thr Asp Lys
        130                 135                 140

Thr Tyr Ser Phe Gly Asn Ala Pro Val Arg Gly Leu Asp Ile Thr Glu
145                 150                 155                 160

Glu Gly Leu Gln Ile Gly Thr Asp Glu Ser Gly Gly Lys Ser Lys Lys
                165                 170                 175

Ile Phe Ala Asp Lys Thr Tyr Gln Pro Glu Pro Gln Leu Gly Asp Glu
                180                 185                 190

Glu Trp His Asp Thr Ile Gly Ala Glu Asp Lys Tyr Gly Gly Arg Ala
            195                 200                 205

Leu Lys Pro Ala Thr Asn Met Lys Pro Cys Tyr Gly Ser Phe Ala Lys
        210                 215                 220

Pro Thr Asn Ala Lys Gly Gly Gln Ala Lys Ser Arg Thr Lys Asp Asp
225                 230                 235                 240

Gly Thr Thr Glu Pro Asp Ile Asp Met Ala Phe Phe Asp Asp Arg Ser
                245                 250                 255

Gln Gln Ala Ser Phe Ser Pro Glu Leu Val Leu Tyr Thr Glu Asn Val
                260                 265                 270

Asp Leu Asp Thr Pro Asp Thr His Ile Ile Tyr Lys Pro Gly Thr Asp
            275                 280                 285

Glu Thr Ser Ser Ser Phe Asn Xaa Gly Gln Gln Ser Met Pro Asn Arg
        290                 295                 300

Pro Asn Tyr Ile Gly Phe Arg Asp Asn Phe Ile Gly Leu Met Tyr Tyr
305                 310                 315                 320

Asn Ser Thr Gly Asn Met Gly Val Leu Ala Gly Gln Ala Ser Gln Leu
                325                 330                 335

Asn Ala Val Val Asp Leu Gln Asp Arg Asn Thr Glu Leu Ser Tyr Gln
                340                 345                 350
```

```
Leu Leu Leu Asp Ser Leu Gly Asp Arg Thr Arg Tyr Phe Ser Met Trp
            355                 360                 365

Asn Gln Ala Val Asp Ser Tyr Asp Pro Asp Val Arg Ile Ile Glu Asn
    370                 375                 380

His Gly Val Glu Asp Glu Leu Pro Asn Tyr Cys Phe Pro Leu Asn Gly
385                 390                 395                 400

Val Gly Phe Thr Asp Thr Phe Gln Gly Ile Lys Val Lys Thr Thr Asn
                405                 410                 415

Asn Gly Thr Ala Asn Ala Thr Glu Trp Glu Ser Asp Thr Ser Val Asn
            420                 425                 430

Asn Ala Asn Glu Ile Ala Lys Gly Asn Pro Phe Ala Met Glu Ile Asn
        435                 440                 445

Ile Gln Ala Asn Leu Trp Arg Asn Phe Leu Tyr Ala Asn Val Ala Leu
    450                 455                 460

Tyr Leu Pro Asp Ser Tyr Lys Tyr Thr Pro Ala Asn Ile Thr Leu Pro
465                 470                 475                 480

Thr Asn Thr Asn Thr Tyr Asp Tyr Met Asn Gly Arg Val Val Ala Pro
                485                 490                 495

Ser Leu Val Asp Ala Tyr Ile Asn Ile Gly Ala Arg Trp Ser Leu Asp
            500                 505                 510

Pro Met Asp Asn Val Asn Pro Phe Asn His His Arg Asn Ala Gly Leu
        515                 520                 525

Arg Tyr Arg Ser Met Leu Leu Gly Asn Gly Arg Tyr Val Pro Phe His
    530                 535                 540

Ile Gln Val Pro Gln Lys Phe Phe Ala Ile Lys Asn Leu Leu Leu Leu
545                 550                 555                 560

Pro Gly Ser Tyr Thr Tyr Glu Trp Asn Phe Arg Lys Asp Val Asn Met
                565                 570                 575

Ile Leu Gln Ser Ser Leu Gly Asn Asp Leu Arg Thr Asp Gly Ala Ser
            580                 585                 590

Ile Ala Phe Thr Ser Ile Asn Leu Tyr Ala Thr Phe Phe Pro Met Ala
        595                 600                 605

His Asn Thr Ala Ser Thr Leu Glu Ala Met Leu Arg Asn Asp Thr Asn
    610                 615                 620

Asp Gln Ser Phe Asn Asp Tyr Leu Ser Ala Ala Asn Met Leu Tyr Pro
625                 630                 635                 640

Ile Pro Ala Asn Ala Thr Asn Val Pro Ile Ser Ile Pro Ser Arg Asn
                645                 650                 655

Trp Ala Ala Phe Arg Gly Trp Ser Phe Thr Arg Leu Lys Thr Arg Glu
            660                 665                 670

Thr Pro Ser Leu Gly Ser Gly Phe Asp Pro Tyr Phe Val Tyr Ser Gly
        675                 680                 685

Ser Ile Pro Tyr Leu Asp Gly Thr Phe Tyr Leu Asn His Thr Phe Lys
    690                 695                 700

Lys Val Ser Ile Thr Phe Asp Ser Ser Val Ser Trp Pro Gly Asn Asp
705                 710                 715                 720

Arg Leu Leu Thr Pro Asn Glu Phe Glu Ile Lys Arg Thr Val Asp Gly
                725                 730                 735

Glu Gly Tyr Asn Val Ala Gln Cys Asn Met Thr Lys Asp Trp Phe Leu
            740                 745                 750

Val Gln Met Leu Ala His Tyr Asn Ile Gly Tyr Gln Gly Phe Tyr Val
        755                 760                 765
```

```
Pro Glu Gly Tyr Lys Asp Arg Met Tyr Ser Phe Phe Arg Asn Phe Gln
    770                 775                 780

Pro Met Ser Arg Gln Val Val Asp Glu Val Asn Tyr Lys Asp Tyr Gln
785                 790                 795                 800

Ala Val Thr Leu Ala Tyr Gln His Asn Asn Ser Gly Phe Val Gly Tyr
                805                 810                 815

Leu Ala Pro Thr Met Arg Gln Gly Gln Pro Tyr Pro Ala Asn Tyr Pro
            820                 825                 830

Tyr Pro Leu Ile Gly Lys Ser Ala Val Ala Ser Val Thr Gln Lys Lys
            835                 840                 845

Phe Leu Cys Asp Arg Val Met Trp Arg Ile Pro Phe Ser Ser Asn Phe
    850                 855                 860

Met Ser Met Gly Ala Leu Thr Asp Leu Gly Gln Asn Met Leu Tyr Ala
865                 870                 875                 880

Asn Ser Ala His Ala Leu Asp Met Asn Phe Glu Val Asp Pro Met Asp
                885                 890                 895

Glu Ser Thr Leu Leu Tyr Val Val Phe Glu Val Phe Asp Val Val Arg
            900                 905                 910

Val His Gln Pro His Arg Gly Val Ile Glu Ala Val Tyr Leu Arg Thr
            915                 920                 925

Pro Phe Ser Ala Gly Asn Ala Thr Thr
930                 935

<210> SEQ ID NO 24
<211> LENGTH: 937
<212> TYPE: PRT
<213> ORGANISM: Adenoviridae - Mastadenovirus
<220> FEATURE:
<221> NAME/KEY: misc_feature
<222> LOCATION: (538)..(538)
<223> OTHER INFORMATION: Xaa can be any naturally occurring amino acid

<400> SEQUENCE: 24

Met Ala Thr Pro Ser Met Leu Pro Gln Trp Ala Tyr Met His Ile Ala
1               5                   10                  15

Gly Gln Asp Ala Ser Glu Tyr Leu Ser Pro Gly Leu Val Gln Phe Ala
            20                  25                  30

Arg Ala Thr Asp Thr Tyr Phe Ser Leu Gly Asn Lys Phe Arg Asn Pro
        35                  40                  45

Thr Val Ala Pro Thr His Asp Val Thr Thr Asp Arg Ser Gln Arg Leu
50                  55                  60

Thr Leu Arg Phe Val Pro Val Asp Arg Glu Asp Asn Thr Tyr Ser Tyr
65                  70                  75                  80

Lys Val Arg Tyr Thr Leu Ala Val Gly Asp Asn Arg Val Leu Asp Met
                85                  90                  95

Ala Ser Thr Tyr Phe Asp Ile Arg Gly Val Leu Asp Arg Gly Pro Ser
            100                 105                 110

Phe Lys Pro Tyr Ser Gly Thr Ala Tyr Asn Ser Leu Ala Pro Lys Gly
        115                 120                 125

Ala Pro Asn Thr Ser Gln Trp Val Thr Lys Asp Asn Gly Thr Asp Lys
130                 135                 140

Thr Tyr Ser Phe Gly Asn Ala Pro Val Arg Gly Leu Asp Ile Thr Glu
145                 150                 155                 160

Glu Gly Leu Gln Ile Gly Thr Asp Asp Ser Ser Thr Glu Ser Lys Lys
                165                 170                 175

Ile Phe Ala Asp Lys Thr Tyr Gln Pro Glu Pro Gln Val Gly Asp Glu
```

```
            180                 185                 190
Glu Trp His Asp Thr Ile Gly Ala Glu Asp Lys Tyr Gly Gly Arg Ala
            195                 200                 205
Leu Lys Pro Ala Thr Asn Met Lys Pro Cys Tyr Gly Ser Phe Ala Lys
            210                 215                 220
Pro Thr Asn Ala Lys Gly Gln Ala Lys Thr Arg Thr Lys Asp Asp
225                 230                 235                 240
Gly Thr Thr Glu Pro Asp Ile Asp Met Ala Phe Phe Asp Asp Arg Ser
                    245                 250                 255
Gln Gln Ala Ser Phe Ser Pro Glu Leu Val Leu Tyr Thr Glu Asn Val
                260                 265                 270
Asp Leu Glu Thr Pro Asp Thr His Ile Ile Tyr Lys Pro Gly Thr Asp
                275                 280                 285
Glu Thr Ser Ser Ser Phe Asn Leu Gly Gln Gln Ser Met Pro Asn Arg
                290                 295                 300
Pro Asn Tyr Ile Gly Phe Arg Asp Asn Phe Ile Gly Leu Met Tyr Tyr
305                 310                 315                 320
Asn Ser Thr Gly Asn Met Gly Val Leu Ala Gly Gln Ala Ser Gln Leu
                    325                 330                 335
Asn Ala Val Val Asp Leu Gln Asp Arg Asn Thr Glu Leu Ser Tyr Gln
                340                 345                 350
Leu Leu Leu Asp Ser Leu Gly Asp Arg Thr Arg Tyr Phe Ser Met Trp
                355                 360                 365
Asn Gln Ala Val Asp Ser Tyr Asp Pro Asp Val Arg Ile Ile Glu Asn
                370                 375                 380
His Gly Val Glu Asp Glu Leu Pro Asn Tyr Cys Phe Pro Leu Asn Gly
385                 390                 395                 400
Val Gly Phe Thr Asp Thr Phe Gln Gly Ile Lys Val Lys Thr Thr Asn
                    405                 410                 415
Asn Gly Thr Ala Asn Ala Thr Glu Trp Glu Ser Asp Thr Ser Val Asn
                420                 425                 430
Asn Ala Asn Glu Ile Ala Lys Gly Asn Pro Phe Ala Met Glu Ile Asn
                435                 440                 445
Ile Gln Ala Asn Leu Trp Arg Asn Phe Leu Tyr Ala Asn Val Ala Leu
450                 455                 460
Tyr Leu Pro Asp Ser Tyr Lys Tyr Thr Pro Ala Asn Val Thr Leu Pro
465                 470                 475                 480
Thr Asn Thr Asn Thr Tyr Glu Tyr Met Asn Gly Arg Val Val Ala Pro
                    485                 490                 495
Ser Leu Val Asp Ser Tyr Ile Asn Ile Gly Ala Arg Trp Ser Leu Asp
                500                 505                 510
Pro Met Asp Asn Val Asn Pro Phe Asn His His Arg Asn Ala Gly Leu
                515                 520                 525
Arg Tyr Arg Ser Met Leu Leu Gly Asn Xaa Arg Phe Val Pro Phe His
                530                 535                 540
Ile Gln Val Pro Gln Lys Phe Phe Ala Ile Lys Ser Leu Leu Leu Leu
545                 550                 555                 560
Pro Gly Ser Tyr Thr Tyr Glu Trp Asn Phe Arg Lys Asp Val Asn Met
                    565                 570                 575
Ile Leu Gln Ser Ser Leu Gly Asn Asp Leu Arg Thr Asp Gly Ala Ser
                580                 585                 590
Ile Ser Phe Thr Ser Ile Asn Leu Tyr Ala Thr Phe Phe Pro Met Ala
                595                 600                 605
```

His Asn Thr Ala Ser Thr Leu Glu Ala Met Leu Arg Asn Asp Thr Asn
            610                 615                 620

Asp Gln Ser Phe Asn Asp Tyr Leu Ser Ala Ala Asn Met Leu Tyr Pro
625                 630                 635                 640

Ile Pro Ala Asn Ala Thr Asn Val Pro Ile Ser Ile Pro Ser Arg Asn
                645                 650                 655

Trp Ala Ala Phe Arg Gly Trp Ser Phe Thr Arg Leu Lys Thr Lys Glu
            660                 665                 670

Thr Pro Ser Leu Gly Ser Gly Phe Asp Pro Tyr Phe Val Tyr Ser Gly
        675                 680                 685

Ser Ile Pro Tyr Leu Asp Gly Thr Phe Tyr Leu Asn His Thr Phe Lys
    690                 695                 700

Lys Val Ser Ile Thr Phe Asp Ser Ser Val Ser Trp Pro Gly Asn Asp
705                 710                 715                 720

Arg Leu Leu Thr Pro Asn Glu Phe Glu Ile Lys Arg Thr Val Asp Gly
                725                 730                 735

Glu Gly Tyr Asn Val Ala Gln Cys Asn Met Thr Lys Asp Trp Phe Leu
            740                 745                 750

Val Gln Met Leu Ala His Tyr Asn Ile Gly Tyr Gln Gly Phe Tyr Val
        755                 760                 765

Pro Glu Gly Tyr Lys Asp Arg Met Tyr Ser Phe Phe Arg Asn Phe Gln
    770                 775                 780

Pro Met Ser Arg Gln Val Val Asp Glu Val Asn Tyr Lys Asp Tyr Gln
785                 790                 795                 800

Ala Val Thr Leu Ala Tyr Gln His Asn Asn Ser Gly Phe Val Gly Tyr
                805                 810                 815

Leu Ala Pro Thr Met Arg Gln Gly Gln Pro Tyr Pro Ala Asn Tyr Pro
            820                 825                 830

Tyr Pro Leu Ile Gly Lys Ser Ala Val Thr Ser Val Thr Gln Lys Lys
        835                 840                 845

Phe Leu Cys Asp Arg Val Met Trp Arg Ile Pro Phe Ser Ser Asn Phe
    850                 855                 860

Met Ser Met Gly Ala Leu Thr Asp Leu Gly Gln Asn Met Leu Tyr Ala
865                 870                 875                 880

Asn Ser Ala His Ala Leu Asp Met Asn Phe Glu Val Asp Pro Met Asp
                885                 890                 895

Glu Ser Thr Leu Leu Tyr Val Val Phe Glu Val Phe Asp Val Val Arg
            900                 905                 910

Val His Gln Pro His Arg Gly Val Ile Glu Ala Val Tyr Leu Arg Thr
        915                 920                 925

Pro Phe Ser Ala Gly Asn Ala Thr Thr
    930                 935

<210> SEQ ID NO 25
<211> LENGTH: 962
<212> TYPE: PRT
<213> ORGANISM: Adenoviridae - Mastadenovirus

<400> SEQUENCE: 25

Met Ala Thr Pro Ser Met Met Pro Gln Trp Ser Tyr Met His Ile Ser
1               5                   10                  15

Gly Gln Asp Ala Ser Glu Tyr Leu Ser Pro Gly Leu Val Gln Phe Ala
            20                  25                  30

Arg Ala Thr Asp Ser Tyr Phe Ser Leu Ser Asn Lys Phe Arg Asn Pro

```
            35                  40                  45
Thr Val Ala Pro Thr His Asp Val Thr Thr Asp Arg Ser Gln Arg Leu
 50                  55                  60
Thr Leu Arg Phe Ile Pro Val Asp Arg Glu Asp Thr Ala Tyr Ser Tyr
 65                  70                  75                  80
Lys Ala Arg Phe Thr Leu Ala Val Gly Asp Asn Arg Val Leu Asp Met
                 85                  90                  95
Ala Ser Thr Tyr Phe Asp Ile Arg Gly Val Leu Asp Arg Gly Pro Thr
             100                 105                 110
Phe Lys Pro Tyr Ser Gly Thr Ala Tyr Asn Ser Leu Ala Pro Lys Gly
             115                 120                 125
Ala Pro Asn Ser Cys Glu Trp Glu Gln Val Glu Pro Ala Glu Glu Ala
 130                 135                 140
Ala Glu Asn Glu Asp Glu Glu Glu Glu Asp Val Val Asp Pro Gln
 145                 150                 155                 160
Glu Gln Glu Pro Thr Thr Lys Thr His Val Tyr Ala Gln Ala Pro Leu
                 165                 170                 175
Ser Gly Glu Lys Ile Thr Lys Asp Gly Leu Gln Ile Gly Thr Glu Ala
             180                 185                 190
Thr Ala Ala Gly Gly Thr Lys Asp Leu Phe Ala Asp Pro Thr Phe Gln
             195                 200                 205
Pro Glu Pro Gln Val Gly Glu Ser Gln Trp Asn Glu Ala Asp Ala Thr
 210                 215                 220
Ala Ala Gly Gly Arg Val Leu Lys Lys Thr Thr Pro Met Lys Pro Cys
 225                 230                 235                 240
Tyr Gly Ser Tyr Ala Arg Pro Thr Asn Ala Asn Gly Gln Gly Val
                 245                 250                 255
Leu Lys Ala Asn Ala Gln Gly Val Leu Glu Ser Gln Val Glu Met Gln
             260                 265                 270
Phe Phe Ser Thr Ser Thr Asn Ala Thr Asn Glu Gln Asn Asn Ile Gln
             275                 280                 285
Pro Lys Leu Val Leu Tyr Ser Glu Asp Val His Met Glu Thr Pro Asp
 290                 295                 300
Thr His Ile Ser Tyr Lys Pro Thr Lys Ser Asp Asp Asn Ser Lys Val
 305                 310                 315                 320
Met Leu Gly Gln Gln Ser Met Pro Asn Arg Pro Asn Tyr Ile Ala Phe
                 325                 330                 335
Arg Asp Asn Phe Ile Gly Leu Met Tyr Tyr Asn Ser Thr Gly Asn Met
             340                 345                 350
Gly Val Leu Ala Gly Gln Ala Ser Gln Leu Asn Ala Val Val Asp Leu
             355                 360                 365
Gln Asp Arg Asn Thr Glu Leu Ser Tyr Gln Leu Leu Asp Ser Met
 370                 375                 380
Gly Asp Arg Thr Arg Tyr Phe Ser Met Trp Asn Gln Ala Val Asp Ser
 385                 390                 395                 400
Tyr Asp Pro Asp Val Arg Ile Ile Glu Asn His Gly Thr Glu Asp Glu
                 405                 410                 415
Leu Pro Asn Tyr Cys Phe Pro Leu Gly Gly Ile Gly Ile Thr Asp Thr
             420                 425                 430
Tyr Gln Ala Ile Lys Thr Asn Gly Asn Gly Ala Gly Asp Gln Ala Thr
             435                 440                 445
Thr Trp Gln Lys Asp Ser Gln Phe Ala Asp Arg Asn Glu Ile Gly Val
 450                 455                 460
```

-continued

Gly Asn Asn Phe Ala Met Glu Ile Asn Leu Ser Ala Asn Leu Trp Arg
465                 470                 475                 480

Asn Phe Leu Tyr Ser Asn Val Ala Leu Tyr Leu Pro Asp Lys Leu Lys
            485                 490                 495

Tyr Asn Pro Ser Asn Val Glu Ile Ser Asp Asn Pro Asn Thr Tyr Asp
        500                 505                 510

Tyr Met Asn Lys Arg Val Val Ala Pro Gly Leu Val Asp Cys Tyr Ile
            515                 520                 525

Asn Leu Gly Ala Arg Trp Ser Leu Asp Tyr Met Asp Asn Val Asn Pro
530                 535                 540

Phe Asn His His Arg Asn Ala Gly Leu Arg Tyr Arg Ser Met Leu Leu
545                 550                 555                 560

Gly Asn Gly Arg Tyr Val Pro Phe His Ile Gln Val Pro Gln Lys Phe
            565                 570                 575

Phe Ala Ile Lys Asn Leu Leu Leu Pro Gly Ser Tyr Thr Tyr Glu
            580                 585                 590

Trp Asn Phe Arg Lys Asp Val Asn Met Val Leu Gln Ser Ser Leu Gly
            595                 600                 605

Asn Asp Leu Arg Val Asp Gly Ala Ser Ile Lys Phe Glu Ser Ile Cys
610                 615                 620

Leu Tyr Ala Thr Phe Phe Pro Met Ala His Asn Thr Ala Ser Thr Leu
625                 630                 635                 640

Glu Ala Met Leu Arg Asn Asp Thr Asn Asp Gln Ser Phe Asn Asp Tyr
                645                 650                 655

Leu Ser Ala Ala Asn Met Leu Tyr Pro Ile Pro Ala Asn Ala Thr Asn
            660                 665                 670

Val Pro Ile Ser Ile Pro Ser Arg Asn Trp Ala Ala Phe Arg Gly Trp
            675                 680                 685

Ala Phe Thr Arg Leu Lys Thr Lys Glu Thr Pro Ser Leu Gly Ser Gly
            690                 695                 700

Phe Asp Pro Tyr Tyr Thr Tyr Ser Gly Ser Ile Pro Tyr Leu Asp Gly
705                 710                 715                 720

Thr Phe Tyr Leu Asn His Thr Phe Lys Lys Val Ser Val Thr Phe Asp
                725                 730                 735

Ser Ser Val Ser Trp Pro Gly Asn Asp Arg Leu Leu Thr Pro Asn Glu
            740                 745                 750

Phe Glu Ile Lys Arg Ser Val Asp Gly Glu Gly Tyr Asn Val Ala Gln
            755                 760                 765

Cys Asn Met Thr Lys Asp Trp Phe Leu Ile Gln Met Leu Ala Asn Tyr
770                 775                 780

Asn Ile Gly Tyr Gln Gly Phe Tyr Ile Pro Glu Ser Tyr Lys Asp Arg
785                 790                 795                 800

Met Tyr Ser Phe Phe Arg Asn Phe Gln Pro Met Ser Arg Gln Val Val
                805                 810                 815

Asp Glu Thr Lys Tyr Lys Asp Tyr Gln Gln Val Gly Ile Ile His Gln
            820                 825                 830

His Asn Asn Ser Gly Phe Val Gly Tyr Leu Ala Pro Thr Met Arg Glu
            835                 840                 845

Gly Gln Ala Tyr Pro Ala Asn Phe Pro Tyr Pro Leu Ile Gly Lys Thr
            850                 855                 860

Ala Val Asp Ser Ile Thr Gln Lys Lys Phe Leu Cys Asp Arg Thr Leu
865                 870                 875                 880

```
Trp Arg Ile Pro Phe Ser Ser Asn Phe Met Ser Met Gly Ala Leu Thr
                885                 890                 895

Asp Leu Gly Gln Asn Leu Leu Tyr Ala Asn Ser Ala His Ala Leu Asp
            900                 905                 910

Met Thr Phe Glu Val Asp Pro Met Asp Glu Pro Thr Leu Leu Tyr Val
        915                 920                 925

Leu Phe Glu Val Phe Asp Val Arg Val His Gln Pro His Arg Gly
    930                 935                 940

Val Ile Glu Thr Val Tyr Leu Arg Thr Pro Phe Ser Ala Gly Asn Ala
945                 950                 955                 960

Thr Thr

<210> SEQ ID NO 26
<211> LENGTH: 531
<212> TYPE: PRT
<213> ORGANISM: Adenoviridae - Mastadenovirus

<400> SEQUENCE: 26

Met Met Arg Arg Val Tyr Pro Glu Gly Pro Pro Ser Tyr Glu Ser
1               5                   10                  15

Val Met Gln Gln Ala Val Ala Ala Met Gln Pro Pro Leu Glu Ala
            20                  25                  30

Pro Tyr Val Pro Pro Arg Tyr Leu Ala Pro Thr Glu Gly Arg Asn Ser
        35                  40                  45

Ile Arg Tyr Ser Glu Leu Ala Pro Leu Tyr Asp Thr Thr Arg Leu Tyr
    50                  55                  60

Leu Val Asp Asn Lys Ser Ala Asp Ile Ala Ser Leu Asn Tyr Gln Asn
65                  70                  75                  80

Asp His Ser Asn Phe Leu Thr Thr Val Val Gln Asn Asn Asp Phe Thr
                85                  90                  95

Pro Thr Glu Ala Ser Thr Gln Thr Ile Asn Phe Asp Glu Arg Ser Arg
            100                 105                 110

Trp Gly Gly Gln Leu Lys Thr Ile Met His Thr Asn Met Pro Asn Val
        115                 120                 125

Asn Glu Phe Met Tyr Ser Asn Lys Phe Lys Ala Arg Val Met Val Ser
130                 135                 140

Arg Lys Thr Pro Asn Gly Val Ala Val Gly Asp Asp Tyr Asp Gly Gly
145                 150                 155                 160

Gln Asp Glu Leu Thr Tyr Glu Trp Val Glu Phe Glu Leu Pro Glu Gly
                165                 170                 175

Asn Phe Ser Val Thr Met Thr Ile Asp Leu Met Asn Asn Ala Ile Ile
            180                 185                 190

Asp Asn Tyr Leu Ala Val Gly Arg Gln Asn Gly Val Leu Glu Ser Asp
        195                 200                 205

Ile Gly Val Lys Phe Asp Thr Arg Asn Phe Arg Leu Gly Trp Asp Pro
    210                 215                 220

Val Thr Glu Leu Val Met Pro Gly Val Tyr Thr Asn Glu Ala Phe His
225                 230                 235                 240

Pro Asp Ile Val Leu Leu Pro Gly Cys Gly Val Asp Phe Thr Glu Ser
                245                 250                 255

Arg Leu Ser Asn Leu Leu Gly Ile Arg Lys Arg Gln Pro Phe Gln Glu
            260                 265                 270

Gly Phe Gln Ile Leu Tyr Glu Asp Leu Glu Gly Gly Asn Ile Pro Ala
        275                 280                 285
```

```
Leu Leu Asp Val Glu Ala Tyr Glu Lys Ser Lys Glu Ser Ala Ala
    290                 295                 300

Ala Ala Thr Ala Ala Val Ala Thr Ala Ser Thr Glu Val Arg Gly Asp
305                 310                 315                 320

Asn Phe Ala Ser Ala Ala Val Ala Glu Ala Ala Glu Thr Glu Ser
                325                 330                 335

Lys Ile Val Ile Gln Pro Val Glu Lys Asp Ser Lys Asp Arg Ser Tyr
                340                 345                 350

Asn Val Leu Ala Asp Lys Lys Asn Thr Ala Tyr Arg Ser Trp Tyr Leu
                355                 360                 365

Ala Tyr Asn Tyr Gly Asp Pro Glu Lys Gly Val Arg Ser Trp Thr Leu
    370                 375                 380

Leu Thr Thr Ser Asp Val Thr Cys Gly Val Glu Gln Val Tyr Trp Ser
385                 390                 395                 400

Leu Pro Asp Met Met Gln Asp Pro Val Thr Phe Arg Ser Thr Arg Gln
                405                 410                 415

Val Ser Asn Tyr Pro Val Val Gly Ala Glu Leu Leu Pro Val Tyr Ser
                420                 425                 430

Lys Ser Phe Phe Asn Glu Gln Ala Val Tyr Ser Gln Gln Leu Arg Ala
                435                 440                 445

Phe Thr Ser Leu Thr His Val Phe Asn Arg Phe Pro Glu Asn Gln Ile
    450                 455                 460

Leu Val Arg Pro Pro Ala Pro Thr Ile Thr Thr Val Ser Glu Asn Val
465                 470                 475                 480

Pro Ala Leu Thr Asp His Gly Thr Leu Pro Leu Arg Ser Ser Ile Arg
                485                 490                 495

Gly Val Gln Arg Val Thr Val Thr Asp Ala Arg Arg Thr Cys Pro
                500                 505                 510

Tyr Val Tyr Lys Ala Leu Gly Val Val Ala Pro Arg Val Leu Ser Ser
                515                 520                 525

Arg Thr Phe
    530

<210> SEQ ID NO 27
<211> LENGTH: 541
<212> TYPE: PRT
<213> ORGANISM: Adenoviridae - Mastadenovirus

<400> SEQUENCE: 27

Met Met Arg Arg Val Tyr Pro Glu Gly Pro Pro Pro Ser Tyr Glu Ser
1               5                   10                  15

Val Met Gln Gln Ala Val Ala Val Ala Met Gln Pro Pro Leu Glu Ala
                20                  25                  30

Pro Tyr Val Pro Pro Arg Tyr Leu Ala Pro Thr Glu Gly Arg Asn Ser
            35                  40                  45

Ile Arg Tyr Ser Glu Leu Ala Pro Leu Tyr Asp Thr Thr Arg Leu Tyr
        50                  55                  60

Leu Val Asp Asn Lys Ser Ala Asp Ile Ala Ser Leu Asn Tyr Gln Asn
65                  70                  75                  80

Asp His Ser Asn Phe Leu Thr Thr Val Val Gln Asn Asn Asp Phe Thr
                85                  90                  95

Pro Thr Glu Ala Ser Thr Gln Thr Ile Asn Phe Asp Glu Arg Ser Arg
            100                 105                 110

Trp Gly Gly Gln Leu Lys Thr Ile Met His Thr Asn Met Pro Asn Val
        115                 120                 125
```

```
Asn Glu Phe Met Tyr Ser Asn Lys Phe Lys Ala Arg Val Met Val Ser
    130                 135                 140

Arg Lys Thr Pro Asn Gly Val Thr Val Gly Asp Asp Tyr Asp Gly Ser
145                 150                 155                 160

Gln Asp Glu Leu Thr Tyr Glu Trp Val Glu Phe Glu Leu Pro Glu Gly
                165                 170                 175

Asn Phe Ser Val Thr Met Thr Ile Asp Leu Met Asn Asn Ala Ile Ile
                180                 185                 190

Asp Asn Tyr Leu Ala Val Gly Arg Gln Asn Gly Val Leu Glu Ser Asp
            195                 200                 205

Ile Gly Val Lys Phe Asp Thr Arg Asn Phe Arg Leu Gly Trp Asp Pro
210                 215                 220

Val Thr Glu Leu Val Met Pro Gly Val Tyr Thr Asn Glu Ala Phe His
225                 230                 235                 240

Pro Asp Ile Val Leu Leu Pro Gly Cys Gly Val Asp Phe Thr Glu Ser
                245                 250                 255

Arg Leu Ser Asn Leu Leu Gly Ile Arg Lys Arg Gln Pro Phe Gln Glu
                260                 265                 270

Gly Phe Gln Ile Leu Tyr Glu Asp Leu Glu Gly Gly Asn Ile Pro Ala
                275                 280                 285

Leu Leu Asp Val Glu Ala Tyr Glu Lys Ser Lys Glu Asp Ser Ala Ala
            290                 295                 300

Ala Thr Thr Ala Ala Val Ala Thr Ala Thr Thr Asp Ala Asp Ala
305                 310                 315                 320

Thr Thr Thr Arg Gly Asp Thr Phe Ala Thr Gln Ala Glu Glu Ala Ala
                325                 330                 335

Ala Leu Ala Ala Thr Asp Asp Ser Glu Ser Lys Ile Val Ile Lys Pro
            340                 345                 350

Val Glu Lys Asp Ser Lys Asp Arg Ser Tyr Asn Val Leu Ala Asp Lys
                355                 360                 365

Lys Asn Thr Ala Tyr Arg Ser Trp Tyr Leu Ala Tyr Asn Tyr Gly Asp
    370                 375                 380

Pro Glu Lys Gly Val Arg Ser Trp Thr Leu Leu Thr Thr Ser Asp Val
385                 390                 395                 400

Thr Cys Gly Val Glu Gln Val Tyr Trp Ser Leu Pro Asp Met Met Gln
                405                 410                 415

Asp Pro Val Thr Phe Arg Ser Thr Arg Gln Val Ser Asn Tyr Pro Val
                420                 425                 430

Val Gly Ala Glu Leu Leu Pro Val Tyr Ser Lys Ser Phe Asn Glu
            435                 440                 445

Gln Ala Val Tyr Ser Gln Gln Leu Arg Ala Phe Thr Ser Leu Thr His
    450                 455                 460

Val Phe Asn Arg Phe Pro Glu Asn Gln Ile Leu Val Arg Pro Pro Ala
465                 470                 475                 480

Pro Thr Ile Thr Thr Val Ser Glu Asn Val Pro Ala Leu Thr Asp His
                485                 490                 495

Gly Thr Leu Pro Leu Arg Ser Ser Ile Arg Gly Val Gln Arg Val Thr
                500                 505                 510

Val Thr Asp Ala Arg Arg Thr Cys Pro Tyr Val Tyr Lys Ala Leu
            515                 520                 525

Gly Val Val Ala Pro Arg Val Leu Ser Ser Arg Thr Phe
530                 535                 540
```

<210> SEQ ID NO 28
<211> LENGTH: 532
<212> TYPE: PRT
<213> ORGANISM: Adenoviridae - Mastadenovirus

<400> SEQUENCE: 28

```
Met Met Arg Arg Val Tyr Pro Glu Gly Pro Pro Ser Tyr Glu Ser
1               5                   10                  15

Val Met Gln Gln Ala Val Ala Ala Met Gln Pro Leu Glu Ala
            20                  25                  30

Pro Tyr Val Pro Pro Arg Tyr Leu Ala Pro Thr Glu Gly Arg Asn Ser
            35                  40                  45

Ile Arg Tyr Ser Glu Leu Ala Pro Leu Tyr Asp Thr Thr Arg Leu Tyr
        50                  55                  60

Leu Val Asp Asn Lys Ser Ala Asp Ile Ala Ser Leu Asn Tyr Gln Asn
65                  70                  75                  80

Asp His Ser Asn Phe Leu Thr Thr Val Val Gln Asn Asn Asp Phe Thr
                85                  90                  95

Pro Thr Glu Ala Ser Thr Gln Thr Ile Asn Phe Asp Glu Arg Ser Arg
            100                 105                 110

Trp Gly Gly Gln Leu Lys Thr Ile Met His Thr Asn Met Pro Asn Val
        115                 120                 125

Asn Glu Phe Met Tyr Ser Asn Lys Phe Lys Ala Arg Val Met Val Ser
130                 135                 140

Arg Lys Thr Pro Asn Gly Val Thr Val Thr Asp Gly Ser Gln Asp Glu
145                 150                 155                 160

Leu Thr Tyr Glu Trp Val Glu Phe Glu Leu Pro Glu Gly Asn Phe Ser
                165                 170                 175

Val Thr Met Thr Ile Asp Leu Met Asn Asn Ala Ile Ile Asp Asn Tyr
            180                 185                 190

Leu Ala Val Gly Arg Gln Asn Gly Val Leu Glu Ser Asp Ile Gly Val
        195                 200                 205

Lys Phe Asp Thr Arg Asn Phe Arg Leu Gly Trp Asp Pro Val Thr Glu
210                 215                 220

Leu Val Met Pro Gly Val Tyr Thr Asn Glu Ala Phe His Pro Asp Ile
225                 230                 235                 240

Val Leu Leu Pro Gly Cys Gly Val Asp Phe Thr Glu Ser Arg Leu Ser
                245                 250                 255

Asn Leu Leu Gly Ile Arg Lys Arg Gln Pro Phe Gln Glu Gly Phe Gln
            260                 265                 270

Ile Leu Tyr Glu Asp Leu Glu Gly Gly Asn Ile Pro Ala Leu Leu Asp
        275                 280                 285

Val Glu Ala Tyr Glu Lys Ser Lys Glu Asp Ser Thr Ala Val Ala Thr
290                 295                 300

Ala Ala Thr Val Ala Asp Ala Thr Val Thr Arg Gly Asp Thr Phe Ala
305                 310                 315                 320

Thr Gln Ala Glu Glu Ala Ala Ala Leu Ala Ala Thr Asp Asp Ser Glu
                325                 330                 335

Ser Lys Ile Val Ile Lys Pro Val Glu Lys Asp Ser Lys Asp Arg Ser
            340                 345                 350

Tyr Asn Val Leu Ser Asp Gly Lys Asn Thr Ala Tyr Arg Ser Trp Tyr
        355                 360                 365

Leu Ala Tyr Asn Tyr Gly Asp Pro Glu Lys Gly Val Arg Ser Trp Thr
370                 375                 380
```

```
Leu Leu Thr Thr Ser Asp Val Thr Cys Gly Val Glu Gln Val Tyr Trp
385                 390                 395                 400

Ser Leu Pro Asp Met Met Gln Asp Pro Val Thr Phe Arg Ser Thr Arg
            405                 410                 415

Gln Val Ser Asn Tyr Pro Val Val Gly Ala Glu Leu Leu Pro Val Tyr
        420                 425                 430

Ser Lys Ser Phe Phe Asn Glu Gln Ala Val Tyr Ser Gln Gln Leu Arg
    435                 440                 445

Ala Phe Thr Ser Leu Thr His Val Phe Asn Arg Phe Pro Glu Asn Gln
450                 455                 460

Ile Leu Val Arg Pro Pro Ala Pro Thr Ile Thr Thr Val Ser Glu Asn
465                 470                 475                 480

Val Pro Ala Leu Thr Asp His Gly Thr Leu Pro Leu Arg Ser Ser Ile
            485                 490                 495

Arg Gly Val Gln Arg Val Thr Val Thr Asp Ala Arg Arg Thr Cys
        500                 505                 510

Pro Tyr Val Tyr Lys Ala Leu Gly Val Val Ala Pro Arg Val Leu Ser
        515                 520                 525

Ser Arg Thr Phe
    530

<210> SEQ ID NO 29
<211> LENGTH: 528
<212> TYPE: PRT
<213> ORGANISM: Adenoviridae - Mastadenovirus

<400> SEQUENCE: 29

Met Met Arg Arg Val Tyr Pro Glu Gly Pro Pro Ser Tyr Glu Ser
1               5                   10                  15

Val Met Gln Gln Ala Val Ala Ala Met Gln Pro Pro Leu Glu Ala
            20                  25                  30

Pro Tyr Val Pro Pro Arg Tyr Leu Ala Pro Thr Glu Gly Arg Asn Ser
        35                  40                  45

Ile Arg Tyr Ser Glu Leu Ala Pro Leu Tyr Asp Thr Thr Arg Leu Tyr
50                  55                  60

Leu Val Asp Asn Lys Ser Ala Asp Ile Ala Ser Leu Asn Tyr Gln Asn
65                  70                  75                  80

Asp His Ser Asn Phe Leu Thr Thr Val Val Gln Asn Asn Asp Phe Thr
                85                  90                  95

Pro Thr Glu Ala Ser Thr Gln Thr Ile Asn Phe Asp Glu Arg Ser Arg
            100                 105                 110

Trp Gly Gly Gln Leu Lys Thr Ile Met His Thr Asn Met Pro Asn Val
        115                 120                 125

Asn Glu Phe Leu Tyr Ser Asn Lys Phe Lys Ala Arg Val Met Val Ser
130                 135                 140

Arg Lys Thr Pro Asn Gly Val Thr Val Thr Asp Gly Ser Gln Asp Glu
145                 150                 155                 160

Leu Thr Tyr Glu Trp Val Glu Phe Glu Leu Pro Glu Gly Asn Phe Ser
                165                 170                 175

Val Thr Met Thr Ile Asp Leu Met Asn Asn Ala Ile Ile Asp Asn Tyr
            180                 185                 190

Leu Ala Val Gly Arg Gln Asn Gly Val Leu Glu Ser Asp Ile Gly Val
        195                 200                 205

Lys Phe Asp Thr Arg Asn Phe Arg Leu Gly Trp Asp Pro Val Thr Glu
```

Leu Val Met Pro Gly Val Tyr Thr Asn Glu Ala Phe His Pro Asp Ile
225                 230                 235                 240

Val Leu Leu Pro Gly Cys Gly Val Asp Phe Thr Glu Ser Arg Leu Ser
                245                 250                 255

Asn Leu Leu Gly Ile Arg Lys Arg Gln Pro Phe Gln Glu Gly Phe Gln
                260                 265                 270

Ile Met Tyr Glu Asp Leu Glu Gly Gly Asn Ile Pro Ala Leu Leu Asp
            275                 280                 285

Val Glu Ala Tyr Glu Lys Ser Lys Glu Asp Ser Ala Ala Ala Ala Thr
290                 295                 300

Ala Ala Val Ala Thr Ala Ser Thr Glu Val Arg Gly Asp Asn Phe Ala
305                 310                 315                 320

Ser Ala Ala Ala Val Ala Glu Ala Ala Glu Thr Glu Ser Lys Ile Val
                325                 330                 335

Ile Gln Pro Val Glu Lys Asp Ser Lys Asp Arg Ser Tyr Asn Val Leu
                340                 345                 350

Ala Asp Lys Lys Asn Thr Ala Tyr Arg Ser Trp Tyr Leu Ala Tyr Asn
                355                 360                 365

Tyr Gly Asp Pro Glu Lys Gly Val Arg Ser Trp Thr Leu Leu Thr Thr
            370                 375                 380

Ser Asp Val Thr Cys Gly Val Glu Gln Val Tyr Trp Ser Leu Pro Asp
385                 390                 395                 400

Met Met Gln Asp Pro Val Thr Phe Arg Ser Thr Arg Gln Val Ser Asn
                405                 410                 415

Tyr Pro Val Val Gly Ala Glu Leu Leu Pro Val Tyr Ser Lys Ser Phe
                420                 425                 430

Phe Asn Glu Gln Ala Val Tyr Ser Gln Gln Leu Arg Ala Phe Thr Ser
            435                 440                 445

Leu Thr His Val Phe Asn Arg Phe Pro Glu Asn Gln Ile Leu Val Arg
            450                 455                 460

Pro Pro Ala Pro Thr Ile Thr Thr Val Ser Glu Asn Val Pro Ala Leu
465                 470                 475                 480

Thr Asp His Gly Thr Leu Pro Leu Arg Ser Ser Ile Arg Gly Val Gln
                485                 490                 495

Arg Val Thr Val Thr Asp Ala Arg Arg Thr Cys Pro Tyr Val Tyr
                500                 505                 510

Lys Ala Leu Gly Val Val Ala Pro Arg Val Leu Ser Ser Arg Thr Phe
            515                 520                 525

<210> SEQ ID NO 30
<211> LENGTH: 535
<212> TYPE: PRT
<213> ORGANISM: Adenoviridae - Mastadenovirus

<400> SEQUENCE: 30

Met Met Arg Arg Ala Tyr Pro Glu Gly Pro Pro Ser Tyr Glu Ser
1               5                   10                  15

Val Met Gln Gln Ala Met Ala Ala Ala Ala Met Gln Pro Pro Leu
                20                  25                  30

Glu Ala Pro Tyr Val Pro Pro Arg Tyr Leu Ala Pro Thr Glu Gly Arg
                35                  40                  45

Asn Ser Ile Arg Tyr Ser Glu Leu Ala Pro Leu Tyr Asp Thr Thr Arg
50                  55                  60

```
Leu Tyr Leu Val Asp Asn Lys Ser Ala Asp Ile Ala Ser Leu Asn Tyr
 65                  70                  75                  80

Gln Asn Asp His Ser Asn Phe Leu Thr Thr Val Val Gln Asn Asn Asp
                 85                  90                  95

Phe Thr Pro Thr Glu Ala Ser Thr Gln Thr Ile Asn Phe Asp Glu Arg
            100                 105                 110

Ser Arg Trp Gly Gly Gln Leu Lys Thr Ile Met His Thr Asn Met Pro
        115                 120                 125

Asn Val Asn Glu Phe Met Tyr Ser Asn Lys Phe Lys Ala Arg Val Met
    130                 135                 140

Val Ser Arg Lys Thr Pro Asn Gly Val Thr Val Thr Glu Asp Tyr Asp
145                 150                 155                 160

Gly Ser Gln Asp Glu Leu Lys Tyr Glu Trp Val Glu Phe Glu Leu Pro
                165                 170                 175

Glu Gly Asn Phe Ser Val Thr Met Thr Ile Asp Leu Met Asn Asn Ala
            180                 185                 190

Ile Ile Asp Asn Tyr Leu Ala Val Gly Arg Gln Asn Gly Val Leu Glu
        195                 200                 205

Ser Asp Ile Gly Val Lys Phe Asp Thr Arg Asn Phe Arg Leu Gly Trp
    210                 215                 220

Asp Pro Val Thr Glu Leu Val Met Pro Gly Val Tyr Thr Asn Glu Ala
225                 230                 235                 240

Phe His Pro Asp Ile Val Leu Leu Pro Gly Cys Gly Val Asp Phe Thr
                245                 250                 255

Glu Ser Arg Leu Ser Asn Leu Leu Gly Ile Arg Lys Arg Gln Pro Phe
            260                 265                 270

Gln Glu Gly Phe Gln Ile Met Tyr Glu Asp Leu Glu Gly Gly Asn Ile
        275                 280                 285

Pro Ala Leu Leu Asp Val Asp Ala Tyr Glu Lys Ser Lys Glu Glu Ser
    290                 295                 300

Ala Ala Ala Ala Thr Ala Ala Val Ala Thr Ala Ser Thr Glu Val Arg
305                 310                 315                 320

Gly Asp Asn Phe Ala Ser Ala Ala Ala Val Ala Ala Ala Glu Ala Ala
                325                 330                 335

Glu Thr Glu Ser Lys Ile Val Ile Gln Pro Val Glu Lys Asp Ser Lys
            340                 345                 350

Asp Arg Ser Tyr Asn Val Leu Pro Asp Lys Ile Asn Thr Ala Tyr Arg
        355                 360                 365

Ser Trp Tyr Leu Ala Tyr Asn Tyr Gly Asp Pro Glu Lys Gly Val Arg
    370                 375                 380

Ser Trp Thr Leu Leu Thr Thr Ser Asp Val Thr Cys Gly Val Glu Gln
385                 390                 395                 400

Val Tyr Trp Ser Leu Pro Asp Met Met Gln Asp Pro Val Thr Phe Arg
                405                 410                 415

Ser Thr Arg Gln Val Ser Asn Tyr Pro Val Val Gly Ala Glu Leu Leu
            420                 425                 430

Pro Val Tyr Ser Lys Ser Phe Phe Asn Glu Gln Ala Val Tyr Ser Gln
        435                 440                 445

Gln Leu Arg Ala Phe Thr Ser Leu Thr His Val Phe Asn Arg Phe Pro
    450                 455                 460

Glu Asn Gln Ile Leu Val Arg Pro Pro Ala Pro Thr Ile Thr Thr Val
465                 470                 475                 480

Ser Glu Asn Val Pro Ala Leu Thr Asp His Gly Thr Leu Pro Leu Arg
```

```
                         485                 490                 495
Ser Ser Ile Arg Gly Val Gln Arg Val Thr Val Thr Asp Ala Arg Arg
            500                 505                 510

Arg Thr Cys Pro Tyr Val Tyr Lys Ala Leu Gly Ile Val Ala Pro Arg
            515                 520                 525

Val Leu Ser Ser Arg Thr Phe
            530                 535

<210> SEQ ID NO 31
<211> LENGTH: 581
<212> TYPE: PRT
<213> ORGANISM: Adenoviridae - Mastadenovirus

<400> SEQUENCE: 31

Met Arg Arg Ala Ala Met Tyr His Glu Gly Pro Pro Ser Tyr Glu
1               5                   10                  15

Ser Val Val Gly Ala Ala Ala Ser Pro Phe Ala Ser Gln Leu Glu
            20                  25                  30

Pro Pro Tyr Val Pro Pro Arg Tyr Leu Arg Pro Thr Gly Gly Arg Asn
            35                  40                  45

Ser Ile Arg Tyr Ser Glu Leu Ala Pro Leu Tyr Asp Thr Thr Arg Val
50                  55                  60

Tyr Leu Val Asp Asn Lys Ser Ala Asp Val Ala Ser Leu Asn Tyr Gln
65                  70                  75                  80

Asn Asp His Ser Asn Phe Leu Thr Thr Val Ile Gln Asn Asn Asp Tyr
                85                  90                  95

Thr Pro Ser Glu Ala Ser Thr Gln Thr Ile Asn Leu Asp Asp Arg Ser
            100                 105                 110

His Trp Gly Gly Asp Leu Lys Thr Ile Leu His Thr Asn Met Pro Asn
            115                 120                 125

Val Asn Glu Phe Met Phe Thr Asn Lys Phe Lys Ala Arg Val Met Val
            130                 135                 140

Ser Arg Ser His Thr Lys Asp Asp Arg Val Glu Leu Lys Tyr Glu Trp
145                 150                 155                 160

Val Glu Phe Glu Leu Pro Glu Gly Asn Tyr Ser Glu Thr Met Thr Ile
                165                 170                 175

Asp Leu Met Asn Asn Ala Ile Val Glu His Tyr Leu Lys Val Gly Arg
            180                 185                 190

Gln Asn Gly Val Leu Glu Ser Asp Ile Gly Val Lys Phe Asp Thr Arg
            195                 200                 205

Asn Phe Arg Leu Gly Leu Asp Pro Val Thr Gly Leu Val Met Pro Gly
            210                 215                 220

Val Tyr Thr Asn Glu Ala Phe His Pro Asp Ile Ile Leu Leu Pro Gly
225                 230                 235                 240

Cys Gly Val Asp Phe Thr Tyr Ser Arg Leu Ser Asn Leu Leu Gly Ile
                245                 250                 255

Arg Lys Arg Gln Pro Phe Gln Glu Gly Phe Arg Ile Thr Tyr Glu Asp
            260                 265                 270

Leu Glu Gly Gly Asn Ile Pro Ala Leu Leu Asp Val Glu Ala Tyr Gln
            275                 280                 285

Asp Ser Leu Lys Glu Glu Glu Ala Gly Glu Gly Ser Gly Gly Gly Ala
            290                 295                 300

Gly Gln Glu Glu Gly Gly Ala Ser Ser Glu Ala Ser Ala Asp Pro Ala
305                 310                 315                 320
```

```
Ala Ala Ala Glu Ala Glu Ala Asp Pro Ala Met Val Val Glu Glu
            325                 330                 335

Glu Lys Asp Met Asn Asp Glu Ala Val Arg Gly Asp Thr Phe Ala Thr
            340                 345                 350

Arg Gly Glu Glu Lys Lys Ala Glu Ala Glu Ala Ala Glu Glu Ala
            355                 360                 365

Ala Ala Ala Ala Ala Val Glu Ala Ala Glu Ala Glu Lys Pro
            370                 375                 380

Pro Lys Glu Pro Val Ile Lys Pro Leu Thr Glu Asp Ser Lys Lys Arg
385                 390                 395                 400

Ser Tyr Asn Val Leu Lys Asp Ser Thr Asn Thr Glu Tyr Arg Ser Trp
            405                 410                 415

Tyr Leu Ala Tyr Asn Tyr Gly Asp Pro Ala Thr Gly Val Arg Ser Trp
            420                 425                 430

Thr Leu Leu Cys Thr Pro Asp Val Thr Cys Gly Ser Glu Gln Val Tyr
            435                 440                 445

Trp Ser Leu Pro Asp Met Met Gln Asp Pro Val Thr Phe Arg Ser Thr
            450                 455                 460

Arg Gln Val Ser Asn Phe Pro Val Val Gly Ala Glu Leu Leu Pro Val
465                 470                 475                 480

His Ser Lys Ser Phe Tyr Asn Asp Gln Ala Val Tyr Ser Gln Leu Ile
            485                 490                 495

Arg Gln Phe Thr Ser Leu Thr His Val Phe Asn Arg Phe Pro Glu Asn
            500                 505                 510

Gln Ile Leu Ala Arg Pro Pro Ala Pro Thr Ile Thr Thr Val Ser Glu
            515                 520                 525

Asn Val Pro Ala Leu Thr Asp His Gly Thr Leu Pro Leu Arg Asn Ser
            530                 535                 540

Ile Gly Gly Val Gln Arg Val Thr Val Thr Asp Ala Arg Arg Arg Thr
545                 550                 555                 560

Cys Pro Tyr Val Tyr Lys Ala Leu Gly Ile Val Ser Pro Arg Val Leu
            565                 570                 575

Ser Ser Arg Thr Phe
            580

<210> SEQ ID NO 32
<211> LENGTH: 1323
<212> TYPE: DNA
<213> ORGANISM: Adenoviridae - Mastadenovirus

<400> SEQUENCE: 32
atgtccaaaa agcgcgtccg ggtggatgat gacttcgacc ccgtctaccc ctacgatgca      60
gacaacgcac cgaccgtgcc cttcatcaac cctcccttcg tctcttcaga tggattccaa     120
gaaaagcccc tgggggtgtt gtccctgcga ctggctgacc ccgtcaccac caagaacggg     180
gaaatcaccc tcaagctggg agaggggtg gacctcgacg actcgggaaa actcatctcc     240
aaaaatgcca ccaaggccac tgcccctctc agtatttcca acagcaccat ttcccttaac     300
atggatgccc ctctttacaa caacaatgga aagttaggca taagaatagg agcacctcta     360
aaggtagtag acttactaaa cactttagct gtagcctatg gatcgggtct aggtctcaag     420
aataatgccc ttacagttca gttagtttct ccactcactt ttgataacaa aggcaatgta     480
aaaattaact tagggaatgg cccattaaca gttgcggcaa accgactgag tgttacctgc     540
aaaagaggtt tatatgtcac tactacagga gatgcactcg aaagcaacat aagctgggct     600
```

| aaaggtataa gatttgaagg aaatgcaata gcagcaaata ttggcaaagg gcttgaattt | 660 |
| ggtactacta gttcagagtc agatgtcagc aatgcttatc ctatccaagt aaaactaggt | 720 |
| actggtctca cctttgacag cacaggtgca attgtcgctt ggaacaaaga agatgacaaa | 780 |
| cttacactgt ggaccacagc cgatccatct ccaaactgtc acatatattc tgacaaggat | 840 |
| gctaagctta cactctgctt gacaaagtgt ggcagtcaga tactgggcac tgtttctctc | 900 |
| atagctgttg atactggtag cttaaatcca ataacaggac aagtaaccac tgctcttgtt | 960 |
| tcacttaaat tcgatgccaa tggagttttg caaaccagtt caacattgga caaagaatat | 1020 |
| tggaattttta gaaaggaga tgtgacacct gctgagccat atactaatgc tataggtttt | 1080 |
| atgcccaata taaaggcata tccgaaaaac acaaattcag ctgcaaaaag tcacattgtg | 1140 |
| ggaaaagtat acctacatgg ggaagtaagc aagccactag acttgataat tacatttaat | 1200 |
| gaaaccagta atgaaacctg tacctattgc attaactttc agtggcagtg gggaactgac | 1260 |
| aaatataaaa atgaaacgct tgctgtcagt tcattcacct tttcctacat tgcccaagaa | 1320 |
| taa | 1323 |

<210> SEQ ID NO 33
<211> LENGTH: 1332
<212> TYPE: DNA
<213> ORGANISM: Adenoviridae - Mastadenovirus

<400> SEQUENCE: 33

| atgtccaaaa agcgcgtccg ggtggatgat gacttcgacc ccgtctaccc ctacgatgca | 60 |
| gacaacgcac cgaccgtgcc cttcatcaac ccccccttcg tctcttcaga tggattccaa | 120 |
| gagaagcccc tgggggtgtt gtccctgcga ctggccgacc ccgtcaccac caagaacggg | 180 |
| gaaatcaccc tcaagctggg agaggggtg gacctcgacg actcgggaaa actcatctcc | 240 |
| aaaaatgcca ccaaggccac tgcccctctc agtatttcca acagcaccat ttcccttaac | 300 |
| atggctgccc ttttttacaa caacaatgga acgttaagtc tcaatgtttc tacaccatta | 360 |
| gcagtatttc ccacttttaa cactttaggt atcagtcttg caacggtct tcaaacttct | 420 |
| aataagttgc tggctgtaca gttaactcat cctcttacat tcagctcaaa tagcatcaca | 480 |
| gtaaaaacag acaaaggact ctatattaat tctagtggaa acagagggct tgaggctaac | 540 |
| ataagcctaa aagaggact gattttgat ggtaatgcta ttgcaacata ccttggaagt | 600 |
| ggtttagact atggatccta tgatagcgat ggaaaaacaa gacccatcat caccaaaatt | 660 |
| ggagcaggct tgaattttga ttctaataat gccatggctg tgaagctagg cacaggttta | 720 |
| agttttgact ctgccggtgc cttaacagct ggaaacaaag aggatgacaa gctaacactt | 780 |
| tggactacac ctgaccccag ccctaattgt caattacttt cagacagaga tgccaaattt | 840 |
| accctatgtc ttacaaaatg cggtagtcaa atactaggca ctgttgcagt agctgctgtt | 900 |
| actgtaagtt cagcactaaa tccaattaat gacacagtaa aagcgccat agtattcctt | 960 |
| agattgact ctgacggtgt gctcatgtca aactcatcaa tggtaggtga ttactggaac | 1020 |
| tttagggaag acagaccac ccaaagtgtg gcctatacaa atgctgtggg attcatgccc | 1080 |
| aatctaggtg catatcctaa aacccaaagc aaaacaccaa aaatagtat agtaagccag | 1140 |
| gtatatttaa atggagaaac tactatgcca atgacactga caataacttt caatggcact | 1200 |
| gatgaaaaag acacaacacc tgtcagcact tactctatga cttttacatg gcagtggact | 1260 |
| ggagactata aggacaagaa tattaccttt gctaccaact cctttacttt ctcctacatg | 1320 |
| gcccaagaat aa | 1332 |

<210> SEQ ID NO 34
<211> LENGTH: 1278
<212> TYPE: DNA
<213> ORGANISM: Adenoviridae - Mastadenovirus

<400> SEQUENCE: 34

| | | | | | |
|---|---|---|---|---|---|
| atgtccaaaa | agcgcgtccg | ggtggatgat | gacttcgacc | ccgtctaccc ctacgatgca | 60 |
| gacaacgcac | cgaccgtgcc | cttcatcaac | ccccccttcg | tctcttcaga tggattccaa | 120 |
| gagaagcccc | tgggggtgtt | gtccctgcga | ctggccgacc | ccgtcaccac caagaacggg | 180 |
| gaaatcaccc | tcaagctggg | agaggggggtg | gacctcgact | cctcgggaaa actcatctcc | 240 |
| aacacggcca | ccaaggccgc | tgcccctctc | agttttttcca | acaacaccat ttcccttaac | 300 |
| atggatcacc | cctttttacac | taaagatgga | aaattagcct | acaagtttc tccaccatta | 360 |
| aatatactga | gaacaagcat | tctaaacaca | ctagctttag | gttttggatc aggtttagga | 420 |
| ctccgtggct | ctgccttggc | agtacagtta | gtctctccac | ttacatttga tactgatgga | 480 |
| aacataaagc | ttaccttaga | cagaggtttg | catgttacaa | caggagatgc aattgaaagc | 540 |
| aacataagct | gggctaaagg | tttaaaattt | gaagatggag | ccatagcaac caacattgga | 600 |
| aatgggttag | agtttggaag | cagtagtaca | gaaacaggtg | tcgatgatgc ttacccaatc | 660 |
| caagttaaac | ttggatctgg | ccttagcttt | gacagtacag | gagccataat ggctggtaac | 720 |
| aaagaagacg | ataaactcac | tttgtggaca | acacctgatc | catcaccaaa ctgtcaaata | 780 |
| ctcgcagaaa | atgatgcaaa | actaacactt | tgcttgacta | atgtggtag tcaaatactg | 840 |
| gccactgtgt | cagtcttagt | tgtaggaagt | ggaaacctaa | accccattac tggcaccgta | 900 |
| agcagtgctc | aggtgtttct | acgttttgat | gcaaacggtg | ttctttttaac agaacattct | 960 |
| acactaaaaa | aatactgggg | gtataggcag | ggagatagca | tagatggcac tccatatgtc | 1020 |
| aatgctgtag | gattcatgcc | caatttaaaa | gcttatccaa | agtcacaaag ttctactact | 1080 |
| aaaaataata | tagtagggca | agtatacatg | aatggagatg | tttcaaaacc tatgcttctc | 1140 |
| actataaccc | tcaatggtac | tgatgacagc | aacagtacat | attcaatgtc attttcatac | 1200 |
| acctggacta | atggaagcta | tgttggagca | acatttggag | ctaactctta taccttctcc | 1260 |
| tacatcgccc | aagaatga | | | | 1278 |

<210> SEQ ID NO 35
<211> LENGTH: 1278
<212> TYPE: DNA
<213> ORGANISM: Adenoviridae - Mastadenovirus

<400> SEQUENCE: 35

| | | | | | |
|---|---|---|---|---|---|
| atgtccaaaa | agcgcgtccg | ggtggatgat | gacttcgacc | ccgtctaccc ctacgatgca | 60 |
| gacaacgcac | cgaccgtgcc | cttcatcaac | ccccccttcg | tctcttcaga tggattccaa | 120 |
| gagaagcccc | tgggggtgct | gtccctgcga | ctggccgacc | ccgtcaccac caagaacggg | 180 |
| gaaatcaccc | tcaagctggg | agaggggctg | gacctcgact | cctcgggaaa actcatctcc | 240 |
| aacacggcca | ccaaggccgc | cgcccctctc | agttttttcca | acaacaccat ttcccttaac | 300 |
| atggatcacc | cctttttacac | taaagatgga | aaattatcct | acaagtttc tccaccatta | 360 |
| aatatactga | gaacaagcat | tctaaacaca | ctagctttag | gttttggatc aggtttagga | 420 |
| ctccgtggct | ctgccttggc | agtacagtta | gtctctccac | ttacatttga tactgatgga | 480 |
| aacataaagc | ttaccttaga | cagaggtttg | catgttacaa | caggagatgc aattgaaagc | 540 |

| | | |
|---|---|---|
| aacataagct | gggctaaagg tttaaaattt gaagatggag ccatagcaac caacattgga | 600 |
| aatgggttag | agtttggaag cagtagtaca gaaacaggtg ttgatgatgc ttacccaatc | 660 |
| caagttaaac | ttggatctgg ccttagcttt gacagtacag gagccataat ggctggtaac | 720 |
| aaagaagacg | ataaacttac tttgtggaca acacctgatc catcaccaaa ctgtcaaata | 780 |
| ctcgcagaaa | atgatgcaaa actaacactt tgcttgacta aatgtggtag tcaaatactg | 840 |
| gccactgtgt | cagtcttagt tgtaggaagt ggaaacctaa accccattac tggcaccgta | 900 |
| agcagtgctc | aggtgtttct acgttttgat gcaaacggtg ttcttttaac agaacattct | 960 |
| acactaaaaa | aatactgggg gtataggcag ggagatagca tagatggcac tccatatacc | 1020 |
| aatgctgtag | gattcatgcc caatttaaaa gcttatccaa agtcacaaag ttctactact | 1080 |
| aaaaataata | tagtagggca agtatacatg aatggagatg tttcaaaacc tatgcttctc | 1140 |
| actataaccc | tcaatggtac tgatgacagc aacagtacat attcaatgtc attttcatac | 1200 |
| acctggacta | atggaagcta tgttggagcg acatttgggg ctaactctta taccttctca | 1260 |
| tacatcgccc | aagaatga | 1278 |

<210> SEQ ID NO 36
<211> LENGTH: 1329
<212> TYPE: DNA
<213> ORGANISM: Adenoviridae - Mastadenovirus

<400> SEQUENCE: 36

| | | |
|---|---|---|
| atgtccaaaa | agcgcgcgcg ggtggatgat ggcttcgacc ccgtgtaccc ctacgatgca | 60 |
| gacaacgcac | cgactgtgcc cttcatcaac cctcccttcg tctcttcaga tggattccaa | 120 |
| gaaaagcccc | tggggtgtgtt gtccctgcgt ctggccgacc ccgtcaccac caagaatggg | 180 |
| gctgtccccc | tcaagctcgg ggaggggggtg gacctcgacg actcgggaaa actcatctcc | 240 |
| aaaaaatcca | ccaaggccaa ttcccctctc agtatttcca caacaccat ttcccttaac | 300 |
| atggataccc | ttttttatac caaagatgga aaattaacca tgcaggtaac tgcaccatta | 360 |
| aagttagcaa | acacggccat actaaacaca ctagctatgg cctatggaaa tggtttaggt | 420 |
| ctaaacaaca | atgctctcac tgttcaggta acatctccac tcacatttga taatagcaaa | 480 |
| gtcaagatta | acctagggaa tggaccacta atggtatctg ctaacaagct ttcaatcaac | 540 |
| tgcttacggg | gtctatatgt tgcccctaat aataccggac tagaaaccaa cataagctgg | 600 |
| gcaaacgcaa | tgcgctttga gggtaatgca atggctgttt atatagacac aaataaaggc | 660 |
| ctacaatttg | gcactactag cacagaaaca ggtgtcacca atgcttaccc catacaagtc | 720 |
| aaacttggcg | caggccttgc atttgatagc acaggagcta ttgttgcttg gaacaaagaa | 780 |
| aatgacagcc | tcactttgtg gactacacca gatccctctc caaattgtaa atagcatct | 840 |
| gaaaaggatg | caaaactcac actttgcttg acaaagtgtg gtagtcaaat cctaggcact | 900 |
| gtctccctat | tagcagtcag tggcagcttg gctcctatca caggggctgt tagtactgca | 960 |
| cttgtatcac | tcaaattcaa tgctaatgga gccctttggg acaaatcaac tctgaacaaa | 1020 |
| gaatactgga | actacagaca aggagatcta attccaggta caccatatac acatgctgtg | 1080 |
| ggtttcatgc | ctaacaaaaa agcctaccct aaaaacacaa ctgcagcttc caagagccac | 1140 |
| attgtgggtg | atgtgtattt agatggagat gcagataagc ctttatctct tatcatcact | 1200 |
| ttcaatgaaa | ctgatgatga aacctgtgat tactgcatca actttcaatg gaaatgggga | 1260 |
| gctgatcaat | ataaggataa gacactcgca accagttcat tcaccttctc atacatcgcc | 1320 |
| caagaataa | | 1329 |

<210> SEQ ID NO 37
<211> LENGTH: 1731
<212> TYPE: DNA
<213> ORGANISM: Adenoviridae - Mastadenovirus

<400> SEQUENCE: 37

```
atgaagcgcg ccaaaacgtc tgacgagacc ttcaaccccg tgtacccta tgacacggaa      60
aacgggcctc cctccgtccc tttcctcacc cctcccttcg tgtcccccga cggatttcaa     120
gaaagccccc caggggtcct gtctctgcgc ctgtcagagc cctggtcac ttcccacggc      180
atgcttgccc tgaaaatggg aaatggcctc tccctggatg acgccggcaa cctcacctct     240
caagatgtca ccaccgtcac ccctcccctc aaaaaaacca agaccaacct cagcctccag     300
acctcagccc cctgaccgt tagctctggg tccctcaccg tcgcggccgc cgctccactg      360
gcggtggccg gcacctctct caccatgcaa tctcaggccc ccttgacagt gcaagatgca     420
aaactcggcc tggccaccca gggacccctg accgtgtctg aaggcaaaact caccttgcag    480
acatcggctc cactgacggc cgctgacagc agcactctca ctgttagtgc cacacctccc     540
ctcagcacaa gcaatggtag tttgagcatt gacatgcagg ccccgattta taccaccaat     600
ggaaaactgg cacttaacat tggtgctccc ctgcatgtgg tagacaccct aaatgcacta     660
actgtagtaa ctggccaggg tcttaccata aatggaagag ccctgcaaac tagagtcacg     720
ggtgccctca gttatgacac agaaggcaac atccaactgc aagccggagg gggtatgcgc     780
attgacaata tggccaact tatccttaat gtagcttatc catttgatgc tcaaaacaac     840
ctcagcctta gacttggcca aggtcccta attgttaact ctgcccacaa cttggatctt     900
aaccttaaca gaggccttta cttatttaca tctggaaaca cgaaaaaact ggaagttaac     960
ataaaaacag ccaaaggtct atttttacgat ggcaccgcta tagcaatcaa tgcaggtgac    1020
gggctacagt ttgggtctgg ttcagataca aatccattgc aaactaaact tggattgggg    1080
ctggaatatg actccaacaa agctataatc actaaacttg gaactggcct aagctttgac    1140
aacacaggtg ccatcacagt aggcaacaaa atgatgaca gcttaccttt gtggaccaca    1200
ccagacccct ccccaaactg cagaattaat tcagaaaaag atgctaaact cacactagtt    1260
ttgactaaat gcggcagcca ggtgttagcc agcgtttctg ttttatctgt aaaaggcagc    1320
cttgccccca tcagcggcac agtaactagc gcccagattg ttttaagatt tgatgaaaac    1380
ggagttttat tgagcaattc ttctcttgac ccccaatact ggaactatag aaaaggcgat    1440
tctacagaag gcactgcata tactaatgct gtgggattta tgcccaacct cacagcatac    1500
cctaaaacac agagccagac tgctaaaagc aacattgtaa gtcaagttta cttgaatggg    1560
gacaaaacaa aacccatgac cctaaccatc accctcaatg gaactaatga acagggggat    1620
gctacagtaa gcacatactc catgtcattt tcatggaact ggaatggaag taattacatt    1680
aatgacacct tccaaaccaa ctcctttacc ttctcctaca tcgcccaaga a              1731
```

<210> SEQ ID NO 38
<211> LENGTH: 2814
<212> TYPE: DNA
<213> ORGANISM: Adenoviridae - Mastadenovirus
<220> FEATURE:
<221> NAME/KEY: misc_feature
<222> LOCATION: (345)..(345)
<223> OTHER INFORMATION: n is a, c, g, or t
<220> FEATURE:
<221> NAME/KEY: misc_feature
<222> LOCATION: (360)..(360)

<223> OTHER INFORMATION: n is a, c, g, or t

<400> SEQUENCE: 38

```
atggccaccc catcgatgct gccccagtgg gcgtacatgc acatcgccgg acaggacgct    60
tcggagtacc tgagtccggg tctggtgcag ttcgcccgcg ccacagacac ctacttcagt   120
ctggggaaca agtttaggaa ccccacggtg gcgcccacgc acgatgtgac caccgaccgc   180
agccagcggc tgacgctgcg cttcgtgccc gtggaccgcg aggacaacac ctactcgtac   240
aaagtgcgct acacgctggc cgtgggcgac aaccgcgtgc tggacatggc cagcacctac   300
tttgacatcc gcggcgtgct ggatcggggc cccagcttca accntactc cggcaccgcn   360
tacaacagcc tggctcccaa gggagcgccc aacacctcac agtggataac caaagacaat   420
ggaactgata agacatacag ttttggaaat gctccagtca gaggattgga cattacagaa   480
gagggtctcc aaataggacc cgatgagtca ggggtgaaa gcaagaaaat ttttgcagac   540
aaaacctatc agcctgaacc tcagcttgga gatgaggaat ggcatgatac tattggagct   600
gaagacaagt atggaggcag agcgcttaaa cctgccacca catgaaacc ctgctatggg   660
tctttcgcca agccaactaa tgctaaggga ggtcaggcta aaagcagaac caaggacgat   720
ggcactactg agcctgatat tgacatggcc ttctttgacg atcgcagtca gcaagctagt   780
ttcagtccag aacttgtttt gtatactgag aatgtcgatc tggacacccc ggatacccac   840
attatttaca aacctggcac tgatgaaaca agttcttctt tcaacttggg tcagcagtcc   900
atgcccaaca gacccaacta catcggcttc agagacaact ttatcggtct catgtactac   960
aacagtactg caatatgggt gtactagct ggacaggcct cccagctgaa tgctgtggtg  1020
gacttgcagg acagaaacac tgaactgtcc taccagctct tgcttgactc tctgggtgac  1080
agaaccaggt atttcagtat gtggaaccag gcggtggaca gctacgaccc cgatgtgcgc  1140
attattgaaa tcacggtgt ggaggatgaa ctacccaact attgcttccc tttgaatggt  1200
gtgggcttta cagatacatt ccagggaatt aaggttaaaa ctaccaataa cggaacagca  1260
aatgctacag agtgggaatc tgatacctct gtcaataatg ctaatgagat tgccaagggc  1320
aatcctttcg ccatggagat caacatccag gccaacctgt ggcggaactt cctctacgcg  1380
aacgtggcgc tgtacctgcc cgactcctac aagtacacgc cggccaacat cacgctgccc  1440
accaacacca cacctacga ttacatgaac ggccgcgtgg tagcgccctc gctggtggac  1500
gcctacatca acatcggggc gcgctggtcg ctggacccca tggacaacgt caacccttc  1560
aaccaccacc gcaacgcggg cctgcgctac cgctccatgc tcctgggcaa cgggcgctac  1620
gtgcccttcc acatccaggt gccccaaaag ttttcgcca tcaagagcct cctgctcctg  1680
cccgggtcct acacctacga gtggaacttc cgcaaggacg tcaacatgat cctgcagagc  1740
tccctcggca acgacctgcg cacggacggg gcctccatcg ccttcaccag catcaacctc  1800
tacgccacct tcttcccat ggcgcacaac accgcctcca cgctcgaggc catgctgcgc  1860
aacgacacca cgaccagtc cttcaacgac tacctctcgg cggccaacat gctctacccc  1920
atcccggcca acgccaccaa cgtgcccatc tccatcccct cgcgcaactg gccgccttc  1980
cgcggctggt ccttcacgcg cctcaagacc cgcgagacgc cctcgctggg ctccgggttc  2040
gaccccact tcgtctactc gggctccatc ccctacctcg acggcacctt ctacctcaac  2100
cacaccttca gaaggtctc catcaccttc gactcctccg tcagctggcc cggcaacgac  2160
cgcctcctga cgcccaacga gttcgaaatc aagcgcaccg tcgacggaga ggggtacaac  2220
gtgccccagt gcaacatgac caaggactgg ttcctggttc agatgctggc ccactacaac  2280
```

```
atcggctacc agggcttcta cgtgcccgag ggctacaagg accgcatgta ctccttcttc      2340
cgcaacttcc agcccatgag ccgccaggtc gtggacgagt caactacaa ggactaccag       2400 gccgtcaccc tggcctacca gcacaacaac tcgggcttcg tcggctacct cgcgccacc       2460 atgcgccagg acagcccta ccccgccaac taccctacc cgctcatcgg caagagcgcc        2520
gtcgccagcg tcacccagaa aaagttcctc tgcgaccggg tcatgtggcg catccccttc      2580
tccagcaact tcatgtccat gggcgcgctc accgacctcg ccagaacat gctctacgcc       2640 aactccgccc acgcgctaga catgaatttc gaagtcgacc ccatggatga gtccaccctt     2700
ctctatgttg tcttcgaagt cttcgacgtc gtccgagtgc accagcccca ccgcggcgtc      2760
atcgaggccg tctacctgcg cacgcccttc tcggccggta acgccaccac ctaa            2814

<210> SEQ ID NO 39
<211> LENGTH: 2814
<212> TYPE: DNA
<213> ORGANISM: Adenoviridae - Mastadenovirus

<400> SEQUENCE: 39
atggccaccc catcgatgct gccccagtgg gcgtacatgc acatcgccgg acaggacgct        60
tcggagtacc tgagtccggg tctggtgcag tttgcccgcg ccacagacac ctacttcagt       120
ctggggaaca gtttaggaa ccccacggtg gcgcccacgc acgatgtgac caccgaccgc        180
agccagcggc tgacgctgcg cttcgtgccc gtggacggcg aggacaacac ctactcgtac       240
aaagtgcgct acacgctggc cgtgggcgac aaccgcgtgc tggacatggc cagcacctac       300
tttgacatcc gcggcgtgct ggatcggggc cccagcttca aaccctactc cggcaccgcc       360
tacaacgctc tggctcccaa gggagcgccc aacacctcac agtggataac caaagacaat       420
ggaactgata agacatacag ttttggaaat gctccagtca gaggattgga cattacagaa       480
gagggtctcc aaataagaac cgatgagtca ggggtgaaa gcaagaaaat ttttgcagac        540
aaaacctatc agcctgaacc tcagcttgga gatgaggaat ggcatgatac tattggagct       600
gaagacaagt atggaggcag agcgcttaaa cctgccacca acatgaaacc ctgctatggg       660
tctttcgcca agcaactaa tgctaaggga ggtcaggcta aaagcagaac caaggacgat       720
ggcactactg agcctgatat tgacatggcc ttctttgacg atcgcagtca gcaagctagt      780
ttcagtccag aacttgtttt gtatactgag aatgtcgatc tggacacccc ggatacccac       840
attatttaca aacctggcac tgatgaaaca agttcttctt caacttgggt cagcagtcc        900 atgcccaaca gacccaacta cattgggttc agagacaact tatcgggct catgtactac        960 aacagcactg gcaatatggg tgtactggct ggtcaggcct cccagctgaa tgctgtggtg     1020
gacttgcagg acagaaacac cgaactgtcc taccagctct tgcttgactc tctgggtgac     1080
agaaccaggt atttcagtat gtggaatcag gcggtggaca gttatgaccc cgatgtgcgc     1140
attattgaaa tcacggtgt ggaggatgaa ctccccaact attgcttccc tttgaatggt      1200 gtgggctta cagatacatt ccagggaatt aaggttaaaa ctaccaataa cggaacagca      1260
aatgctacag agtgggaatc tgataccct gtcaataatg ctaatgagat tgccaagggc      1320 aatccttcg ccatggagat caacatccag gccaacctgt ggcggaactt cctctacgcg      1380
aacgtggcgc tgtacctgcc cgactcctac aagtacacgc cggccaacat cacgctgccg      1440
accaacacca cacctacga ttacatgaac ggccgcgtgg tggcgccctc gctggtggac      1500
gcctacatca acatcggggc gcgctggtcg ctggacccca tggacaacgt caaccccttc     1560
```

```
aaccaccacc gaaacgcggg cctgcgatac cgctccatgc tcctgggcaa cgggcgctac    1620
gtgcccttcc acatccaggt gccccaaaag ttttcgcca tcaagagcct cctgctcctg    1680
cccgggtcct acacctacga gtggaacttc cgcaaggacg tcaacatgat cctgcagagc    1740
tccctcggca cgacctgcg cacggacggg gcttccatcg ccttcaccag catcaacctc    1800
tacgccacct tcttccccat ggcgcacaac accgcctcca cgctcgaggc catgctgcgc    1860
aacgacacca cgaccagtc cttcaacgac tacctctcgg cggccaacat gctctacccc    1920
atcccggcca acgccaccaa cgtgcccatc tccatccct cgcgcaactg gccgccttc     1980 cgcggmtggt ccttcacgcg cctcaagacc cgcgagacgc cctcgctagg ctccgggttc    2040 gaccccctact tcgtctactc gggctccatc ccctaccttg acggcacctt ctacctcaac    2100
cacaccttca agaaggtctc catcaccttc gactcctccg tcagctggcc cggcaacgac    2160
cgcctcctga cgcccaacga gttcgaaatc aagcgcaccg tcgacggaga ggggtacaac    2220
gtggcccagt gcaacatgac caaggactgg ttcctggtcc agatgctggc ccactacaac    2280
atcggctacc agggcttcta cgtgcccgag ggctacaagg accgcatgta ctccttcttc    2340
cgcaacttcc agcccatgag ccgccaggtc gtggacgagg tcaactacaa ggactaccag    2400
gccgtcaccc tggcctacca gcacaacaac tcgggcttcg tcggctacct cgcgcccacc    2460
atgcgccagg acagcccta ccccgccaac taccctacc cgctcatcgg caagagcgcc    2520
gtcgccagcg tcacccagaa aaagttcctc tgcgaccggg tcatgtggcg catcccttc    2580 tccagcaact tcatgtccat gggcgcgctc accgacctcg ccaaacat gctttacgcc    2640 aactccgccc acgcgctaga catgaatttc gaagtcgacc ccatggatga gtccaccctt    2700
ctctatgttg tcttcgaagt cttcgacgtc gtccgagtgc accagcccca ccgcggcgtc    2760
atcaaggccg tctacctgcg cacccccttc tcggccggta acgccaccac ctaa         2814
```

<210> SEQ ID NO 40
<211> LENGTH: 2814
<212> TYPE: DNA
<213> ORGANISM: Adenoviridae - Mastadenovirus

<400> SEQUENCE: 40

```
atggccaccc catcgatgct gccccagtgg gcgtacatgc acatcgccgg acaggacgct     60
tcggagtacc tgagtccggg tctggtgcag ttcgcccgcg ccacagacac ctacttcagt    120
ctggggaaca gtttaggaa ccccacggtg gcacccacgc acgatgtgac caccgaccgc    180
agccagcggc tgacgctgcg cttcgtgccc gtggaccgcg aggacaacac ctactcgtac    240
aaagtgcgct acacgctggc cgtgggcgac aaccgcgtgc tggacatggc cagcacctac    300
tttgacatcc gcggcgtgct ggatcggggc cccagcttca accctactc cggcaccgcc    360 tacaacagcc tggctcccaa gggagcgccc aacacctcac agtggataac caaagacaat    420
ggaactgata agcatacag ttttggaaat gctccagtca gaggattgga cattacagaa    480
gagggtctcc aaataggaac cgatgagtca gggggtgaaa gcaagaaaat ttttgcagac    540
aaaacctatc agcctgaacc tcagcttgga gatgaggaat ggcatgatac tattggagct    600
gaagacaagt atggaggcag agcgcttaaa cctgccacca catgaaacc ctgctatggg    660 tctttcgcca agccaactaa tgctaaggga ggtcaggcta aaagcagaac caaggacgat    720
ggcactactg agcctgatat tgacatggcc ttctttgacg atcgcagtca gcaagctagt    780
ttcagtccag aacttgtttt gtatactgag aatgtcgatc tggacacccc ggatacccac    840
attatttaca aacctggcac tgatgaaaca agttcttctt tcaacttggg tcagcagtcc    900
```

```
atgcccaaca gacccaacta cattggcttc agagacaact ttatcgggct catgtactac      960
aacagcactg gcaatatggg tgtactggcc ggtcaggcct cccagctgaa tgctgtggtg     1020
gacttgcagg acagaaacac tgaactgtcc taccagctct tgcttgactc tctgggtgac     1080
agaaccaggt atttcagtat gtggaatcag gcggtggaca gctatgaccc cgatgtgcgc     1140
attattgaaa tcacggtgt ggaggatgaa ctccccaact attgcttccc tttgaatggt      1200
gtgggcttta cagatacatt ccagggaatt aaggttaaaa ctacaaataa cggaacagca     1260
aatgctacag agtgggaatc tgatacctct gtcaataatg ctaatgagat tgccaagggc     1320
aatcctttcg ccatggagat caacatccag gccaacctgt ggcggaactt cctctacgcg     1380
aacgtggcgc tgtacctgcc cgactcctac aagtacacgc cggccaacat cacgctgccc     1440
accaacacca cacctacga ttacatgaac ggccgcgtgg tggcgccctc gctggtggac      1500
gcctacatca acatcggggc gcgctggtcg ctggacccca tggacaacgt caacccttc     1560
aaccaccacc gcaacgcggg cctgcgctac cgctccatgc tcctgggcaa cgggcgctac     1620
gtgcccttcc acatccaggt gccccaaaag ttttcgcca tcaagagcct cctgctcctg     1680
cccgggtcct acacctacga gtggaacttc cgcaaggacg tcaacatgat cctgcagagc     1740
tccctcggca acgacctgcg cacggacggg gcctccatcg ccttcaccag catcaacctc     1800
tacgccacct tcttccccat ggcgcacaac accgcctcca cgctcgaggc catgctgcgc     1860
aacgacacca acgaccagtc cttcaacgac tacctctcgg cggccaacat gctctacccc     1920
atcccggcca acgccaccaa cgtgcccatc tccatcccct cgcgcaactg gccgccttc      1980
cgcggatggt ccttcacgcg cctcaagacc cgcgagacgc cctcgctcgg ctccgggttc     2040
gacccctact tcgtctactc gggctccatc ccctacctcg acggcacctt ctacctcaac     2100
cacaccttca agaaggtctc catcaccttc gactcctccg tcagctggcc cggcaacgac     2160
cgcctcctga cgcccaacga gttcgaaatc aagcgcaccg tcgacggaga ggggtacaac     2220
gtggcccagt gcaacatgac caaggactgg ttcctggtcc agatgctggc ccactacaac     2280
atcggctacc agggcttcta cgtgcccgag ggctacaagg accgcatgta ctccttcttc     2340
cgcaacttcc agcccatgag ccgccaggtc gtggacgagg tcaactacaa ggactaccag     2400
gccgtcaccc tggcctacca gcacaacaac tcgggcttcg tcggctacct cgcgcccacc     2460
atgcgccagg ccagcccta ccccgccaac taccccacc cgctcatcgg caagagcgcc      2520
gtcgccagcg tcacccagaa aaagttcctc tgcgaccggg tcatgtggcg catccccttc     2580
tccagcaact tcatgtccat gggcgcgctc accgacctcg ccagaacat gctctacgcc      2640
aactccgccc acgcgctaga catgaatttc gaagtcgacc ccatggatga gtccacccctt    2700
ctctatgttg tcttcgaagt cttcgacgtc gtccgagtgc accagcccca ccgcggcgtc     2760
atcgaggccg tctacctgcg cacgcccttc tcggccggca acgccaccac ctaa           2814
```

<210> SEQ ID NO 41
<211> LENGTH: 2814
<212> TYPE: DNA
<213> ORGANISM: Adenoviridae - Mastadenovirus
<220> FEATURE:
<221> NAME/KEY: misc_feature
<222> LOCATION: (297)..(297)
<223> OTHER INFORMATION: n is a, c, g, or t
<220> FEATURE:
<221> NAME/KEY: misc_feature
<222> LOCATION: (360)..(360)
<223> OTHER INFORMATION: n is a, c, g, or t
<220> FEATURE:

<221> NAME/KEY: misc_feature
<222> LOCATION: (887)..(887)
<223> OTHER INFORMATION: n is a, c, g, or t

<400> SEQUENCE: 41

```
atggccaccc catcgatgct gccccagtgg gcgtacatgc acatcgccgg acaggacgct        60
tcggagtacc tgagtccggg tctggtgcag ttcgcccgcg ccacagacac ctacttcagt       120
ctggggaaca gtttaggaa ccccacggtg gcgcccacgc acgatgtgac caccgaccgc        180
agccagcggc tgacgctgcg cttcgtgccc gtggaccgcg aggacaacac ctactcgtac       240
aaagtgcgct acacgctggc cgtgggcgac aaccgcgtgc tggacatggc cagcacntac       300
tttgacatcc gcggcgtgct ggatcggggc cccagcttca aaccctactc cggcaccgcn       360
tacaacagcc tggctcccaa gggagcgccc aacacctcac agtggataac caaagacaat       420
ggaactgata agacatacag ttttggaaat gctccagtca gaggattgga cattacagaa       480
gagggtctcc aaataggaac cgatgagtca gggggtaaaa gcaagaaaat ttttgcagac       540
aaaacctatc agcctgaacc tcagcttgga gatgaggaat ggcatgatac tattggagct       600
gaagacaagt atggaggcag agcgcttaaa cctgccacca acatgaaacc ctgctatggg       660
tctttcgcca agccaactaa tgctaaggga ggtcaggcta aaagcagaac caaggacgat       720
ggcactactg agcctgatat tgacatggcc ttttttgacg atcgcagtca gcaagctagt       780
ttcagtccag aacttgtttt gtatactgag aatgtcgatc tggacacccc ggatacccac       840
attatttaca aacctggcac tgatgaaaca agttcttctt tcaactnggg tcagcagtcc       900
atgcccaaca gacccaatta cattggcttc agagacaact ttatcggact catgtactac       960
aacagcactg gcaatatggg tgtactggct ggacaggcct cccagctgaa tgctgtggtg      1020
gacttgcagg acagaaacac cgaactgtcc taccagctct tgcttgactc tctgggcgac      1080
agaaccaggt atttcagtat gtggaatcag gcggtggaca gctatgaccc cgatgtgcgc      1140
attattgaaa atcacggtgt ggaggatgaa cttcccaact attgcttccc tttgaatggt      1200
gtgggcttta cagatacatt ccagggaatt aaggttaaaa ctaccaataa cggaacagca      1260
aacgctacag agtgggaatc tgatacctct gtcaataatg ctaatgagat tgccaagggc      1320
aatcctttcg ccatggagat caacatccag gccaacctgt ggcggaactt cctctacgcg      1380
aacgtggcgc tgtacctgcc cgactcctac aagtacacgc cggccaacat cacgctgccc      1440
accaacacca caccctacga ttacatgaac ggccgcgtgg tggcgccctc gctggtggac      1500
gcctacatca catcggggc gcgctggtcg ctggacccca tggacaacgt caaccccttc      1560
aaccaccacc gcaacgcggg cctgcgatac cgctccatgc tcctgggcaa cgggcgctac      1620
gtgcccttcc acatccaggt gccccaaaag ttttcgcca tcaagaacct cctgctcctg      1680
cccgggtcct acacctacga gtggaacttc cgcaaggacg tcaacatgat cctgcagagc      1740
tccctcggca cgacctgcg cacggacggg gcctccatcg ccttcaccag catcaacctc      1800
tacgccacct tcttccccat ggcgcacaac accgcctcca cgctcgaggc catgctgcgc      1860
aacgacacca acgaccagtc cttcaacgac tacctctcgg cggccaacat gctctacccc      1920
atcccggcca acgccaccaa cgtgcccatc tccatcccct cgcgcaactg gccgccttc      1980
cgcggatggt ccttcacgcg cctcaagacc cgcgagacgc cctcgctcgg ctccgggttt      2040
gaccccctact tcgtctactc gggctccatc ccctacctcg acggcacctt ctacctcaac      2100
cacaccttca gaaggtctc catcaccttc gactcctccg tcagctggcc cggcaacgac      2160
cgcctcctga cgcccaacga gttcgaaatc aagcgcaccg tcgacggaga ggggtacaac      2220
```

```
gtggcccagt gcaacatgac caaggactgg ttcctggtcc agatgctggc ccactacaac    2280
atcggctacc agggcttcta cgtgcccgag ggctacaagg accgcatgta ctccttcttc    2340
cgcaacttcc agcccatgag ccgccaggtc gtggacgagg tcaactacaa ggactaccag    2400
gccgtcaccc tggcctacca gcacaacaac tcgggcttcg tcggctacct cgcgcccacc    2460
atgcgccagg gccagcccta ccccgccaac taccccctacc cgctcatcgg caagagcgcc    2520
```
(Note: preserve as shown)

atgcgccagg gccagcccta ccccgccaac taccccctacc cgctcatcgg caagagcgcc   2520
gttgccagcg tcacccagaa aaagttcctc tgcgaccggg tcatgtggcg catcccttc    2580 tccagcaact tcatgtccat gggcgcgctc accgacctcg gccagaacat gctctacgcc    2640
aactccgccc acgcgctaga catgaatttc gaagtcgacc ccatggatga gtccacccct   2700
ctctatgttg tcttcgaagt cttcgacgtc gtccgagtgc accagcccca ccgcggcgtc    2760
atcgaggccg tctacctgcg cacgcccttc tcggccggca cgccaccac ctaa          2814

<210> SEQ ID NO 42
<211> LENGTH: 2814
<212> TYPE: DNA
<213> ORGANISM: Adenoviridae - Mastadenovirus
<220> FEATURE:
<221> NAME/KEY: misc_feature
<222> LOCATION: (1612)..(1612)
<223> OTHER INFORMATION: n is a, c, g, or t

<400> SEQUENCE: 42
atggccaccc catcgatgct gccccagtgg gcgtacatgc acatcgccgg acaggacgct      60
tcggagtacc tgagtccggg tctggtgcag ttcgcccgcg ccacagacac ctacttcagt     120
ctggggaaca agtttaggaa ccccacggtg gcgcccacgc acgatgtgac caccgaccgc     180
agccagcgac tgacgctgcg cttcgtgccc gtggaccgcg aggacaacac ctactcgtac     240
aaagtgcgct acacgctggc cgtgggcgac aaccgcgtgc tggacatggc cagcacctac     300
tttgacatcc gcggcgtgct ggaccggggc cctagcttca accctactc cggcaccgcc     360 tacaacagcc tggcccccaa gggagcaccc aacacctcac agtgggtgac caaagacaat     420
gggactgata aaacatacag cttttggtaat gctcctgtca gaggcttgga cattacagaa     480
gagggtctcc aaataggaac cgatgactct tcaaccgaaa gcaagaaaat ttttgcagac     540
aaaacatatc agcctgaacc tcaggttgga gatgaggaat ggcatgacac cattgggct     600 gaagacaaat atggaggcag agctcttaaa cctgccacca acatgaaacc ctgttatggt     660
tcttttgcca agccaactaa tgctaaggga ggtcaggcta aaaccagaac caaagacgat     720
ggaactaccg agcctgatat tgacatggcc ttctttgacg atcgcagtca gcaggctagt     780
ttcagcccag aacttgtttt gtatactgag aatgtggatt tggagacccc agatacccac     840
attatttaca aacccggtac tgatgaaaca agttcttctt tcaacttggg tcagcaatcc     900
atgcccaaca gacccaacta cattggtttc agagacaact ttattggctt gatgtactac     960
aacagcactg gcaacatggg tgtgctggct ggtcaggctt ctcagctgaa tgccgtggtt    1020
gacttgcaag acagaaacac cgagctgtcc taccagctct tgcttgactc tctgggcgac    1080
agaacccggt atttcagtat gtggaatcag gcgtggaca gctatgatcc tgatgtgcgc    1140
attattgaaa accatggtgt ggaagatgaa ctgccaaact attgcttccc tttaaatggt    1200
gtggctttta cagacacatt ccagggaatt aaggttaaaa ctaccaacaa cggtactgct    1260
aatgctacag agtgggaatc tgatacttct gtcaataatg ccaatgagat tgccaagggt    1320
aatccattcg ccatggaaat caacatccaa gccaacctgt ggaggaactt cctctatgcc    1380

```
aacgtggccc tgtacttgcc cgattcttac aagtacacgc cggccaacgt caccctgccc    1440
accaacacca acacctacga gtacatgaac ggccgggtgg tggcgccctc gctggtggac    1500
tcctacatca acatcggggc gcgctggtcg ctggaccccca tggacaacgt caatcccttc    1560
aaccaccacc gcaatgcggg gctgcgctac cgctccatgc tcctgggcaa cnggcgcttc    1620
gtgcccttcc acatccaggt gccccagaaa ttttttcgcca tcaagagcct cctgctcctg    1680
cccgggtcct acacctacga gtggaacttc cgcaaggacg tcaacatgat cctgcagagc    1740
tccctcggca acgacctgcg cacggacggg gcctccatct ccttcaccag catcaacctc    1800
tacgccacct tcttccccat ggcgcacaac acggcctcca ctctcgaggc catgctgcgc    1860
aacgacacca acgaccagtc cttcaacgac tacctctcgg cggccaacat gctctacccc    1920
atcccggcca acgccaccaa cgtgcccatc tccatcccct cgcgcaactg gccgccttc     1980
cgcggctggt ccttcacgcg cctcaagacc aaggagacgc cctcgctggg ctccgggttc    2040
gaccccctact tcgtctactc gggctccatc ccctacctcg acggcacctt ctacctcaac    2100
cacaccttca agaaggtctc catcaccttc gactcctccg tcagctggcc cggcaacgac    2160
cggctcctga cgcccaacga gttcgaaatc aagcgcaccg tcgacggcga gggatacaac    2220
gtggcccagt gcaacatgac caaggactgg ttcctggtcc agatgctggc ccactacaac    2280
atcggctacc agggcttcta cgtgcccgag ggctacaagg accgcatgta ctccttcttc    2340
cgcaacttcc agcccatgag ccgccaggtg gtggacgagt caactacaa ggactaccag     2400
gccgtcaccc tggcctacca gcacaacaac tcgggcttcg tcggctacct cgcgcccacc    2460
atgcgtcagg gccagcccta ccccgccaac taccctacc cgctcatcgg caagagcgcc     2520
gtcaccagcg tcacccagaa aaagttcctc tgcgaccgcg tcatgtggcg catcccttc     2580
tccagcaact tcatgtccat gggcgcgctc accgacctcg ccagaacat gctctatgcc     2640
aactccgccc acgcgctaga catgaatttc gaagtcgacc ccatggatga gtccacccctt    2700
ctctatgttg tcttcgaagt cttcgacgtc gtccgagtgc accagcccca ccgcggcgtc    2760
atcgaggccg tctacctgcg caccccctttc tcggccggta acgccaccac ctaa          2814
```

<210> SEQ ID NO 43
<211> LENGTH: 2886
<212> TYPE: DNA
<213> ORGANISM: Adenoviridae - Mastadenovirus

<400> SEQUENCE: 43

```
atggcgaccc catcgatgat gccgcagtgg tcgtacatgc acatctcggg ccaggacgcc      60
tcggagtacc tgagccccgg gctggtgcag ttcgcccgcg ccaccgacag ctacttcagc     120
ctgagtaaca agtttaggaa ccccacggtg gcgcccacgc acgatgtgac caccgaccgg    180
tcccagcgcc tgacgctgcg gttcatcccc gtggaccgcg aggacaccgc gtactcttac    240
aaggcgcggt tcaccctggc cgtgggcgac aaccgcgtgc tggacatggc ctccacctac    300
tttgacatcc gcggcgtgct ggacagggc cccaccttca gccctactc cggcaccgcc     360
tacaactccc tggccccaa gggcgccccc aactcctgcg agtgggagca agtggagcca     420
gctgaagagg cagcagaaaa tgaagatgaa gaagaagaag aggatgttgt tgatcctcag    480
gaacaggagc ccactactaa aacacatgta tatgctcaag ctccccttc tggcgagaaa     540
attaccaaag atggtctgca aataggaact gaggctacgg cagcaggagg cactaaagac    600
ttatttgcag accctacatt ccagccagaa ccccaagttg gcgaatctca gtggaatgag    660
gcggatgcta cagcagctgg aggtagagtg ctcaaaaaga ccactcccat gaaaccttgc    720
```

```
tatggctcat atgcccgccc cacaaatgcc aatgggggcc aaggtgtgct aaaggcaaat      780
gcccagggag tgctcgagtc tcaggttgag atgcagttct tttccacttc tacaaatgcc      840
acaaacgagc aaaacaacat ccagcccaaa ttggtgctgt acagcgagga tgtgcatatg      900
gagaccccag acacacacat ctcctacaag cctacaaaaa gcgatgataa ttcaaaagtc      960
atgctgggtc agcagtccat gcccaacagg ccaaattaca tcgccttcag agacaacttt     1020
atcgggctca tgtattataa cagcactggc aacatggggg tgctggcagg tcaggcctca     1080
cagttgaatg cagtggtgga cctgcaagac agaaacacag aactgtccta ccagctcttg     1140
cttgattcca tgggagacag aaccagatac ttttccatgt ggaatcaggc cgtggacagt     1200
tatgacccag atgtcagaat tattgaaaat catggaaccg aagatgagct gcccaactat     1260
tgtttccctc tgggaggcat agggataact gacacttacc aggccattaa gactaatggc     1320
aatggggcag agatcaagcc caccacgtgg cagaaagact cacaatttgc agaccgcaac     1380
gaaatagggg tgggaaacaa cttcgccatg gagatcaacc tcagtgccaa cctgtggagg     1440
aacttcctct actccaacgt ggccctgtac ctgccagaca agcttaagta caacccctcc     1500
aacgtggaaa tctctgacaa ccccaacacc tacgactaca tgaacaagcg agtggtggcc     1560
ccggggctgg tggactgcta catcaacctg ggcgcgcgct ggtccctgga ctacatggac     1620
aacgtcaacc ccttcaacca ccaccgcaat gcgggcctgc gctaccgctc catgcttctg     1680
ggcaacgggc gctacgtgcc cttccacatc caggtgcccc agaagttctt tgccatcaag     1740
aacctcctcc tcctgccggg ctcctacacc tacgagtgga cttcaggaa ggatgtcaac     1800 atggtcctgc agagctctct gggcaacgac ctcagggtcg acggggccag catcaagttc     1860
gagagcatct gcctctacgc caccttcttc cccatggccc acaacacggc ctccacgctc     1920
gaggccatgc tcaggaacga caccaacgac cagtccttca cgactacct ctccgccgcc     1980 aacatgctct accccatccc cgccaacgcc accaacgtcc catctccat ccctcgcgc     2040 aactgggcgg ccttccgcgg ctgggccttc acccgcctta agaccaagga gaccccctcc     2100
ctgggctcgg gtttcgaccc ctactacacc tactcgggct ccataccta cctggacgga     2160 accttctacc tcaaccacac tttcaagaag gtctcggtca ccttcgactc ctcggtcagc     2220
tggccgggca acgaccgcct gctcaccccc aacgagttcg agatcaagcg ctcggtcgac     2280
ggggagggct acaacgtagc ccagtgcaac atgaccaagg actggttcct catccagatg     2340
ctggccaact acaacatcgg ctatcagggc ttctacatcc agagagcta caaggacagg     2400 atgtactcct tctttaggaa cttccagccc atgagccggc aggtggtgga cgaaaccaag     2460
tacaaggact accagcaggt gggcatcatc caccagcaca caactcgggg cttcgtgggc     2520
tacctcgccc ccaccatgcg cgagggacag gcctacccg ccaacttccc ctacccgctc     2580
attggcaaga ccgcggtcga cagcatcacc cagaaaaagt tcctctgcga ccgcaccctc     2640
tggcgcatcc ccttctccag caacttcatg tccatgggtg cgctcacgga cctgggccag     2700
aacctgctct atgccaactc cgcccacgcg ctcgacatga ccttcgaggt cgaccccatg     2760
gacgagccca cccttctcta tgttctgttc gaagtctttg acgtggttcg ggtccaccag     2820
ccgcaccgcg gcgtcatcga gaccgtgtac ctgcgcacgc ccttctcggc cggcaacgcc     2880
accacc                                                                2886
```

<210> SEQ ID NO 44
<211> LENGTH: 1596
<212> TYPE: DNA

<213> ORGANISM: Adenoviridae - Mastadenovirus

<400> SEQUENCE: 44

```
atgatgaggc gcgtgtaccc ggagggtcct cctccctcgt acgagagcgt gatgcagcag      60
gcggtggcgg cggcgatgca gccccgctg gaggcgcctt acgtgccccc gcggtacctg     120
gcgcctacgg aggggcggaa cagcattcgt tactcggagc tggcacccTT gtacgatacc     180
acccggttgt acctggtgga caacaagtcg gcggacatcg cctcgctgaa ctaccagaac     240
gaccacagca acttcctgac caccgtggtg cagaacaacg atttcacccc cacggaggcc     300
agcacccaga ccatcaactt tgacgagcgc tcgcggtggg gcggccagct gaaaaccatc     360
atgcacacca acatgcccaa cgtgaacgag ttcatgtaca gcaacaagtt caaggcgcgg     420
gtgatggtct cgcgcaagac ccccaacggg gtcgcggtag gggatgatta tgatggtggt     480
caggacgagc tgacctacga gtgggtggag tttgagctgc ccgagggcaa cttctcggtg     540
accatgacca tcgatctgat gaacaacgcc atcatcgaca actacttggc ggtggggcgg     600
cagaacgggg tgctggagag cgacatcggc gtgaagttcg acacgcgcaa cttccggctg     660
ggctgggacc ccgtgaccga gctggtgatg ccgggcgtgt acaccaacga ggccttccac     720
cccgacattg tcctgctgcc cggctgcggc gtggacttca ccgagagccg cctcagcaac     780
ctgctgggca tccgcaagcg gcagcccttc caggagggct tccagatcct gtacgaggac     840
ctggaggggg gcaacatccc cgcgctcttg gatgtcgaag cctacgagaa agcaaggag      900
gagagcgccg ccgcggcgac cgcagccgta gccaccgcct ctaccgaggt gcggggcgat     960
aattttgcta cgccgcagc agtggccgag gcggctgaaa ccgaaagtaa gatagtgatc    1020
cagccggtgg agaaggacag caaggacagg agctacaacg tgctcgcgga caagaaaaac    1080
accgcctacc gcagctggta cctggcctac aactacggcg accccgagaa gggcgtgcgc    1140
tcctggacgc tgctcaccac ctcggacgtc acctgcggcg tggagcaagt ctactggtcg    1200
ctgcccgaca tgatgcaaga cccggtcacc ttccgctcca cgcgtcaagt tagcaactac    1260
ccggtggtgg gcgccgagct cctgcccgtc tactccaaga gcttcttcaa cgagcaggcc    1320
gtctactcgc agcagctgcg cgccttcacc tcgctcacgc acgtcttcaa ccgcttcccc    1380
gagaaccaga tcctcgtccg cccgcccgcg cccaccatta ccaccgtcag tgaaaacgtt    1440
cctgctctca cagatcacgg gaccctgccg ctgcgcagca gtatccgggg agtccagcgc    1500
gtgaccgtca ctgacgccag acgccgcacc tgcccctacg tctacaaggc cctgggcgta    1560
gtcgcgccgc gcgtcctctc gagccgcacc ttctaa                              1596
```

<210> SEQ ID NO 45
<211> LENGTH: 1626
<212> TYPE: DNA
<213> ORGANISM: Adenoviridae - Mastadenovirus

<400> SEQUENCE: 45

```
atgatgaggc gcgtgtaccc ggagggtcct cctccctcgt acgagagcgt gatgcagcag      60
gcggtggcgg tggcgatgca gccccgctg gaggcgcctt acgtgccccc gcggtacctg     120
gcgcctacgg aggggcggaa cagcattcgt tactcggagc tggcacccTT gtacgatacc     180
acccggttgt acctggtgga caacaagtcg gcggacatcg cctcgctgaa ctaccagaac     240
gaccacagca acttcctgac caccgtggtg cagaacaacg atttcacccc cacggaggcc     300
agcacccaga ccatcaactt tgacgagcgc tcgcggtggg gcggccagct gaaaaccatc     360
atgcacacca acatgcccaa cgtgaacgag ttcatgtaca gcaacaagtt caaggcgcgg     420
```

```
gtgatggtct cgcgcaagac ccccaacggg gtgacggtag gggatgatta tgatggtagt    480
caggacgagc tgacctacga gtgggtggag tttgagctgc ctgagggcaa cttctcggtg    540
accatgacca tcgatctgat gaacaacgcc atcatcgaca actacttggc ggtggggcgg    600
cagaacgggg tgctggaaag cgacatcggc gtgaagttcg acacgcgcaa cttccggctg    660
ggctgggacc ccgtgaccga gctggtgatg ccgggcgtgt acaccaacga ggccttccac    720
cccgacatcg tcctgctgcc cggctgcggc gtggacttca ccgagagccg cctcagcaac    780
ctgctgggca tccgcaagcg gcagcccttc caggagggct tccagatcct gtacgaggac    840
ctggaggggg gcaacatccc cgcgctcttg gatgtcgaag cctatgagaa agcaaggag    900 gatagcgccg cagcgacgac cgcagccgtg gctactgccg cgaccaccga tgcagatgca    960
actactacca ggggcgatac atttgccacc caggcggagg aagcagccgc cctagcggcg   1020
accgatgata gtgaaagtaa gatagtcatc aagccggtgg agaaggacag caaggacagg   1080
agctacaacg tgctcgcgga caagaaaaac accgcctacc gcagctggta cctggcctac   1140
aactacggcg accccgagaa gggcgtgcgc tcctggacgc tgctcaccac ctcggacgtc   1200
acctgcggcg tggagcaagt ctactggtcg ctgcccgaca tgatgcaaga cccggtcacc   1260
ttccgctcca cgcgtcaagt tagcaactac ccggtggtgg gcgccgagct cctgcccgtc   1320
tactccaaga gcttcttcaa cgagcaggcc gtctactcgc agcagctgcg cgccttcacc   1380
tcgctcacgc acgtcttcaa ccgcttcccc gagaaccaga tcctcgttcg cccgcccgcg   1440
cccaccatta ccaccgtcag tgaaaacgtt cctgctctca cagatcacgg gaccctgccg   1500
ctgcgcagca gtatccgggg agtccagcgc gtgaccgtca ctgacgccag acgccgcacc   1560
tgcccctacg tctacaaggc cctgggcgta gtcgcgccgc cgtcctctc gagccgcacc   1620 ttctaa                                                              1626

<210> SEQ ID NO 46
<211> LENGTH: 1599
<212> TYPE: DNA
<213> ORGANISM: Adenoviridae - Mastadenovirus

<400> SEQUENCE: 46
atgatgaggc gcgtgtaccc ggagggtcct cctccctcgt acgagagcgt gatgcagcag     60
gcggtggcgc cggcgatgca gcccccgctg gaggcgcctt acgtgccccc gcggtacctg    120
gcgcctacgg aggggcggaa cagcattcgt tactcggagc tggcacccct gtacgatacc    180
acccggttgt acctggtgga caacaagtcg gcggacatcg cctcgctgaa ctaccagaac    240
gaccacagca acttcctgac caccgtggtg cagaacaacg atttcacccc cacggaggcc    300
agcacccaga ccatcaactt tgacgagcgc tcgcggtggg gcggccagct gaaaaccatc    360
atgcacacca acatgcccaa cgtgaacgag ttcatgtaca gcaacaagtt caaggcgcgg    420
gtgatggtct cgcgcaagac ccccaacggg gtcacagtaa cagatggtag tcaggacgag    480
ctgacctacg agtgggtgga gtttgagctg ccgagggca acttctcggt gaccatgacc    540
atcgatctga tgaacaacgc catcatcgac aactacttgg cggtggggcg gcagaacggg    600
gtgctggaga gcgacatcgg cgtgaagttc gacacgcgca acttccggct gggctgggac    660
cccgtgaccg agctggtgat gccgggcgtg tacaccaacg aggccttcca ccccgacatc    720
gtcctgctgc ccggctgcgg cgtggacttc accgagagcc gcctcagcaa cctgctgggc    780
atccgcaagc ggcagccctt ccaggagggc ttccagatcc tgtacgagga cctggagggg    840
```

-continued

```
ggcaacatcc ccgcgctctt ggatgtcgaa gcctacgaga aaagcaagga ggatagcacc      900
gccgtggcta ccgccgcgac tgtggcagat gccactgtca ccaggggcga tacattcgcc      960
acccaggcgg aggaagcagc cgccctagcg gcgaccgatg atagtgaaag taagatagtt     1020
atcaagccgg tggagaagga cagcaaggac aggagctaca cgttctatc ggatggaaag      1080
aacaccgcct accgcagctg gtacctggcc tacaactacg gcgaccccga agggcgtg       1140
cgctcctgga cgctgctcac cacctcggac gtcacctgcg cgtggagca agtctactgg      1200
tcgctgcccg acatgatgca agacccggtc accttccgct ccacgcgtca gttagcaac     1260
tacccggtgg tgggcgccga gctcctgccc gtctactcca agagcttctt caacgagcag     1320
gccgtctact cgcagcagct gcgcgccttc acctcgctca cgcacgtctt caaccgcttc     1380
cccgagaacc agatcctcgt ccgcccgccc gcgcccacca ttaccaccgt cagtgaaaac     1440
gttcctgctc tcacagatca cgggaccctg ccgctgcgca gcagtatccg gggagtccag     1500
cgcgtgaccg tcactgacgc cagacgccgc acctgcccct acgtctacaa ggccctgggc     1560
gtagtcgcgc cgcgcgtcct ctcgagccgc accttctaa                            1599
```

<210> SEQ ID NO 47
<211> LENGTH: 1587
<212> TYPE: DNA
<213> ORGANISM: Adenoviridae - Mastadenovirus

<400> SEQUENCE: 47

```
atgatgaggc gcgtgtaccc ggagggtcct cctccctcgt acgagagcgt gatgcagcag       60
gcggtggcgc cggcgatgca gccccgctg gaggcgcctt acgtgccccc gcggtacctg       120
gcgcctacgg aggggcggaa cagcattcgt tactcggagc tggcacccett gtacgatacc     180
acccggttgt acctggtgga caacaagtcg gcggacatcg cctcgctgaa ctaccagaac      240
gaccacagca acttcctgac caccgtggtg cagaacaacg atttcacccc cacggaggcc     300
agcacccaga ccatcaactt tgacgagcgc tcgcggtggg gcggccagct gaaaaccatc      360
atgcacacca acatgcccaa cgtgaacgag ttcctgtaca gcaacaagtt caaggcgcgg     420
gtgatggtct cgcgcaagac ccccaacggg gtcacagtaa cagatggtag tcaggacgag    480
ctgacctacg agtgggtgga gtttgagctg cccgagggca acttctcggt gaccatgacc      540
atcgatctga tgaacaacgc cattatcgac aattacttgg cggtggggcg gcagaacggg     600
gtgctggaga gcgacatcgg cgtgaagttc gacacgcgca acttcaggct cggttgggac    660
cccgtgaccg agctggtcat gccgggcgtg tacaccaacg aggccttcca ccccgacatc      720
gtcctgctgc ccggctgcgg cgtggacttc accgagagcc gcctcagcaa cctgctgggc     780
attcgcaaga ggcagcccct tccaggaggg ttccagatca tgtacgagga tctgaggggg    840
ggcaacatcc ccgcgctcct ggatgtcgag gcctacgaga aaagcaagga ggatagcgcc    900
gccgcggcga ccgcagccgt ggccaccgcc tctaccgagg tgcggggcga taattttgct     960
agcgccgcgg cagtggccga gcggctgaa accgaaagta agatagtgat ccagccggtg    1020
gagaaggaca gcaaggacag gagctacaac gtgctcgcgg acaagaaaaa caccgcctac    1080
cgcagctggt acctggccta caactacggc gaccccgaga agggcgtgcg ctcctggacg    1140
ctgctcacca cctcggacgt cacctgcggc gtggagcaag tctactggtc gctgcccgac    1200
atgatgcaag acccggtcac cttccgctcc acgcgtcaag ttagcaacta cccggtggtg    1260
ggcgccgagc tcctgcccgt ctactccaag agcttcttca acgagcaggc cgtctactcg    1320
cagcagctgc gcgccttcac ctcgctcacg cacgtcttca accgcttccc cgagaaccag    1380
```

```
atcctcgtcc gcccgcccgc gcccaccatt accaccgtca gtgaaaacgt tcctgctctc   1440
acagatcacg ggaccctgcc gctgcgcagc agtatccggg gagtccagcg cgtgaccgtc   1500
actgacgcca acgccgcac ctgcccctac gtctacaagg ccctgggcgt agtcgcgccg   1560
cgcgtcctct cgagccgcac cttctaa                                       1587

<210> SEQ ID NO 48
<211> LENGTH: 1608
<212> TYPE: DNA
<213> ORGANISM: Adenoviridae - Mastadenovirus

<400> SEQUENCE: 48
atgatgaggc gtgcgtaccc ggagggtcct cctccctcgt acgagagcgt gatgcagcag     60
gcgatggcgg cggcggcggc gatgcagccc ccgctggagg ctccttacgt gccccgcgg    120 tacctggcgc ctacggaggg gcggaacagc attcgttact cggagctggc acccttgtac    180
gataccaccc ggttgtacct ggtggacaac aagtcggcgg acatcgcctc gctgaactac    240
cagaacgacc acagcaactt cctgaccacc gtggtgcaga caatgactt caccccacg     300 gaggccagca cccagaccat caactttgac gagcgctcgc ggtggggcgg ccagctgaaa    360
accatcatgc acaccaacat gcccaacgtg aacgagttca tgtacagcaa caagttcaag    420
gcgcgggtca tggtctcccg caagacccc aacggggtga cagtgacaga ggattatgat    480
ggtagtcagg atgagctgaa atacgagtgg gtggagtttg agctgcccga aggcaacttc    540
tcggtgacca tgactatcga cctgatgaac aacgccatca tcgacaatta cttggcggtg    600
gggcggcaga acggggtgct ggagagcgac atcggcgtga agttcgacac taggaacttc    660
aggctgggct gggacccgt gaccgagctg gtcatgcccg gggtgtacac caacgaggcc    720
ttccatcccg atattgtctt gctgcccggc tgcggggtgg acttcaccga gagccgcctc    780
agcaacctgc tgggcattcg caagaggcag cccttccagg agggcttcca gatcatgtac    840
gaggatctgg agggggggtaa catccccgcg ctcctggatg tcgacgccta tgagaaaagc    900
aaggaggaga cgccgccgc ggcgaccgca gccgtagcca ccgcctctac cgaggtcagg    960
ggcgataatt ttgctagcgc cgcagcagtg gcagcggcc aggcggctga aaccgaaagt   1020
aagatagtca ttcagccggt ggagaaggat agcaaagaca ggagctacaa cgtgctgccg   1080
gacaagataa acaccgccta ccgcagctgg tacctggcct acaactatgg cgaccccgag   1140
aagggcgtgc gctcctggac gctgctcacc acctcggacg tcacctgcgg cgtggagcaa   1200
gtctactggt cgctgcccga catgatgcaa gacccggtca ccttccgctc cacgcgtcaa   1260
gttagcaact acccggtggt gggcgccgag ctcctgcccg tctactccaa gagcttcttc   1320
aacgagcagg ccgtctactc gcagcagctg cgcgccttca cctcgctcac gcacgtcttc   1380
aaccgcttcc ccgagaacca gatcctcgtc cgcccgcccg cgcccaccat taccaccgtc   1440
agtgaaaacg ttcctgctct cacagatcac gggaccctgc cgctgcgcag cagtatccgg   1500
ggagtccagc gcgtgaccgt tactgacgcc agacgccgca cctgcccta cgtctacaag   1560 gccctgggca tagtcgcgcc gcgcgtcctc tcgagccgca ccttctaa              1608

<210> SEQ ID NO 49
<211> LENGTH: 1743
<212> TYPE: DNA
<213> ORGANISM: Adenoviridae - Mastadenovirus

<400> SEQUENCE: 49
```

```
atgcggcgcg cggcgatgta ccacgaggga cctcctccct cttatgagag cgtggtgggc    60
gcggcggcgg cctctccctt tgcgtcgcag ctggagccgc cgtacgtgcc tccgcggtac   120
ctgcggccta cggggggaag aaacagcatc cgttactcgg agctggcgcc cctgtacgac   180
accacccggg tgtacctggt ggacaacaag tcggcggacg tggcctccct gaactaccag   240
aacgaccaca gcaattttt gaccacggtc atccagaaca atgactacac cccgagcgag   300
ccagcaccc agaccatcaa tctggatgac cggtcgcact ggggcggcga cctgaaaacc   360
atcctgcaca ccaacatgcc caacgtgaac gagttcatgt tcaccaataa gttcaaggcg   420
cgggtgatgg tgtcgcgctc gcacaccaag gacgaccggg tggagctgaa gtacgagtgg   480
gtagagttcg agctgcccga gggcaactac tcggagacca tgaccataga cctgatgaac   540
aacgcgatcg tggagcacta tctgaaagtg ggcaggcaga acgggtcct ggagagcgac   600
atcggggtca agttcgacac caggaacttc cgcctggggc tggacccggt caccgggctg   660
gttatgcccg ggtctacac caacgaggcc ttccaccccg acatcatcct gctgcccggc   720
tgcggggtgg acttcaccta cagccgcctg agcaacctgc tgggcatccg caagcggcag   780
cccttccagg agggcttcag gatcacctac gaggacctgg aggggggcaa catccccgcg   840
ctcctggatg tggaggccta ccaggatagc ttgaaggaag aagaggcggg agagggcagc   900
ggcggtggcg ccggtcagga ggagggcggg gcctcctctg aggcctctgc ggacccagcc   960
gctgccgcca ggcggaggc ggccgacccc gcgatggtgg tagaggaaga aaggatatg  1020
aacgacgagg cggtgcgcgg cgacaccttt gccactcggg gggaggagaa gaaagcggag  1080
gccgaggccg cggcagagga ggcggcagca gcggcggcgg cagtagaggc ggcggccgag  1140
gcggagaagc cccccaagga gcccgtgatt aagcccctga ccgaagatag caagaagcgc  1200
agttacaacg tgctcaagga cagcaccaac accgagtacc gcagctggta cctggcctac  1260
aactacggcg accggcgac gggggtgcgc tcctggaccc tgctgtgtac gccggacgtg  1320
acctgcgggct cggagcaggt gtactggtcg ctgcccgaca tgatgcaaga ccccgtgacc  1380
ttccgctcca cgcggcaggt cagcaacttc ccggtggtgg gcgccgagct gctgcccgtg  1440
cactccaaga gcttctacaa cgaccaggcc gtcactccc agctcatccg ccagttcacc  1500
tctctgaccc acgtgttcaa cgctttcct gagaaccaga ttctggcgcg cccgcccgcc  1560
cccaccatca ccaccgtcag tgaaaacgtt cctgctctca cagatcacgg gacgctaccg  1620
ctgcgcaaca gcatcggagg agtccagcga gtgaccgtaa ctgacgccag acgccgcacc  1680
tgccctacg tttacaaggc cctgggcata gtctcgccgc cgtcctttc cagccgcact  1740
ttt                                                                1743

<210> SEQ ID NO 50
<211> LENGTH: 577
<212> TYPE: PRT
<213> ORGANISM: Adenoviridae - Mastadenovirus

<400> SEQUENCE: 50

Met Lys Arg Ala Lys Thr Ser Asp Glu Thr Phe Asn Pro Val Tyr Pro
1               5                   10                  15

Tyr Asp Thr Glu Asn Gly Pro Pro Ser Val Pro Phe Leu Thr Pro Pro
            20                  25                  30

Phe Val Ser Pro Asp Gly Phe Gln Glu Ser Pro Pro Gly Val Leu Ser
        35                  40                  45

Leu Arg Leu Ser Glu Pro Leu Val Thr Ser His Gly Met Leu Ala Leu
    50                  55                  60
```

-continued

```
Lys Met Gly Asn Gly Leu Ser Leu Asp Asp Ala Gly Asn Leu Thr Ser
 65              70                  75                  80

Gln Asp Val Thr Thr Val Thr Pro Pro Leu Lys Lys Thr Lys Thr Asn
                 85                  90                  95

Leu Ser Leu Gln Thr Ser Ala Pro Leu Thr Val Ser Ser Gly Ser Leu
            100                 105                 110

Thr Val Ala Ala Ala Pro Leu Ala Val Ala Gly Thr Ser Leu Thr
            115                 120                 125

Met Gln Ser Gln Ala Pro Leu Thr Val Gln Asp Ala Lys Leu Gly Leu
    130                 135                 140

Ala Thr Gln Gly Pro Leu Thr Val Ser Glu Gly Lys Leu Thr Leu Gln
145                 150                 155                 160

Thr Ser Ala Pro Leu Thr Ala Ala Asp Ser Ser Thr Leu Thr Val Ser
                165                 170                 175

Ala Thr Pro Pro Leu Ser Thr Ser Asn Gly Ser Leu Ser Ile Asp Met
                180                 185                 190

Gln Ala Pro Ile Tyr Thr Thr Asn Gly Lys Leu Ala Leu Asn Ile Gly
            195                 200                 205

Ala Pro Leu His Val Val Asp Thr Leu Asn Ala Leu Thr Val Val Thr
210                 215                 220

Gly Gln Gly Leu Thr Ile Asn Gly Arg Ala Leu Gln Thr Arg Val Thr
225                 230                 235                 240

Gly Ala Leu Ser Tyr Asp Thr Glu Gly Asn Ile Gln Leu Gln Ala Gly
                245                 250                 255

Gly Gly Met Arg Ile Asp Asn Asn Gly Gln Leu Ile Leu Asn Val Ala
            260                 265                 270

Tyr Pro Phe Asp Ala Gln Asn Asn Leu Ser Leu Arg Leu Gly Gln Gly
            275                 280                 285

Pro Leu Ile Val Asn Ser Ala His Asn Leu Asp Leu Asn Leu Asn Arg
    290                 295                 300

Gly Leu Tyr Leu Phe Thr Ser Gly Asn Thr Lys Lys Leu Glu Val Asn
305                 310                 315                 320

Ile Lys Thr Ala Lys Gly Leu Phe Tyr Asp Gly Thr Ala Ile Ala Ile
                325                 330                 335

Asn Ala Gly Asp Gly Leu Gln Phe Gly Ser Gly Ser Asp Thr Asn Pro
            340                 345                 350

Leu Gln Thr Lys Leu Gly Leu Gly Leu Glu Tyr Asp Ser Asn Lys Ala
    355                 360                 365

Ile Ile Thr Lys Leu Gly Thr Gly Leu Ser Phe Asp Asn Thr Gly Ala
    370                 375                 380

Ile Thr Val Gly Asn Lys Asn Asp Lys Leu Thr Leu Trp Thr Thr
385                 390                 395                 400

Pro Asp Pro Ser Pro Asn Cys Arg Ile Asn Ser Glu Lys Asp Ala Lys
                405                 410                 415

Leu Thr Leu Val Leu Thr Lys Cys Gly Ser Gln Val Leu Ala Ser Val
                420                 425                 430

Ser Val Leu Ser Val Lys Gly Ser Leu Ala Pro Ile Ser Gly Thr Val
            435                 440                 445

Thr Ser Ala Gln Ile Val Leu Arg Phe Asp Glu Asn Gly Val Leu Leu
    450                 455                 460

Ser Asn Ser Ser Leu Asp Pro Gln Tyr Trp Asn Tyr Arg Lys Gly Asp
465                 470                 475                 480
```

-continued

```
Ser Thr Glu Gly Thr Ala Tyr Thr Asn Ala Val Gly Phe Met Pro Asn
                485                 490                 495

Leu Thr Ala Tyr Pro Lys Thr Gln Ser Gln Thr Ala Lys Ser Asn Ile
            500                 505                 510

Val Ser Gln Val Tyr Leu Asn Gly Asp Lys Thr Lys Pro Met Thr Leu
        515                 520                 525

Thr Ile Thr Leu Asn Gly Thr Asn Glu Thr Gly Asp Ala Thr Val Ser
    530                 535                 540

Thr Tyr Ser Met Ser Phe Ser Trp Asn Trp Asn Gly Ser Asn Tyr Ile
545                 550                 555                 560

Asn Asp Thr Phe Gln Thr Asn Ser Phe Thr Phe Ser Tyr Ile Ala Gln
                565                 570                 575

Glu

<210> SEQ ID NO 51
<211> LENGTH: 955
<212> TYPE: PRT
<213> ORGANISM: Adenoviridae - Mastadenovirus

<400> SEQUENCE: 51

Met Ala Thr Pro Ser Met Met Pro Gln Trp Ser Tyr Met His Ile Ser
1               5                   10                  15

Gly Gln Asp Ala Ser Glu Tyr Leu Ser Pro Gly Leu Val Gln Phe Ala
            20                  25                  30

Arg Ala Thr Asp Ser Tyr Phe Ser Leu Ser Asn Lys Phe Arg Asn Pro
        35                  40                  45

Thr Val Ala Pro Thr His Asp Val Thr Thr Asp Arg Ser Gln Arg Leu
    50                  55                  60

Thr Leu Arg Phe Ile Pro Val Asp Arg Glu Asp Thr Ala Tyr Ser Tyr
65                  70                  75                  80

Lys Ala Arg Phe Thr Leu Ala Val Gly Asp Asn Arg Val Leu Asp Met
                85                  90                  95

Ala Ser Thr Tyr Phe Asp Ile Arg Gly Val Leu Asp Arg Gly Pro Thr
            100                 105                 110

Phe Lys Pro Tyr Ser Gly Thr Ala Tyr Asn Ser Leu Ala Pro Lys Gly
        115                 120                 125

Ala Pro Asn Pro Cys Glu Trp Asp Glu Ala Val Thr Ala Val Asp Ile
    130                 135                 140

Asn Leu Asp Glu Leu Gly Glu Asp Asp Ala Glu Gly Glu Ala
145                 150                 155                 160

Glu Gln Gln Lys Ser His Val Phe Gly Gln Ala Pro Tyr Ser Gly Gln
                165                 170                 175

Asn Ile Thr Lys Glu Gly Ile Gln Ile Gly Val Asp Thr Thr Ser Gln
            180                 185                 190

Ala Gln Thr Pro Leu Tyr Ala Asp Lys Thr Phe Gln Pro Glu Pro Gln
        195                 200                 205

Val Gly Glu Ser Gln Trp Asn Glu Thr Glu Ile Asn Tyr Gly Ala Gly
    210                 215                 220

Arg Val Leu Lys Lys Thr Thr Leu Met Lys Pro Cys Tyr Gly Ser Tyr
225                 230                 235                 240

Ala Arg Pro Thr Asn Glu Asn Gly Gly Gln Gly Ile Leu Leu Glu Lys
                245                 250                 255

Glu Gly Gly Lys Pro Glu Ser Val Glu Met Gln Phe Phe Ser Thr
            260                 265                 270
```

```
Thr Gln Ala Ala Ala Gly Asn Ser Asp Asn Leu Thr Pro Lys Val
            275                 280                 285

Val Leu Tyr Ser Glu Asp Val His Leu Glu Thr Pro Asp Thr His Ile
    290                 295                 300

Ser Tyr Met Pro Thr Ser Asn Glu Ala Asn Ser Arg Glu Leu Leu Gly
305                 310                 315                 320

Gln Gln Ala Met Pro Asn Arg Pro Asn Tyr Ile Ala Phe Arg Asp Asn
                325                 330                 335

Phe Ile Gly Leu Met Tyr Tyr Asn Ser Thr Gly Asn Met Gly Val Leu
                340                 345                 350

Ala Gly Gln Ala Ser Gln Leu Asn Ala Val Asp Leu Gln Asp Arg
            355                 360                 365

Asn Thr Glu Leu Ser Tyr Gln Leu Leu Leu Asp Ser Met Gly Asp Arg
    370                 375                 380

Thr Arg Tyr Phe Ser Met Trp Asn Gln Ala Val Asp Ser Tyr Asp Pro
385                 390                 395                 400

Asp Val Arg Ile Ile Glu Asn His Gly Thr Glu Asp Glu Leu Pro Asn
                405                 410                 415

Tyr Cys Phe Pro Leu Gly Gly Ile Ile Asn Thr Glu Thr Leu Thr Lys
                420                 425                 430

Val Lys Pro Lys Thr Gly Gln Asp Ala Gln Trp Glu Lys Asp Thr Glu
    435                 440                 445

Phe Ser Glu Lys Asn Glu Ile Arg Val Gly Asn Asn Phe Ala Met Glu
    450                 455                 460

Ile Asn Leu Asn Ala Asn Leu Trp Arg Asn Phe Leu Tyr Ser Asn Val
465                 470                 475                 480

Ala Leu Tyr Leu Pro Asp Lys Leu Lys Tyr Thr Pro Ala Asn Val Gln
                485                 490                 495

Ile Ser Ser Asn Ser Asn Ser Tyr Asp Tyr Met Asn Lys Arg Val Val
                500                 505                 510

Ala Pro Gly Leu Val Asp Cys Tyr Ile Asn Leu Gly Ala Arg Trp Ser
                515                 520                 525

Leu Asp Tyr Met Asp Asn Val Asn Pro Phe Asn His His Arg Asn Ala
530                 535                 540

Gly Leu Arg Tyr Arg Ser Met Leu Leu Gly Asn Gly Arg Tyr Val Pro
545                 550                 555                 560

Phe His Ile Gln Val Pro Gln Lys Phe Phe Ala Ile Lys Asn Leu Leu
                565                 570                 575

Leu Leu Pro Gly Ser Tyr Thr Tyr Glu Trp Asn Phe Arg Lys Asp Val
                580                 585                 590

Asn Met Val Leu Gln Ser Ser Leu Gly Asn Asp Leu Arg Val Asp Gly
                595                 600                 605

Ala Ser Ile Lys Phe Glu Ser Ile Cys Leu Tyr Ala Thr Phe Phe Pro
            610                 615                 620

Met Ala His Asn Thr Ala Ser Thr Leu Glu Ala Met Leu Arg Asn Asp
625                 630                 635                 640

Thr Asn Asp Gln Ser Phe Asn Asp Tyr Leu Ser Ala Ala Asn Met Leu
                645                 650                 655

Tyr Pro Ile Pro Ala Asn Ala Thr Asn Val Pro Ile Ser Ile Pro Ser
                660                 665                 670

Arg Asn Trp Ala Ala Phe Arg Gly Trp Ala Phe Thr Arg Leu Lys Thr
                675                 680                 685

Lys Glu Thr Pro Ser Leu Gly Ser Gly Phe Asp Pro Tyr Tyr Thr Tyr
```

```
                690                 695                 700
Ser Gly Ser Ile Pro Tyr Leu Asp Gly Thr Phe Tyr Leu Asn His Thr
705                 710                 715                 720

Phe Lys Lys Val Ser Val Thr Phe Asp Ser Ser Val Ser Trp Pro Gly
                725                 730                 735

Asn Asp Arg Leu Leu Thr Pro Asn Glu Phe Glu Ile Lys Arg Ser Val
                740                 745                 750

Asp Gly Glu Gly Tyr Asn Val Ala Gln Cys Asn Met Thr Lys Asp Trp
                755                 760                 765

Phe Leu Ile Gln Met Leu Ala Asn Tyr Asn Ile Gly Tyr Gln Gly Phe
                770                 775                 780

Tyr Ile Pro Glu Ser Tyr Lys Asp Arg Met Tyr Ser Phe Phe Arg Asn
785                 790                 795                 800

Phe Gln Pro Met Ser Arg Gln Val Val Asp Glu Thr Lys Tyr Lys Asp
                805                 810                 815

Tyr Gln Gln Val Gly Ile Ile His Gln His Asn Asn Ser Gly Phe Val
                820                 825                 830

Gly Tyr Leu Ala Pro Thr Met Arg Glu Gly Gln Ala Tyr Pro Ala Asn
                835                 840                 845

Phe Pro Tyr Pro Leu Ile Gly Lys Thr Ala Val Asp Ser Val Thr Gln
                850                 855                 860

Lys Lys Phe Leu Cys Asp Arg Thr Leu Trp Arg Ile Pro Phe Ser Ser
865                 870                 875                 880

Asn Phe Met Ser Met Gly Ala Leu Thr Asp Leu Gly Gln Asn Leu Leu
                885                 890                 895

Tyr Ala Asn Ser Ala His Ala Leu Asp Met Thr Phe Glu Val Asp Pro
                900                 905                 910

Met Asp Glu Pro Thr Leu Leu Tyr Val Leu Phe Glu Val Phe Asp Val
                915                 920                 925

Val Arg Val His Gln Pro His Arg Gly Val Ile Glu Thr Val Tyr Leu
                930                 935                 940

Arg Thr Pro Phe Ser Ala Gly Asn Ala Thr Thr
945                 950                 955

<210> SEQ ID NO 52
<211> LENGTH: 582
<212> TYPE: PRT
<213> ORGANISM: Adenoviridae - Mastadenovirus

<400> SEQUENCE: 52

Met Arg Arg Ala Ala Met Tyr His Glu Gly Pro Pro Ser Tyr Glu
1                5                   10                  15

Ser Val Val Gly Ala Ala Ala Ser Pro Phe Ala Ser Gln Leu Glu
                20                  25                  30

Pro Pro Tyr Val Pro Pro Arg Tyr Leu Arg Pro Thr Gly Gly Arg Asn
                35                  40                  45

Ser Ile Arg Tyr Ser Glu Leu Ala Pro Leu Tyr Asp Thr Thr Arg Val
                50                  55                  60

Tyr Leu Val Asp Asn Lys Ser Ala Asp Val Ala Ser Leu Asn Tyr Gln
65                  70                  75                  80

Asn Asp His Ser Asn Phe Leu Thr Thr Val Ile Gln Asn Asn Asp Tyr
                85                  90                  95

Thr Pro Ser Glu Ala Ser Thr Gln Thr Ile Asn Leu Asp Asp Arg Ser
                100                 105                 110
```

```
His Trp Gly Gly Asp Leu Lys Thr Ile Leu His Thr Asn Met Pro Asn
            115                 120                 125

Val Asn Glu Phe Met Phe Thr Asn Lys Phe Lys Ala Arg Val Met Val
    130                 135                 140

Ser Arg Ser His Thr Lys Asp Asp Arg Val Glu Leu Lys Tyr Glu Trp
145                 150                 155                 160

Val Glu Phe Glu Leu Pro Gly Asn Tyr Ser Glu Thr Met Thr Ile
                165                 170                 175

Asp Leu Met Asn Asn Ala Ile Val Glu His Tyr Leu Lys Val Gly Arg
            180                 185                 190

Gln Asn Gly Val Leu Glu Ser Asp Ile Gly Val Lys Phe Asp Thr Arg
            195                 200                 205

Asn Phe Arg Leu Gly Leu Asp Pro Val Thr Gly Leu Val Met Pro Gly
    210                 215                 220

Val Tyr Thr Asn Glu Ala Phe His Pro Asp Ile Ile Leu Leu Pro Gly
225                 230                 235                 240

Cys Gly Val Asp Phe Thr Tyr Ser Arg Leu Ser Asn Leu Leu Gly Ile
                245                 250                 255

Arg Lys Arg Gln Pro Phe Gln Glu Gly Phe Arg Ile Thr Tyr Glu Asp
            260                 265                 270

Leu Glu Gly Gly Asn Ile Pro Ala Leu Leu Asp Val Glu Ala Tyr Gln
            275                 280                 285

Asn Ser Leu Lys Glu Glu Glu Ala Glu Gly Ser Gly Gly Gly Gly
    290                 295                 300

Ala Gly Gln Glu Glu Gly Gly Ala Ser Ser Glu Ala Ser Ala Asp Ala
305                 310                 315                 320

Ala Ala Ala Glu Ala Glu Ala Ala Asp Pro Ala Met Val Val Glu
                325                 330                 335

Glu Glu Lys Asp Met Asn Asp Glu Ala Val Arg Gly Asp Thr Phe Ala
            340                 345                 350

Thr Arg Gly Glu Glu Lys Lys Ala Glu Ala Ala Ala Glu Glu
                355                 360                 365

Ala Ala Ala Ala Ala Ala Ala Val Glu Ala Ala Ala Glu Ala Glu Lys
370                 375                 380

Pro Pro Lys Glu Pro Val Ile Lys Pro Leu Thr Glu Asp Ser Lys Lys
385                 390                 395                 400

Arg Ser Tyr Asn Val Leu Lys Asp Ser Thr Asn Thr Glu Tyr Arg Ser
                405                 410                 415

Trp Tyr Leu Ala Tyr Asn Tyr Gly Asp Pro Ala Thr Gly Val Arg Ser
                420                 425                 430

Trp Thr Leu Leu Cys Thr Pro Asp Val Thr Cys Gly Ser Glu Gln Val
                435                 440                 445

Tyr Trp Ser Leu Pro Asp Met Met Gln Asp Pro Val Thr Phe Arg Ser
    450                 455                 460

Thr Arg Gln Val Ser Asn Phe Pro Val Val Gly Ala Glu Leu Leu Pro
465                 470                 475                 480

Val His Ser Lys Ser Phe Tyr Asn Asp Gln Ala Val Tyr Ser Gln Leu
                485                 490                 495

Ile Arg Gln Phe Thr Ser Leu Thr His Val Phe Asn Arg Phe Pro Glu
                500                 505                 510

Asn Gln Ile Leu Ala Arg Pro Pro Ala Pro Thr Ile Thr Thr Val Ser
            515                 520                 525

Glu Asn Val Pro Ala Leu Thr Asp His Gly Thr Leu Pro Leu Arg Asn
```

```
                530             535             540
Ser Ile Gly Gly Val Gln Arg Val Thr Val Thr Asp Ala Arg Arg
545                 550             555                 560

Thr Cys Pro Tyr Val Tyr Lys Ala Leu Gly Ile Val Ser Pro Arg Val
                565             570             575

Leu Ser Ser Arg Thr Phe
            580

<210> SEQ ID NO 53
<211> LENGTH: 542
<212> TYPE: PRT
<213> ORGANISM: Adenoviridae - Mastadenovirus

<400> SEQUENCE: 53

Met Lys Arg Ala Lys Thr Ser Asp Glu Thr Phe Asn Pro Val Tyr Pro
1               5                   10                  15

Tyr Asp Thr Glu Asn Gly Pro Pro Ser Val Pro Phe Leu Thr Pro Pro
            20                  25                  30

Phe Val Ser Pro Asp Gly Phe Gln Glu Ser Pro Pro Gly Val Leu Ser
        35                  40                  45

Leu Arg Leu Ser Glu Pro Leu Val Thr Ser His Gly Met Leu Ala Leu
    50                  55                  60

Lys Met Gly Asn Gly Leu Ser Leu Asp Asp Ala Gly Asn Leu Thr Ser
65                  70                  75                  80

Gln Asp Val Thr Thr Val Thr Pro Pro Leu Lys Lys Thr Lys Thr Asn
                85                  90                  95

Leu Ser Leu Gln Thr Ser Ala Pro Leu Thr Val Ser Ser Gly Ser Leu
            100                 105                 110

Thr Val Ala Ala Ala Pro Leu Ala Val Ala Gly Thr Ser Leu Thr
        115                 120                 125

Met Gln Ser Gln Ala Pro Leu Thr Val Gln Asp Ala Lys Leu Gly Leu
130                 135                 140

Ala Thr Gln Gly Pro Leu Thr Val Ser Glu Gly Lys Leu Thr Leu Gln
145                 150                 155                 160

Thr Ser Ala Pro Leu Thr Ala Ala Asp Ser Ser Thr Leu Thr Val Gly
                165                 170                 175

Thr Thr Pro Pro Ile Ser Val Ser Ser Gly Ser Leu Gly Leu Asp Met
            180                 185                 190

Glu Asp Pro Met Tyr Thr His Asp Gly Lys Leu Gly Ile Arg Ile Gly
        195                 200                 205

Gly Pro Leu Gln Val Val Asp Ser Leu His Thr Leu Thr Val Val Thr
    210                 215                 220

Gly Asn Gly Ile Thr Val Ala Asn Asn Ala Leu Gln Thr Lys Val Ala
225                 230                 235                 240

Gly Ala Leu Gly Tyr Asp Ser Ser Gly Asn Leu Glu Leu Arg Ala Ala
                245                 250                 255

Gly Gly Met Arg Ile Asn Thr Gly Gly Gln Leu Ile Leu Asp Val Ala
            260                 265                 270

Tyr Pro Phe Asp Ala Gln Asn Asn Leu Ser Leu Arg Leu Gly Gln Gly
        275                 280                 285

Pro Leu Tyr Val Asn Thr Asn His Asn Leu Asp Leu Asn Cys Asn Arg
    290                 295                 300

Gly Leu Thr Thr Thr Thr Ser Ser Asn Thr Thr Lys Leu Glu Thr Lys
305                 310                 315                 320
```

-continued

```
Ile Asp Ser Gly Leu Asp Tyr Asn Ala Asn Gly Ala Ile Ile Ala Lys
            325                 330                 335

Leu Gly Thr Gly Leu Thr Phe Asp Asn Thr Gly Ala Ile Thr Val Gly
            340                 345                 350

Asn Thr Gly Asp Asp Lys Leu Thr Leu Trp Thr Thr Pro Asp Pro Ser
            355                 360                 365

Pro Asn Cys Arg Ile His Ala Asp Lys Asp Cys Lys Phe Thr Leu Val
370                 375                 380

Leu Thr Lys Cys Gly Ser Gln Ile Leu Ala Ser Val Ala Ala Leu Ala
385                 390                 395                 400

Val Ser Gly Asn Leu Ser Ser Met Thr Gly Thr Val Ser Ser Val Thr
            405                 410                 415

Ile Phe Leu Arg Phe Asp Gln Asn Gly Val Leu Met Glu Asn Ser Ser
            420                 425                 430

Leu Asp Lys Glu Tyr Trp Asn Phe Arg Asn Gly Asn Ser Thr Asn Ala
            435                 440                 445

Thr Pro Tyr Thr Asn Ala Val Gly Phe Met Pro Asn Leu Ser Ala Tyr
            450                 455                 460

Pro Lys Thr Gln Ser Gln Thr Ala Lys Asn Asn Ile Val Ser Glu Val
465                 470                 475                 480

Tyr Leu His Gly Asp Lys Ser Lys Pro Met Ile Leu Thr Ile Thr Leu
            485                 490                 495

Asn Gly Thr Asn Glu Ser Ser Glu Thr Ser Gln Val Ser His Tyr Ser
            500                 505                 510

Met Ser Phe Thr Trp Ser Trp Asp Ser Gly Lys Tyr Ala Thr Glu Thr
            515                 520                 525

Phe Ala Thr Asn Ser Phe Thr Phe Ser Tyr Ile Ala Glu Gln
            530                 535                 540

<210> SEQ ID NO 54
<211> LENGTH: 964
<212> TYPE: PRT
<213> ORGANISM: Adenoviridae - Mastadenovirus

<400> SEQUENCE: 54

Met Ala Thr Pro Ser Met Met Pro Gln Trp Ser Tyr Met His Ile Ser
1               5                   10                  15

Gly Gln Asp Ala Ser Glu Tyr Leu Ser Pro Gly Leu Val Gln Phe Ala
            20                  25                  30

Arg Ala Thr Asp Ser Tyr Phe Ser Leu Ser Asn Lys Phe Arg Asn Pro
        35                  40                  45

Thr Val Ala Pro Thr His Asp Val Thr Thr Asp Arg Ser Gln Arg Leu
    50                  55                  60

Thr Leu Arg Phe Ile Pro Val Asp Arg Glu Asp Thr Ala Tyr Ser Tyr
65                  70                  75                  80

Lys Ala Arg Phe Thr Leu Ala Val Gly Asp Asn Arg Val Leu Asp Met
                85                  90                  95

Ala Ser Thr Tyr Phe Asp Ile Arg Gly Val Leu Asp Arg Gly Pro Thr
            100                 105                 110

Phe Lys Pro Tyr Ser Gly Thr Ala Tyr Asn Ser Leu Ala Pro Lys Gly
        115                 120                 125

Ala Pro Asn Ser Cys Glu Trp Glu Gln Glu Glu Thr Gln Thr Ala Glu
    130                 135                 140

Glu Ala Gln Asp Glu Glu Glu Asp Glu Ala Glu Ala Glu Glu Glu Met
145                 150                 155                 160
```

Pro Gln Glu Glu Gln Ala Pro Val Lys Lys Thr His Val Tyr Ala Gln
            165                 170                 175

Ala Pro Leu Ser Gly Glu Lys Ile Thr Lys Asp Gly Leu Gln Ile Gly
            180                 185                 190

Thr Asp Ala Thr Ala Thr Glu Gln Lys Pro Ile Tyr Ala Asp Pro Thr
            195                 200                 205

Phe Gln Pro Glu Pro Gln Ile Gly Glu Ser Gln Trp Asn Glu Ala Asp
        210                 215                 220

Ala Ser Val Ala Gly Gly Arg Val Leu Lys Lys Thr Thr Pro Met Lys
225                 230                 235                 240

Pro Cys Tyr Gly Ser Tyr Ala Arg Pro Thr Asn Ala Asn Gly Gly Gln
                245                 250                 255

Gly Val Leu Val Glu Lys Asp Gly Gly Lys Met Glu Ser Gln Val Asp
            260                 265                 270

Met Gln Phe Phe Ser Thr Ser Glu Asn Ala Arg Asn Glu Ala Asn Asn
        275                 280                 285

Ile Gln Pro Lys Leu Val Leu Tyr Ser Glu Asp Val His Met Glu Thr
        290                 295                 300

Pro Asp Thr His Ile Ser Tyr Lys Pro Ala Lys Ser Asp Asp Asn Ser
305                 310                 315                 320

Lys Val Met Leu Gly Gln Gln Ser Met Pro Asn Arg Pro Asn Tyr Ile
                325                 330                 335

Gly Phe Arg Asp Asn Phe Ile Gly Leu Met Tyr Tyr Asn Ser Thr Gly
                340                 345                 350

Asn Met Gly Val Leu Ala Gly Gln Ala Ser Gln Leu Asn Ala Val Val
            355                 360                 365

Asp Leu Gln Asp Arg Asn Thr Glu Leu Ser Tyr Gln Leu Leu Leu Asp
        370                 375                 380

Ser Met Gly Asp Arg Thr Arg Tyr Phe Ser Met Trp Asn Gln Ala Val
385                 390                 395                 400

Asp Ser Tyr Asp Pro Asp Val Arg Ile Ile Glu Asn His Gly Thr Glu
                405                 410                 415

Asp Glu Leu Pro Asn Tyr Cys Phe Pro Leu Gly Gly Ile Gly Val Thr
            420                 425                 430

Asp Thr Tyr Gln Ala Ile Lys Thr Asn Gly Asn Gly Asn Gly Gly Gly
        435                 440                 445

Asn Thr Thr Trp Thr Lys Asp Glu Thr Phe Ala Asp Arg Asn Glu Ile
        450                 455                 460

Gly Val Gly Asn Asn Phe Ala Met Glu Ile Asn Leu Ser Ala Asn Leu
465                 470                 475                 480

Trp Arg Asn Phe Leu Tyr Ser Asn Val Ala Leu Tyr Leu Pro Asp Lys
                485                 490                 495

Leu Lys Tyr Asn Pro Ser Asn Val Glu Ile Ser Asp Asn Pro Asn Thr
            500                 505                 510

Tyr Asp Tyr Met Asn Lys Arg Val Val Ala Pro Gly Leu Val Asp Cys
        515                 520                 525

Tyr Ile Asn Leu Gly Ala Arg Trp Ser Leu Asp Tyr Met Asp Asn Val
530                 535                 540

Asn Pro Phe Asn His His Arg Asn Ala Gly Leu Arg Tyr Arg Ser Met
545                 550                 555                 560

Leu Leu Gly Asn Gly Arg Tyr Val Pro Phe His Ile Gln Val Pro Gln
                565                 570                 575

```
Lys Phe Phe Ala Ile Lys Asn Leu Leu Leu Pro Gly Ser Tyr Thr
                580                 585                 590

Tyr Glu Trp Asn Phe Arg Lys Asp Val Asn Met Val Leu Gln Ser Ser
        595                 600                 605

Leu Gly Asn Asp Leu Arg Val Asp Gly Ala Ser Ile Lys Phe Glu Ser
    610                 615                 620

Ile Cys Leu Tyr Ala Thr Phe Phe Pro Met Ala His Asn Thr Ala Ser
625                 630                 635                 640

Thr Leu Glu Ala Met Leu Arg Asn Asp Thr Asn Asp Gln Ser Phe Asn
                645                 650                 655

Asp Tyr Leu Ser Ala Ala Asn Met Leu Tyr Pro Ile Pro Ala Asn Ala
        660                 665                 670

Thr Asn Val Pro Ile Ser Ile Pro Ser Arg Asn Trp Ala Ala Phe Arg
    675                 680                 685

Gly Trp Ala Phe Thr Arg Leu Lys Thr Lys Glu Thr Pro Ser Leu Gly
690                 695                 700

Ser Gly Phe Asp Pro Tyr Tyr Thr Tyr Ser Gly Ser Ile Pro Tyr Leu
705                 710                 715                 720

Asp Gly Thr Phe Tyr Leu Asn His Thr Phe Lys Lys Val Ser Val Thr
                725                 730                 735

Phe Asp Ser Ser Val Ser Trp Pro Gly Asn Asp Arg Leu Leu Thr Pro
        740                 745                 750

Asn Glu Phe Glu Ile Lys Arg Ser Val Asp Gly Glu Gly Tyr Asn Val
    755                 760                 765

Ala Gln Cys Asn Met Thr Lys Asp Trp Phe Leu Ile Gln Met Leu Ala
770                 775                 780

Asn Tyr Asn Ile Gly Tyr Gln Gly Phe Tyr Ile Pro Glu Ser Tyr Lys
785                 790                 795                 800

Asp Arg Met Tyr Ser Phe Phe Arg Asn Phe Gln Pro Met Ser Arg Gln
                805                 810                 815

Val Val Asp Glu Thr Lys Tyr Lys Asp Tyr Gln Gln Val Gly Ile Ile
        820                 825                 830

His Gln His Asn Asn Ser Gly Phe Val Gly Tyr Leu Ala Pro Thr Met
    835                 840                 845

Arg Glu Gly Gln Ala Tyr Pro Ala Asn Phe Pro Tyr Pro Leu Ile Gly
850                 855                 860

Lys Thr Ala Val Asp Ser Val Thr Gln Lys Lys Phe Leu Cys Asp Arg
865                 870                 875                 880

Thr Leu Trp Arg Ile Pro Phe Ser Ser Asn Phe Met Ser Met Gly Ala
                885                 890                 895

Leu Thr Asp Leu Gly Gln Asn Leu Leu Tyr Ala Asn Ser Ala His Ala
        900                 905                 910

Leu Asp Met Thr Phe Glu Val Asp Pro Met Asp Glu Pro Thr Leu Leu
    915                 920                 925

Tyr Val Leu Phe Glu Val Phe Asp Val Val Arg Val His Gln Pro His
930                 935                 940

Arg Gly Val Ile Glu Thr Val Tyr Leu Arg Thr Pro Phe Ser Ala Gly
945                 950                 955                 960

Asn Ala Thr Thr

<210> SEQ ID NO 55
<211> LENGTH: 584
<212> TYPE: PRT
<213> ORGANISM: Adenoviridae - Mastadenovirus
```

<400> SEQUENCE: 55

Met Arg Arg Ala Ala Met Tyr His Glu Gly Pro Pro Ser Tyr Glu
1               5                   10                  15

Ser Val Val Gly Ala Ala Ala Ser Pro Phe Ala Ser Gln Leu Glu
            20                  25                  30

Pro Pro Tyr Val Pro Pro Arg Tyr Leu Arg Pro Thr Gly Gly Arg Asn
        35                  40                  45

Ser Ile Arg Tyr Ser Glu Leu Ala Pro Leu Tyr Asp Thr Thr Arg Val
    50                  55                  60

Tyr Leu Val Asp Asn Lys Ser Ala Asp Val Ala Ser Leu Asn Tyr Gln
65                  70                  75                  80

Asn Asp His Ser Asn Phe Leu Thr Thr Val Ile Gln Asn Asn Asp Tyr
                85                  90                  95

Thr Pro Ser Glu Ala Ser Thr Gln Thr Ile Asn Leu Asp Asp Arg Ser
            100                 105                 110

His Trp Gly Gly Asp Leu Lys Thr Ile Leu His Thr Asn Met Pro Asn
            115                 120                 125

Val Asn Glu Phe Met Phe Thr Asn Lys Phe Lys Ala Arg Val Met Val
130                 135                 140

Ser Arg Ser His Thr Lys Asp Asp Arg Val Glu Leu Lys Tyr Glu Trp
145                 150                 155                 160

Val Glu Phe Glu Leu Pro Glu Gly Asn Tyr Ser Glu Thr Met Thr Ile
                165                 170                 175

Asp Leu Met Asn Asn Ala Ile Val Glu His Tyr Leu Lys Val Gly Arg
            180                 185                 190

Gln Asn Gly Val Leu Glu Ser Asp Ile Gly Val Lys Phe Asp Thr Arg
        195                 200                 205

Asn Phe Arg Leu Gly Leu Asp Pro Val Thr Gly Leu Val Met Pro Gly
210                 215                 220

Val Tyr Thr Asn Glu Ala Phe His Pro Asp Ile Ile Leu Leu Pro Gly
225                 230                 235                 240

Cys Gly Val Asp Phe Thr Tyr Ser Arg Leu Ser Asn Leu Leu Gly Ile
                245                 250                 255

Arg Lys Arg Gln Pro Phe Gln Glu Gly Phe Arg Ile Thr Tyr Glu Asp
            260                 265                 270

Leu Glu Gly Gly Asn Ile Pro Ala Leu Leu Asp Val Glu Ala Tyr Gln
        275                 280                 285

Asp Ser Leu Lys Glu Glu Ala Gly Glu Gly Ser Gly Gly Gly
290                 295                 300

Gly Ala Gly Gln Glu Glu Gly Ala Ser Ser Glu Ala Ser Ala Asp
305                 310                 315                 320

Ala Ala Ala Ala Glu Ala Glu Ala Ala Asp Pro Ala Met Val Val
            325                 330                 335

Glu Glu Glu Lys Asp Met Asn Asp Glu Ala Val Arg Gly Asp Thr Phe
            340                 345                 350

Ala Thr Arg Gly Glu Glu Lys Lys Ala Glu Ala Glu Ala Ala Glu
            355                 360                 365

Glu Ala Ala Ala Ala Ala Ala Val Glu Ala Ala Glu Ala
            370                 375                 380

Glu Lys Pro Pro Lys Glu Pro Val Ile Lys Ala Leu Thr Glu Asp Ser
385                 390                 395                 400

Lys Lys Arg Ser Tyr Asn Val Leu Lys Asp Ser Thr Asn Thr Ala Tyr

```
                    405                 410                 415
Arg Ser Trp Tyr Leu Ala Tyr Asn Tyr Gly Asp Pro Ala Thr Gly Val
            420                 425                 430

Arg Ser Trp Thr Leu Leu Cys Thr Pro Asp Val Thr Cys Gly Ser Glu
            435                 440                 445

Gln Val Tyr Trp Ser Leu Pro Asp Met Met Gln Asp Pro Val Thr Phe
        450                 455                 460

Arg Ser Thr Arg Gln Val Ser Asn Phe Pro Val Val Gly Ala Glu Leu
465                 470                 475                 480

Leu Pro Val His Ser Lys Ser Phe Tyr Asn Asp Gln Ala Val Tyr Ser
                485                 490                 495

Gln Leu Ile Arg Gln Phe Thr Ser Leu Thr His Val Phe Asn Arg Phe
            500                 505                 510

Pro Glu Asn Gln Ile Leu Ala Arg Pro Pro Ala Pro Thr Ile Thr Thr
        515                 520                 525

Val Ser Glu Asn Val Pro Ala Leu Thr Asp His Gly Thr Leu Pro Leu
    530                 535                 540

Arg Asn Ser Ile Gly Gly Val Gln Arg Val Thr Val Thr Asp Ala Arg
545                 550                 555                 560

Arg Arg Thr Cys Pro Tyr Val Tyr Lys Ala Leu Gly Ile Val Ser Pro
                565                 570                 575

Arg Val Leu Ser Ser Arg Thr Phe
            580

<210> SEQ ID NO 56
<211> LENGTH: 1734
<212> TYPE: DNA
<213> ORGANISM: Adenoviridae - Mastadenovirus

<400> SEQUENCE: 56
atgaagcgcg ccaaaacgtc tgacgagacc ttcaaccccg tgtaccccta tgacacggaa        60
aacgggcctc cctccgtccc tttcctcacc cctcccttcg tgtccccga cggatttcaa       120 gaaagccccc caggggtcct gtctctgcgc ctgtcagagc cctggtcac ttcccacggc        180 atgcttgccc tgaaaatggg aaatggcctc tccctggatg acgccggcaa cctcacctct       240
caagatgtca ccaccgtcac ccctcccctc aaaaaaacca agaccaacct cagcctccag       300
acctcagccc cctgaccgt tagctctggg tccctcaccg tcgcggccgc cgctccactg       360
gcggtggccg gcacctctct caccatgcaa tctcaggccc ccttgacagt gcaagatgca       420
aaactcggcc tggccaccca gggacccctg accgtgtctg aaggcaaact caccttgcag       480
acatcggctc cactgacggc cgctgacagc agcactctca ctgttagtgc cacacctccc       540
ctcagcacaa gcaatggtag tttgagcatt gacatgcagg ccccgattta taccaccaat       600
ggaaaactgg cacttaacat tggtgctccc ctgcatgtgg tagacaccct aaatgcacta       660
actgtagtaa ctggccaggg tcttaccata aatggaagag ccctgcaaac tagagtcacg       720
ggtgccctca gttatgacac agaaggcaac atccaactgc aagccggagg gggtatgcgc       780
attgacaata atggccaact tatccttaat gtagcttatc catttgatgc tcaaaacaac       840
ctcagcctta gacttggcca aggtcccta attgttaact ctgccacaa cttggatctt       900 aaccttaaca gaggccttta cttatttaca tctggaaaca cgaaaaaact ggaagttaac       960
ataaaaacag ccaaaggtct attttacgat ggcaccgcta tagcaatcaa tgcaggtgac      1020
gggctacagt ttgggtctgg ttcagataca aatccattgc aaactaaact ggattgggg       1080
```

```
ctggaatatg actccaacaa agctataatc actaaacttg gaactggcct aagctttgac      1140
aacacaggtg ccatcacagt aggcaacaaa aatgatgaca agcttacctt gtggaccaca      1200
ccagacccct ccccaaactg cagaattaat tcagaaaaag atgctaaact cacactagtt      1260
ttgactaaat gcggcagcca ggtgttagcc agcgtttctg ttttatctgt aaaaggcagc      1320
cttgccccca tcagcggcac agtaactagc gcccagattg ttttaagatt tgatgaaaac      1380
ggagttttat tgagcaattc ttctcttgac ccccaatact ggaactatag aaaaggcgat      1440
tctacagaag gcactgcata tactaatgct gtgggattta tgcccaacct cacagcatac      1500
cctaaaacac agagccagac tgctaaaagc aacattgtaa gtcaagttta cttgaatggg      1560
gacaaaacaa aacccatgac cctaaccatc accctcaatg aactaatga aacagggat       1620 gctacagtaa gcacatactc catgtcattt tcatggaact ggaatggaag taattacatt      1680
aatgacacct tccaaaccaa ctcctttacc ttctcctaca tcgcccaaga ataa            1734

<210> SEQ ID NO 57
<211> LENGTH: 2868
<212> TYPE: DNA
<213> ORGANISM: Adenoviridae - Mastadenovirus

<400> SEQUENCE: 57
atggcgaccc catcgatgat gccgcagtgg tcgtacatgc acatctcggg ccaggacgcc       60
tcggagtacc tgagccccgg gctggtgcag ttcgcccgcg ccaccgacag ctacttcagc      120
ctgagtaaca agtttaggaa ccccacggtg gcgcccacgc acgatgtgac caccgaccgg      180
tcccagcgcc tgacgctgcg gttcatcccc gtggaccgcg aggacaccgc gtactcttac      240
aaggcgcggt tcaccctggc cgtgggcgac aaccgcgtgc tggacatggc ctccacctac      300
tttgacatcc gcgcgtgct ggacaggggc cccacccttta gccctactc cggcactgcc      360 tacaactccc tggccccaa gggcgccccc aaccctgtg agtgggatga agccgttact       420
gctgttgaca ttaacctgga tgagctcggc gaagatgaag acgacgccga aggggaagca      480
gaacagcaaa aaagtcatgt atttggtcaa gcgccctact caggacaaaa cattcgaag       540 gagggcatac aaattggggt agataccacc agccaagccc aaacaccttt atacgctgac      600
aaaacattcc aacccgaacc tcaggttgga gaatcccaat ggaatgagac agaaatcaat      660
tatggagcgg gacgagtgct aaaaaagacc accctcatga accatgcta tgggtcatat       720 gcaagaccta ctaatgaaaa cggcggtcag gcatactgc tggagaaaga gggtggtaaa      780
ccagaaagtc aagttgaaat gcaatttttt tctactactc aggccgccgc ggctggtaat       840
tcagataatc ttactccaaa agttgttttg tatagcgagg atgttcacct ggaaacgcca      900
gatacacaca tttcatatat gcccactagc aacgaagcca attcaagaga actgttggga      960
caacaagcta tgcccaacag acccaactac attgccttca gagacaactt tattggcctt     1020
atgtattaca cagcactgg caacatggga gtgctggcag tcaggcctc acagttgaat       1080 gcagtggtgg acttgcaaga cagaaacaca gaactgtcct accagctctt gcttgattcc      1140
atgggagaca gaaccagata cttttccatg tggaatcagg cggtggacag ttatgatcca      1200
gatgttagaa ttattgaaaa tcatggaact gaagatgagc tgcccaacta ttgtttccc       1260 ctgggcggca taattaacac cgaaacttta actaaagtga aacctaagac tggacaagac      1320
gctcagtggg aaaagatac tgagttttca gagaaaaatg aaataagggt gggaaacaac      1380
ttcgccatgg agattaacct caatgccaac ctgtggagga atttcctgta ctccaacgtg     1440
gccctgtacc tgccagacaa acttaagtac actccagcca acgtgcagat tccagcaac      1500
```

```
tccaactcct acgactacat gaacaagcga gtggtggccc cggggctggt ggactgctac    1560
atcaacctgg gcgcgcgctg gtccctggac tacatggaca cgtcaaccc cttcaaccac    1620 caccgcaatg cgggcctgcg ctaccgctcc atgcttctgg caacgggcg ctacgtgccc    1680 ttccacatcc aggtgcccca gaagttcttt gccatcaaga acctcctcct cctgccgggc    1740
tcctacacct acgagtggaa cttcaggaag gatgtcaaca tggtcctcca gagctctctg    1800
ggtaacgacc tcagggtcga cggggccagc atcaagttcg agagcatctg cctctacgcc    1860
accttcttcc ccatggccca caacacggcc tccacgctcg aggccatgct caggaacgac    1920
accaacgacc agtccttcaa cgactacctc tccgccgcca catgctcta ccccatcccc    1980 gccaacgcca ccaacgtccc catctccatc ccctcgcgca ctgggcggc cttccgcgc    2040 tgggccttca ctcgcctcaa gaccaaggag accccctccc tgggctcggg tttcgacccc    2100
tactacacct actcgggctc catacccta ctggacggaa ccttctacct caaccacacc    2160
ttcaagaagg tctcggtcac cttcgactcc tcggtcagct ggccgggcaa cgaccgcctg    2220 ctcacccca acgagttcga gatcaagcgc tcggtcgacg gggagggcta caacgtggcc    2280
cagtgcaaca tgaccaagga ctggttcctc atccagatgc tggccaacta caacatcggc    2340
tatcagggct tctacatccc agagagctac aaggacagga tgtactcctt ctttaggaac    2400
ttccagccca tgagccggca ggtggtggac gaaaccaagt acaaggacta ccagcaggtg    2460
ggcatcatcc accagcacaa caactcgggc ttcgtgggct acctcgcccc caccatgcgc    2520
gagggacagg cctaccccgc caacttcccc tacccgctca ttggcaagac cgcggtcgac    2580
agcgtcaccc agaaaaagtt cctctgcgac cgcaccctct ggcgcatccc cttctccagc    2640
aacttcatgt ccatgggtgc gctcacggac ctgggccaga acctgctcta tgccaactcc    2700
gcccacgcgc tcgacatgac cttcgaggtc gaccccatgg acgagcccac ccttctctat    2760
gttctgttcg aagtctttga cgtggtccgg gtccaccagc cgcaccgcgg cgtcatcgag    2820
accgtgtacc tgcgcacgcc cttctcggcc ggcaacgcca ccacctaa                2868
```

<210> SEQ ID NO 58
<211> LENGTH: 1749
<212> TYPE: DNA
<213> ORGANISM: Adenoviridae - Mastadenovirus

<400> SEQUENCE: 58

```
atgcggcgcg cggcgatgta ccacgaggga cctcctccct cttatgagag cgtggtgggc     60
gcggcggcgg cctctcccct tgcgtcgcag ctggagccgc cgtacgtgcc tccgcggtac    120
ctgcggccta cgggggggaag aaacagcatc cgttactcgg agctggcgcc cctgtacgac    180
accacccggg tgtacctggt ggacaacaag tcggcggacg tggcctccct gaactaccag    240
aacgaccaca gcaattttt gaccacggtc atccagaaca atgactacac cccgagcgag    300
gccagcaccc agaccatcaa tctggatgac cggtcgcact ggggcggcga cctgaaaacc    360
atcctgcaca ccaacatgcc caacgtgaac gagttcatgt tcaccaataa gttcaaggcg    420
cgggtgatgg tgtcgcgttc gcacaccaag gacgaccggg tggagctgaa gtacgagtgg    480
gtagagttcg agctgcccga gggcaactac tcggagacca tgaccataga cctgatgaac    540
aacgcgatcg tggagcacta tctgaaagtg ggcaggcaga acggggtcct ggagagcgac    600 atcgggtca gttcgacac caggaacttc cgcctgggc tggacccggt caccgggctg    660
gtcatgcccg gggtctacac caacgaggcc ttccaccccg acatcatcct gctgcccggc    720
```

```
tgcggggtgg acttcaccta cagccgcctg agcaacctgc tgggcatccg caagcggcag     780
cccttccagg agggctttag gatcacctac gaggacctgg aggggggcaa catccccgcg     840
ctcctggatg tggaggccta ccagaatagc ttgaaggaag aagaggcggg agagggcagc     900
ggcggcggcg gcgccggtca ggaggagggc ggggcctcct ctgaggcctc tgcggacgca     960
gctgccgccg aggcggagga ggcggccgac cccgcgatgg tggtagagga agagaaggat    1020
atgaatgacg aggcggtgcg cggcgacacc tttgccaccc ggggggagga gaagaaagcg    1080
gaggccgagg ccgcggcaga ggaggcggca gcagcggcg  cggcagtaga ggcggcggcc    1140
gaggcggaga agccccccaa ggagcccgtg attaagcccc tgaccgaaga tagcaagaag    1200
cgcagttaca acgtgctcaa ggacagcacc aacaccgagt accgcagctg gtacctggcc    1260
tacaactacg cgacccggc  gacggggtg  cgctcctgga ccctgctgtg tacgccggac    1320
gtgacctgcg gctcggagca ggtgtactgg tcgctgcccg acatgatgca agaccccgtg    1380
accttccgct ccacgcggca ggtcagcaac tttccggtgg tgggcgccga gctgctgccc    1440
gtgcactcca agagcttcta caacgaccag gccgtctact cccagctcat ccgccagttc    1500
acctctctga cccacgtgtt caatcgcttt cctgagaacc agattctggc gcgcccgccc    1560
gcccccacca tcaccaccgt cagtgaaaac gttcctgctc tcacagatca cgggacgcta    1620
ccgctgcgca acagcatcgg aggagtccag cgagtgaccg taactgacgc cagacgccgc    1680
acctgtccct acgtttacaa ggccctgggc atagtctcgc cgcgcgtcct ttccagccgc    1740
acttttaa                                                             1749

<210> SEQ ID NO 59
<211> LENGTH: 1629
<212> TYPE: DNA
<213> ORGANISM: Adenoviridae - Mastadenovirus

<400> SEQUENCE: 59
atgaagcgcg ccaaaacgtc tgacgagacc ttcaaccccg tgtacccta  tgacacggaa      60
aacgggcctc cctccgttcc tttcctcacc cctcccttcg tgtccccga  cggatttcaa     120
gaaagccccc caggggtcct gtctctgcgc ctgtcagagc cctggtcac  ttcccacggc     180
atgcttgccc tgaaaatggg aaatggcctc tccctggatg acgccggcaa cctcacctct     240
caagatgtca ccaccgtcac ccctcccctc aaaaaaacca agaccaacct cagcctccag     300
acctcagccc ccctgaccgt tagctctggg tccctcaccg tcggccgcgc cgctccactg     360
gcggtggccg gcacctctct caccatgcaa tctcaggccc ccttgacggt gcaagatgca     420
aaactgggtc tggccaccca gggaccctg  accgtgtctg aaggcaaact caccttgcag     480
acatcggctc cactgacggc cgccgacagc agcactctca ctgttggcac cacaccgcca     540
atcagtgtga gcagtggaag tctaggctta gatatggaag accccatgta tactcacgat     600
ggaaaactgg gaatcagaat tggtggccca ctgcaagtag tagacagctt gcacacactc     660
actgtagtta ctggaaacgg aataactgta gctaacaatg cccttcaaac taaagttgcg     720
ggtgccctgg ttatgactc  atctggcaat ctagaattgc gagccgcagg gggtatgcga     780
attaacacag ggggtcaact cattcttgat gtggcttatc catttgatgc tcagaacaat     840
ctcagcctta gactcggcca gggacctta  tatgtgaaca ccaatcacaa cctagattta     900
aattgcaaca gaggtctgac cacaaccacc agcagtaaca accaaaaact gaaactaaa      960
atcgattcgg gcttagacta taacgccaat ggggctatca ttgctaaact ggcactggg     1020
ttaacctttg acaacacagg tgccataact gtgggaaaca ctggggatga caaactcact    1080
```

```
ctgtggacta ccccagatcc ctctcctaac tgcagaattc acgcagacaa agactgcaag    1140
tttactctag tcctgactaa gtgtggaagt caaattctgg cctccgtcgc cgccctggcg    1200
gtgtctggaa acctatcatc aatgacaggc actgtctcca gcgttaccat ctttctcaga    1260
ttcgatcaga atggagttct tatggaaaat tcctcgctag acaaggagta ctggaacttc    1320
agaaatggta attccaccaa tgccaccccc tacaccaatg cggttgggtt catgcccaac    1380
ctcagcgcct accccaaaac ccagagtcaa actgcaaaaa acaacattgt aagtgaggtt    1440
tacttacatg gggacaaatc taaacccatg atccttacca ttacccttaa tggcacaaat    1500
gaatccagtg aaactagtca ggtgagtcac tactccatgt catttacatg gtcctgggac    1560
agtgggaaat atgccaccga aacctttgcc accaactctt ttaccttctc ctacattgct    1620
gaacaataa                                                            1629

<210> SEQ ID NO 60
<211> LENGTH: 2895
<212> TYPE: DNA
<213> ORGANISM: Adenoviridae - Mastadenovirus

<400> SEQUENCE: 60
atggcgaccc catcgatgat gccgcagtgg tcgtacatgc acatctcggg ccaggacgcc      60
tcggagtacc tgagccccgg gctggtgcag ttcgcccgcg ccaccgacag ctacttcagc     120
ctgagtaaca agtttaggaa ccccacggtg gcgcccacgc acgatgtgac caccgaccgg     180
tcccagcgcc tgacgctgcg gttcatcccc gtggaccgcg aggacaccgc gtactcttac     240
aaggcgcggt tcaccctggc cgtgggcgac aaccgcgtgc tggacatggc ctccacctac     300
tttgacatcc gcggcgtgct ggacaggggc cccaccttca gccctactc cggcaccgcc     360 tacaactccc tggcccccaa gggcgccccc aactcctgcg agtgggagca agaggagact     420
cagacagctg aagaggcaca agacgaagaa gaagatgaag ctgaagctga ggaggaaatg     480
cctcaggaag agcaagcacc tgtcaaaaag actcatgtat atgctcaggc tccccttcct     540
ggcgaaaaaa ttactaaaga cggtctgcag ataggaacgg acgctacagc taccgaacaa     600
aaacctattt atgcagatcc cacattccag ccagaacccc aaattggtga atctcagtgg     660
aatgaggcag atgcttcagt tgccggcggt agagtgctga agaaaactac tcccatgaaa     720
ccctgttatg gttcctatgc caggcccaca atgccaatgg aggtcagggt gtattggtg     780 gagaaagacg tggaaagatg gaaagccaa gtagatatgc aattcttttc gacttctgaa     840
aacgcccgta cgaggctaa caacattcag cccaaattgg tgctgtacag cgaggatgtg     900
catatggaga ccccagacac acacatttct tacaagcctg caaaaagcga tgataattcg     960
aaagtcatgc tgggtcagca gtccatgccc aacaggccaa attacatcgg cttcagagac    1020
aactttatcg ggctcatgta ttacaacagc actggcaaca tggggggtgct ggcaggtcag    1080 gcctcacagt tgaatgcggt ggtggacttg caagacagaa acacagaact gtcctaccag    1140
ctcttgcttg attccatggg agacagaacc agatactttt ccatgtggaa tcaggcggtg    1200
gacagttatg atccagatgt cagaattatt gaaaatcatg aactgaaga tgagctgccc    1260 aactattgtt tccctctggg aggcataggg gtaactgaca cttaccaggc cattaagact    1320
aatggcaatg gcaacggcgg gggcaatacc acttggacca aggatgaaac ttttgcagac    1380
cgcaacgaga taggggtggg aaacaatttc gccatggaga tcaacctcag tgccaacctg    1440
tggaggaact tcctctactc caacgtggcc ctgtacctgc cagacaagct taagtacaac    1500
```

```
cgctccaacg tggaaatctc tgacaacccc aacacctacg actacatgaa caagcgagtg   1560
gtggccccgg ggctggtgga ctgctacatc aacctgggcg cgcgctggtc cctggactac   1620
atggacaacg tcaacccctt caaccaccac cgcaacgcgg gcctgcgcta ccgctccatg   1680
cttctgggca cgggcgcta cgtgcccttc cacatccagg tgccccagaa gttcttttgcc   1740 atcaagaacc tcctcctcct gccgggctcc tacacctacg agtggaactt caggaaggat   1800
gtcaacatgg tcctccagag ctctctgggt aacgacctca gggtcgacgg ggccagcatc   1860
aagttcgaga gcatctgcct ctacgccacc ttcttcccca tggcccacaa cacggcctcc   1920
acgctcgagg ccatgctcag gaacgacacc aacgaccagt ccttcaacga ctacctctcc   1980
gccgccaaca tgctctaccc catccccgcc aacgccacca cgttcccat ctccatcccc   2040 tcgcgcaact gggcggcctt ccgcggctgg gccttcaccc gcctcaagac caaggagacc   2100
ccctccctgg gctcgggttt cgaccctac tacacctact cgggctccat accctacctg   2160
gacgaaccct tctacctcaa ccacactttc aagaaggtct cggtcacctt cgactcctcg   2220
gtcagctggc cgggcaacga tcgcctgctc accccaacg agttcgagat caagcgctcg   2280
gtcgacgggg agggctacaa cgtggcccag tgcaacatga ccaaggactg gttcctcatc   2340
caaatgctgg ccaactacaa catcggctat cagggcttct acatcccaga gagctacaag   2400
gacaggatgt actccttctt taggaacttc cagcccatga ccggcaggt ggtggacgaa   2460 accaagtaca aggactacca gcaggtgggc atcatccacc agcacaacaa ctcgggcttc   2520
gtgggctacc tcgcccccac catgcgcgag ggacaggcct accccgccaa cttcccctac   2580
ccgctcattg gcaagaccgc ggtcgacagc gtcacccaga aaaagttcct ctgcgaccgc   2640
accctctggc gcatccctt ctccagcaac ttcatgtcca tgggtgcgct cacggacctg   2700
ggccagaacc tgctctatgc caactccgcc cacgcgctcg acatgaccttc cgaggtcgac   2760 cccatggacg agcccaccct ctctatgtt ctgttcgaag tctttgacgt ggtccgggtc   2820
caccagccgc accgcggcgt catcgagacc gtgtacctgc gcacgccctt ctcggccggc   2880
aacgccacca cctaa                                                    2895

<210> SEQ ID NO 61
<211> LENGTH: 1755
<212> TYPE: DNA
<213> ORGANISM: Adenoviridae - Mastadenovirus

<400> SEQUENCE: 61
atgcggcgcg cggcgatgta ccacgaggga cctcctccct cttatgagag cgtggtgggc     60
gcggcggcgg cctctccctt tgcgtcgcag ctggagccgc cgtacgtgcc tccgcggtac    120
ctgcggccta cggggggaag aaacagcatc cgttactcgg agctggcgcc cctgtacgac    180
accacccggg tgtacctggt ggacaacaag tcggcggacg tggcctccct gaactaccag    240
aacgaccaca gcaattttttt gaccacggtc atccagaaca tgactacac cccgagcgag    300 gccagcaccc agaccatcaa tctggatgac cggtcgcact gggcggcga cctgaaaacc    360 atcctgcaca ccaacatgcc caacgtgaac gagttcatgt tcaccaataa gttcaaggcg    420
cgggtgatgt gtcgcgttc gcacaccaag gacgaccggg tggagctgaa gtacgagtgg    480
gtagagttcg agctgcccga gggcaactac tcggagacca tgaccataga cctgatgaac    540
aacgcgatcg tggagcacta tctgaaaagtg gcaggcaga acggggtcct ggagagcgac    600
atcggggtca agttcgacac caggaacttc cgcctgggc tggaccccggt caccgggctg    660 gtcatgcccg gggtctacac caacgaggcc ttccaccccg acatcatcct gctgcccggc    720
```

```
tgcggggtgg acttcaccta cagccgcctg agcaacctgc tgggcatccg caagcggcag      780
cccttccagg agggctttag gatcacctac gaggacctgg aggggggcaa catccccgcg      840
ctcctggatg tggaggccta ccaggatagc ttgaaggaag aagaggcggg agagggcagc      900
ggcggcggcg gcggcgccgg tcaggaggag gcggggcct cctctgaggc tctgcggac       960 gccgccgctg ccgccgaggc ggaggcggcc gaccccgcga tggtggtaga ggaagagaag     1020
gatatgaatg acgaggcggt gcgcggcgac acctttgcca ccggggggga ggagaagaaa     1080
gcggaggccg aggccgcggc agaggaggcg gcagcggcgg cggcggcggc agtagaggcg     1140
gcggccgagg cggagaagcc ccccaaggag cccgtgatta aggccctgac cgaagatagc     1200
aagaagcgca gttacaacgt gctcaaggac agcaccaaca ccgcgtaccg cagctggtac     1260
ctggcctaca actacggcga cccggcgacg ggggtgcgct cctggaccct gctgtgtacg     1320
ccggacgtga cctgcggctc ggagcaggtg tactggtcgc tgcccgacat gatgcaagac     1380
cccgtgacct tccgctccac gcggcaggtc agcaacttcc cggtggtggg cgccgagctg     1440
ctgcccgtgc actccaagag cttctacaac gaccaggccg tctactccca gctcatccgc     1500
cagttcacct ctctgaccca cgtgttcaat cgctttcctg agaaccagat tctggcgcgc     1560
ccgcccgccc ccaccatcac caccgtcagt gaaaacgttc ctgctctcac agatcacggg     1620
acgctaccgc tgcgcaacag catcggagga gtccagcgag tgaccgtaac tgacgccaga     1680
cgccgcacct gtccctacgt ttacaaggcc ctgggcatag tctcgccgcg cgtcctttcc     1740
agccgcactt tttaa                                                     1755

<210> SEQ ID NO 62
<211> LENGTH: 37776
<212> TYPE: DNA
<213> ORGANISM: Adenoviridae - Mastadenovirus

<400> SEQUENCE: 62
catcatcaat aatataccct attttggatt gaagccaata tgataatgag gtgggcggag      60
cggggcgggg cggggaggag cggcggcgcg gggcgggccg ggaggtgtgg cggaagttga     120
gtttgtaagt gtggcggatg tgacttgcta gcgccggatg tggtaaaagt gacgtttttg     180
gagtgcgaca acgcccacgg gaagtgacat tttttcccgcg gttttttaccg gatgtcgtag     240 tgaatttggg cgttaccaag taagatttgg ccatttttcgc gggaaaactg aaatggggaa     300
gtgaaatctg attaatttcg cgttagtcat accgcgtaat atttgccgag gccgaggga     360 cttttgaccga ttacgtggag gaatcgccca ggtgtttttt gaggtgaatt ccgcgttcc     420 gggtcaaagt ctccgtttta ttattatagt cagctgacgc ggagtgtatt tatacccgct     480
gatctcgtca agaggccact cttgagtgcc agcgagtaga gttttctcct ctgccgctcc     540
gctccgctct gacaccgggg gaaaaatgag acatttcacc tacgatggcg gtgtgcttac     600 cggcagctg gctgcctcgg tcctggacgc cctgattgag gacgtattgg ccgacaatta     660
tcctcctcca gctcattttg agccacctac tcttcacgaa ctgtatgatt tggacgtggt     720
ggcacctagc gacccgaacg agcaggcggt ttccagtttt tttcctgact ctatgctgtt     780
ggccagccag gaggggtcg agctcgagac ccctcctcca atcgccgttt ctcctgagcc     840 tccgacctg accaggcagc ccgatcgccg tgttggacct gcgactatgc ccatctgct       900 gcccgaggtg atcgatctca cctgtaacga gtctggtttt ccaccagcg aggatgagga     960 cgaagagggt gagcagtttg tgttagattc tgtggaggaa cccgggcgcg gttgcagatc    1020
```

```
ttgtcaatac catcggaaaa atacaggaga cccccaaatt atgtgttccc tgtgttatat    1080
gaagacgacc tgtatgttta tttacagtaa gtttgtgatt ggtgggtcgg tgggctgtag    1140
tgtgggtagg tggtctgtgg ttttttttt ttttaatatc agcttgggct aaaaaactgc    1200
tatggtaatt tttttaaggt ccggtgtctg aacctgagca ggaagctgaa ccggagcctg    1260
agagtcgccc caggagaagg cctgcaattc taactagacc gagtgcacct gtagcgaggg    1320
acctcagcag tgcagagacc accgattccg gtccttcctc atcccctcca gagattcatc    1380
ccgtggtgcc tttgtgtccc ctcaagcccg ttgccgtgag agttagtggg cggagggccg    1440
ccgtggagag cattgaggac ttgcttaatg agacacagga acctttggac ttgagctgta    1500
aacgccctag gcaataaacc tgcttacctg gactgaatga gttgacgcct atgtttgctt    1560
ttgaatgact taatgtgtat ataataaaga gtgagataat gtttaattgc atggtgtgtt    1620
tgattggggc ggggtttgtt gggtatataa gcttccctgg gctaaacttg gttacacttg    1680
acctcatgga ggcctgggag tgtttagaga gctttgccga agtgcgtgcc ttgctggaag    1740
agagctctaa taatacctct gggtggtgga ggtattttg gggctctccc caggctaagt    1800
tagtttgtag aatcaaggag gattacaagt gggaatttga acagcttttg aaatcctgtg    1860
gtgagctctt ggattctttg aatctgggcc accaggctct tttccaggac aagatcatca    1920
ggactttgga tttttccaca ccggggcgca ttgctgccgg ggttgctttt ctagcttttt    1980
tgaaggataa atggagcgaa gagacccact tgagttcggg atacgtcctg gattttctgg    2040
ccatacaact gtggagagca tggatcaggc acaagaacag aatgcaactg ttgtcttccg    2100
tccgtccgtt gctgattcag ccggaggagc agcagaccgg gccggaggac cgggctcgtc    2160
tggaaccaga agagagggcg ccggagagga gcgcgtggaa cctgggagcc ggcctgaacg    2220
gccatccaca tcgggagtga atgttggaca ggtggcggat ctctttccag aactgcgacg    2280
aatcttaact atcagggagg atggacaatt tgttaagggg cttaagaggg agcgggggc    2340 ttctgaacat aacgaggagg ccagtaattt agcttttagt ctgatgacca gacaccgtcc    2400
cgagtgcatt acttttcagc agattaagga taattgtgcc aatgagttag atctgctggg    2460
tcagaagtac agcatagagc agttgaccac ttactggctg cagccgggtg atgatctgga    2520
ggaagctatt agggtgtatg ccaaggtggc cctgaggccc gattgcaagt acaagctcaa    2580
ggggctggtg aatatcagga attgttgcta catttctggg aacggggcgg aggtggagat    2640
agagaccgat gacagggtgg cctttaggtg cagcatgatg aatatgtggc ctggggtgct    2700
gggcatggac ggggtggtga ttatgaatgt gaggttcacg gggcccaatt ttaatggcac    2760
ggtgttcctg ggcaacacca acttggtgct gcacggggtg agcttctatg ctttaacaa    2820 cacctgtgtg gaggcctgga ccgatgtgaa ggtccgtggc tgtgccttct acggatgttg    2880
gaaggcggta gtgtgtcgcc ccaagagcag gagttccatt aaaaaatgct tgtttgagag    2940
gtgcaccctg ggggtgctgg cggagggcaa ctgtcgggtg cgccacaatg tggcctcaga    3000
atgcggttgc ttcatgctag tcaagagcgt ggcggtcatc aagcataaca tggtgtgcgg    3060
caacagcgag gacaaggcct cgcagatgct gacctgctcg gatggcaact gccacttact    3120
gaagaccgta catataacca gccacagccg caaggcctgg cccgtgttcg agcacaacgt    3180
gttgacccgc tgctctttgc atctgggcaa caggaggggt gtgttcctgc cctatcaatg    3240
caacttgagc cacaccaaga tcttgctaga gcccgaaagc atgtccaagg tgaacctgaa    3300
cggggtgttt gacatgaccc tgaagatatg gaaggtgctg aggtacgacg agaccaggtc    3360
tcgatgcagg ccctgcgagt gcggggggcaa gcatatgagg aaccagcctg tgatgctgga    3420
```

```
tgtgaccgag gagctgaggc ctgaccactt ggttctggcc tgcaccaggg ccgagtttgg    3480
ttctagcgat gaagacacag actgaggtgg gtgagtgggc gtggtctggg ggtgggaagc    3540
aatatataag ttgggggtct tagggtctct gtgtctgttt tgcagaggga ccgccggcgc    3600
catgagcggg agcagtagca gcaacgcctt ggatggcagc atcgtgagcc cttatttgac    3660
gacgcgcatg ccccactggg ccggggtgcg tcagaatgtg atgggctcca gcatcgacgg    3720 acgaccgtg ctgcccgcaa attccgccac gctgacctac gcgaccgtcg cggggacccc    3780
gttggacgcc accgccgccg ccgccgccac cgccgccgcc tcggccgtgc gcagcctggc    3840
cacggacttt gcattcttgg gacccttggc caccggggcg ccgcccgtg ccgccgttcg    3900 cgatgacaag ctgaccgccc tgctggcgca gttggatgcg cttacccggg aactgggtga    3960
cctttcgcag caggtcgtgg ccctgcgcca gcaggtctcc gccctgcagg ctagcgggaa    4020
tgcttctcct gcaaatgccg tttaagataa ataaaaccag actctgtttg gattaaagaa    4080
aagtagcaag tgcattgctc tctttatttc ataattttcc gcgcgcgata ggcccgagtc    4140
cagcgttctc ggtcgttgag ggtgcggtgt atcttctcca ggacgtggta gaggtggctc    4200
tggacgttga gatacatggg catgagcccg tcccgggggt ggaggtagca ccactgcaga    4260
gcttcatgct ccggggtggt gttgtagatg atccagtcgt agcaggagcg ctgggcatgg    4320
tgcctaaaaa tgtccttaag cagcaggccg atggccaggg ggaggcccct ggtgtaagtg    4380
tttacaaaac ggttgagttg ggaagggtgc atgcggggtg agatgatgtg catcttagat    4440 tgtatttta gattggcgat gtttcctccc agatcccttc tgggattcat gttgtggagg    4500
accaccagca cagtatatcc ggtgcacttg ggaaatttgt catgcagctt agagggaaat    4560
gcgtggaaga acttggagac gcccttgtgg cctcccagat tctccatgca ttcgtccatg    4620
atgatggcaa tgggcccgcg ggaggcggcc tgggcaaaga tgtttctggg gtcactgaca    4680
tcgtagttgt gttccagggt gagatcgtca taggccattt ttataaagcg cgggcggagg    4740
gtgcccgact gggggatgat ggttccctcg ggccccgggg cgtagttgcc ttcgcagatc    4800
tgcatttccc aggccttaat ctctgagggg ggaatcatat ccacttgcgg ggcgatgaag    4860
aaaacggttt ccggagccgg ggagattaac tgggatgaga gcaggtttct cagcagctgt    4920
gactttccac agccggtggg gccataaata acacctataa ccggctgcag ctggtagttg    4980
agcgagctgc agctgccgtc gtcccggagg aggggggcca cctcattgag catgtcccgg    5040
acgcgcttgt tctcctcgac caggtccgcc agaaggcgct cgccgcccag ggacagcagc    5100
tcttgcaagg aagcaaagtt tttcagcggc ttgaggccgt ccgccgtggg catgtttttc    5160
agggtctggc cgagcagctc caggcggtcc cagagctcgg tgacgtgctc tacggcatct    5220
ctatccagca tatctcctcg tttgcgggt tgggcggct ttcgctgtag ggcaccaggc    5280
gatggtcgtc cagcgcggcc agagtcatgt ccttccatgg gcgcagggtc ctcgtcaggg    5340
tggtctgggt cacggtgaag gggtgcgccc cggctgggc gctggccagg gtgcgcttga    5400
gactggtcct gctggtgctg aagcgctgcc ggtcttcgcc ctgcgcgtcg ccaggtagc    5460 atttgaccat ggtgtcgtag tccagcccct ccgcggcgtg tcccttggcg cgcagcttgc    5520
ccttggaggt ggcgccgcac gcggggcact gcaggtcttt gagcgcgtag agcttggggg    5580
cgaggaagac cgattcgggg gagtaggcgt ccgcgccgca ggcccccgcac acggtctcgc    5640 actccaccag ccaggtgagc tcggggcgct cggggtcaaa aaccaggttt cccccatgct    5700
ttttgatgcg tttcttacct cgggtctcca tgaggcggtg tccccgctcg gtgacgaaga    5760
```

```
ggctgtccgt gtctccgtag accgacttga ggggtctgtc ctccaggggg gtccctcggt   5820
cctcttcgta gagaaactcg gaccactctg agacgaaggc ccgcgtccag gccaggacga   5880
aggaggccag gtgggagggg tagcggtcgt tgtccactag ggggtccacc ttctccaagg   5940
tgtgaagaca catgtcgccc tcctcggcgt ccaggaaggt gattggcttg taggtgtagg   6000
ccacgtgacc cggggttccg gacgggggggg tataaaaggg ggtgggggcg cgctcgtcct   6060
cactctcttc cgcatcgctg tctgcgaggg ccagctgctg gggtgagtat tccctctcga   6120
aggcgggcat gacctcagcg ctgaggctgt cagtttctaa aaacgaggag gatttgatgt   6180
tcacctgtcc cgagctgatg cctttgaggg tgcccgcgtc catctggtca gaaaacacga   6240 tcttttatt gtccagcttg gtggcgaacg acccgtagag ggcgttggag agcagcttgg   6300
cgatggagcg cagggtctga ttcttgtccc ggtcggcgcg ctccttggcc gcgatgttga   6360
gctgcacgta ctcgcgcgcg acgcagcgcc actcggggaa gacggtggtg cgctcgtcgg   6420
gcaccaggcg cacgcgccag ccgcggttgt gcagggtgac gaggtccacg ctggtggcga   6480
cctcgccgcg caggcgctcg ttggtccagc agaggcgccc gccccttgcgc gagcagaagg   6540 ggggcagggg gtcgagttgg gtttcgtccg ggggtccgc gtccaccgtg aagaccccgg   6600
ggcgcaggcg cgcgtcgaag tagtcgatct tgcatccttg caagtccagc gcctgctgcc   6660
agtcgcgggc ggcgagcgcg cgctcgtagg ggttgagcgg cgggcccag ggcatggggt   6720 gggtgagcgc ggaggcgtac atgccgcaga tgtcatagac gtagaggggc tcccggagga   6780
tgcccaggta ggtggggtag cagcggccgc cgcggatgct ggcgcgcacg tagtcgtaga   6840
gctcgtgcga ggggcgagg aggtcgggc ccaggttggt gcgggcgggg cgctccgcgc   6900
ggaagacgat ctgcctgaag atggcatgcg agttggaaga gatggtgggg cgctggaaga   6960
cgttgaagct ggcgtcctgc aggccgacgg cgtcgcgcac gaaggaggcg taggactcgc   7020
gcagcttgtg caccagctcg gcggtgacct gcacgtcgag cgcgcagtag tcgagggtct   7080
cgcggatgat gtcatactta gcctgcccct tctttttcca cagctcgcgg ttgaggacga   7140
actcttcgcg gtctttccag tactcttgga tcgggaaacc gtccggctcc gaacggtaag   7200
agcccagcat gtagaactgg ttgacggcct ggtaggcgca gcagcccttc tccacgggca   7260
gggcgtaggc ctgcgcggcc ttgcggagcg aggtgtgggt cagggcgaag gtgtccctga   7320
ccatgacctt gaggtactgg tgtttgaagt cggagtcgtc gcagccgccc cgctcccaga   7380
gcgagaagtc ggtgcgcttt ttggagcggg ggttgggcag cgcgaaggtg acatcgttgt   7440
agaggatctt gcccgcgcga ggcatgaagt tgcgggtgat gcggaagggc cccggcactt   7500
ccgagcggtt gttgatgacc tgggcggcga gcacgatctc gtcgaagccg ttgatgttgt   7560
ggcccacgat gtagagttcc aggaagcggg gccggccctt gacgctgggc agcttctttta   7620 gctcttcgta ggtgagctcc tcgggcgagg cgaggccgtg ctcggccagg gcccagtccg   7680
ccaggtgcgg gttgtccgcg aggaaggacc gccagaggtc gcgggccagg agggtctgca   7740
ggcggtccct gaaggtcctg aactggcggc ctacggccat ctttttcgggg gtgacgcagt   7800 agaaggtgag ggggtcttgc tgccaggggt cccagtcgag ctccagggcg aggtcgcgcg   7860
cggcggcgac caggcgctcg tcgcccccga atttcatgac cagcatgaag ggcacgagct   7920
gctttccgaa ggcgcccatc caagtgtagg tctctacatc gtaggtgaca aagagacgtt   7980
ccgtgcgagg atgcgagccg atcgggaaga actggatctc ccgccaccag ttggaggagt   8040
ggctgttgat gtggtgaaag tagaagtccc gtcggcgggc cgagcactcg tgctggcttt   8100
tgtaaaagcg agcgcagtac tggcagcgct gcacgggctg tacctcttgc acgagatgca   8160
```

```
cctgccgacc gcggacgagg aagctgagtg ggaatctgag ccccccgcat ggctcgcggc    8220
ctggctggtg ctcttctact ttggatgcgt ggccgtcacc gtctggctcc tcgaggggtg    8280
ttacggtgga gcggatcacc acgccgcgcg agccgcaggt ccagatatcg gcgcgcggcg    8340
gtcggagttt gatgacgaca tcgcgcagct gggagctgtc catggtctgg agctcccgcg    8400
gcggcggcag gtcagccggg agttcttgca ggtttacctc gcagagacgg gccagggcgc    8460
ggggcaggtc caggtggtac ttgaattcga gaggcgtgtt ggtggcggcg tcgatggctt    8520
gcaggaggcc gcagcccggg ggcgcgacga cggtgccccg cggggcggtg aagctcccgc    8580
cgccgctcct gctgtcgccg ccggtggcgg ggcttagaag cggtgccgcg gtcgggcccc    8640
cggaggtagg gggggctccg gtcccgcggg caggggcggc agcggcacgt cggcgccgcg    8700
cgcgggcagg agctggtgct gcgcccggag gttgctggcg aaggcgacga cgcggcggtt    8760
gatctcctgg atctggcgcc tctgcgtgaa gacgacgggt ccggtgagct tgaacctgaa    8820
agagagttcg acagaatcaa tctcggtgtc attgaccgcg acctggcgca ggatctcctg    8880
cacgtcgccc gagttgtctt ggtaggcgat ctcggccatg aactgttcga tctcttcctc    8940
ctggaggtct ccgcgtccgg cgcgctccac ggtggccgcc aggtcgttgg agatgcgcgc    9000
catgagctgc gagaaggcgt tgagtccgcc ctcgttccag actcggctgt agaccacgcc    9060
gccctggtcg tcgcgggcgc gcatgaccac ctgcgcgagg ttgagttcca cgtggcgcgc    9120
aaagacggcg tagttgcgca ggcgctggaa gaggtagttg agggtggtgg cggtgtgctc    9180
ggccacgaag aagtacatga cccagcgcgc caacgtggat tcgttgatgt cccccaaggc    9240
ctccagtcgc tccatggcct cgtagaagtc cacggcgaag ttgaaaaact gggagttgcg    9300
cgccgacacg gtcaactcct cctccagaag acggatgagc tcggcgacgg tgtcgcgcac    9360
ctcgcgctcg aaggctatgg gaatctcttc ctccgccagc atcaccacct cttcctcttc    9420
ttcctcctct ggcacttcca tgatggcttc ctcctcttcg gggggtggcg gcggggagg    9480 gggcgctcgg cgccggcggc ggcgcaccgg gaggcggtcc acgaagcgct cgatcatctc    9540
cccgcggcgg cgacgcatgg tctcggtgac ggcgcggccg ttctctcggg gacgcagctg    9600
gaagacgccg ccggtcatct ggtgctgggg cgggtggccg tggggcagcg agaccgcgct    9660
gacgatgcat cttaacaatt gctgcgtagg tacgccgccg agggacctga gggagtccag    9720
atccaccgga tccgaaaacc tttcgaggaa ggcatctaac cagtcgcagt cgcaaggtag    9780
gctgagcacc gtggcgggcg gcggggggtg ggggagtgt ctggcggagg tgctgctgat    9840
gatgtaattg aagtaggcgg tcttgacacg gcggatggtc gacaggagca ccatatcttt    9900
gggcccggcc tgctggatgc ggaggcggtc ggccatgccc caggcttcgt tctggcatct    9960
gcgcaggtct ttgtagtagt cttgcatgag cctttccacc ggcacctctt ctccttcttc   10020
ttctgacatc tctgctgcat ctgcggccct ggggcgacgg cgcgcgcccc tgccccccat   10080
gcgcgtcacc ccgaacccc tgagcggctg gagcagggcc aggtcggcga cgacgcgctc   10140
ggccaggatg gcctgctgga cctgcgtgag ggtggtttgg aagtcatcca agtccacgaa   10200
gcggtggtag gcgcccgtgt tgatggtgta ggtgcagttg gccatgacgg accagttgac   10260
ggtctggtgg cccggttgcg tcatctcggt gtacctgagg cgcgagtagg cgcgcgagtc   10320
gaagatgtag tcgttgcaag tccgcaccag gtactggtag cccaccagga agtgcgggcgg   10380 cggctggcgg tagaggggcc agcggagggt ggcggggct ccgggggcca ggtcttccag   10440
catgaggcgg tggtattcgt agatgtacct ggacatccag gtgatgcccg cggcggtggt   10500
```

```
ggaggcgcgc gggaagtcgc gcacccggtt ccagatgttg cgcagcggca gaaagtgctc   10560
catggtaggc gtgctctggc cggtcaggcg cgcgcagtcg ttgatactct agaccaggga   10620
aaacgaaagc cggtcagcgg gcactcttcc gtggtctggt ggataaattc gcaagggtat   10680
catggcggag ggcctcggtt cgagcccggg gcccgggccg gacggtccgc catgatccac   10740
gcggttaccg cccgcgtgtc gaacccaggt ggcgacgtca gacaacggtg gagtgttcct   10800
tttgggtttt ttttaatttt tctggccggg cgccgacgcc gccgcgtaag agactagagt   10860
gcaaaagcga aagcagtaag tggctcgctc cctgtagccc ggaggatcct tgctaagggt   10920
tgcgttgcgg cgaaccccgg ttcgagtctg gctctcgctg ggccgctcgg gtcggcggga   10980
accgcggcta aggcgggatt ggcctccccc tcattaaaga ccccgcttgc ggattcctcc   11040
ggacacaggg gacgagcccc tttttacttt tgcttttctc agatgcatcc ggtgctgcgg   11100
cagatgcgcc ccccgcccca gcagcagcag cagcaacatc agcaagagcg gcaccagcag   11160
cagcgggagt catgcagggc cccctcgccc acgctcggcg gtccggcgac ctcggcgtcc   11220
gcggccgtgt ctggagccgg cggcggtggg ctggcggacg accggaggga gccccgcgcg   11280
cgcagggcca gacagtacct ggacctggag gagggcgagg gcctggcgcg actgggggcg   11340
ccgtcccccg agcgccaccc gcgggtgcag ctgaagcgcg actcgcgcga ggcgtacgtg   11400
cctcggcaga acctgttcag agaccgcgcg ggcgaggagc ccgaggagat gcgggaccgc   11460
aggttcgccg cggggcggga gctgcggcag gggctgaacc gggagcggct gctgcgcgag   11520
gaggactttg agcccgacgc gcggacgggg atcagccccg cgcgcgcgca cgtggcggcc   11580
gccgacctgg tgacgcgta cgagcagacg gtgaaccagg agatcaactt ccaaaaaagc   11640
ttcaacaacc acgtgcgcac gctggtggcg cgcgaggagg tgaccatcgg cctgatgcac   11700
ctgtgggact tgtgagcgc gctggagcag aaccccaaca gcaagcctct gacgcgcag   11760
ctgttcctga tagtgcagca cagcagggac aacgaggcgt tcagggacgc gctgctgaac   11820
atcaccgagc ccgagggtcg gtggctcctg gacctgatta acatcttgca gagcatagtg   11880
gtgcaggagc gcagcctgag cctggccgac aaggtggcgg ccatcaatta ctcgatgctc   11940
agtctgggca gttttacgc gcgcaagatc taccagacgc cgtacgtgcc catagacaag   12000
gaggtgaaga tcgacggctt ctacatgcgc atggcgctga aggtgctgac cctgagcgac   12060
gacctgggcg tgtaccgcaa cgagcgcatc cacaaggccg tgagcgtgag ccggcggcgc   12120
gagctgagcg accgcgagct gatgcacagc ctgcagcggg cgctggcggg ggccggcagc   12180
ggcgacaggg aggccgagtc ctacttcgag gcggggcgg acctgcgctg ggtgcccagc   12240
cggagggccc tggaggccgc gggggcccgc cgcgaggact atgcagacga ggaggaggag   12300
gatgacgagg agtacgagct agaggagggc gagtacctgg actaaaccgc aggtggtgtt   12360
tttggtagat gcaagacccg aacgtggtgg accggcgct gcgggcggct ctgcagagcc   12420
agccgtccgg ccttaactct acagacgact ggcgacaggt catggaccgc atcatgtcgc   12480
tgacggcgcg caatccggac gcgttccggc agcagccgcga ggccaacagg ctctccgcca   12540
tcttggaggc ggtggtgcct gcgcgcgcga accccacgca cgagaaggtg ctggccatag   12600
tgaacgcgct cgccgagaac agggccatcc gcccggacga ggccgggctg gtgtacgacg   12660
cgctgctgca gcgcgtggcc cgctacaaca gcggcaacgt gcagaccaac ctggaccggc   12720
tggtggggga cgtgcgcgag gcggtggcgc agcgggagcg cgcggagcgg cagggaaacc   12780
tgggctccat ggtggcgctg aacgccttcc tgagcacgca gccggccaac gtgccgcggg   12840
gcaggaggaa ctacaccaac tttgtgagcg cgctgcggct gatggtgacc gagacccccc   12900
```

```
agagcgaggt gtaccagtcg gggccggact acttttttcca gaccagcaga cagggcctgc  12960
agacggtgaa cctgagccag gctttcaaga acctgcgggg gctgtggggc gtgaaggcgc  13020
ccaccgggga ccgggcgacg gtgtccagcc tgctgacgcc caactcgcgc ctgctgctgc  13080
tgctgatcgc gccgttcacg gacagcggca gcgtgtcccg ggagacctac ctcgggcacc  13140
tgctgacgct gtaccgcgag gccatcgggc agacccaggt ggacgagcac accttccagg  13200
agatcaccag cgtgagccgc gcgctggggc aggaggacac gggcagcctg gaggcgaccc  13260
tgaactacct gctgaccaac cggcggcaga agatcccctc gctgcatagt ttgaccaccg  13320
aggaggagcg catcctgcgc tacgtgcagc agagcgtgag cctgaacctg atgcgcgacg  13380
gggtgacgcc cagcgtggcg ctggacatga ccgcgcgcaa catggaaccg gcatgtacg   13440
ccgcgcatcg gccttacatc aaccgcctga tggactactt gcatcgcgcg gcggccgtga  13500
accccgagta cttcaccaac gccatcctga acccgcactg gctcccgccg cccgggttct  13560
acagcggggg cttcgaggtc cccgaggcca cgacggctt cctgtgggac gacatggacg   13620
acagcgtgtt ctccccgcgg ccgcaggcgc tggcggaggc gtcgctgctc cgcctcccca  13680
agaaagaaga gagccgccgg cccagcagcg cggcggcctc tctgtccgag ctgggggcgg  13740
cggccgcgcg gcccgggtcc ctgggggggca gccccttttcc cagtctggtg gggtctctgc  13800
agagcgggcg caccacccgg ccccggctgc tgggcgagga cgagtacctg aacaactccc  13860
tgatgcagcc ggtgcgggag aaaaacctgc ccccccgcctt ccccaacaac gggatagaga  13920
gcctggtaga caagatgagc agatggaaga cctatgcgca ggagcacagg gactcgcccg  13980
tgctccgtcc gcccacgcgg cgccagcgcc acgaccggca gcgggggctg gtatgggatg  14040
acgaggactc cgcggacgat agcagcgtgc tggacctggg ggggagcggc ggtaacccgt  14100
tcgcgcacct gcgcccccgc ctggggagga tgtttcaata agaaaaatca agcatgatgc  14160
aaggttttt aagcggataa ataaaaaact caccaaggcc atggcgaccg agcgttgttg   14220
gtttcttgtt gtgttcccctt agtatgcggc gcgcggcgat gtaccacgag ggacctcctc  14280
cctcttatga gagcgtggtg ggcgcggcg cggcctctcc ctttgcgtcg cagctggagc   14340
cgccgtacgt gcctccgcgg tacctgcggc ctacggggggg aagaaacagc atccgttact  14400
cggagctggc gcccctgtac gacaccaccc gggtgtacct ggtggacaac aagtcggcgg  14460
acgtggcctc cctgaactac cagaacgacc acagcaattt tttgaccacg gtcatccaga  14520
acaatgacta caccccgagc gaggccagca cccagaccat caatctggat gaccggtcgc  14580
actggggcgg cgacctgaaa accatcctgc acaccaacat gccaacgtg aacgagttca    14640
tgttcaccaa taagttcaag gcgcgggtga tggtgtcgcg ttcgcacacc aaggacgacc  14700
gggtggagct gaagtacgag tgggtagagt tcgagctgcc cgaggcaac tactcggaga    14760
ccatgaccat agacctgatg aacaacgcga tcgtggagca ctatctgaaa gtgggcaggc  14820
agaacggggt cctggagagc gacatcgggg tcaagttcga caccaggaac ttccgcctgg  14880
ggctggaccc ggtcaccggg ctggtcatgc ccggggtcta caccaacgag gccttccacc  14940
ccgacatcat cctgctgccc ggctgcgggg tggacttcac ctacagccgc ctgagcaacc  15000
tgctgggcat ccgcaagcgg cagcccttcc aggagggctt taggatcacc tacgaggacc  15060
tggagggggg caacatcccc gcgctcctgg atgtggaggc ctaccagaat agcttgaagg  15120
aagaagaggc gggagagggc agcggcgcg cggcgccgg tcaggaggag ggcggggcct   15180
cctctgaggc ctctgcggac gcagctgccg ccgaggcgga ggaggcggcc gaccccgcga  15240
```

```
tggtggtaga ggaagagaag gatatgaatg acgaggcggt gcgcggcgac acctttgcca   15300
cccgggggga ggaagagaaa gcggaggccg aggccgcggc agaggaggcg gcagcagcgg   15360
cggcggcagt agaggcggcg gccgaggcgg agaagccccc caaggagccc gtgattaagc   15420
ccctgaccga agatagcaag aagcgcagtt acaacgtgct caaggacagc accaacaccg   15480
agtaccgcag ctggtacctg gcctacaact acggcgaccc ggcgacgggg gtgcgctcct   15540
ggaccctgct gtgtacgccg gacgtgacct gcggctcgga gcaggtgtac tggtcgctgc   15600
ccgacatgat gcaagacccc gtgaccttcc gctccacgcg gcaggtcagc aactttccgg   15660
tggtgggcgc cgagctgctg cccgtgcact ccaagagctt ctacaacgac caggccgtct   15720
actcccagct catccgccag ttcacctctc tgacccacgt gttcaatcgc tttcctgaga   15780
accagattct ggcgcgcccg cccgccccca ccatcaccac cgtcagtgaa aacgttcctg   15840
ctctcacaga tcacgggacg ctaccgctgc gcaacagcat cggaggagtc cagcgagtga   15900
ccgtaactga cgccagacgc cgcacctgtc cctacgttta caaggccctg gcatagtct    15960 cgccgcgcgt cctttccagc cgcacttttt aagcatgtcc atcctcatct cgcccagcaa   16020
taacaccggc tggggcctgc tgcgcgcgcc cagcaagatg ttcggagggg cgaggaagcg   16080
ctccgaccag caccccgtgc gcgtgcgcgg gcactaccgc gcccctgggg gcgcgcacaa   16140
acgcgggcgc accggcaccg cggggcgcac caccgtggac gaagccatcg actcggtggt   16200
ggagcaggcg cgcaactaca cgcccgcggt ctccaccgtg gacgcggcta tcgagagcgt   16260
ggtgcgaggc gcgcggcggt acgccaaggc gaagagccgc cggaggcgcg tggcccgccg   16320
ccaccgccgc cgaccgggga gcgccgccaa gcgcgccgcc gccgccttgc ttcgccgggc   16380
cagacgcacg gccgccgcg ccgccatgag ggccgcgcgc cgcctggccg ccggcatcac   16440
caccgtggcc ccccgcgcca gaagacgcgc ggccgctgcc gccgctgcgg ccatcagcga   16500
cctggccacc aggcgccggg gcaacgtgta ctgggtgcgc gactcggtga gcggcacgcg   16560
cgtgcccgtg cgcttccgcc ccccgcggac ttgagaggag aggacaggaa aaaagcatca   16620
acaacaacac cactgagtct cctgctgttg tgtgtatccc agcggcgcgc gcgcacacgg   16680
cgacatgtcc aagcgcaaaa tcaaagaaga gatgctccag gtcgtcgcgc cggagatcta   16740
tgggcccccg aagaaggaag agcaggattt caagccccgc aagataaagc gggtcaaaaa   16800
gaaaaagaaa gatgacgatg atggcgaggt ggagtttctg cgcgccacgg cgcccaggcg   16860
cccgctgcag tggaagggtc ggcgcgtaaa gcgcgttctg cgccccggca ccgcggtggt   16920
cttcacgccc ggcgagcgct ccacccgcac tttcaagcgc gtctatgacg aggtgtacgg   16980
cgacgaagac ctgctggagc aggccaacga tcgctccgga gagtttgctt acgggaagcg   17040
gcaccgggcg atggagaagg acgaggtgct ggcgctgccg ctggaccggg gcaaccccac   17100
ccccagcctg aagcccgtga ccttgcagca ggtgctgccg agcagcgcgc cctccgagat   17160
gaagcggggc ctgaagcgcg agggcggcga cctggcgccc accgtgcagc tgatggtgcc   17220
caagcggcag aggctggagg acgtgctgga gaaaatgaaa gtagacccg gcctgcagcc    17280 ggacatcagg gtccgcccca tcaagcaggt ggcgccgggc ctcggcgtgc agaccgtgga   17340
cgtggtcatc cccaccggcg cctcctcttc cagcgccgcc gccgccacta gcaccgcgga   17400
catggagacg cagactagct ccgccctcgc cgccccgcg gccgccgccg ccgccgccac     17460
ctcctcggcg gaggtacaga cggacccctg gatgccgccg ccggcggccg ccccctcgcg   17520
cgcacgccgc gggcgcagga agtacggtgc cgccagcgcg ctcatgcccg agtacgcctt   17580
gcatccttcc atcgcgccca ccccggcta ccgaggctac agctaccgcc cgcgaagagc     17640
```

```
caagggctcc acccgccgca gccgccgcgc cgccacctct acccgccgcc gcagtcgccg   17700
ccgccgccgc cggcagcccg cgctggctcc gatctccgtg aggagagtgg cgcgcaacgg   17760
ggacaccttg gtgctgccca gggcgcgcta ccaccccagc atcgtttaaa agcctgttgt   17820
ggttcttgca gatatggccc tcacttgccg cctccgtttc ccggtgccgg ataccgagg    17880 aagatcgcgc cgtagaaggg gtatggccgg acgcggcctg agcggaggca gccgccgtgc   17940
gcaccggcgg cgacgcgcca ccagccgacg catgcgcggc ggggtgctgc ctctgctgat   18000 cccctgatc gccgcggcga tcggcgccgt gcccgggatc gcctccgtgg ccttgcaggc    18060
gtcccagagg cgttgacaca gacttcttgc aagcttgcaa atatggaaa aaatcccccc    18120 aataaaaaag tctagactct cacgctcgct tggtcctgtg actattttgt agaaaaaga    18180 tggaagacat caactttgcg tcgctggccc cgcgtcacgg ctcgcgcccg ttcctgggac   18240
actggaacga tatcggcacc agcaacatga gcggtggcgc cttcagttgg ggctctctgt   18300
ggagcggcat taaaaatatc ggttctgccg ttaagaatta cggcaccaag gcctggaaca   18360
gcagcacggg ccagatgttg agagacaagt tgaaagagca gaacttccag cagaaggtgg   18420
tggagggcct ggcctccggc atcaacgggg tggtggacct ggccaatcag gccgtgcaaa   18480
ataagatcaa cagcaaactg gaccccggc cgccggtgga agagctgccg ccggcgctgg    18540
agacggtgtc ccccgatggg cggggcgaaa agcgccgcg gcccgacagg gaagagacca    18600
ctctggtcac gcacaccgat gagccgcccc cctacgagga agccctgaag caaggcttgc   18660
ccaccactcg gcccatcgcg cccatggcca ccggggtggt gggccgccac accccccgcca   18720 cgctggacct gcctcctcct cctgtttctt cttcggccgc cgatgcgcag cagcagaagg   18780
cggcgctgcc cggtccgccc gcggccgccc cccgtccac cgccagtcga gcgcccctgc    18840
gtcgcgcggc cagcggcccc cgcggggtcg cgaggcacag cagcggcaac tggcagaaca   18900
cgctgaacag catcgtgggt ctgggggtgc agtccgtgaa cgccgccga tgctactgaa    18960 tagcttagct aacggtgttg tatgtgtgta tgcgtcctat gtcaccgcca gaggagctgc   19020
tgagtcgccg ccgttcgcgc gcccaccgcc actaccaccg ccgtactac tccagcgccc    19080 ctcaagatgg cgacccatc gatgatgccg cagtggtcgt acatgcacat ctcgggccag   19140
gacgcctcgg agtacctgag ccccgggctg gtgcagttcg cccgcgccac cgacagctac   19200
ttcagcctga gtaacaagtt taggaacccc acggtgcgc ccacgcacga tgtgaccacc    19260
gaccggtccc agcgcctgac gctgcggttc atccccgtgg accgcgagga caccgcgtac   19320
tcttacaagg cgcggttcac cctggccgtg ggcgacaacc gcgtgctgga catggcctcc   19380
acctactttg acatccgcgg cgtgctggac aggggcccca cctttaagcc ctactccggc   19440
actgcctaca actccctggc ccccaagggc gcccccaacc cctgtgagtg ggatgaagcc   19500
gttactgctg ttgacattaa cctggatgag ctcggcgaag atgaagacga cgccgaaggg   19560
gaagcagaac agcaaaaaac tcatgtattt ggtcaagcgc cctactcagg acaaaacatt   19620
acgaaggagg gcatacaaat tggggtagat accaccagcc aagcccaaac acctttatac   19680
gctgacaaaa cattccaacc cgaacctcag gttggagaat cccaatggaa tgagacagaa   19740
atcaattatg gagcgggacg agtgctaaaa aagaccaccc tcatgaaacc atgctatggg   19800
tcatatgcaa gacctactaa tgaaaacggc ggtcagggca tactgctgga gaagagggt    19860 ggtaaaccag aaagtcaagt tgaaatgcaa ttttttttcta ctactcaggc cgccgcggct   19920
ggtaattcag ataatcttac tccaaaagtt gttttgtata gcgaggatgt tcacctggaa   19980
```

```
acgccagata cacacatttc atatatgccc actagcaacg aagccaattc aagagaactg    20040
ttgggacaac aagctatgcc caacagaccc aactacattg ccttcagaga caactttatt    20100
ggccttatgt attacaacag cactggcaac atgggagtgc tggcaggtca ggcctcacag    20160
ttgaatgcag tggtggactt gcaagacaga aacacagaac tgtcctacca gctcttgctt    20220
gattccatgg gagacagaac cagatacttt tccatgtgga atcaggcggt ggacagttat    20280
gatccagatg ttagaattat tgaaaatcat ggaactgaag atgagctgcc caactattgt    20340 ttcccccctgg gcggcataat aacaccgaa actttaacta aagtgaaacc taagactgga    20400
caagacgctc agtgggaaaa agatactgag ttttcagaga aaaatgaaat aagggtggga    20460
aacaacttcg ccatggagat taacctcaat gccaacctgt ggaggaattt cctgtactcc    20520
aacgtggccc tgtacctgcc agacaaactt aagtacactc cagccaacgt gcagatttcc    20580
agcaactcca actcctacga ctacatgaac aagcgagtgg tggccccggg gctggtggac    20640
tgctacatca acctgggcgc gcgctggtcc ctggactaca tggacaacgt caacccctcc    20700
aaccaccacc gcaatgcggg cctgcgctac cgctccatgc ttctgggcaa cgggcgctac    20760
gtgcccttcc acatccaggt gccccagaag ttctttgcca tcaagaacct cctcctcctg    20820
ccgggctcct acacctacga gtggaacttc aggaaggatg tcaacatggt cctccagagc    20880
tctctgggta cgacctcag ggtcgacggg ccagcatca agttcgagag catctgcctc    20940
tacgccacct tcttccccat ggcccacaac acggcctcca cgctcgaggc catgctcagg    21000
aacgacacca cgaccagtc cttcaacgac tacctctccg ccgccaacat gctctacccc    21060
atccccgcca acgccaccaa cgtccccatc tccatcccct cgcgcaactg gcggccttc    21120 cgcggctggg ccttcactcg cctcaagacc aaggagaccc cctccctggg ctcgggtttc    21180
gacccctact acacctactc gggctccata cctacctgg acggaacctt ctacctcaac    21240
cacaccttca agaaggtctc ggtcaccttc gactcctcgg tcagctggcc gggcaacgac    21300
cgcctgctca ccccaacga gttcgagatc aagcgctcgg tcgacgggga gggctacaac    21360
gtggcccagt gcaacatgac caaggactgg ttcctcatcc agatgctggc caactacaac    21420
atcggctatc agggcttcta catcccagag agctacaagg acaggatgta ctccttcttt    21480
aggaacttcc agcccatgag ccggcaggtg gtggacgaaa ccaagtacaa ggactaccag    21540
caggtgggca tcatccacca gcacaacaac tcgggcttcg tgggctacct cgccccccac    21600
atgcgcgagg acaggcta ccccgccaac ttccctacc cgctcattgg caagaccgcg    21660
gtcgacagcg tcacccagaa aagttcctc tgcgaccgca ccctctggcg catcccttc    21720 tccagcaact tcatgtccat gggtgcgctc acggacctgg gccagaacct gctctatgcc    21780
aactccgccc acgcgctcga catgaccttc gaggtcgacc ccatggacga gcccacccct    21840
ctctatgttc tgttcgaagt cttttgacgtg gtccgggtcc accagccgca ccgcggcgtc    21900
atcgagaccg tgtacctgcg cacgcccttc tcggccggca cgccaccac ctaaagaagc    21960 aagccgccac cgccaccacc tgcatgtcgt cgggttccac cgagcaggag ctcaaggcca    22020
tcgtcagaga cctgggatgc gggccctatt ttttgggcac cttcgacaaa cgcttcccgg    22080
gcttcgtcgc cccgcacaag ctggcctgcg ccatcgtcaa cacggccggc cgcgagaccg    22140
ggggcgtgca ctggctggcc ttcgcctgga acccgcgctc aaacatgc acctctttg    22200 accccttcgg attctcggac cagcggctca agcagatcta ccagttcgag tacgagggcc    22260
tgctgcgccc cagcgccatc gcctcctcgc ccgaccgctg cgtcaccctc gagaagtcca    22320
cccagaccgt gcaggggccc gactcggccg cctgcgtct cttctgctgc atgttcctgc    22380
```

```
atgcctttgt gcgctggccc cagagtccca tggaccgcaa ccccaccatg aacttgctga    22440
cggggatccc caactccatg ctccagagcc cccaggccgc cccacccctg cgccgcaatc    22500
aggagcgact ctacagcttc ctggagcgcc actcgcccta cttccgccgc cacagcgcgc    22560
agatcagggg ggccacctct ttctgccgca tgcaagagat gcaagggaaa atgcaatgat    22620
gtacacagac acttttctt ttctcaataa atggcaactt tatttataca tgctctctct    22680
ctcgggtatt catttcccca ccacccacca cccgccgccg ccgtaaccat ctgctgctgg    22740
cttttttaaa aatcgaaagg gttctgccgg gaatcgccgt gcgccacggg cagggacacg    22800
ttgcggaact ggtagcgggt gccccacttg aactcgggca ccaccatgcg gggcaagtcg    22860
gggaagttgt cggcccacag gccgcgggtc agcaccagcg cgttcatcag gtcgggcgcc    22920
gagatcttga gtcgcagtt ggggccgccg ccctgcgcgc gcgagttgcg gtacaccggg    22980
ttgcaacact ggaacaccag cagcgccgga taattcacgc tggccagcac gctccggtcg    23040
gagatcagct cggcgtccag gtcctccgcg ttgctcagcg cgaacggggt cagcttgggc    23100
acctgccgcc ccaggaaggg agcgtgtccc ggcttggaat tgcagtcgca gcgcagcggg    23160
atcagcaggt gcccgcggcc ggactcggcg ttggggtaca gcgcgcgcat gaaggcctcc    23220
atctggcgga aggccatctg ggccttggcg ccctccgaga aaaacatgcc gcaggacttg    23280
cccgagaact ggttcgcggg gcagctcgcg tcgtgcaggc agcagcgcgc gtcggtgttg    23340
gcgatctgca ccacgttgcg ccccaccgg ttcttcacga tcttggcctt ggaagcctgc    23400
tccttcagcg cgcgctgccc gttctcgctg gtcacatcca tctcgatcac gtgctccttg    23460
ttcaccatgc tgctgccgtg cagacacttc agctcgccct ccacctcggt gcagcggtgc    23520
tgccacagcg cgcagcccgt gggctcgaaa tgcttgtagg tcacctccgc gtaggactgc    23580
aggtaggcct gcaggaagcg ccccatcatg gtcacgaagg tcttgttgct gctgaaggtc    23640
agctgcagcc cgcggtgctc ctcgttcagc caggccttgc acacggccgc cagcgcctcc    23700
acctggtcgg gcagcatctt gaagttcagc ttcagctcat tctccacatg gtacttgtcc    23760
atcagcgcgc gcgcagcctc catgcccttc tcccaggccg acaccagcgg caggctcaag    23820
gggttcacca ccgtcgcagt cgccgccgcg ctttcgcttt ccgctccgct gttctcttct    23880
tcctcctcct cctcttcttc ctcgccgccc gcgcgcagcc cccgcaccac ggggtcgtct    23940
tcctgcaggc gccgcaccga gcgcttgccg ctcctgccct gcttgatgcg cacgggcggg    24000
ttgctgaagc ctaccatcac cagcgcggcc tcttcttgct cgtcctcgct gtccactatg    24060
acctcggggg agggcgacct cagtaccgtg gcgcgctgcc tcttctttt cctggggcg    24120 tttgcaagct ccgcggccgc ggccgccgcc gaggtcgaag gccgagggct gggcgtgcgc    24180
ggcaccagcg cgtcctgcga gccgtcctcg tcctcggact cgaggcggca gcgagcccgc    24240
ttcttcgggg gcgcgcgggg cggcggcggc ggggcggcg gcgacggaga cggggacgag    24300
acatcgtcca gggtgggagg acggcgggcc gcgccgcgtc cgcgctcggg ggtggtttcg    24360
cgctggtcct cttcccgact ggccatctcc cactgctcct tctcctatag gcagaaagag    24420
atcatggagt ctctcatgca agtcgagaag gaggaggaca gcctaaccac caccgccccc    24480
tctgagcccc ccgccgccgc cgccgcggac gacgcgccca ccaccgccgc cgccaccacc    24540
accattacca ccctacccgg cgacgcagcc ccgatcgaga aggaagtgtt gatcgagcag    24600 gacccggggtt ttgtgagcga agaggaggat gaggaggatg aaaaggagaa ggataccgcc    24660
gcctcagtgc caaaagagga taaaaagcaa gaccaggacg acgcagagac agatgaggca    24720
```

| | | | | |
|---|---|---|---|---|
| gcagtcgggc | ggggggacga | gaggcatgat | gatgatgacg | gctacctaga cgtgggagac 24780 |
| gacgtgctgc | ttaagcacct | gcaccgccag | tgcgtcatcg | tctgcgacgc gctgcaggag 24840 |
| cgctgcgaag | tgcccctgga | cgtggcggag | gtcagccgcg | cctacgagcg gcacctcttc 24900 |
| gcgccacacg | tgcccccccaa | gcgcgggag | aacggcacct | gcgagcccaa cccgcgcctc 24960 |
| aacttctacc | cggtcttcgc | ggtacccgag | gtgctggcca | cctaccacat cttcttccaa 25020 |
| aactgcaaga | tcccctctc | ctgccgcgcc | aaccgcaccc | gcgccgacaa gacgctggcc 25080 |
| ctgcggcagg | gcgcccacat | acctgatatc | gcctctctgg | aggaggtgcc caagatcttc 25140 |
| gagggtctcg | gtcgcgacga | gaaacgggcg | gcgaacgctc | tgcaaggaga cagcgaaaac 25200 |
| gagagtcact | cggggggtgct | ggtggagctc | gagggcgaca | acgcgcgcct ggccgtgctc 25260 |
| aagcgcagca | tcgaagtcac | ccacttcgcc | tacccggcgc | tcaacctgcc ccccaaggtc 25320 |
| atgagtgtgg | tcatgagcga | gctcatcatg | cgccgcgccc | agccctgga cgcggatgca 25380 |
| aacttgcaag | agccctccga | ggaaggcctg | cccgcggtca | gcgacgagca gctggcgcgc 25440 |
| tggctggaga | cccgcgaccc | cgcccagctg | gaggagcggc | gcaagctcat gatggccgcg 25500 |
| gtgctcgtca | ccgtggagct | cgagtgtctg | cagcgcttct | tcggggaccc cgagatgcag 25560 |
| cgcaagctcg | aggagaccct | gcactacacc | ttccgccagg | gctacgtgcg ccaggcctgc 25620 |
| aagatctcca | acgtggagct | ctgcaacctg | gtctcctacc | tgggcatcct gcacgagaac 25680 |
| cgcctcgggc | agaacgtcct | gcactccacc | ctcaaagggg | aggcgcgccg cgactacgtc 25740 |
| cgcgactgcg | tctacctctt | cctctgctac | acgtggcaga | cagccatggg ggtctggcag 25800 |
| cagtgcctgg | aggagcgcaa | cctcaaggag | ctggagaagc | tcctccggcg cgccctcagg 25860 |
| gacctctgga | cgggcttcaa | cgagcgctcg | gtggccgccg | cgctggcgga catcatcttc 25920 |
| cccgagcgcc | tgctcaaaac | cctgcagcag | ggcctgcccg | acttcaccag ccagagcatg 25980 |
| ctgcagaact | tcaggacctt | catcctggag | cgctcgggca | tcctgccggc cacctgctgc 26040 |
| gcgctgccca | gcgacttcgt | gcccatcagg | tacaggagt | gcccgccgcc gctctggggc 26100 |
| cactgctacc | tcttccagct | ggccaactac | ctcgcctacc | actcggatct catggaagac 26160 |
| gtgagcggcg | agggcctgct | cgagtgccac | tgccgctgca | acctgtgcac gccccaccgc 26220 |
| tctctagtct | gcaacccgca | gctgctcagc | gagagtcaga | ttatcggtac ctttgagctg 26280 |
| cagggtccct | cgcccgacga | aaagtccgcg | gctccggggt | tgaaactcac tccggggctg 26340 |
| tggacttccg | cctacctacg | caaatttgta | cctgaagact | accacgccca cgagatcagg 26400 |
| ttttacgaag | accaatcccg | cccgcccaag | gcggagctca | ccgcctgcgt cattacccag 26460 |
| ggccacatcc | tgggccaatt | gcaagccatc | aacaaagccc | gccaagagtt cttgctgaaa 26520 |
| aagggtcggg | gggtgtacct | ggaccccag | tccggcgagg | agctaaaccc gctacccccg 26580 |
| ccgccgcccc | agcagcggga | ccttgcttcc | caggatggca | cccagaaaga agcagccgcc 26640 |
| gccgccgcca | gcatacatgc | ttctggagga | agaggaggac | tgggacagtc aggcagagga 26700 |
| ggtttcggac | gaggacgagg | aggaggagat | gatggaagac | tgggaggagg acagcctaga 26760 |
| cgaggaagct | tcagaggccg | aagaggtggc | agacgcaaca | ccatcaccct cggccgcagc 26820 |
| cccctcgccg | gcgcccccga | aatcctccga | ccccagcagc | agcgctataa cctccgctcc 26880 |
| tccggcgccg | gcgcccaccc | gcagcagacc | caaccgtaga | tgggacacta caggaaccgg 26940 |
| ggtcggtaag | tccaagtgcc | ccccagcgcc | gccccgcaa | caggagcaac agcagcagca 27000 |
| gcggcgacag | ggctaccgct | cgtggcgcgg | acacaaaaac | gccatagtcg cctgcttgca 27060 |
| agactgcggg | ggcaacatct | ccttcgcccg | ccgcttcctg | ctcttccacc acggggtggc 27120 |

```
ttttccccgc aatgtcctgc attactaccg tcatctctac agcccctact gcggcggcag    27180
cggcgaccca gagggagcgg cggcagcagc agcgccagcc acagcggcga ccacctagga    27240
agacctccgc gggcaagacg gcgggagccg ggagacccgc ggcggcggcg gtagcggcgg    27300
cggcgggcgc actgcgcctc tcgcccaacg aaccccctctc gacccgggag ctcagacaca   27360
ggatcttccc cactctgtat gctatcttcc agcagagcag aggccaggaa caggagctga    27420
aaataaaaaa cagatctctg cgctccctca cccgcagctg tctgtatcac aaaagcgaag    27480
atcagcttcg gcgcacgctg gaggacgcgg aggcactctt cagcaaatac tgcgcgctga    27540
ctcttaagga ctagccgcgc gcccttctcg aatttaggcg ggagaaagac tacgtcatcg    27600
ccgaccgccg cccagcccac ccagccgaca tgagcaaaga gattcccacg ccctacatgt    27660
ggagctacca gccgcagatg ggactcgcgg cgggagcggc ccaagactac tccacccgca    27720
tgaactacat gagcgcgggg ccccacatga tctcacgggt taatgggatc cgcgcccagc    27780
gaaaccaaat actgctggaa caggcggcca taaccgccac accccgtcat gacctcaatc    27840
cccgaaattg gcccgccgcc ctcgtgtacc aggaaacccc ctctgccacc accgtggtac    27900
ttccgcgtga cacccaggcc gaagtccaga tgactaactc aggggcgcag ctcgcgggcg    27960
gctttcgtca cggggtgcgg ccgcaccggc cgggtatatt acacctggcg atcagaggcc    28020
gaggtattca gctcaacgac gagtcggtga gctcttcgct cggtctccgt ccggacggaa    28080
ccttccagat cgccggatca ggtcgctcct cattcacgcc tcgccaggcg tatctgactc    28140
tgcagacctc ctcctcggag cctcgctccg gcggcatcgg cacctccag ttcgtggagg    28200
agttcgtgcc ctcggtctac ttcaacccct tctcgggacc tccggacgc taccccgacc    28260
agttcatccc gaactttgac gcggtgaagg actcggcgga cggctacgac tgaatgtcaa    28320
gtgctgaggc agagagcgtt cgcctgaaac acctccagca ctgccgccgc ttcgcctgct    28380
tcgcccgcag ctccggtgag ttctgctact ttcagctgcc cgaggagcat accgaggggc    28440
cggcgcacgg cgtccgccta accacccagg gcgaggttac ctgtaccctt atccgggagt    28500
ttaccctccg tcccctgcta gtggagcggg agcggggttc ttgtgtcata actatcgcct    28560
gcaactgccc taaccctgga ttacatcaag atctttgttg tcacctgtgc gctgagtata    28620
ataaacgctg agatcagact ctactggggc tcctgtcgcc atcctgtgaa cgccaccgtc    28680
ttcacccacc ccgagcagcc ccaggcgaac ctcacctgcg gcctgcgtcg gagggccaag    28740
aagtacctca cctggtactt caacggcacc cccttttgtgg tttacaacag cttcgaccag    28800
gacgagttg ccttgagaga cgacctttcc ggtctcagct actccattca caagaacacc     28860
accctccacc tcttccctcc ctacctgccg ggaacctacg agtgcgtcac cggccgctgc    28920
acccacctcc tccgcctgat cgtaaaccag acctttccgg gaacacacct cttccccaga    28980
acaggaggtg agctcaggaa accccctggg gcccagggcg gagacttacc ttcgaccctt    29040
gtggggttag gatttttttat cgccgggttg ctggctctcc tgatcaaagc ttccttcaga    29100
tttgttctct ccctttactt ttatgaacag ctcaacttct aataacacta ccttttctca    29160
ggaatcgggt agtgacttct cttctgaaat cgggctgggt gtgctgctta ctctgttgat    29220
tttttttcctt atcatactta gccttctgtg cctcaggctc gccgcctgct gcgcacatat    29280
ctacatctac agccggttgc ttaactgctg gggtcgccat ccaagatgaa cggggctcag    29340
gtgctatgtc tgctggccct ggtggcctgc agtgccgccc tcaatttga ggaacccgct     29400
tgcaatgtga ctttcaagcc tgagggcgca cattgcacca ctctggttaa atgtgtgacc    29460
```

```
tctcatgaaa aactgctcat cgcctacaaa aacaaaacag gcgagttcgc ggtctatagt   29520
gtgtggcaac ccggagacca taataactac tcagtcaccg tcttcgaggg tgcggagtct   29580
aagaaattcg attacaccct tcccttcgag gagatgtgtg atgcggtcat gtacctgtcc   29640
aaacagcaca agctgtggcc ccccaccccc gaggcgtgtg tggaaaacac tgggtctttc   29700
tgctgtctct ctctggcaat cactgtgctt gctctaatct gcacgctgct atacatgaga   29760
ttcaggcaga ggcgaatctt tatcgatgag aaaaaaatgc cttgatcgct aacaccggct   29820
ttctgtctgc agaatgaaag caatcacctc cctactaatc agcaccaccc tccttgcgat   29880
tgcccatggg ttgacacgaa tcgaagtgcc agtggggtcc aatgtcacca tggtgggccc   29940
cgccggcaat tcctccctga tgtgggaaaa atatgtccgt aatcaatggg atcattactg   30000
ctctaatcga atctgtatca agcccagagc catctgcgac gggcaaaatc taactttgat   30060
tgatgtgcaa atgacggatg ctgggtacta ttacgggcag cggggagaaa tgattaatta   30120
ctggcgaccc cacaaggact acatgctgca tgtagtcaag gcagtcccca ctactaccac   30180
ccccaccact accactccca ctactaccac cccactact accactagca ctgctactac   30240
cgctgcccgc aaagctatta cccgcaaaag caccatgctt agcaccaagc cccattctca   30300
ctcccacgcc ggcgggccca ccggtgcggc ctcagaaacc accgagcttt gcttctgcca   30360
atgcactaac gccagcgccc acgaactgtt cgacctggag aatgaggacg atgaccagct   30420
gagctccgct tgcccggtcc cgctgcccgc agagccggtc gccctgaagc agctcggtga   30480
tccatttaat gactctcctg tttatccctc tcccgaatac ccgcccgact ctaccttcca   30540
catcacgggc accaacgacc ccaacctctc cttctacctg atgctgctgc tttgtatctc   30600
tgtggtatct ccgcgctca tgttactggg catgttctgc tgcctcatct gccgcagaaa   30660
gagaaagtct cgctctcagg gccaaccact gatgcccttc ccctaccccc cagatttgc   30720 agataacaag atatgagcac gctgctgaca ctaaccgctt tactcgcctg cgctctaacc   30780
cttgtcgctt gcgaatccag ataccacaat gtcacagttg tgacaggaga aaatgttaca   30840
ttcaactcca cggccgacac ccagtggtcg tggagcggcc acggtagcta tgtatacatc   30900
tgcaatagct ccacctcccc tagcatgtcc tctcccaagt accactgcaa tgccagcctg   30960
ttcaccctca tcaacgcctc cacctcggac aatggactct atgtaggcta tgtgacaccc   31020
ggtgggcggg gaaagaccca cgcctacaac ctgcaagttc gccacccctc caccaccgcc   31080
accacctctg ccgcccctac ccgcagcagc agcagcatca gcagcagcag cagcagcagc   31140
agattcctga ctttaatcct agccagctca acaaccaccg ccaccgctga gaccaccac   31200 agctccgcgc ccgaaaccac ccacacccac cacccagaga cgaccgcggc ctccagtgac   31260
cagatgtcgg ccaacatcac cgcctcgggt cttgaacttg cttcaaccccc cacccccaaaa   31320 ccagtggatg cagccgacgt ctccgccctc gtcaatgact gggcggggct gggaatgtgg   31380
tggttcgcca taggcatgat ggcgctctgc ctgcttctgc tctggctcat ctgctgcctc   31440
aaccgcaggc gggccagacc catctataga cccatcattg ttctcaaccc cgctgatgat   31500
gggatccata gattggatgg tctgaaaaac ctactttct cttttacagt atgataaatt   31560
gagacatgcc tcgcatttt atgtacttga cacttctccc acttttctg gggtgttcta   31620 cgctggccgc cgtctctcac ctcgaggtag actgcctcac acccttcact gtctacctga   31680
tttacggatt ggtcaccctc actctcatct gcagcctaat cacagtagtc atcgccttca   31740
tccagtgcat tgactacatc tgtgtgcgcc tcgcatacct gagacaccac ccgcagtacc   31800
gagacaggaa cattgcccaa ctcctaagac tgctctaatc atgcataaga ctgtgatctg   31860
```

```
cctcctcatc ctcctctccc tgcccgctct cgtctcatgc cagcccacca caaaacctcc    31920
acgaaaaaga catgcctcct gtcgcttgag ccaactgtgg aatattccca aatgctacaa    31980
tgaaaagagc gagctttccg aagcctggct atatgcggtc atgtgtgtcc ttgtcttctg    32040
cagcacaatc tttgccctca tgatctaccc ccactttgat ttgggatgga atgcggtcga    32100
tgccatgaat taccctacct ttcccgcgcc cgatatgatt ccactccgac aggttgtggt    32160
gcccgtcgcc ctcaatcaac gcccccatc ccctacaccc actgaggtca gctactttaa    32220
tctaacaggc ggagatgact gacactctag atctagaaat ggacggcatc ggcaccgagc    32280
agcgtctcct acagaggcgc aagcaggcgg ctgaacaaga gcgcctcaat caggagctcc    32340
gagatctcat taacctgcac cagtgcaaaa aaggcatctt ttgcctggtc aagcaggccg    32400
atgtcaccta cgagaaaacc ggtaacagcc accgcctcag ctacaagctg cccacccaac    32460
gccagaagtt ggtgctcatg gtgggtcaga atcccatcac cgtcacccag cactcggtgg    32520
agaccgaggg gtgtctgcac tcccctgtc agggtccgga agacctctgc accctggtaa    32580
agaccctgtg tggtcttaga gatttaatcc cctttaacta atcaaacact ggaatcaata    32640
aaaagaatca cttactttaa atcagtcagc aggtctctgt ccactttatt cagcagcacc    32700
tccttcccct cctcccaact ctggtactcc aaacgcctcc tggcggcaaa cttcctccac    32760
accctgaagg gaatgtcaga ttcttgctcc tgtccctccg cacccactat cttcatgttg    32820
ttgcagatga agcgcgccaa aacgtctgac gagaccttca accccgtgta ccctatgac    32880 acggaaaacg ggcctccctc cgtccctttc ctcacccctc ccttcgtgtc cccgacgga    32940 tttcaagaaa gccccccagg ggtcctgtct ctgcgcctgt cagagcccct ggtcacttcc    33000
cacggcatgc ttgccctgaa aatgggaaat ggcctctccc tggatgacgc cggcaacctc    33060
acctctcaag atgtcaccac cgtcacccct cccctcaaaa aaccaagac caacctcagc    33120 ctccagacct cagcccccct gaccgttagc tctgggtccc tcaccgtcgc ggccgccgct    33180
ccactggcgg tggccggcac ctctctcacc atgcaatctc aggcccctt gacagtgcaa    33240 gatgcaaaac tcggcctggc cacccaggga cccctgaccg tgtctgaagg caaactcacc    33300
ttgcagacat cggctccact gacggccgct gacagcagca ctctcactgt tagtgccaca    33360
cctcccctca gcacaagcaa tggtagtttg agcattgaca tgcaggcccc gatttatacc    33420
accaatggaa aactggcact taacattggt gctcccctgc atgtggtaga caccctaaat    33480
gcactaactg tagtaactgg ccagggtctt accataaatg gaagagccct gcaaactaga    33540
gtcacgggtg ccctcagtta tgacacagaa ggcaacatcc aactgcaagc cggaggggggt    33600 atgcgcattg acaataatgg ccaacttatc cttaatgtag cttatccatt tgatgctcaa    33660
aacaacctca gccttagact tggccaaggt cccctaattg ttaactctgc ccacaacttg    33720
gatcttaacc ttaacagagg cctttactta tttacatctg gaaacacgaa aaaactggaa    33780
gttaacataa aaacagccaa aggtctattt tacgatggca ccgctatagc aatcaatgca    33840
ggtgacgggc tacagtttgg gtctggttca gatacaaatc cattgcaaac taaacttgga    33900
ttggggctgg aatatgactc caacaaagct ataatcacta aacttggaac tggcctaagc    33960
tttgacaaca caggtgccat cacagtaggc aacaaaaatg atgacaagct taccttgtgg    34020
accacaccag acccctcccc aaactgcaga attaattcag aaaaagatgc taaactcaca    34080
ctagttttga ctaaatgcgg cagccaggtg ttagccagcg tttctgtttt atctgtaaaa    34140
ggcagccttg ccccatcag cggcacagta actagcgccc agattgtttt aagatttgat    34200
```

```
gaaaacggag ttttattgag caattcttct cttgacccc  aatactggaa ctatagaaaa  34260
ggcgattcta cagaaggcac tgcatatact aatgctgtgg gatttatgcc caacctcaca  34320 gcataccta  aaacacagag ccagactgct aaaagcaaca ttgtaagtca agtttacttg  34380
aatggggaca aaacaaaacc catgacccta accatcaccc tcaatggaac taatgaaaca  34440
ggggatgcta cagtaagcac atactccatg tcattttcat ggaactggaa tggaagtaat  34500
tacattaatg acaccttcca aaccaactcc tttaccttct cctacatcgc caagaataa   34560 aaaagcatga cgctttgttc tctgattcag tgtgtttctt ttattttttt ttcaattaca  34620
acagaatcat tcaagtcatt ctccatttag cttaatagac ccagtagtgc aaagccccat  34680
actagcttat ttcagacagt ataaattaaa ccataccttt tgatttcaat attaaaaaaa  34740
tcatcacagg atcctagtcg tcaggccgcc cctccctgc  caagacacag aatacacaat  34800
cctctccccc cggctggctt taaacaacac catctggttg gtgacagaca ggttcttcgg  34860
ggttatattc cacacggtct cctggcgggc caggcgctcg tcggtgatgc tgataaactc  34920
tcccggcagc tcgctcaagt tcacgtcgct gtccagcggc tgaacctcat gctgacgcgg  34980
taactgcgcg accggctgct gaacaaacgg aggccgcgcc tacaagggg  tagagtcata  35040 atcctccgtc aggatagggc ggttatgcag cagcagcgag cgaatcatct gctgccgccg  35100
ccgctccgtc cggcaggaaa acaacatccc ggtggtctcc tccgctataa tccgcaccgc  35160
ccgcagcata agcctcctcg ttctccgcgc gcagcaccgc accctgatct cgctcaggtt  35220
ggcgcagtag gtacagcaca tcaccacgat gttattcatg atcccacagt gcaaggcgct  35280
gtatccaaag ctcatgcccg ggaccaccgc ccccacgtga ccgtcgtacc agaagcgcag  35340
gtaaatcaag tgacgacccc tcatgaacgt gctggacata acatcaccct ccttgggcat  35400
gttgtaattc accacctccc ggtaccagat gaatctctga ttgaacacgg ccccttccac  35460
caccatcctg aaccaagagg ctaggacctg cccaccggct atgcactgca gggaacccgg  35520
gttggaacaa tgacaatgca gactccaggg ctcgtaaccg tggatcatcc ggctgctgaa  35580
gacatcgatg ttggcgcaac acagacacac gtgcatacac ttcctcatga ttagcagctc  35640
ctccctcgtc aggatcatat cccaagggat aacccattct tgaatcaacg taaagcccac  35700
agagcaggga aggcctcgca cataactcac gttgtgcatg gtcagcgtgt tgcattccgg  35760
aaacagcgga tgatcctcca gtatcgaggc gcggtctcg  ttctcacagg gaggtaaagg  35820
ggccctgctg tacggactgt ggcgggacga ccgagatcgt gttgagcgta acgtcatgga  35880
aaagggaacg ccggacgtgg tcatacttct tgaagcagaa ccaggctcgc gcgtgacaga  35940
cctccttgcg tctacggtct cgccgcttag ctcgctccgt gtgatagttg tagtacagcc  36000
actctctcaa agcgtcgagg cgacacctgg cgtcaggatg tatgtagact ccgtcttgca  36060
ccgcggccct gataatatcc accaccgtag aataagccac accaagccaa gcaatacact  36120
cgctttgcga gcggcagaca ggaggagcgg ggagagacgg aaggaccatc ataaaatttt  36180
aaagaatatt ttccaatatt tcgaaatcaa gatctaccaa atggcagcgc tcccctccac  36240
tggcgcggtc aaactctacg gccaaagaac agataacggc attttttaaga tgttcccgga  36300 cggcgtctaa aagacaaacc gctctcaagt cgacataaat tataagccaa aagcatcgg   36360 gttcaagatc cactatggac gcgccggcgg cgtccaccaa acccaaataa ttttcttctc  36420
tccagcgctg caaaatccca gtaagcaact ccctgatatt aagatgaacc atgccaaaaa  36480
tctgttcaag agcgccctcc accttcattc tcaagcagcg catcatgatt gcaaaaattc  36540
aggttcctca gacacctgta tgagattcaa aacgggaata ttaacaaaaa ttcctctgtc  36600
```

```
gcgcagatcc cttcgcaggg caagctgaac ataatcagac aggtctgaac gaaccagcga   36660
ggccaaatcc ccgccaggaa ccagatccag agaccctatg ctgattatga cgcgcatact   36720
cggggctatg ctaaccagcg tagcgccgat gtaggcgtgc tgcatgggcg gcgaaataaa   36780
atgcaaggtg ctggttaaaa aatcaggcaa agcctcgcgc aaaaaagcta agacatcata   36840
atcatgctca tgcaggtagt tgcaggtaag ctcaggaacc aaaacggaat aacacacgat   36900
tttcctctca acatgactt ccaggtgact gcataagaaa aaaattataa ataataaata   36960
ttaattaaat aaattaaaca ttggaagcct gtctcacaac aggaaaaacc actctgatca   37020
acataagacg ggccacgggc atgcccgcgt gaccataaaa aaatcggtct ccgtgattac   37080
aaagcaccac agatagctcc ccggtcatgt cgggggtcat catgtgagac tgtgtataca   37140
cgtccgggct gttgacatcg gtcaaagaaa gaaatcgagc tacatagccc ggaggaatca   37200 acaccccgcac gcggaggtac agcaaaacgg tccccatagg aggaatcaca aaattagtag   37260
gagaaaaaaa aacataaaca ccagaaaaac cctcttgccg aggcaaaaca gcgccctccc   37320
gttccaaaac aacataaagc gcttccacag gagcagccat gacaaagacc cgagtcttac   37380
caggaaaatt ttaaaaaaga ttcctcaacg cagcaccagc accaacacct gtcagtgtaa   37440
aatgccaagc gccgagcgag tatatatagg aataaaaagt gacgtaaacg gttaaagtcc   37500
agaaaacgcc cagaaaaacc gcacgcgaac ctacgccccg aaacgaaagc caaaaaacag   37560
tgaacacgcc ctttcggcgt caacttccgg tttcccacgg tacgtcactt ccgcatataa   37620
gaaaactacg ctacccaaca tgcaagaagc cacgccccaa aaaacgtcac acctcccggc   37680
ccgccccgcg ccgccgctcc tccccgcccc gccccgctcc gcccacctca ttatcatatt   37740
ggcttcaatc caaaataagg tatattattg atgatg   37776

<210> SEQ ID NO 63
<211> LENGTH: 37713
<212> TYPE: DNA
<213> ORGANISM: Adenoviridae - Mastadenovirus

<400> SEQUENCE: 63
catcatcaat aatatacctt attttggatt gaagccaata tgataatgag gtgggcggag     60
cggggcgggg cggggaggag cggcggcgcg gggcgggccg ggaggtgtgg cggaagttga    120
gtttgtaagt gtggcggatg tgacttgcta gcgccggatg tggtaaaagt gacgtttttg    180
gagtgcgaca acgcccacgg gaagtgacat ttttcccgcg gtttttaccg gatgtcgtag    240
tgaatttggg cgttaccaag taagatttgg ccattttcgc gggaaaactg aaatggggaa    300
gtgaaatctg attaatttcg cgttagtcat accgcgtaat atttgccgag ggccgaggga    360 cttgaccga ttacgtggag gaatcgccca ggtgttttg aggtgaattt ccgcgttccg    420
ggtcaaagtc tccgttttat tattatagtc agctgacgcg gagtgtattt atacccgctg    480
atctcgtcaa gaggccactc ttgagtgcca gcgagtagaa ttttctcctc tgccgctccg    540
ctccgctctg acaccggggg aaaaaaatga gacatttcac ctacgatggc ggtgtgctta    600
ccggccagct ggctgcctcg gtcctggacg ccctgattga ggacgtattg gccgacaatt    660
atcctcctcc agctcatttt gagccaccta ctcttcacga actgtatgat ttggacgtgg    720
tggcacctag cgacccgaac gagcaggcgg tttccagttt ttttcctgac tctatgctgt    780
tggccagcca ggagggggtc gagctcgaga cccctcctcc aatcgccgtt tctcctgagc    840
ctccgaccct gaccaggcag cccgatcgcc gtgttggacc tgcgactatg ccccatctgc    900
```

```
tgcccgaggt gatcgatctc acctgtaacg agtctggttt tccacccagc gaggatgagg    960
acgaagaggg tgagcagttt gtgttagatt ctgtggagga acccgggcgc ggttgcagat   1020
cttgtcaata ccatcggaaa aatacaggag accccccaaat tatgtgttcc ctgtgttata  1080
tgaagacgac ctgtatgttt atttacagta agtttgtgat tggtgggtcg gtgggctgta   1140
gtgtgggtaa gtggtctgtg gttttttttt tttaatatca gcttgggcta aaaaactgct   1200
atggtaattt ttttaaggtc cggtgtctga acctgagcag gaagctgaac cggagcctga   1260
gagtcgcccc aggagaaggc ctgcaattct aactagaccg agtgcacctg tagcgaggga   1320
cctcagcagt gcagagacca ccgattctgg tccttcctca tcccctccag agattcatcc   1380
cgtggtgcct ttgtgtcccc tcaagcccgt tgccgtgaga gttagtgggc ggagggccgc   1440
cgtggagagc attgaggact tgcttaatga gacacaggaa cctttggact tgagctgtaa   1500
acgccctagg caataaacct gcttacctgg actgaatgag ttgacgccta tgtttgcttt   1560
tgaatgactt aatgtgtata taataaagag tgagataatg tttaattgca tggtgtgttt   1620
gattggggcg gggtttgttg ggtatataag cttccctggg ctaaacttgg ttacacttga   1680
cctcatggag gcctgggagt gtttagagag cttttgccgaa gtgcgtgcct tgctggaaga   1740
gagctctaat aatacctctg ggtggtggag gtattttttgg ggctctcccc aggctaagtt   1800
agttgtgtaga atcaaggagg attacaagtg ggaatttgaa cagcttttga aatcctgtgg   1860
tgagctcttg gattctttga atctgggcca ccaggctctt ttccaggaca agatcatcag   1920
gactttggat ttttccacac cggggcgcat tgctgccggg gttgcttttc tagcttttt    1980
gaaggataaa tggagcgaag agacccactt gagttcggga tacgtcctgg atttctggc    2040
catacaactg tggagagcat ggatcaggca caagaacaga atgcaactgt tgtcttccgt   2100
ccgtccgttg ctgattcagc cggaggagca gcagaccggg ccggaggacc gggctcgtct   2160
ggaaccagaa gagagggcac cggagaggag cgcgtggaac ctgggagccg gcctgaacgg   2220
ccatccacat cgggagtgaa tgttggacag gtggcggatc tctttccaga actgcgacga   2280
atcttaacta tcagggagga tggacaattt gttaaggggc ttaagaggga gcgggggggct  2340
tctgaacata acgaggaggc cagtaattta gcttttagtc tgatgaccag acaccgtccc   2400
gagtgcatta cttttcagca gattaaggat aattgtgcca atgagttaga tctgctgggt   2460
cagaagtaca gcatagagca gttgaccact tactggctgc agccgggtga tgatctggag   2520
gaagctatta gggtgtatgc caaggtggcc ctgaggcccg attgcaagta caagctcaag   2580
gggctggtga atatcaggaa ttgttgctac atttctggga acggggcgga ggtggagata   2640
gagaccgatg acagggtggc ctttaggtgt agcatgatga atatgtggcc tggggtgctg   2700
ggcatggacg gggtggtgat tatgaatgtg aggttcacgg ggcccaattt taatggcacg   2760
gtgttcctgg gcaacaccaa cttggtgctg cacggggtga gcttctatgg ctttaacaac   2820
acctgtgtgg aggcctggac cgatgtgaag gtccgtggct gtgccttcta cggatgttgg   2880
aaggcggtag tgtgtcgccc caagagcagg agttccatta aaaaatgctt gtttgagagg   2940
tgcaccctgg gggtgctggc ggagggcaac tgtcgggtgc gccacaatgt ggcctcagaa   3000
tgcggttgct tcatgctagt caagagcgtg gcggtcatca agcataacat ggtgtgcggc   3060
aacagcgagg acaaggcctc gcagatgctg acctgctcgg atggcaactg ccacttactg   3120
aagaccgtac atataaccag ccacagccgc aaggcctggc ccgtgttcga gcacaacgtg   3180
ttgacccgct gctctttgca tctgggcaac aggaggggtg tgttcctgcc ctatcaatgc   3240
aacttgagcc acaccaagat cttgctagag cccgaaagca tgtccaaggt gaacctgaac   3300
```

```
ggggtgtttg acatgaccct gaagatatgg aaggtgctga ggtacgacga gaccaggtct    3360
cgatgcaggc cctgcgagtg cgggggcaag catatgagga accagcctgt gatgctggat    3420
gtgaccgagg agctgaggcc tgaccacttg gttctggcct gcaccagggc cgagtttggt    3480
tctagcgatg aagacacaga ctgaggtggg tgagtgggcg tggtctgggg gtgggaagca    3540
atatataagt tgggggtctt agggtctctg tgtctgtttt gcagagggac cgccggcgcc    3600
atgagcggga gcagtagcag caacgccttg gatggcagca tcgtgagccc ttatttgacg    3660
acgcgcatgc cccactgggc cggggtgcgt cagaatgtga tgggctccag catcgacgga    3720
cgacccgtgc tgcccgcaaa ttccgccacg ctgacctacg cgaccgtcgc ggggaccccg    3780
ttggacgcca ccgccgccgc cgccgccacc gccgccgcct cggccgtgcg cagcctggcc    3840
acggactttg cattcttggg acccttggcc accggggcgg ccgcccgtgc cgccgttcgc    3900
gatgacaagc tgaccgccct gctggcgcag ttggatgcgc ttacccggga actgggtgac    3960
cttccgcagc aggtcgtggc cctgcgccag caggtctccg ccctgcaggc tagcgggaat    4020
gcttctcctg caaatgccgt ttaagataaa taaaaccaga ctctgtttgg attaaagaaa    4080
agtagcaagt gcattgctct ctttatttca taattttccg cgcgcgatag gcccgagtcc    4140
agcgttctcg gtcgttgagg gtgcggtgta tcttctccag gacgtggtag aggtggctct    4200
ggacgttgag atacatgggc atgagcccgt cccgggggtg gaggtagcac cactgcagag    4260
cttcatgctc cggggtggtg ttgtagatga tccagtcgta gcaggagcgc tgggcatggt    4320
gcctaaaaat gtccttaagc agcaggccga tggccagggg gaggcccttg gtgtaagtgt    4380
ttacaaaacg gttgagttgg aagggtgca tgcggggtga gatgatgtgc atcttagatt    4440
gtatttttag attggcgatg tttcctccca gatcccttct gggattcatg ttgtggagga    4500
ccaccagcac agtatatccg gtgcacttgg gaaatttgtc atgcagctta gagggaaatg    4560
cgtggaagaa cttggagacg cccttgtggc ctcccagatt ctccatgcat cgtccatga    4620 tgatggcaat gggcccgcgg gaggcggcct gggcaaagat gtttctgggg tcactgacat    4680
cgtagttgtg ttccagggtg agatcgtcat aggccatttt tataaagcgc gggcggaggg    4740
tgcccgactg ggggatgatg gttccctcgg gccccggggc gtagttgcct tcgcagatct    4800
gcatttccca ggccttaatc tctgagggg gaatcatatc cacttgcggg gcgatgaaga    4860
aaacggtttc cggagccggg gagattaact gggatgagag caggtttctc agcagctgtg    4920
actttccaca gccggtgggt ccataaataa cacctataac cggctgcagc tggtagttga    4980
gcgagctgca gctgccgtcg tcccggagga gggggccac tcattgagc atgtcccgga    5040 cgcgcttgtt ctcctcgacc aggtccgcca aaggcgctc gccgcccagg acagcagct    5100 cttgcaagga agcaaagttt ttcagcggtt tgaggccgtc cgccgtgggc atgttttca    5160 gggtctggcc gagcagctcc aggcggtccc agagctcggt gacgtgctct acggcatctc    5220
tatccagcat atctcctcgt ttcgcgggtt ggggcggctt tcgctgtagg caccaggcg    5280 atggtcgtcc agcgcggcca gagtcatgtc cttccatggg cgcagggtcc tcgtcagggt    5340
ggtctgggtc acggtgaagg ggtgcgcccc gggctgggcg ctggccaggg tgcgcttgag    5400
actggtcctg ctggtgctga agcgctgccg gtcttcgccc tgcgcgtcgg ccaggtagca    5460
tttgaccatg gtgtcgtagt ccagcccctc cgcggcgtgt cccttggcgc gcagcttgcc    5520 cttgaggtg gcgccgcacg cggggcactg caggctcttg agcgcgtaga gcttgggggc    5580
gaggaagacc gattcggggg agtaggcgtc cgcgccgcag gccccgcaca cggtctcgca    5640
```

```
ctccaccagc caggtgagct cggggcgctc ggggtcaaaa accaggtttc ccccatgctt    5700
tttgatgcgt ttcttacctc gggtctccat gaggcggtgt cccgttcgg tgacgaagag     5760
gctgtccgtg tctccgtaga ccgacttgag gggtctgtcc tccagggggg tccctcggtc    5820
ctcttcgtag agaaactcgg accactctga gacaaaggcc cgcgtccagg ccaggacgaa    5880
ggaggccagg tgggagggt accggtcgtt gtccactagg gggtccacct tctccaaggt    5940
gtgaagacac atgtcgccct cctcggcgtc caggaaggtg attggcttgt aggtgtaggc    6000
cacgtgaccc ggggttccgg acgggggggt ataaaagggg gtggggcgc gctcgtcctc    6060
actctcttcc gcatcgctgt ctgcgagggc cagctgctgg ggtgagtatt ccctctcgaa    6120
ggcgggcatg acctcagcgc tgaggctgtc agtttctaaa aacgaggagg atttgatgtt    6180
cacctgtccc gagctgatgc ctttgagggt gcccgcgtcc atctggtcag aaaacacgat    6240
cttttattg tccagcttgg tggcgaacga cccgtagagg gcgttggaga gcagcttggc     6300
gatggagcgc agggtctgat tcttgtcccg gtcggcgcgc tccttggccg cgatgttgag    6360
ctgcacgtac tcgcgcgcga cgcagcgcca ctcggggaag acgtggtgc gctcgtcggg     6420
caccaggcgc acgcgccagc cgcggttgtg cagggtgacg aggtccacgc tggtggcgac    6480
ctcgccgcgc aggcgctcgt tggtccagca gaggcgcccg cccttgcgcg agcagaaggg    6540
gggcaggggg tcgagttggg tttcgtccgg ggggtccgcg tccaccgtga gaccccggg    6600
gcgcaggcgc gcgtcgaagt agtcgatctt gcatccttgc aagtccagcg cccgctgcca    6660
gtcgcgggcg gcgagcgcgc gctcgtaggg gttgagcggc gggccccagg gcatggggtg    6720
ggtgagcgcg gaggcgtaca tgccgcagat gtcatagacg tagaggggct cccggaggat    6780
gcccaggtag gtggggtagc agcggccgcc gcggatgctg gcgcgcacgt agtcgtagag    6840
ctcgtgcgag ggggcgagga ggtcggggcc caggttggtg cgggcggggc gctccgcgcg    6900
gaagacgatc tgcctgaaga tggcatgcga gttggaagag atggtggggc gctggaagac    6960
gttgaagctg gcgtcctgca ggccgacggc gtcgcgcacg aaggaggcgt aggactcgcg    7020
cagcttgtgc accagctcgg cggtgacctg cacgtcgagc gcgcagtagt cgagggtctc    7080
gcggatgatg tcatacttag cctgccccctt ctttttccac agctcgcggt tgaggacgaa    7140
ctcttcgcgg tctttccagt actcttggat cgggaaaccg tccggctccg aacggtaaga    7200
gcccagcatg tagaactggt tgacggcctg gtaggcgcag cagcccttct ccacgggcag    7260
ggcgtaggcc tgcgcggcct tgcggagcga ggtgtgggtc agggcgaagg tgtccctgac    7320
catgaccttg aggtactggt gtttgaagtc ggagtcgtcg cagccgcccc gctcccagag    7380
cgagaagtcg gtgcgctttt tggagcgggg gttgggcagc gcgaaggtga catcgttgta    7440
gaggatcttg cccgcgcgag gcatgaagtt gcggtgatg cggaagggcc ccggcacttc     7500
cgagcggttg ttgatgacct gggcggcgag cacgatctcg tcgaagccgt tgatgttgtg    7560
gcccacgatg tagagttcca ggaagcgggg ccggcccttg acgctgggca gcttctttag    7620
ctcttcgtag gtgagctcct cgggcgaggc gaggccgtgc tcggccaggg cccagtccgc    7680
caggtgcggg ttgtccgcga ggaaggaccg ccagaggtcg cgggccagga gggtctgcag    7740
gcggtccctg aaggtcctga actgcgcgcc tacggccatc ttttcggggg tgacgcagta    7800
gaaggtgagg gggtcttgct gccagggtc ccagtcgagc tccagggcga ggtcgcgcgc     7860
ggcggcgacc aggcgctcgt cgccccccgaa tttcatgacc agcatgaagg gcacgagctg    7920
cttttccgaag gcgcccatcc aagtgtaggt ctctacatcg taggtgacaa agagacgttc    7980
cgtgcgagga tgcgagccga tcgggaagaa ctggatctcc cgccaccagt tggaggagtg     8040
```

```
gctgttgatg tggtgaaagt agaagtcccg tcggcgggcc gagcactcgt gctggctttt    8100
gtaaaagcga gcgcagtact ggcagcgctg cacgggctgt acctcttgca cgagatgcac    8160
ctgccgaccg cggacgagga agctgagtgg gaatctgagc cccccgcatg gctcgcggcc    8220
tggctggtgc tcttctactt tggatgcgtg gccgtcaccg tctggctcct cgaggggtgt    8280
tacggtggag cggatcacca cgccgcgcga ccgcaggtc cagatatcgg cgcgcggcgg     8340
tcggagtttg atgacgacat cgcgcagctg ggagctgtcc atggtctgga gctcccgcgg    8400
cggcggcagg tcagccggga gttcttgcag gtttacctcg cagagacggg ccagggcgcg    8460
gggcaggtcc agtggtact tgaattcgag aggcgtgttg gtggcggcgt cgatggcttg     8520
cagtatgccg cagccccggg gcgcgacgac ggtgccccgc ggggcggtga agctcccgcc    8580
gccgctcctg ctgtcgccgc cggtggcggg gcttagaagc ggtgccgcgg tcgggccccc    8640
ggaggtaggg ggggctccgg tcccgcgggc aggggcggca gcggcacgtc ggcgccgcgc    8700
gcgggcagga gctggtgctg cgcccggagg ttgctggcga aggcgacgac gcggcggttg    8760
atctcctgga tctggcgcct ctgcgtgaag acgacgggtc cggtgagctt gaacctgaaa    8820
gagagttcga cagaatcaat ctcggtgtca ttgaccgcga cctggcgcag gatctcctgc    8880
acgtcgcccg agttgtcttg gtaggcgatc tcggccatga actgttcaat ctcttcctcc    8940
tggaggtctc cgcgtccggc gcgctccacg gtggccgcca ggtcgttgga gatgcgcgcc    9000
atgagctgcg agaaggcgtt gagtccgccc tcgttccaca ctcggctgta gaccacgccg    9060
ccctggtcgt cgcgggcgcg catgaccacc tgcgcgaggt tgagttccac gtggcgcgca    9120
aagacggcgt agttgcgcag gcgctggaag aggtagttga gggtggtggc ggtgtgctcg    9180
gccacaaaga agtacatgac ccagcggcgc aacgtggatt cgttgatgtc ccccaaggcc    9240
tccagtcgct ccatggcctc gtagaagtcc acggcgaagt tgaaaaactg ggagttgcgc    9300
gccgacacgg tcaactcctc ctccagaaga cggatgagct cggcgacggt gtcgcgcacc    9360
tcgcgctcga aggctatggg aatctcttcc tccgccagca tcaccacctc ttcctcttct    9420
tcctcctctg gcacttccat gatgcttcc tcctcttcgg ggggtggcgg cggggggagg     9480
ggcgctcggc gccggcggcg gcgcaccggg aaggcggtcca cgaagcgctc gatcatctcc    9540
ccgcggcggc gacgcatggt ctcggtgacg gcgcggccgt tctctcgggg acgcagctgg    9600
aagacgccgc cggtcatctg gtgctgggc gggtggccgt ggggcagcga gaccgcgctg     9660
acgatgcatc ttaacaattg ctgcgtaggt acgccgccga gggacctgag ggagtccaga    9720
tccaccggat ccgaaaacct ttcgaggaag gcatctaacc agtcgcagtc gcaaggtagg    9780
ctgagcaccg tggcgggcgg cggggggtgg ggggagtgtc tggcggaggt gctgctgatg    9840
atgtaattga agtaggcggt cttgacacgg cggatggtcg acaggagcac catgtctttg    9900
ggcccggcct gctggatgcg gaggcggtcg gccatgcccc aggcttcgtt ctggcatctg    9960
cgcaggtctt tgtagtagtc ttgcatgagc ctttccaccg gcacctcttc tccttcttct   10020
tctgacatct ctgctgcatc tgcggccctg gggcgacggc gcgcgcccct gcccccccatg   10080
cgcgtcaccc cgaaccccct gagcggctgg agcagggcca ggtcggcgac gacgcgctcg   10140
gccaggatgg cctgctggac ctgcgtgagg gtggtttgga agtcatccaa gtccacgaag   10200
cggtggtagg cgcccgtgtt gatggtgtag gtgcagttgg ccatgacgga ccagttgacg   10260
gtctggtggc ccggttgcgt catctcggtg tacctgaggc gcgagtaggc gcgcgagtcg   10320
aagatgtagt cgttgcaagt ccgcaccagg tactggtagc ccaccaggaa gtgcggcggc   10380
```

```
ggctggcggt agaggggcca gcggaggtg gcggggctc cggggccag gtcttccagc    10440 atgaggcggt ggtattcgta gatgtacctg gacatccagg tgatgcccgc ggcggtggtg    10500
gaggcgcgcg ggaagtcgcg cacccggttc agatgttgc gcagcggcag aaagtgctcc    10560
atggtaggcg tgctctggcc ggtcaggcgc gcgcagtcgt tgatactcta gaccagggaa    10620
aacgaaagcc ggtcagcggg cactcttccg tggtctggtg gataaattcg caagggtatc    10680
atggcggagg gcctcggttc gagcccgggg cccgggccgg acgtccgcc atgatccacg    10740 cggttaccgc ccgcgtgtcg aacccaggtg gcgacgtcag acaacggtgg agtgttcctt    10800
ttgggttttt ttccaaattt ttctggccgg gcgccgacgc cgccgcgtaa gagactagag    10860
tgcaaaagcg aaagcagtaa gtggctcgct ccctgtagcc cggaggatcc ttgctaaggg    10920
ttgcgttgcg gcgaaccccg gttcgagtct ggctctcgct gggccgctcg ggtcggccgg    10980
aaccgcggct aaggcgggat tggcctcccc ctcattaaag accccgcttg cggattcctc    11040
cggacacagg ggacgagccc cttttttactt ttgcttttct cagatgcatc cggtgctgcg    11100
gcagatgcgc ccccgccc agcagcagca gcagcaacat cagcaagagc ggcaccagca    11160
gcagcgggag tcatgcaggg ccccctcgcc cacgctcggc ggtccggcga cctcggcgtc    11220
cgcggccgtg tctggagccg gcggcggtgg gctggcggac gacccggagg agcccccgcg    11280
gcgcagggcc agacagtacc tggacctgga ggagggcgag ggcctggcgc gactggggc    11340 gccgtccccc gagcgccacc cgcggtgca gctgaagcgc gactcgcgcg aggcgtacgt    11400
gcctcggcag aacctgttca gagaccgcgc gggcgaggag cccgaggaga tgcgggaccg    11460
caggttcgcc gcggggcggg agctgcggca ggggctgaac cggagcggc tgctgcgcga    11520 ggaggacttt gagcccgacg cgcggacggg gatcagcccc gcgcgcgcgc acgtggcggc    11580
cgccgacctg tgacggcgt acgagcagac ggtgaaccag gagatcaact tccaaaaaag    11640
cttcaacaac cacgtgcgca cgctggtggc gcgcgaggag gtgaccatcg gcctgatgca    11700
cctgtgggac tttgtgagcg cgctggagca gaaccccaac agcaagcctc tgacggcgca    11760
gctgttcctg atagtgcagc acagcaggga caacgaggcg ttcagggacg cgctgctgaa    11820
catcaccgag cccgagggtc ggtggctgct ggacctgatt aacatcttgc agagcatagt    11880
ggtgcaggag cgcagcctga gcctggccga caaggtggcg gccatcaatt actcgatgct    11940
cagtctgggc aagttttacg cgcgcaagat ctaccagacg ccgtacgtgc ccatagacaa    12000
ggaggtgaag atcgacggct tctacatgcg catggcgctg aaggtgctga ccctgagcga    12060
cgacctgggc gtgtaccgca acgagcgcat ccacaaggcc gtgagcgtga gccggcggcg    12120
cgagctgagc gaccgcgagc tgatgcacag cctgcagcgg gcgctggcgg gggccggcag    12180
cggcgacagg gaggccgagt cctacttcga ggcgggggcg gacctgcgct gggtgccag    12240 ccggagggcc ctggaggccg cggggcccg ccgcgaggac tatgcagacg aggaggagga    12300
ggatgacgag gagtacgagc tagaggaggg cgagtacctg gactaaaccg caggtggtgt    12360
ttttggtaga tgcaagaccc gaacgtggtg gacccgcgcg tgcgggcggc tctgcagagc    12420
cagccgtccg gccttaactc tacagacgac tggcgacagg tcatggaccg catcatgtcg    12480
ctgacgcgcg gcaatccgga gcgcgttccg cagcagccgc aggccaacag gctctccgcc    12540
atcttggagg cggtggtgcc tgcgcgcgcg aaccccacgc acgagaaggt gctggccata    12600
gtgaacgcgc tggccgagaa cagggccatc cgcccggacg aggccgggct ggtgtacgac    12660
gcgctgctgc agcgcgtggc ccgctacaac agcggcaacg tgcagaccaa cctgaccggg    12720
ctggtggggg acgtgcgcga ggcggtggcg cagcgggagc gcgcggagcg gcagggaaac    12780
```

```
ctgggctcca tggtggcgct gaacgccttc ctgagcacgc agccggccaa cgtgccgcgg    12840
gggcaggagg actacaccaa ctttgtgagc gcgctgcggc tgatggtgac cgagaccccc    12900
cagagcgagg tgtaccagtc ggggccggac tactttttcc agaccagcag acagggcctg    12960
cagacggtga acctgagcca ggctttcaag aacctgcggg gctgtgtggg cgtgaaggcg    13020
cccaccgggg accgggcgac ggtgtccagc ctgctgacgc ccaactcgcg cctgctgctg    13080
ctgctgatcg cgccgttcac ggacagcggc agcgtgtccc gggagaccta cctcgggcac    13140
ctgctgacgc tgtaccgcga ggccatcggg cagacccagg tggacgagca caccttccag    13200
gagatcacca gcgtgagccg cgcgctgggg caggaggaca cgggcagcct ggaggcgacc    13260
ctgaactacc tgctgaccaa ccggcggcag aagatcccct cgctgcatag tttgaccacc    13320
gaggaggagc gcatcctgcg ctacgtgcag cagagcgtga gcctgaacct gatgcgcgac    13380
ggggtgacgc ccagcgtggc gctggacatg accgcgcgca acatggaacc gggcatgtac    13440
gccgcgcatc ggccttacat caaccgcctg atggactact tgcatcgcgc ggcggccgtg    13500
aaccccgagt acttcaccaa cgccatcctg aacccgcact ggctcccgcc gcccgggttc    13560
tacagcgggg gcttcgaggt ccccgaggcc aacgacggct tcctgtggga cgacatggac    13620
gacagcgtgt tctccccgcg gccgcaggcg ctggcggagg cgtcgctgct ccgcctcccc    13680
aagaaagaag agagccgccg gcccagcagc gcggcggcct ctctgtccga gctggggcg    13740 gcggccgcgc ggcccgggtc cctgggggc agcccctttc ccagtctggt ggggtctctg    13800
cagagcgggc gcaccacccg gccccggctg ctgggcgagg acgagtacct gaacaactcc    13860
ctgatgcagc cggtgcggga gaaaaacctg ccccccgcct tccccaacaa cgggatagag    13920
agcctggtag acaagatgag cagatggaag acctatgcgc aggagcacag ggactcgccc    13980
gtgctccgtc cgcccacgcg cgccagcgc cacgaccggc agcgggggct ggtatgggat    14040
gacgaggact ccgcggacga tagcagcgtg ctggacctgg gggggagcgg cggtaacccg    14100
ttcgcgcacc tgcgcccccg cctggggagg atgtttcaat aagaaaaatc aagcatgatg    14160
caaggttttt taagcggata aataaaaaac tcaccaaggc catggcgacc gagcgttgtt    14220
ggtttcttgt tgtgttccct tagtatgcgg cgcgcggcga tgtaccacga gggacctcct    14280
ccctcttatg agagcgtggt gggcgcggcg gcggcctctc cctttgcgtc gcagctggag    14340
ccgccgtacg tgcctccgcg gtacctgcgg cctacggggg gaagaaacag catccgttac    14400
tcggagctgg cgcccctgta cgacaccacc cgggtgtacc tggtggacaa caagtcggcg    14460
gacgtggcct ccctgaacta ccagaacgac cacagcaatt ttttgaccac ggtcatccag    14520
aacaatgact acacccccgag cgaggccagc acccagacca tcaatctgga tgaccggtcg    14580
cactggggcg cgacctgaa aaccatcctg cacaccaaca tgcccaacgt gaacgagttc    14640
atgttcacca ataagttcaa ggcgcgggtg atggtgtcgc gttcgcacac caaggacgac    14700
cgggtggagc tgaagtacga gtgggtagag ttcgagctgc cgagggcaa ctactcgag    14760 accatgacca tagacctgat gaacaacgcg atcgtggagc actatctgaa agtgggcagg    14820
cagaacgggg tcctggagag cgacatcggg gtcaagttcg acaccaggaa cttccgcctg    14880
gggctggacc cggtcaccgg gctggtcatg cccgggtct acaccaacga ggccttccac    14940
cccgacatca tcctgctgcc cggctgcggg gtggacttca cctacagccg cctgagcaac    15000 ctgctggca tccgcaagcg gcagcccttc caggagggct ttaggatcac ctacgaggac    15060
ctggaggggg gcaacatccc cgcgctcctg gatgtggagg cctaccagga tagcttgaag    15120
```

```
gaagaagagg cgggagaggg cagcggcggc ggcggcggcg ccggtcagga ggagggcggg   15180
gcctcctctg aggcctctgc ggacgccgcc gctgccgccg aggcggaggc ggccgacccc   15240
gcgatggtgg tagaggaaga gaaggatatg aatgacgagg cggtgcgcgg cgacaccttt   15300
gccacccggg gggaggagaa gaaagcggag gccgaggccg cggcagagga ggcggcagcg   15360
gcggcggcgg cggcagtaga ggcggcggcc gaggcggaga agccccccaa ggagcccgtg   15420
attaaggccc tgaccgaaga tagcaagaag cgcagttaca acgtgctcaa ggacagcacc   15480
aacaccgcgt accgcagctg gtacctggcc tacaactacg gcgacccggc gacggggtg    15540 cgctcctgga ccctgctgtg tacgccgac gtgacctgcg gctcggagca ggtgtactgg   15600
tcgctgcccg acatgatgca agaccccgtg accttccgct ccacgcggca ggtcagcaac   15660
ttcccggtgg tgggcgccga gctgctgccc gtgcactcca agagcttcta caacgaccag   15720
gccgtctact cccagctcat ccgccagttc acctctctga cccacgtgtt caatcgcttt   15780
cctgagaacc agattctggc gcgcccgccc gcccccacca tcaccaccgt cagtgaaaac   15840
gttcctgctc tcacagatca cgggacgcta ccgctgcgca acagcatcgg aggagtccag   15900
cgagtgaccg taactgacgc cagacgccgc acctgtccct acgtttacaa ggccctgggc   15960
atagtctcgc cgcgcgtcct ttccagccgc acttttttaag catgtccatc ctcatctcgc   16020
ccagcaataa caccggctgg ggcctgctgc gcgcgcccag caagatgttt ggaggggcga   16080
ggaagcgctc cgaccagcac cccgtgcgcg tgcgcgggca ctaccgcgcc ccctggggcg   16140
cgcacaaacg cgggcgcacc ggcaccgcgg ggcgcaccac cgtggacgaa gccatcgact   16200
cggtggtgga gcaggcgcgc aactacacgc ccgcggtctc caccgtggac gcggctatcg   16260
agagcgtggt gcgaggcgcg cggcggtacg ccaaggcgaa gagccgccgg aggcgcgtgg   16320
cccgccgcca ccgccgtcga cccggaagcg ccgccaagcg cgccgccgcc gccttgcttc   16380
gtcgggccag acgcacgggc cgccgcgccg ccatgagggc cgcgcgccgc ctggccgccg   16440
gcatcaccac cgtggccccc cgcgccagaa gacgcgcggc cgctgccgcc gccgcggcca   16500
tcagcgacct ggccaccagg cgccggggca acgtgtactg ggtgcgcgac tcggtgagcg   16560
gcacgcgcgt gcccgtgcgc ttccgccccc cgcggacttg agaggagagg acaggaaaaa   16620
agcatcaaca acaccaccac tgagtctcct gctgttgtgt gtatcccagc ggcgcgcgcg   16680
cacacgcgca catgtccaag cgcaaaaatca aagaagagat gctccaggtc gtcgcgccgg   16740
aaatctatgg gcccccgaag aaggaagagc aggatttcaa gccccgcaag ataaagcggg   16800
tcaaaaagaa aaagaaagat gacgatgatg gcgaggtgga gtttctgcgc gccacggcgc   16860
ccaggcgccc gctgcagtgg aagggtcggc gcgtaaagcg cgttctgcgc cccggcaccg   16920
cggtggtctt cacgcccggc gagcgctcca cccgcacttt caagcgcgtc tatgacgagg   16980
tgtacggcga cgaagacctg ctggagcagg ccaacgatcg ctccggagag tttgcttacg   17040
ggaagcggca ccgggcgatg gagaaggacg aggtgctggc gctgccgctg accggggca    17100 acccccacccc cagcctgaag cccgtgaccc tgcagcaggt gctgccggcc agcgcgccct   17160
ccgagatgaa gcggggcctg aagcgcgagg cggcgacct ggcgcccacc gtgcagctga    17220
tggtgcccaa gcggcagagg ctggaggacg tgctggagaa aatgaaagta gaccccggcc   17280
tgcagccgga catcagggtc cgccccatca agcaggtggc gccgggcctc ggcgtgcaga   17340
ccgtggacgt ggtcatcccc accggcgcct cctcttccag cgccgccgcc gccactagca   17400
ccgcggacat ggagacgcag actagctccg ccctcgccgc ccccgcggcc gccgccgccg   17460
ccacctcctc ggcggaggta cagacggacc cctggatgcc gccgccggcg gccgccccct   17520
```

```
cgcgcgcacg ccgcgggcgc aggaagtacg gcgccgccag cgcgctcatg cccgagtacg    17580
ccttgcatcc ttccatcgcg cccacccccg gctaccgagg ctacagctac cgcccgcgaa    17640
gagccaaggg ctccacccgc cgcagccgcc gcgccgccac ctctacccgc cgccgcagtc    17700
gccgccgccg ccggcagccc gcgctggctc cgatctccgt gaggagagtg gcgcgcaacg    17760
gggacacctt ggtgctgccc agggcgcgct accaccccag catcgtttaa aagcctgttg    17820
tggttcttgc agatatggcc ctcacttgcc gcctccgttt cccggtgccg ggataccgag    17880
gaagatcgcg ccgtagaagg ggtatggccg gacgcggcct gagcggaggc agccgccgtg    17940
cgcaccggcg gcgacgcgcc accagccgac gcatgcgcgg cggggtgctg cctctgctga    18000 tcccctgat cgccgcggcg atcggcgccg tgcccgggat cgcctccgtg gccttgcagg    18060
cgtcccagag gcgttgacac agacttcttg caagcttgca aaaatatgga aaaaatcccc    18120
ccaataaaaa agtctagact ctcacgctcg cttggtcctg tgactattt gtagaaaaaa    18180 agatggaaga catcaacttt gcgtcgctgg ccccgcgtca cggctcgcgc ccgttcctgg    18240
gacactggaa cgatatcggc accagcaaca tgagcggtgg cgccttcagt tggggctctc    18300
tgtggagcgg cattaaaaat atcggttctg ccgttaagaa ttacggctcc aaggcctgga    18360
acagcagcac gggccagatg ttgagagaca agttgaaaga gcagaacttc cagcagaagg    18420
tggtggaggg cctggcctcc ggcatcaacg gggtggtgga cctggccaat caggccgtgc    18480
aaaataagat caacagcaga ctggaccccc ggccgccggt ggaagagctg ccgccggcgc    18540
tggagacggt gtcccccgat gggcggggcg aaaagcgccc gcggcccgac agggaagaga    18600
ccactctggt cacgcacacc gatgagccgc cccctacga ggaagctctg aagcaaggct    18660
tgcccaccac tcggcccatc gcgcccatgg ccaccggggt ggtgggccgc cacacccccg    18720
ccaggctgga cctgcctcct cctcctgttt cttcttcggc cgccgatgcg cagcagcaga    18780
aggcggcgct gccccggtccg cccgcggccg cccccccgtcc caccgccagt cgagcgcccc    18840
tgcgtcgcgc ggccagcggc ccccgcgggg tcgcgaggca cagcagcggc aactggcaga    18900
acacgctgaa cagcatcgtg ggtctggggg tgcagtccgt gaagcgccgc cgatgctact    18960
gaatagctta gctaacggtg ttgtatgtgt gtatgcgtcc tatgtcaccg ccagaggagc    19020
tgctgagtcg ccgccgttcg cgcgcccacc gccactacca ccgccggtac cactccagcg    19080
cccctcaaga tggcgacccc atcgatgatg ccgcagtggt cgtacatgca catctcgggc    19140
caggacgcct cggagtacct gagcccccggg ctggtgcagt tcgcccgcgc caccgacagc    19200
tacttcagcc tgagtaacaa gtttaggaac cccacggtgg cgcccacgca cgatgtgacc    19260
accgaccggt cccagcgcct gacgctgcgg ttcatccccg tggaccgcga ggacaccgcg    19320
tactcttaca aggcgcggtt caccctggcc gtgggcgaca accgcgtgct ggacatggcc    19380
tccacctact ttgacatccg cggcgtgctg gacaggggcc ccaccttcaa gccctactcc    19440
ggcaccgcct acaactccct ggcccccaag ggcgccccca ctcctgcga gtgggagcaa    19500 gaggagactc agacagctga agaggcacaa gacgaagaag aagatgaagc tgaagctgag    19560
gaggaaatgc ctcaggaaga gcaagcacct gtcaaaaaga ctcatgtata tgctcaggct    19620
cccctttctg gcgaaaaaat tactaaagac ggtctgcaga taggaacgga cgctacagct    19680
accgaacaaa aacctatttta tgcagatccc acattccagc cagaacccca aattggtgaa    19740
tctcagtgga atgaggcaga tgcttcagtt gccggcggta gagtgctgaa gaaaactact    19800
cccatgaaac cctgttatgg ttcctatgcc aggcccacaa atgccaatgg aggtcagggt    19860
```

```
gtattggtgg agaaagacgg tggaaagatg gaaagccaag tagatatgca attcttttcg   19920
acttctgaaa acgcccgtaa cgaggctaac aacattcagc ccaaattggt gctgtacagc   19980
gaggatgtgc atatggagac cccagacaca cacatttctt acaagcctgc aaaaagcgat   20040
gataattcga aagtcatgct gggtcagcag tccatgccca acaggccaaa ttacatcggc   20100
ttcagagaca actttatcgg gctcatgtat tacaacagca ctggcaacat gggggtgctg   20160
gcaggtcagg cctcacagtt gaatgcggtg gtggacttgc aagacagaaa cacagaactg   20220
tcctaccagc tcttgcttga ttccatggga gacagaacca gatactttc catgtggaat   20280
caggcggtgg acagttatga tccagatgtc agaattattg aaaatcatgg aactgaagat   20340
gagctgccca actattgttt ccctctggga ggcataggg taactgacac ttaccaggcc   20400
attaagacta atggcaatgg caacggcggg ggcaatacca cttggaccaa ggatgaaact   20460
tttgcagacc gcaacgagat aggggtggga aacaatttcg ccatggagat caacctcagt   20520
gccaacctgt ggaggaactt cctctactcc aacgtggccc tgtacctgcc agacaagctt   20580
aagtacaacc cctccaacgt ggaaatctct gacaacccca cacctacga ctacatgaac   20640
aagcgagtgg tggccccggg gctggtggac tgctacatca acctgggcgc gcgctggtcc   20700
ctggactaca tggacaacgt caaccccttc aaccaccacc gcaacgcggg cctgcgctac   20760
cgctccatgc ttctgggcaa cgggcgctac gtgcccttcc acatccaggt gccccagaag   20820
ttctttgcca tcaagaacct cctcctcctg ccgggctcct acacctacga gtggaacttc   20880
aggaaggatg tcaacatggt cctccagagc tctctgggta acgacctcag ggtcgacggg   20940
gccagcatca agttcgagag catctgcctc tacgccacct tcttcccat ggcccacaac   21000
acggcctcca cgctcgaggc catgctcagg aacgacacca cgaccagtc cttcaacgac   21060
tacctctccg ccgccaacat gctctacccc atccccgcca acgccaccaa cgttcccatc   21120
tccatcccct cgcgcaactg ggcggccttc cgcggctggg ccttcacccg cctcaagacc   21180
aaggagaccc cctccctggg ctcgggtttc gacccctact acacctactc gggctccata   21240
ccctacctgg acggaacctt ctacctcaac cacactttca gaaggtctc ggtcaccttc   21300
gactcctcgg tcagctggcc gggcaacgat cgcctgctca cccccaacga gttcgagatc   21360
aagcgctcgg tcgacgggga gggctacaac gtggcccagt gcaacatgac caaggactgg   21420
ttcctcatcc aaatgctggc caactacaac atcggctatc agggcttcta catcccagag   21480
agctacaagg acaggatgta ctccttcttt aggaacttcc agcccatgag ccggcaggtg   21540
gtggacgaaa ccaagtacaa ggactaccag caggtgggca tcatccacca gcacaacaac   21600
tcgggcttcg tgggctacct cgcccccacc atgcgcgagg acaggcccta ccccgccaac   21660
ttcccctacc cgctcattgg caagaccgcg gtcgacagcg tcacccagaa aaagttcctc   21720
tgcgaccgca ccctctggcg catccccttc tccagcaact tcatgtccat gggtgcgctc   21780
acggacctgg gccagaacct gctctatgcc aactccgccc acgcgctcga catgaccttc   21840
gaggtcgacc ccatggacga gcccaccctt ctctatgttc tgttcgaagt ctttgacgtg   21900
gtccgggtcc accagccgca ccgcggcgtc atcgagaccg tgtacctgcg cacgcccttc   21960
tcggccggca acgccaccac ctaaagaagc aagccgccac cgccaccacc tgcatgtcgt   22020
cgggttccac cgagcaggag ctcaaggcca tcgtcagaga cctgggatgc gggccctatt   22080
ttttgggcac cttcgacaaa cgcttcccgg gcttcgtcgc cccgcacaag ctggcctgcg   22140
ccatcgtcaa cacggccggc cgcgagaccg ggggcgtgca ctggctggcc ttcgcctgga   22200
acccgcgctc caaaacatgc tacctctttg accccttcgg attctcggac cagcggctca   22260
```

```
agcagatcta ccagttcgag tacgagggcc tgctgcgccg cagcgccatc gcctcctcgc  22320
ccgaccgctg cgtcaccctc gagaagtcca cccagaccgt gcaggggccc gactcggccg  22380
cctgcggtct cttctgctgc atgttcctgc atgcctttgt gcactggccc cagagtccca  22440
tggaccgcaa ccccaccatg aacttgctga cggggatccc caactccatg ctccagagcc  22500
cccaggtcgc gcccaccctg cgccgcaacc aggagcggct ctacagcttc ctggaacgcc  22560
actcgcccta cttccgccgc cacagcgcgc agatcagggg ggccacctct ttctgccgca  22620
tgcaagagat gcaagggaaa atgcaatgat gtacacagac acttttttctt ttctcaataa  22680 atggcaactt tatttataca tgctctctct cgggtattca tttccccacc acccaccacc  22740
cgccgccgcc gtaaccatct gctgctggct ttttttttttt tttttaaaaa tcgaaagggt  22800
tctgccggga atcgccgtgc gccacgggca gggacacgtt gcggaactgg tagcgggtgc  22860
cccacttgaa ctcgggcacc accatgcggg gcaagtcggg gaagttgtcg gcccacaggc  22920
tgcgggtcag caccagcgcg ttcattaggt cgggcgccga gatcttgaag tcgcagttgg  22980
ggccgccgcc ctgcgcgcgc gagttgcggt acaccgggtt gcaacactgg aacaccagca  23040
gcgccggata attcacactg gccagcacgc tccggtcgga gatcagctcg gcgtccaggt  23100
cctccgcgtt gctcagcgcg aacggggtca gcttgggcac ctgccgcccc aggaagggag  23160
cgtgccccgg cttcgagttg cagtcgcagc gcagcgggat cagcaggtgc ccgcggccgg  23220
actcggcgtt ggggtacagc gcgcgcatga aggcctccat ctggcggaag gccatctggg  23280
ccttggcgcc ctccgagaag aacatgccgc aggacttgcc cgagaactgg ttcgcggggc  23340
agctagcgtc gtgcaggcag cagcgcgcgt cggtgttggc gatctgcacc acgttgcgcc  23400
cccaccggtt cttcacgatt ttggccttgg aagcctgctc cttcagcgcg cgctgcccgt  23460
tctcgctggt cacatccatc tcgatcacgt gctccttgtt caccatgctg ctgccgtgca  23520
gacacttcag ctcgccctcc acctcggtgc agcggtgctg ccatagcgcg cagcccgtgg  23580
gctcgaaatg cttgtaggtc acctccgcgt aggactgcag gtaggcctgc aggaagcgcc  23640
ccatcatggt cacgaaggtc ttgttgctgc tgaaggtcag ctgcagcccg cggtgctcct  23700
cgttcagcca ggccttgcac acggccgcca gcgcctccac ctggtcgggc agcatcttga  23760
agttcagctt cagctcattc tccacatggt acttgtccat cagcgcgcgc gcagcctcca  23820
tgcccttctc ccaggccgac accagcggca ggctcaaggg gttcaccacc gtcgcagccg  23880
ccgctgcgct ttcgctttcc gctccgctgt tctcttcttc ctcctcctct tcttcctcgc  23940
cgcccgcgcg cagcccccgc accacggggt cgtcttcctg caggcgccgc accgagcgct  24000
tgccgctcct gccctgcttg atacgcacgg gcgggttgct gaagcctacc atcaccagcg  24060
cggcctcttc ttgctcgtcc tcgctgtcca ctatgacctc ggggagggc gacctcagaa  24120 ccgtggcgcg ctgcctcttc ttttcctgg gggcgtttgc cagctccgcg gccgcggccg  24180
ccgccgaggt cgaaggccga gggctgggcg tgcgcggcac cagcgcgtcc tgcgagccgt  24240
cctcgtcctc ggactcgagg cggcagcgag cccgcttctt cgggggcgcg cggggcggcg  24300
gcggcggggg cggcggcgac ggagacgggg acgagacatc gtccagggtg ggaggacggc  24360
gggccgcgcc gcgtccgcgc tcgggggtgg tttcgcgctg gtcctcttcc cgactggcca  24420
tctcccactg ctccttctcc tataggcaga aagagatcat ggagtctctc atgcaagtcg  24480
agaaggagga ggacagccta accaccaccg cccctctga gccctccgcc gccgccgcgg  24540
acgacgcgcc caccaccacc gccgccgcca ccaccaccat taccaccta cccggcgacg  24600
```

```
cagccccgat cgagaaggaa gtgttgatcg agcaggaccc gggttttgtg agcgaagagg    24660
aggatgagga ggatgaaaag gagaaggata ccgccgcctc agtgccaaaa gaggataaaa    24720
agcaagacca ggacgacgca gagacagatg aggcagcagt cgggcggggg gacggaaggc    24780
atgatgatga tgacggctac ctagacgtgg gagacgacgt gctgcttaag cacctgcacc    24840
gccagtgcgt catcgtctgc gacgcgctgc aggagcgctg cgaagtgccc ctggacgtgg    24900
cggaggtcag ccgcgcctac gagcggcacc tcttcgcgcc acacgtgccc ccaagcgcc     24960 gggagaacgg cacctgcgag cccaacccgc gcctcaactt ctacccggtc ttcgcggtac    25020
ccgaggtgct ggccacctac cacatcttct tccaaaactg caagatcccc ctctcctgcc    25080
gcgccaaccg cacccgcgcc gacaagacgc tggccctgcg gcagggcgcc cacatacctg    25140
atatcgcctc tctggaggag gtgcccaaga tcttcgaggg tctcggtcgc gacgagaaac    25200
gggcggcgaa cgctctgcaa ggagacagcg aaaacgagag tcactcgggg gtgctggtgg    25260
agctcgaggg cgacaacgcg cgcctggccg tgctcaagcg cagcatcgaa gtcacccact    25320
tcgcctaccc ggcgctcaac ctgcccccca aggtcatgag tgtggtcatg agtgagctca    25380
tcatgcgccg cgcccagccc ctggacgcgg atgcaaactt gcaagagccc tccgaggaag    25440
gcctgcccgc ggtcagcgac gagcagctgg cgcgctggct ggagacccgc gaccccgccc    25500
agctggagga gcggcgcaag ctcatgatgg ccgcggtgct cgtcaccgtg gagctcgagt    25560
gtctgcagcg cttcttcggg gaccccgaga tgcagcgcaa gctcgaggag accctgcact    25620
acaccttccg ccagggctac gtgcgccagg cctgcaagat ctccaacgtg gagctctgca    25680
acctggtctc ctacctgggc atcctgcacg agaaccgcct cggcagaac gtcctgcact     25740 ccaccctcaa aggggaggcg cgccgcgact acgtccgcga ctgcgtctac ctcttcctct    25800
gctacacgtg gcagacggcc atgggggtct ggcagcagtg cctggaggag cgcaacctca    25860
aggagctgga gaagctcctc cggcgcgccc tcagggacct ctggacgggc ttcaacgagc    25920
gctcggtggc cgccgcgctg gcggacatca tcttccccga gcgcctgctc aaaaccctgc    25980
agcagggcct gcccgacttc accagccaga gcatgctgca gaacttcagg accttcatcc    26040
tggagcgctc gggcatcctg ccggccacct gctgcgcgct gccagcgac ttcgtgccca     26100 tcaggtacag ggagtgcccg ccgccgctct ggggccactg ctacctcttc cagctggcca    26160
actacctcgc ctaccactcg gatctcatgg aagacgtgag cggcgagggc ctgctcgagt    26220
gccactgccg ctgcaacctg tgcacgcccc accgctctct agtctgcaat ccgcagctgc    26280
tcagcgagag tcagattatc ggtaccttcg agctgcaggg tccctcgccc gacgaaaagt    26340
ccgcggctcc ggggttgaaa ctcactccgg ggctgtggac ttccgcctac ctacgcaaat    26400
ttgtacctga agactaccac gcccacgaga tcaggtttta cgaagaccaa tcccgcccgc    26460
ccaaggcgga gctcaccgcc tgcgtcatta cccagggcca catcctgggc caattgcaag    26520
ccatcaacaa agcccgccaa gagttcttgc tgaaaaaggg tcgggggggtg tacctggacc    26580 cccagtccgg cgaggagcta aacccgctac ccccgccgcc gccccagcag cgggaccttg    26640
cttcccagga tggcacccag aaagaagcag ccgccgccgc cgccagcata catgcttctg    26700
gaggaagagg aggactggga cagtcaggca gaggaggttt cggacgagga cgaggaggag    26760
gagatgatgg aagactggga ggaggacagc ctagacgagg aagcttcaga ggccgaagag    26820
gtggcagacg caaaccatc accctcggcc gcagcccct cgccggcgcc ccgaaatcc       26880 tccgaccccca gcagcagcgc tataacctcc gctcctccgg cgccggcgcc cacccgcagc    26940
agacccaacc gtagatggga cactacagga accggggtcg gtaagtccaa gtgcccccca    27000
```

```
gcgccgcccc cgcaacagga gcaacagcag cagcagcggc gacagggcta ccgctcgtgg    27060
cgcggacaca agaacgccat agtcgcctgc ttgcaagact gcgggggcaa catctccttc    27120
gcccgccgct tcctgctctt ccaccacggg gtggcttttc cccgcaatgt cctgcattac    27180
taccgtcatc tctacagccc ctactgcggc ggcagcggcg acccagaggg agcggcggca    27240
gcagcagcgc cagccacagc ggcgaccacc taggaagacc tccgcgggca agacggcggg    27300
agccgggaga cccgcggcgg cggcggtagc ggcggcggcg ggcgcactgc gcctctcgcc    27360
caacgaaccc ctctcgaccc gggagctcag acacaggatc ttccccactc tgtatgctat    27420
cttccagcag agcagaggcc aggaacagga gctcaaaata aaaaacagat ctctgcgctc    27480
cctcacccgc agctgtctgt atcacaaaag cgaagatcag cttcggcgca cgctggagga    27540
cgcggaggca ctcttcagca aatactgcgc gctgactctt aaggactagc cgcgcgccct    27600
tctcgaattt aggcgggaga aagactacgt catcgccgac cgccgcccag cccacccagc    27660
cgacatgagc aaagagattc ccacgcccta catgtggagc taccagccgc agatgggact    27720
cgcggcggga gcggcccaag actactccac ccgcatgaac tacatgagcg cggggcccca    27780
catgatctca cgggttaatg ggatccgcgc ccagcgaaac caaatactgc tggaacaggc    27840
ggccataacc gccacacccc gtcatgacct caatccccga aattggcccg ccgccctcgt    27900
gtaccaggaa accccctctg ccaccaccgt ggtacttccg cgtgacaccc aggccgaagt    27960
ccagatgact aactcagggg cgcagctcgc gggcggcttt cgtcacgggg tgcggccgca    28020
ccggccgggt atattacacc tggcgatcag aggccgaggt attcagctca acgacgagtc    28080
ggtgagctct tcgctcggtc tccgtccgga cggaaccttc cagatcgccg gatcaggtcg    28140
ctcctcattc acgcctcgcc aggcgtatct gactctgcag acctcctcct cggagcctcg    28200
ctccggcggc atcggcaccc tccagttcgt ggaggagttc gtgccctcgg tctacttcaa    28260
cccctccctcg ggacctcccg gacgctaccc cgaccagttc atcccgaact ttgacgcggt    28320
gaaggactcg gcggacggct acgactgaat gtcaagtgct gaggcagaga gcgttcgcct    28380
gaaacacctc cagcactgcc gccgcttcgc ctgctttgcc cgcagctccg gtgagttctg    28440
ctactttcag ctgcccgagg agcataccga agggccggcg cacggcgtcc gcctaaccac    28500
ccagggcgag gttacctgta cccttatccg ggagtttacc ctccgtcccc tgctagtgga    28560
gcgggagcgg ggttcttgtg tcataactat cgcctgcaac tgccctaacc ctggattaca    28620
tcaagatctt tgttgtcacc tgtgcgctga gtataataaa cgctgagatc agactctact    28680
ggggctcctg tcgccatcct gtgaacgcca ccgtcttcac ccaccccgag cagccccagg    28740
cgaacctcac ctgcggcctg cgtcggaggg ccaagaagta cctcacctgg tacttcaacg    28800
gcaccccctt tgtggtttac aacagcttcg accaggacgg agttgccttg agagacgacc    28860
tttccggtct cagctactcc attcacaaga acaccaccct ccacctcttc cctccctacc    28920
tgccgggaac ctacgagtgc gtcaccggcc gctgcaccca cctcctccgc ctgatcgtaa    28980
accagacctt tccgggaaca cacctcttcc ccagaacagg aggtgagctc aggaaaccc    29040
ctggggccca gggcggagac ttaccttcga cccttgtggg gttaggattt tttatcgccg    29100
ggttgctggc tctcctgatc aaagcttcct tcagatttgt tctctccctt tacttttatg    29160
aacagctcaa cttctaataa cgctaccttt tctcaggaat cgagtagtaa cttctcttcc    29220
gaaatcgggc tgggtgtgct gcttactctg ttgatttttt tccttatcat acttagcctt    29280
ctgtgcctca ggctcgccgc ctgctgcgca catatctaca tctacagccg gttgcttaac    29340
```

```
tgctggggtc gccatccaag atgaacgggg ctcaggtgct atgtctgctg gccctggtgg   29400
cctgcagtgc cgccgtcaat tttgaggaac ccgcttgcaa tgtgactttc aagcctgagg   29460
gcgcacattg caccactctg gttaaatgtg tgacctctca tgaaaaactg ctcatcgcct   29520
acaaaaacaa aacaggccag atcgcagtct atagcgagtg gctacccgga gaccataata   29580
actactcagt caccgtcttc gagggtgcgg agtctaagaa attcgattac accttccct   29640
tcgaggagat gtgtgatgcg gtcatgtacc tgtccaaaca gtacaagctg tggccccca   29700
cccccaaggc gtgtgtggaa aacactgggt ctttctgctg tctctctctg gcaatcactg   29760
tgcttgctct aatctgcacg ctgctataca tgagattcag gcagaggcga atctttatcg   29820
atgagaaaaa aatgccttga tcgctaacac cggctttctg tctgcagaat gaaagcaatc   29880
acctccctac taatcagcac caccctcctt gcgattgccc atgggttgac acgaatcgaa   29940
gtgccagtgg ggtccaatgt caccatggtg ggccccgccg gcaattcctc cctgatgtgg   30000
gaaaaatatg tccgtaatca atgggatcat tactgctcta atcgaatctg tatcaagccc   30060
agagccacct gcgacgggca aaatctaact ttgattgatg tgcaaatgac ggatgctggg   30120
tactattacg ggcagcgggg agaaatgatt aattactggc gaccccacaa ggactacatg   30180
ctgcatgtag tcaaggcagt cccaactact accaccccca ccactaccac tcccactacc   30240
accaccccca ccactaccac tagcactgct actaccgctg cccgcaaagc tattacccgc   30300
aaaagcacca tgcttagcac caagcccat tctcactccc acgccggcgg gcccaccggt   30360
gcggcctcag aaaccaccga gctttgcttc tgccaatgca ctaacgccag cgcccacgaa   30420
ctgttcgacc tggagaatga ggacgatgac cagctgagct ccgcttgccc ggtcccgctg   30480
cccgcagagc cggtcgccct gaagcagctc ggtgatccat ttaatgactc tcctgtttat   30540
ccctctcccg aatacccctcc cgactctacc ttccacatca cgggcaccaa agaccccaac   30600
ctctccttct acctgatgct gctgctctgt atctctgtgg tatcttccgc gctcatgtta   30660
ctgggcatgt tctgctgcct catctgccgc agaaaaagaa agtctcgctc tcagggccaa   30720
ccactgatgc ccttccccta ccccccagat tttgcagata caagatatg agcacgctgc   30780
tgacactaac cgctttactc gcctgcgctc taacccttgt cgcttgcgaa tccagatacc   30840
acaatgtcac agttgtgaca ggagaaaatg ttacattcaa ctccacggcc gacacccagt   30900
ggtcgtggag tggccacggt agctatgtat acatctgcaa tagctccacc tcccctagca   30960
tgtcctctcc caagtaccac tgcaatgaca gcctgttcac cctcatcaac gcctccacct   31020
cggacaatgg actctatgta ggctatgtga cacccgtgg gcagggaaag acccacgcct   31080
acaacctgca agttcgccac ccctccacca ccgccaccac ctctgccgcc cctacccgca   31140
gcagcagcag cagcagcagc agcagcagca gcagcagcag cagattcctg actttaatcc   31200
tagccagctc aacaaccacc gccaccgctg agaccaccca cagctccgcg cccgaaacca   31260
cccacacca ccacccagag acgaccgcgg cctccagcga ccagatgtcg gccaacatca   31320
ccgcctcggg tcttgaactt gcttcaaccc ccaccccaaa accagtggat gcagccgacg   31380
tctccgccct cgtcaatgac tgggcggggc tgggaatgtg tgggttcgcc ataggcatga   31440
tggcgctctg cctgcttctg ctctggctca tctgctgcct caaccgcagg cgggccagac   31500
ccatctatag acccatcatt gttctcaacc ccgctgatga tgggatccat agattggatg   31560
gtctgaaaaa cctactttc tctttttacag tatgataaat tgagacatgc ctcgcatttt   31620
catgtacttg acacttctcc cactttttct ggggtgttct acgctggccg ccgtctctca   31680
cctcgaggta gactgcctca caccccttcac tgtctacctg atttacggat tggtcaccct   31740
```

```
cactctcatc tgcagcctaa tcacagtagt catcgccttc atccagtgca ttgactacat    31800
ctgtgtgcgc ctcgcatacc tgagacacca cccgcagtac cgagacagga acattgccca    31860
actcctaaga ctgctctaat catgcataag actgtgatct gcctcctcat cctcctctcc    31920
ctgcccgctc tcgtctcatg ccagcccacc acaaaacctc cacgaaaaag acatgcctcc    31980
tgtcgcttga gccaactgtg gaatattccc aaatgctaca atgaaaagag cgagctttcc    32040
gaagcctggc tatatgcggt catgtgtgtc cttgtcttct gcagcacaat ctttgccctc    32100
atgatctacc cccactttga tttgggatgg aatgcggtcg atgccatgaa ttaccctacc    32160
tttcccgcgc ccgatatgat tccactccga caggttgtgg tgcccgtcgc cctcaatcaa    32220 cgcccccat  ccctacacc cactgaggtc agctactta atctaacagg cggagatgac    32280
tgacactcta gatctagaaa tggacggcat cggcaccgag cagcgtctcc tacagaggcg    32340
caagcaggcg gctgaacaag agcgcctcaa tcaggagctc cgagatctca ttaacctgca    32400
ccagtgcaaa aaaggcatct tttgcctggt caagcaggcc gatgtcacct acgagaaaac    32460
cggtaacagc caccgcctca gctacaagct gcccacccaa cgccagaagt tggtgctcat    32520
ggtgggtcag aatcccatca ccgtcaccca gcactcggtg gagaccgagg ggtgtctgca    32580 ctcccctgt  cagggtccgg aagacctctg caccctggta agacccgtgt gtggtcttag    32640
agatttaatc ccctttaact aatcaaacac tggaatcaat aaaaagaatc acttacttta    32700
aatcagtcag caggtctctg tccactttat tcagcagcac ctccttcccc tcctcccaac    32760
tctggtactc caaacgcctc ctggcggcaa acttcctcca cacctgaag  ggaatgtcag    32820 attcttgctc ctgtccctcc gcacccacta tcttcatgtt gttgcagatg aagcgcgcca    32880
aaacgtctga cgagaccttc aacccgtgt  accctatga  cacggaaaac gggcctccct    32940
ccgttccttt cctcacccct cccttcgtgt ccccgacgg  atttcaagaa agcccccag    33000 gggtcctgtc tctgcgcctg tcagagcccc tggtcacttc ccacggcatg cttgccctga    33060
aaatgggaaa tggcctctcc ctggatgacg ccggcaacct cacctctcaa gatgtcacca    33120
ccgtcacccc tccctcaaa  aaaccaaga  ccaacctcag cctccagacc tcagcccccc    33180
tgaccgttag ctctgggtcc ctcaccgtcg cggccgccgc tccactggcg gtggccggca    33240
cctctctcac catgcaatct caggcccccct tgacggtgca agatgcaaaa ctgggtctgg    33300
ccacccaggg acccctgacc gtgtctgaag gcaaactcac cttgcagaca tcggctccac    33360
tgacggccgc cgacagcagc actctcactg ttggcaccac accgccaatc agtgtgagca    33420
gtggaagtct aggcttagat atggaagacc ccatgtatac tcacgatgga aaactgggaa    33480
tcagaattgg tggcccactg caagtagtag acagcttgca cacactcact gtagttactg    33540
gaaacggaat aactgtagct aacaatgccc ttcaaactaa agttgcgggt gccctgggtt    33600
atgactcatc tggcaatcta gaattgcgag ccgcaggggg tatgcgaatt aacacagggg    33660
gtcaactcat tcttgatgtg gcttatccat ttgatgctca gaacaatctc agccttagac    33720
tcggccaggg acctttatat gtgaacacca atcacaacct agatttaaat tgcaacagag    33780
gtctgaccac aaccaccagc agtaacacaa ccaaacttga aactaaaatc gattcgggct    33840
tagactataa cgccaatggg gctatcattg ctaaacttgg cactgggtta accttttgaca    33900 acacaggtgc cataactgtg ggaaacactg gggatgacaa actcactctg tggactaccc    33960
cagatccctc tcctaactgc agaattcacg cagacaaaga ctgcaagttt actctagtcc    34020
tgactaagtg tggaagtcaa attctggcct ccgtcgccgc cctggcggtg tctggaaacc    34080
```

```
tatcatcaat gacaggcact gtctccagcg ttaccatctt tctcagattc gatcagaatg   34140
gagttcttat ggaaaattcc tcgctagaca aggagtactg gaacttcaga aatggtaatt   34200
ccaccaatgc caccccctac accaatgcgg ttgggttcat gcccaacctc agcgcctacc   34260
ccaaaaccca gagtcaaact gcaaaaaaca acattgtaag tgaggtttac ttacatgggg   34320
acaaatctaa acccatgatc cttaccatta cccttaatgg cacaaatgaa tccagtgaaa   34380
ctagtcaggt gagtcactac tccatgtcat ttacatggtc ctgggacagt gggaaatatg   34440
ccaccgaaac ctttgccacc aactcttta ccttctccta cattgctgaa caataaagaa   34500
gcataacgct gctgttcatt tgtaatcaag tgttactttt ttatttttca attacaacag   34560
aatcattcaa gtcattctcc atttagctta atagacccca gtagtgcaaa gccccatact   34620
agcttatttc agacagtata aattaaacca tacctttga tttcaacatt aaaaaaatca   34680
tcacaggatc ctagtcgtca ggccgccccc tcccttccaa gacacagaat acacaatcct   34740
ctccccccgg ctagctttaa acaacaccat ctgattggtg acagacaggt tcttcggggt   34800
tatattccac acggtctcct ggcgggccag gcgctcgtcg gtgatgctga taaactctcc   34860
cggcagctcg ctcaagttca cgtcgctgtc cagcggctga acctcatgct gacgcggtaa   34920
ctgcgcgacc ggctgctgaa caaacggagg ccgcgcctac aagggggtag agtcataatc   34980
ctccgtcagg atagggcggt tatgcagcag cagcgagcga atcatctgct gccgccgccg   35040
ctccgtccgg caggaaaaca acatcccggt ggtctcctcc gctataatcc gcaccgcccg   35100
cagcataagc ctcctcgttc tccgcgcgca gcaccgcacc ctgatctcgc tcaggttggc   35160
gcagtaggta cagcacatca ccacgatgtt attcatgatc ccacagtgca aggcgctgta   35220
tccaaagctc atgcccggga ccaccgcccc cacgtgaccg tcgtaccaga agcgcaggta   35280
aatcaagtgc cgacccctca tgaacgtgct ggacataaac atcacctcct tgggcatgtt   35340
gtaattcacc acctcccggt accagatgaa tctctgattg aacacggccc cttccaccac   35400
catcctgaac caagaggcta ggacctgccc accggctatg cactgcaggg aacccggggtt   35460 agaacaatga caatgcagac tccagggctc gtaaccgtgg atcatccggc tgctgaagac   35520
atcgatgttg gcgcaacaca gacacacgtg catacacttc ctcatgatta gcagctcctc   35580
cctcgtcagg atcatatccc aagggataac ccattcttga atcaacgtaa agcccacaga   35640
gcagggaagg cctcgcacat aactcacgtt gtgcatggtt agcgtgttgc attccggaaa   35700
cagcggatga tcctccagta tcgaggcgcg ggtctcgttc tcacagggag gtaaaggggc   35760
cctgctgtac ggactgtggc gggacgaccg agatcgtgtt gagcgtaacg tcatggaaaa   35820
gggaacgccg gacgtggtca tacttcttga agcagaacca ggctcgcgcg tgacagacct   35880
ccttgcgtct acggtctcgc cgcttagctc gctccgtgtg atagttgtag tacagccact   35940
ctctcaaagc gtcgaggcga cacctggcgt caggatgtat gtagactccg tcttgcaccg   36000
cggccctgat aatatccacc accgtagaat aagccacacc aagccaagca atacactcgc   36060
tttgcgagcg gcagacagga ggagcgggga gagacggaag gaccatcata aaattttaaa   36120
gaatattttc caatacttcg aaatcaagat ctaccaaatg gcaacgctcc cctccactgg   36180
cgcggtcaaa ctctacggcc aaagaacaga taacggcatt tttaagatgt cccggacgg   36240 cgtctaaaag acaaaccgct ctcaagtcga cataaattat aagccaaaag ccatcgggat   36300
ccatatccac tatggacgcg ccggcggcgt ccaccaaacc caaataattt tcttctctcc   36360
agcgcagcaa aatcccagta agcaactccc tgatattaag atgaaccatg ccaaaaatct   36420
gttcaagagc gccctccacc ttcattctca agcagcgcat catgattgca aaaattcagg   36480
```

```
ttcctcagac acctgtatga gattcaaaac gggaatatta acaaaaattc ctctgtcgcg    36540
cagatccctt cgcagggcaa gctgaacata atcagacagg tctgaacgaa ccagcgaggc    36600
caaatccccg ccaggaacca gatccagaga ccctatgctg attatgacgc gcatactcgg    36660
ggctatgcta accagcgtag cgccgatgta ggcgtgctgc atgggcggcg aaataaaatg    36720
caaggtgctg gttaaaaaat caggcaaagc ctcgcgcaaa aaagctaaga catcataatc    36780
atgctcatgc aggtagttgc aggtaagctc aggaaccaaa acggaataac acacgatttt    36840
cctctcaaac atgacttcca ggtgactgca taagaaaaaa attataaata ataaatatta    36900
attaaataaa ttaaacattg gaagcctgtc tcacaacagg aaaaaccact ctgatcaaca    36960
taagacgggc cacgggcatg cccgcgtgac cataaaaaaa tcggtctccg tgattacaaa    37020
gcaccacaga tagctccccg gtcatgtcgg gggtcatcat gtgagactgt gtatacacgt    37080
ccgggctgtt gacatcggtc aaagaaagaa atcgagctac atagcccgga ggaatcaaca    37140
cccgcacgcg gaggtacagc aaaacggtcc ccataggagg aatcacaaaa ttagtaggag    37200
aaaaaaaaac ataaacacca gaaaaacccct cttgccgagg caaaacagcg ccctcccgtt    37260
ccaaaacaac ataaagcgct tccacaggag cagccatgac aaagacccga gtcttaccag    37320
gaaaatttta aaaagattc ctcaacgcag caccagcacc aacacctgtc agtgtaaaat    37380
gccaagcgcc gagcgagtat atataggaat aaaaagtgac gtaaacggtt aaagtccaga    37440
aaacgcccag aaaaaccgca cgcgaaccta cgccccgaaa cgaaagccaa aaaacagtga    37500 acacgcccctt tcggcgtcaa cttccgcttt cccacggtac gtcacttccg catatagtaa    37560
aactacgcta cccaacatgc aagaagccac gccccaaaaa acgtcacacc tcccggcccg    37620
ccccgcgccg ccgctcctcc ccgccccgcc ccgctccgcc cacctcatta tcatattggc    37680
ttcaatccaa aataaggtat attattgatg atg    37713

<210> SEQ ID NO 64
<211> LENGTH: 882
<212> TYPE: DNA
<213> ORGANISM: Adenoviridae - Mastadenovirus

<400> SEQUENCE: 64
atgactacgt ccggcgttcc atttggcatg acactacgac caacacgatc tcggttgtct      60
cggcgcactc cgtacagtag ggatcgtcta cctccttttg agacagaaac ccgcgctacc     120
atactggagg atcatccgct gctgcccgaa tgtaacactt tgacaatgca caacgtgagt     180
tacgtgcgag gtcttcccct gcagtgtggga tttacgctga ttcaggaatg ggttgttccc     240
tgggatatgg ttctaacgcg ggaggagctt gtaatcctga ggaagtgtat gcacgtgtgc     300
ctgtgttgtg ccaacattga tatcatgacg agcatgatga tccatggtta cgagtcctgg     360
gctctccact gtcattgttc cagtcccggt tccctgcagt gtatagccgg cgggcaggtt     420
ttggccagct ggtttaggat ggtggtggat ggcgccatgt taatcagag gtttatatgg     480 taccgggagg tggtgaatta caacatgcca aaagaggtaa tgtttatgtc cagcgtgttt    540
atgaggggtc gccacttaat ctacctgcgc ttgtggtatg atggccacgt gggttctgtg     600
gtccccgcca tgagctttgg atacagcgcc ttgcactgtg ggattttgaa caatattgtg     660
gtgctgtgct gcagttactg tgctgattta agtgagatca gggtgcgctg ctgtgcccgg     720
aggacaaggc gccttatgct gcgggcggtg cgaatcatcg ctgaggagac cactgccatg     780
ttgtattcct gcaggacgga gcggcggcgg cagcagttta ttcgcgcgct gctgcagcac     840
```
caccgcccta tcctgatgca cgattatgac tctaccccca tg            882

<210> SEQ ID NO 65
<211> LENGTH: 36571
<212> TYPE: DNA
<213> ORGANISM: Adenoviridae - Mastadenovirus

<400> SEQUENCE: 65
catcatcaat aatatacctc aaacttttgg tgcgcgttaa tatgcaaatg agctgtttga      60
atttggggat gcggggcgct gattggctgc gggagcggcg accgttaggg gcggggcggg     120
tgacgttttg atgacgtggc cgtgaggcgg agccggtttg caagttctcg tgggaaaagt     180
gacgtcaaac gaggtgtggt ttgaacacgg aaatactcaa ttttcccgcg ctctctgaca     240
ggaaatgagg tgtttctggg cggatgcaag tgaaaacggg ccattttcgc gcgaaaactg     300
aatgaggaag tgaaaatctg agtaatttcg cgtttatggc agggaggagt atttgccgag     360
ggccgagtag actttgaccg attacgtggg ggtttcgatt accgtatttt tcacctaaat     420
ttccgcgtac ggtgtcaaag tccggtgttt ttacgtaggc gtcagctgat cgccagggta     480
tttaaacctg cgctcactag tcaagaggcc actcttgagt gccagcgagt agagttttct     540
cctccgcgcc gcgagtcaga tctacacttt gaaagatgag gcacttgaga gacctgcccg     600
gtaatgtttt cctggctact gggaacgaga ttctggaatt ggtggtggac gccatgatgg     660
gtgacgaccc tcccgagccc cctacccat ttgaggcgcc ttcgctgtac gatttgtatg     720
atctggaggt ggatgtgccc gagaacgacc ccaacgagga ggcggtgaat gatttgttta     780
gcgatgccgc gctgctggct gccgagcagg ctaatacgga cttggctca gacagcgatt      840
cttctctcca taccccgaga cccggcagag gtgagaaaaa gatccccgag cttaaagggg     900
aagagctcga cctgcgctgc tatgaggaat gcttgcctcc gagcgatgat gaggaggacg     960
aggaggcgat tcgagctgca gcgaaccagg gagtgaaagc tgcgggcgaa agctttagcc    1020
tggactgtcc tactctgccc ggacacggct gtaagtcttg tgaatttcat cgcatgaata    1080
ctggagataa gaatgtgatg tgtgccctgt gctatatgag agcttacaac cattgtgttt    1140
acagtaagtg tgattaactt tagttgggaa ggcagagggt gactgggtgc tgactggttt    1200
atttatgtat atgtttttta tgtgtaggtc ccgtctctga cgcagatgag accccacttt    1260
cagagtgcat ttcatcaccc ccagaaattg gcgaggaacc gcccgaagat attattcata    1320
gaccagttgc agtgagagtc accgggcgga gagcagctgt ggagagtttg gatgacttgc    1380
tacagggtgg ggatgaacct ttggacttgt gtacccggaa acgccccagg cactaagtgc    1440
cacacatgtg tgtttactta aggtgatgtc agtatttata gggtgtggag tgcaataaaa    1500
tccgtgttga ctttaagtgc gtggtttatg actcaggggt ggggactgtg ggtatataag    1560
caggtgcaga cctgtgtggt cagttcagag caggactcat ggagatctgg acggtcttgg    1620
aagactttca ccagactaga cagctgctag agaactcatc ggagggagtc tcttacctgt    1680
ggagattctg cttcggtggg cctctagcta agctagtcta tagggccaag caggattata    1740
aggatcaatt tgaggatatt tgagagagt gtcctggtat ttttgactct ctcaacttgg    1800
gccatcagtc tcacttttaac cagagtattc tgagagccct tgacttttcc actcctggca    1860
gaactaccgc cgcggtagcc ttttttgcct ttatccttga caaatggagt caagaaaccc    1920
atttcagcag ggattaccgt ctggactgct tagcagtagc tttgtggaga acatggaggt    1980
gccagcgcct gaatgcaatc tccggctact tgccagtaca gccggtagac acgctgagga    2040
tcctgagtct ccagtcaccc caggaacacc aacgccgcca gcagccgcag caggagcagc    2100

```
agcaagagga ggaccgagaa gagaacccga gagccggtct ggaccctccg gtggcggagg    2160
aggaggagta gctgacttgt ttcccgagct gcgccgggtg ctgactaggt cttccagtgg    2220
acgggagagg gggattaagc gggagaggca tgaggagact agtcacagaa ctgaactgac    2280
tgtcagtctg atgagccgca ggcgcccaga atcggtgtgg tggcatgagg tgcagtcgca    2340
ggggatagat gaggtctcgg tgatgcatga gaaatattcc ctagaacaag tcaagacttg    2400
ttggttggag cctgaggatg attgggaggt agccatcagg aattatgcca agctagctct    2460
gaagccagac aagaagtaca agattaccaa actgattaat atcagaaatt cctgctacat    2520
ttcagggaat ggggccgagg tggagatcag tacccaggag agggtggcct tcagatgctg    2580
catgatgaat atgtacccgg gggtggtggg catggaggga gtcacctttα tgaacgcgag    2640 gttcaggggc gatgggtata atgggtggt ctttatggcc aacaccaagc tgacagtgca    2700
cggatgctcc ttctttggct tcaataacat gtgcatcgag gcctggggca gtgtttcagt    2760
gaggggatgc agttttttcag ccaactggat ggggtcgtg ggcagaacca agagcaaggt    2820
gtcagtgaag aaatgcctgt tcgagaggtg ccacctgggg gtgatgagcg agggcgaagc    2880
caaagtcaaa cactgcgcct ctactgagac gggctgcttt gtgctgatca agggcaatgc    2940
ccaagtcaag cataacatga tctgtggggc ctcggatgag cgcggctacc agatgctgac    3000
ctgcgccggt gggaacagcc atatgctggc caccgtgcat gtgacctcgc accccgcaa    3060 gacatggccc gagttcgagc acaacgtcat gacccgctgc aatgtgcacc tgggctcccg    3120
ccgaggcatg ttcatgccct accagtgcaa catgcaattt gtgaaggtgc tgctggagcc    3180
cgatgccatg tccagagtga gcctgacggg ggtgtttgac atgaatgtgg agatgtggaa    3240
aattctgaga tatgatgaat ccaagaccag gtgccgggcc tgcgaatgcg gaggcaagca    3300
cgccaggctt cagcccgtgt gtgtggaggt gacgaggac ctgcgacccg atcatttggt    3360
gttgtcctgc aacgggacgg agttcggctc cagcggggaa gaatctgact agagtgagta    3420
gtgtttgggg gaggtggagg gcctggatga ggggcagaat gactaaaatc tgtgtttttc    3480
tgcgcagcag catgagcgga agcgcctcct ttgaggagg ggtattcagc ccttatctga    3540
cggggcgtct cccctcctgg gcgggagtgc gtcagaatgt gatgggatcc acggtggacg    3600
gccggcccgt gcagcccgcg aactcttcaa ccctgaccta cgcgaccctg agctcctcgt    3660
ccgtggacgc agctgccgcc gcagctgctg cttccgccgc cagcgccgtg cgcggaatgg    3720
ccctgggcgc cggctactac agctctctgg tggccaactc gagttccacc aataatcccg    3780
ccagcctgaa cgaggagaag ctgctgctgc tgatggccca gctcgaggcc ctgacccagc    3840
gcctgggcga gctgacccag caggttgctc agctgcaggc ggagacgcgg gccgcggttg    3900
ccacggtgaa aaccaaataa aaatgaatc aataaataaa cggagacggt tgttgatttt    3960
aacacagagt cttgaatctt tatttgattt ttcgcgcgcg gtaggccctg gaccaccggt    4020
ctcgatcatt gagcacccgg tggatctttt ccaggacccg gtagaggtgg gcttggatgt    4080
tgaggtacat gggcatgagc ccgtcccggg ggtggaggta gctccattgc agggcctcgt    4140
gctcgggggt ggtgttgtaa atcacccagt catagcaggg gcgcagggcg tggtgctgca    4200
cgatgtcctt gaggaggaga ctgatggcca cgggcagccc cttggtgtag gtgttgacga    4260
acctgttgag ctgggaggga tgcatgcggg gggagatgag atgcatcttg gcctggatct    4320
tgagattggc gatgttcccg cccagatccc gccgggggtt catgttgtgc aggaccacca    4380
gcacggtgta tccggtgcac ttgggaatt tgtcatgcaa cttggaaggg aaggcgtgaa    4440
```

```
agaatttgga gacgcccttg tggccgccca ggttttccat gcactcatcc atgatgatgg   4500
cgatgggccc gtgggcggcg gcctgggcaa agacgtttcg ggggtcggac acatcgtagt   4560
tgtggtcctg ggtgagctcg tcataggcca ttttaatgaa tttggggcgg agggtgcccg   4620
actggggggac gaaggtgccc tcgatcccgg gggcgtagtt gccctcgcag atctgcatct   4680
cccaggcctt gagctcggag gggggatca tgtccacctg cggggcgatg aaaaaaacgg   4740
tttccggggc gggggagatg agctgcgccg aaagcaggtt ccggagcagc tgggacttgc   4800
cgcagccggt ggggccgtag atgaccccga tgaccggctg caggtggtag ttgagggaga   4860
gacagctgcc gtcctcgcgg aggagggggg ccacctcgtt catcatctcg cgcacatgca   4920
tgttctcgcg cacgagttcc gccaggaggc gctcgccccc cagcgagagg agctcttgca   4980
gcgaggcgaa gttttttcagc ggcttgagcc cgtcggccat gggcattttg gagagggtct   5040
gttgcaagag ttccagacgg tcccagagct cggtgatgtg ctctagggca tctcgatcca   5100
gcagacctcc tcgtttcgcg ggttggggcg actgcgggag tagggcacca ggcgatgggc   5160
gtccagcgag gccagggtcc ggtccttcca gggtcgcagg gtccgcgtca gcgtggtctc   5220
cgtcacggtg aaggggtgcg cgccgggctg ggcgcttgcg agggtgcgct tcaggctcat   5280
ccggctggtc gagaaccgct cccggtcggc gccctgtgcg tcggccaggt agcaattgag   5340
catgagttcg tagttgagcg cctcggccgc gtggcccttg gcgcggagct tacctttgga   5400
agtgtgtccg cagacgggac agaggaggga cttgagggcg tagagcttgg gggcgaggaa   5460
gacggactcg ggggcgtagg cgtccgcgcc gcagctggcg cagacggtct cgcactccac   5520
gagccaggtg aggtcgggc ggtcgggtc aaaaacgagg tttcctccgt gcttttgat   5580
gcgtttctta cctctggtct ccatgagctc gtgtccccgc tgggtgacaa agaggctgtc   5640
cgtgtccccg tagaccgact ttatgggccg gtcctcgagc ggggtgccgc ggtcctcgtc   5700
gtagaggaac cccgcccact ccgagacgaa ggcccgggtc caggccagca cgaaggaggc   5760
cacgtgggag gggtagcggt cgttgtccac cagcgggtcc accttctcca gggtatgcaa   5820
gcacatgtcc ccctcgtcca catccaggaa ggtgattggc ttgtaagtgt aggccacgtg   5880
accgggggtc ccggccgggg gggtataaaa ggggggcggc ccctgctcgt cctcactgtc   5940
ttccggatcg ctgtccagga gcgccagctg ttggggtagg tattccctct cgaaggcggg   6000
catgacctcg gcactcaggt tgtcagtttc tagaaacgag gaggatttga tattgacggt   6060
gccgttggag acgcctttca tgagcccctc gtccatctgg tcagaaaaga cgatctttt   6120
gttgtcgagc ttggtggcga aggagccgta gagggcgttg gagagcagct tggcgatgga   6180
gcgcatggtc tggttctttt ccttgtcggc gcgctccttg gcggcgatgt tgagctgcac   6240
gtactcgcgc gccacgcact tccattcggg gaagacggtg gtgagctcgt cgggcacgat   6300
tctgacccgc cagccgcggt tgtgcagggt gatgaggtcc acgctggtgg ccacctcgcc   6360
gcgcaggggc tcgttggtcc agcagaggcg cccgcccttg cgcgagcaga agggggggcag   6420
cgggtccagc atgagctcgt cgggggggtc ggcgtccacg tgaagatgc cgggcaggag   6480
ctcggggtcg aagtagctga tgcaggtgcc cagatcgtcc agcgccgctt gccagtcgcg   6540
cacgccagc gcgcgctcgt aggggctgag gggcgtgccc cagggcatgg ggtgcgtgag   6600
cgcggaggcg tacatgccgc agatgtcgta gacgtagagg ggctcctcga ggacgccgat   6660
gtaggtgggg tagcagcgcc ccccgcggat gctggcgcgc acgtagtcgt acagctcgtg   6720
cgagggcgcg aggagcccg tgccgaggtt ggagcgttgc ggcttttcgg cgcggtagac   6780
gatctggcgg aagatggcgt gggagttgga ggagatggtg ggcctctgga agatgttgaa   6840
```

```
gtgggcgtgg ggcaggccga ccgagtccct gatgaagtgg gcgtaggagt cctgcagctt    6900
ggcgacgagc tcggcggtga cgaggacgtc cagggcgcag tagtcgaggg tctcttggat    6960
gatgtcgtac ttgagctggc ccttctgctt ccacagctcg cggttgagaa ggaactcttc    7020
gcggtccttc cagtactctt cgaggggaa  cccgtcctga tcggcacggt aagagcccac    7080
catgtagaac tggttgacgg ccttgtaggc gcagcagccc ttctccacgg ggagggcgta    7140
agcttgcgcg gccttgcgca gggaggtgtg ggtgagggcg aaggtgtcgc gcaccatgac    7200
tttgaggaac tggtgcttga agtcgaggtc gtcgcagccg ccctgctccc agagttggaa    7260
gtccgtgcgc ttcttgtagg cggggttggg caaagcgaaa gtaacatcgt tgaagaggat    7320
cttgcccgcg cggggcatga agttgcgagt gatgcggaaa ggctggggca cctcggcccg    7380
gttgttgatg acctgggcgg cgaggacgat ctcgtcgaag ccgttgatgt tgtgcccgac    7440
gatgtagagt tccacgaatc gcgggcagcc cttgacgtgg ggcagcttct tgagctcgtc    7500
gtaggtgagc tcgcggggt  cgctgagccc gtgctgctcg agggcccagt cggcgacgtg    7560
ggggttggcg ctgaggaagg aagtccagag atccacggcc agggcggtct gcaagcggtc    7620
ccggtactga cggaactgct ggcccacggc cattttttcg ggggtgacgc agtagaaggt    7680
gcggggtcg  ccgtgccagc ggtcccactt gagttggagg gcgaggtcgt gggcgagctc    7740
gacgagcggc gggtccccgg agagtttcat gaccagcatg aagggacga  gctgcttgcc    7800
gaaggacccc atccaggtgt aggtttccac atcgtaggtg aggaagagcc tttcggtgcg    7860
aggatgcgag ccgatgggga agaactggat ctcctgccac cagttggagg aatggctgtt    7920
gatgtgatgg aagtagaaat gccgacggcg cgccgagcac tcgtgcttgt gtttatacaa    7980
gcgtccgcag tgctcgcaac gctgcacggg atgcacgtgc tgcacgagct gtacctgggt    8040
tcctttgacg aggaatttca gtgggcagtg gagcgctggc ggctgcatct ggtgctgtac    8100
tacgtcctgg ccatcggcgt ggccatcgtc tgcctgatg  gtggtcatgc tgacgagccc    8160
gcgcgggagg caggtccaga cctcggctcg gacgggtcgg agagcgagga cgagggcgcg    8220
caggccggag ctgtccaggg tcctgagacg ctgcggagtc aggtcagtgg gcagcggcgg    8280
cgcgcggttg acttgcagga gcttttccag ggcgcgcggg aggtccagat ggtacttgat    8340
ctccacggcg ccgttggtgg cgacgtccac ggcttgcagg gtcccgtgcc cctggggcgc    8400
caccaccgtg ccccgtttct tcttgggcgg cggcggctcc atgcttagaa gcggcggcga    8460
ggacgcgcgc cgggcggcag gggcggctcg gggcccggag gcaggggcgg caggggcacg    8520
tcggcgccgc gcgcgggcag gttctggtac tgcgcccgga gaagactggc gtgagcgacg    8580
acgcgacggt tgacgtcctg gatctgacgc ctctgggtga aggccacggg acccgtgagt    8640
ttgaacctga aagagagttc gacagaatca atttcggtat cgttgacggc ggcctgccgc    8700
aggatctctt gcacgtcgcc cgagttgtcc tggtaggcga tctcggtcat gaactgctcg    8760
atctcctcct cctgaaggtc tccgcggccg gcgcgctcga cggtgccgc  gaggtcgttg    8820
gagatgcggc ccatgagctg cgagaaggcg ttcatgccgg cctcgttcca gacgcggctg    8880
tagaccacgg ctccgttggg gtcgcgcgcg cgcatgacca cctgggcgag gttaagctcg    8940
acgtggcgcg tgaagaccgc gtagttgcag aggcgctggt agaggtagtt gagcgtggtg    9000
gcgatgtgct cggtgacgaa gaagtacatg atccagcggc ggagcggcat ctcgctgacg    9060
tcgcccaggc cttccaagcg ctccatggtc tcgtagaagt ccacggcgaa gttgaaaaac    9120
tgggagttgc gcgccgagac ggtcaactcc tcctccagaa gacggatgag ctcggcgatg    9180
```

```
gtggcgcgca cctcgcgctc gaaggccccg gggggctcct cttcttccat ctcctcctcc    9240
tcttcctcct ccactaacat ctcttctact tcctcctcag gaggcggcgg cgggggaggg    9300
gccctgcgtc gccggcggcg cacgggcaga cggtcgatga agcgctcgat ggtctccccg    9360
cgccggcgac gcatggtctc ggtgacggcg cgcccgtcct cgcggggccg cagcgtgaag    9420
acgccgccgc gcatctccag gtggccgccg gggggtctc cgttgggcag ggagagggcg     9480
ctgacgatgc atcttatcaa ttggcccgta gggactccgc gcaaggacct gagcgtctcg    9540
agatccacgg gatccgaaaa ccgctgaacg aaggcttcga gccagtcgca gtcgcaaggt    9600
aggctgagcc cggtttcttg ttcttcgggt atttggtcgg gaggcgggcg ggcgatgctg    9660
ctggtgatga agttgaagta ggcggtcctg agacggcgga tggtggcgag gagcaccagg    9720
tccttgggcc cggcttgctg gatgcgcaga cggtcggcca tgcccaggcc gtggtcctga    9780
cacctggcga ggtccttgta gtagtcctgc atgagccgct ctacgggcac gtcctcctcg    9840
cccgcgcggc cgtgcatgcg cgtgagcccc aacccgcgct gcggctggac gagcgccagg    9900
tcggcgacga cgcgctcggc gaggatggcc tgctggatct gggtgagggt ggtctggaag    9960
tcgtcgaagt cgacgaagcg gtggtaggct ccggtgttga tggtgtagga gcagttggcc    10020
atgacggacc agttgacggt ctggtggccg gggcgcacga gctcgtggta cttgaggcgc    10080
gagtaggcgc gcgtgtcgaa gatgtagtcg ttgcaggtgc gcacgaggta ctggtatccg    10140
acgaggaagt gcggcggcgg ctggcggtag agccggcatc gctcggtggc gggggcgccg    10200
ggcgcgaggt cctcgagcat gaggcggtgg tagccgtaga tgtacctgga catccaggtg    10260
atgccggcgg cggtggtgga ggcgcgcggg aactcgcgga cgcggttcca gatgttgcgc    10320
agcggcagga agtagttcat ggtggccgcg gtctggcccg tgaggcgcgc gcagtcgtgg    10380
atgctctaga catacgggca aaaacgaaag cggtcagcgg ctcgactccg tggcctggag    10440
gctaagcgaa cgggttgggc tgcgcgtgta ccccggttcg aatctcgaat caggctggag    10500
ccgcagctaa cgtggtactg gcactcccgt ctcgacccaa gcctgctaac gaaacctcca    10560
ggatacggag gcgggtcgtt ttttggcctt ggtcgctggt catgaaaaac tagtaagcgc    10620
ggaaagcggc cgcccgcgat ggctcgctgc cgtagtctgg agaaagaatc gccagggttg    10680
cgttgcggtg tgccccggtt cgagcctcag cgctcggtgc cggccggatt ccgcggctaa    10740
cgtgggcgtg gctgccccgt cgtttccaag acccccttagc cagccgactt ctccagttac    10800
ggagcgagcc cctctttttc ttgtgttttt gccagatgca tcccgtactg cggcagatgc    10860
gcccccaccc tccaccacaa ccgccccctac cgcagcagca gcaacagccg gcgcttctgc    10920
ccccgccccca gcagcagcag ccagccacta ccgcggcggc cgccgtgagc ggagccggcg    10980
ttcagtatga cctggccttg gaagagggcg aggggctggc gcggctgggg gcgtcgtcgc    11040
cggagcggca cccgcgcgtg cagatgaaaa gggacgctcg cgaggcctac gtgcccaagc    11100
agaacctgtt cagagacagg agcggcgagg agcccgagga gatgcgcgcc tcccgcttcc    11160
acgcggggcg ggagctgcgg cgcggcctgg accgaaagcg ggtgctgagg gacgaggatt    11220
tcgaggcgga cgagctgacg gggatcagcc ccgcgcgcgc gcacgtggcc gcggccaacc    11280
tggtcacggc gtacgagcag accgtgaagg aggagagcaa cttttcaaaaa tccttcaaca    11340
accacgtgcg cacgctgatc gcgcgcgagg aggtgacccct gggcctgatg cacctgtggg    11400
acctgctgga ggccatcgtg cagaacccca cgagcaagcc gctgacggcg cagctgtttc    11460
tggtggtgca gcacagtcgg gacaacgaga cgttcaggga ggcgctgctg aatatcaccg    11520
agcccgaggg ccgctggctc ctggacctgg tgaacattct gcagagcatc gtggtgcagg    11580
```

```
agcgcgggct gccgctgtcc gagaagctgg cggccatcaa cttctcggtg ctgagcctgg    11640
gcaagtacta cgctaggaag atctacaaga ccccgtacgt gcccatagac aaggaggtga    11700
agatcgacgg gttttacatg cgcatgaccc tgaaagtgct gaccctgagc gacgatctgg    11760
gggtgtaccg caacgacagg atgcaccgcg cggtgagcgc cagccgccgg cgcgagctga    11820
gcgaccagga gctgatgcac agcctgcagc gggccctgac cggggccggg accgaggggg    11880
agagctactt tgacatgggc gcggacctgc gctggcagcc cagccgccgg gccttggaag    11940
ctgccggcgg cgtgccctac gtggaggagg tggacgatga ggaggaggag ggcgagtacc    12000
tggaagactg atggcgcgac cgtattttg ctagatgcag caacagccac cgccgcctcc    12060
tgatcccgcg atgcgggcgg cgctgcagag ccagccgtcc ggcattaact cctcggacga    12120
ttggacccag gccatgcaac gcatcatggc gctgacgacc cgcaatcccg aagcttttag    12180
acagcagcct caggccaacc ggctctcggc catcctggag gccgtggtgc cctcgcgctc    12240
gaaccccacg cacgagaagg tgctggccat cgtgaacgcg ctggtggaga caaggccat    12300 ccgcggcgac gaggccgggc tggtgtacaa cgcgctgctg gagcgcgtgg cccgctacaa    12360
cagcaccaac gtgcagacga acctggaccg catggtgacc gacgtgcgcg aggcggtgtc    12420
gcagcgcgag cggttccacc gcgagtcgaa cctgggctcc atggtggcgc tgaacgcctt    12480
cctgagcacg cagcccgcca acgtgccccg gggccaggag gactacacca acttcatcag    12540
cgcgctgcgg ctgatggtgg ccgaggtgcc ccagagcgag gtgtaccagt cggggccgga    12600
ctacttcttc cagaccagtc gccagggctt gcagaccgtg aacctgagcc aggctttcaa    12660
gaacttgcag ggactgtggg gcgtgcaggc cccggtcggg gaccgcgcga cggtgtcgag    12720
cctgctgacg ccgaactcgc gcctgctgct gctgctggtg gcgcccttca cggacagcgg    12780
cagcgtgagc cgcgactcgt acctgggcta cctgcttaac ctgtaccgcg aggccatcgg    12840
gcaggcgcac gtggacgagc agacctacca ggagatcacc cacgtgagcc gcgcgctggg    12900
ccaggaggac ccgggcaacc tggaggccac cctgaacttc ctgctgacca accggtcgca    12960
gaagatcccg ccccagtacg cgctgagcac cgaggaggag cgcatcctgc gctacgtgca    13020
gcagagcgtg gggctgttcc tgatgcagga gggggccacg cccagcgccg cgctcgacat    13080
gaccgcgcgc aacatggagc ccagcatgta cgcccgcaac cgcccgttca tcaataagct    13140
gatggactac ttgcatcggg cggccgccat gaactcggac tactttacca acgccatctc    13200
gaacccgcac tggctccgc cgcccgggtt ctacacgggc gagtacgaca tgcccgaccc    13260
caacgacggg ttcctgtggg atgacgtgga cagcagcgtg ttctcgccgc gtcccaccac    13320
caccgtgtgg aagaaagagg gcggggaccg gcggccgtcc tcggcgctgt ccggtcgcgc    13380
gggtgctgcc gcggcggtgc ccgaggccgc cagcccttt ccgagcctgc cttttcgct    13440 gaacagcgtg cgcagcagcg agctgggtcg gctgacgcgg ccgcgcctgc tgggcgagga    13500
ggagtacctg aacgactcct tgttgaggcc cgagcgcgaa aagaacttcc ccaataacgg    13560
gatagagagc ctggtggaca agatgagccg ctggaagacg tacgcgcacg agcacaggga    13620
cgagccccga gctagcagcg caggcacccg tagacgccag cggcacgaca ggcagcgggg    13680
tctggtgtgg gacgatgagg attccgccga cgacagcagc gtgttggact ggggtgggag    13740
tggtggtggt aacccgttcg ctcacttgcg cccccgtatc gggcgcctga tgtaagaatc    13800
tgaaaaataa aaacggtac tcaccaaggc catggcgacc agcgtgcgtt cttctctgtt    13860
gtttgtagta gtatgatgag gcgcgtgtac ccggagggtc ctcctccctc gtacgagagc    13920
```

```
gtgatgcagc aggcggtggc ggcggcgatg cagcccccgc tggaggcgcc ttacgtgccc   13980
ccgcggtacc tggcgcctac ggaggggcgg aacagcattc gttactcgga gctggcaccc   14040
ttgtacgata ccacccggtt gtacctggtg acaacaagt cggcggacat cgcctcgctg    14100
aactaccaga acgaccacag caacttcctg accaccgtgg tgcagaacaa cgatttcacc   14160
cccacggagg ccagcaccca gaccatcaac tttgacgagc gctcgcggtg ggcggccag   14220 ctgaaaacca tcatgcacac caacatgccc aacgtgaacg agttcatgta cagcaacaag   14280
ttcaaggcgc gggtgatggt ctcgcgcaag accccaacg gggtcacagt aacagatggt    14340
agtcaggacg agctgaccta cgagtgggtg gagtttgagc tgcccgaggg caacttctcg   14400
gtgaccatga ccatcgatct gatgaacaac gccatcatcg acaactactt ggcggtgggg   14460
cggcagaacg gggtgctgga gagcgacatc ggcgtgaagt tcgacacgcg caacttccgg   14520
ctgggctggg accccgtgac cgagctggtg atgccgggcg tgtacaccaa cgaggccttc   14580
caccccgaca tcgtcctgct gcccggctgc ggcgtggact tcaccgagag ccgcctcagc   14640
aacctgctgg gcatccgcaa gcggcagccc ttccaggagg gcttccagat cctgtacgag   14700
gacctggagg ggggcaacat ccccgcgctc ttggatgtcg aagcctacga gaaaagcaag   14760
gaggatagca ccgccgtggc taccgccgcg actgtggcag atgccactgt caccaggggc   14820
gatacattcg ccacccaggc ggaggaagca gccgccctag cggcgaccga tgatagtgaa   14880
agtaagatag ttatcaagcc ggtggagaag acagcaagg acaggagcta caacgttcta   14940
tcggatggaa agaacaccgc ctaccgcagc tggtacctgg cctacaacta cggcgacccc   15000
gagaagggcg tgcgctcctg gacgctgctc accacctcgg acgtcacctg cggcgtggag   15060
caagtctact ggtcgctgcc cgacatgatg caagacccgg tcaccttccg ctccacgcgt   15120
caagttagca actaccggt ggtgggcgcc gagctcctgc ccgtctactc caagagcttc    15180
ttcaacgagc aggccgtcta ctcgcagcag ctgcgcgcct tcacctcgct cacgcacgtc   15240
ttcaaccgct tccccgagaa ccagatcctc gtccgcccgc ccgcgcccac cattaccacc   15300
gtcagtgaaa acgttcctgc tctcacagat cacgggaccc tgccgctgcg cagcagtatc   15360
cggggagtcc agcgcgtgac cgtcactgac gccagacgcc gcacctgccc ctacgtctac   15420
aaggccctgg gcgtagtcgc gccgcgcgtc ctctcgagcc gcaccttcta aaaaatgtcc   15480
attctcatct cgcccagtaa taacaccggt tggggcctgc gcgcgcccag caagatgtac   15540
ggaggcgctc gccaacgctc cacgcaacac cccgtgcgcg tgcgcgggca cttccgcgct   15600
ccctggggcg ccctcaaggg tcgcgtgcgc tcgcgcacca ccgtcgacga cgtgatcgac   15660
caggtggtgg ccgacgcgcg caactacacg cccgccgccg cgcccgcctc caccgtggac   15720
gccgtcatcg acagcgtggt ggccgacgcg cgccggtacg cccgcgccaa gagccggcgg   15780
cggcgcatcg cccggcggca ccggagcacc cccgccatgc gcgcggcgcg agccttgctg   15840
cgcagggcca ggcgcacggg acgcagggcc atgctcaggg cggccagacg cgcggcctcc   15900
ggcagcagca gcgccggcag gacccgcaga cgcgcggcca cggcggcggc ggcggccatc   15960
gccagcatgt cccgcccgcg gcgcggcaac gtgtactggg tgcgcgacgc cgccaccggt   16020
gtgcgcgtgc ccgtgcgcac ccgccccct cgcacttgaa gatgctgact cgcgatgtt    16080 gatgtgtccc agcggcgagg aggatgtcca agcgcaaata caaggaagag atgctccagg   16140
tcatcgcgcc tgagatctac ggccccgcgg cggcggtgaa ggaggaaaga aagccccgca   16200
aactgaagcg ggtcaaaaag gacaaaaagg aggaggaaga tgtggacgga ctggtggagt   16260
ttgtgcgcga gttcgccccc cggcggcgcg tgcagtggcg cgggcggaaa gtgaaaccgg   16320
```

```
tgctgcggcc cggcaccacg gtggtcttca cgcccggcga gcgttccggc tccgcctcca    16380
agcgctccta cgacgaggtg tacgggacg aggacatcct cgagcaggcg gccgagcgtc    16440
tgggcgagtt tgcttacggc aagcgcagcc gccccgcgcc cttgaaagag gaggcggtgt    16500
ccatcccgct ggaccacggc aaccccacgc cgagcctgaa gccggtgacc ctgcagcagg    16560
tgctgccgag cgcggcgccg cgccggggct tcaagcgcga gggcggcgag gatctgtacc    16620
cgaccatgca gctgatggtg cccaagcgcc agaagctgga ggacgtgctg gagcacatga    16680
aggtggaccc cgaggtgcag cccgaggtca aggtgcggcc catcaagcag gtggcccccg    16740
gcctgggcgt gcagaccgtg gacatcaaga tccccacgga gcccatggaa cgcagaccg    16800 agcccgtgaa gcccagcacc agcaccatgg aggtgcagac ggatccctgg atgccggcgc    16860
cggcttccac caccactcgc cgaagacgca agtacggcgc ggccagcctg ctgatgccca    16920
actacgcgct gcatccttcc atcatcccca cgccgggcta ccgcggcacg cgcttctacc    16980
gcggctacag cagccgccgc aagaccacca cccgccgccg ccgtcgccgc acccgccgca    17040
gcaccaccgc gacttccgcc gccgccttgg tgcggagagt gtaccgcagc gggcgtgagc    17100 ctctgacccct gccgcgcgcg cgctaccacc cgagcatcgc catttaactc tgccgtcgcc    17160
tccttgcaga tatggccctc acatgccgcc tccgcgtccc cattacgggc taccgaggaa    17220
gaaagccgcg ccgtagaagg ctgacgggga acgggctgcg tcgccatcac caccggcggc    17280
ggcgcgccat cagcaagcgg ttgggggag gcttcctgcc cgcgctgatc cccatcatcg    17340
ccgcggcgat cggggcgatc cccggcatag cttccgtggc ggtgcaggcc tctcagcgcc    17400
actgagacac agcttggaaa atttgtaata aaaaaatgga ctgacgctcc tggtcctgtg    17460
atgtgtgttt ttagatgaa gacatcaatt tttcgtccct ggcaccgcga cacggcacgc    17520
ggccgtttat gggcacctgg agcgacatcg gcaacagcca actgaacggg ggcgccttca    17580
attggagcag tctctggagc gggcttaaga atttcgggtc cacgctcaaa acctatggca    17640
acaaggcgtg gaacagcagc acagggcagg cgctgaggga aaagctgaaa gagcagaact    17700
tccagcagaa ggtggtcgat ggcctggcct cgggcatcaa cggggtggtg gacctggcca    17760
accaggccgt gcagaaacag atcaacagcc gcctggacgg ggtcccgccc gcggggtccg    17820
tggagatgcc ccaggtggag gaggagctgc ctcccctgga caagcgcggc gacaagcgac    17880
cgcgtcccga cgcggaggag acgctgctga cgcacacgga cgagccgccc cgtacgagg    17940 aggcggtgaa actgggtctg cccaccacgc ggcccgtggc gcctctggcc accggggtgc    18000
tgaaacccag cagcagcagc agccagcccg cgaccctgga cttgcctcca cctcgccct    18060 ccacagtggc taagcccctg ccgccggtgg ccgtcgcgtc gcgcgccccc cgaggccgcc    18120
cccaggcgaa ctggcagagc actctgaaca gcatcgtggg tctgggagtg cagagtgtga    18180
agcgccgccg ctgctattaa aagacactgt agcgcttaac ttgcttgtct gtgtgtatat    18240
gtatgtccgc cgaccagaag gaggaggaag aggcgcgtcg ccgagttgca agatggccac    18300
cccatcgatg ctgccccagt gggcgtacat gcacatcgcc ggacaggacg cttcggagta    18360
cctgagtccg ggtctggtgc agttcgcccg cgccacagac acctacttca gtctggggaa    18420
caagtttagg aaccccacgg tggcacccac gcacgatgtg accaccgacc gcagccagcg    18480
gctgacgctg cgcttcgtgc ccgtggaccg cgaggacaac acctactcgt acaaagtgcg    18540
ctacacgctg gccgtgggcg acaaccgcgt gctggacatg gccagcacct actttgacat    18600
ccgcggcgtg ctggatcggg gccccagctt caaaccctac tccggcaccg cctacaacag    18660
```

```
cctggctccc aagggagcgc ccaacacctc acagtggata accaaagaca atggaactga   18720
taagacatac agttttggaa atgctccagt cagaggattg gacattacag aagagggtct   18780
ccaaatagga accgatgagt caggggggtga aagcaagaaa attttttgcag acaaaaccta  18840
tcagcctgaa cctcagcttg gagatgagga atggcatgat actattggag ctgaagacaa   18900
gtatggaggc agagcgctta aacctgccac caacatgaaa ccctgctatg ggtctttcgc   18960
caagccaact aatgctaagg gaggtcaggc taaaagcaga accaaggacg atggcactac   19020
tgagcctgat attgacatgg ccttctttga cgatcgcagt cagcaagcta gtttcagtcc   19080
agaacttgtt ttgtatactg agaatgtcga tctggacacc ccggatccc acattattta    19140
caaacctggc actgatgaaa caagttcttc tttcaacttg ggtcagcagt ccatgcccaa   19200
cagacccaac tacattggct tcagagacaa ctttatcggg ctcatgtact acaacagcac   19260
tggcaatatg ggtgtactgg ccggtcaggc ctcccagctg aatgctgtgg tggacttgca   19320
ggacagaaac actgaactgt cctaccagct cttgcttgac tctctgggtg acagaaccag   19380
gtatttcagt atgtggaatc aggcggtgga cagctatgac cccgatgtgc gcattattga   19440
aaatcacggt gtggaggatg aactccccaa ctattgcttc cctttgaatg tgtgggctt    19500
tacagataca ttccagggaa ttaaggttaa aactacaaat aacggaacag caaatgctac   19560
agagtgggaa tctgataccct ctgtcaataa tgctaatgag attgccaagg gcaatccttt   19620
cgccatggag atcaacatcc aggccaacct gtggcgaaac ttcctctacg gaacgtggc    19680
gctgtacctg cccgactcct acaagtacac gccggccaac atcacgctgc ccaccaacac   19740
caacacctac gattacatga acggccgcgt ggtggcgccc tcgctggtgg acgcctacat   19800
caacatcggg gcgcgctggt cgctggaccc catggacaac gtcaaccccct caaccacca   19860
ccgcaacgcg ggcctgcgct accgctccat gctcctgggc aacggcgct acgtgccctt   19920
ccacatccag gtgccccaaa agttttttcgc catcaagagc ctcctgctcc tgcccgggtc   19980
ctacacctac gagtggaact tccgcaagga cgtcaacatg atcctgcaga gctccctcgg   20040
caacgacctg cgcacggacg gggcctccat cgccttcacc agcatcaacc tctacgccac   20100
cttcttcccc atggcgcaca acaccgcctc cacgctcgag gccatgctgc gcaacgacac   20160
caacgaccag tccttcaacg actacctctc ggcggccaac atgctctacc ccatcccggc   20220
caacgccacc aacgtgccca tctccatccc ctcgcgcaac tgggccgcct tccgcggatg   20280
gtccttcacg cgcctcaaga cccgcgagac gccctcgctc ggctccgggt tcgacccta    20340
cttcgtctac tcgggctcca tccctacct cgacggcacc ttctacctca ccacaccttt   20400
caagaaggtc tccatcacct tcgactcctc cgtcagctgg cccggcaacg accgcctcct   20460
gacgcccaac gagttcgaaa tcaagcgcac cgtcgacgga gagggtaca acgtggccca   20520
gtgcaacatg accaaggact ggttcctggt ccagatgctg gcccactaca acatcggcta   20580
ccagggcttc tacgtgcccg agggctacaa ggaccgcatg tactccttct tccgcaactt   20640
ccagcccatg agccgccagg tcgtggacga ggtcaactac aaggactacc aggccgtcac   20700
cctggcctac cagcacaaca actcgggctt cgtcggctac ctcgcgccca ccatgcgcca   20760
gggccagccc taccccgcca actacccct cccgctcatc ggcaagagcg ccgtcgcag    20820
cgtcacccag aaaaagttcc tctgcgaccg ggtcatgtgg cgcatcccct ctccagcaa    20880
cttcatgtcc atgggcgcgc tcaccgacct cggccagaac atgctctacg ccaactccgc   20940
ccacgcgcta gacatgaatt tcgaagtcga ccccatggat gagtccaccc ttctctatgt   21000
tgtcttcgaa gtcttcgacg tcgtccgagt gcaccagccc caccgcggcg tcatcgaggc   21060
```

```
cgtctacctg cgcacgccct tctcggccgg caacgccacc acctaagcct cttgcttctt    21120
gcaagatgac ggcctgtggc tccggcgagc aggagctcag ggccatcctc cgcgacctgg    21180
gctgcgggcc ctacttcctg ggcaccttcg acaagcgctt cccgggattc atggccccgc    21240
acaagctggc ctgcgccatc gtcaacacgg ccggccgcga ccgggggc gagcactggc      21300
tggccttcgc ctggaacccg cgcacccaca cctgctacct cttcgacccc ttcgggttct    21360
cggacgagcg cctcaagcag atctaccagt tcgagtacga gggcctgctg cgccgcagcg    21420
ccctggccac cgaggaccgc tgcgtcaccc tggaaaagtc cacccagacc gtgcagggtc    21480
cgcgctcggc cgcctgcggg ctcttctgct gcatgttcct gcacgccttc gtgcactggc    21540
ccgaccgccc catggacaag aaccccacca tgaacttgct gacggggtg cccaacggca     21600
tgctccagtc gccccaggtg gaacccaccc tgcgccgcaa ccaggaggcg ctctaccgct    21660
tcctcaacgc ccactccgcc tactttcgct cccaccgcgc gcgcatcgag aaggccaccg    21720
ccttcgaccg catgaatcaa gacatgtaaa ctgtgtgtat gtgaatgctt tattcataat    21780
aaacagcaca tgtttatgcc accttctctg aggctctgac tttatttaga aatcgaaggg    21840
gttctgccgg ctctcggcgt gccccgcggg cagggatacg ttgcggaact ggtacttggg    21900
cagccacttg aactcgggga tcagcagctt cggcacgggg aggtcgggga acgagtcgct    21960
ccacagcttg cgcgtgagtt gcagggcgcc cagcaggtcg ggcgcggata tcttgaaatc    22020
acagttggga cccgcgttct gcgcgcgaga gttgcggtac acggggttgc agcactggaa    22080
caccatcagg gccgggtgct tcacgctcgc cagcaccgtc gcgtcggtga tgccctccac    22140
gtccagatcc tcggcgttgg ccatcccgaa gggggtcatc ttgcaggtct gccgcccat    22200
gctgggcacg cagccgggct tgtggttgca atcgcagtgc aggggatca gcatcatctg     22260
ggcctgctcg gagctcatgc ccgggtacat ggccttcatg aaagcctcca gctggcggaa    22320
ggcctgctgc gccttgccgc cctcggtgaa gaagaccccg caggacttgc tagagaactg    22380
gttggtggcg cagccggcgt cgtgcacgca gcagcgcgcg tcgttgttgg ccagctgcac    22440
cacgctgcgc ccccagcggt tctgggtgat cttggcccgg tcggggttct ccttcagcgc    22500
gcgctgcccg ttctcgctcg ccacatccat ctcgatcgtg tgctccttct ggatcatcac    22560
ggtcccgtgc aggcaccgca gcttgccctc ggcttcggtg catccgtgca gccacagcgc    22620
gcagccggtg cactcccagt tcttgtgggc gatctgggag tgcgagtgca cgaagccctg    22680
caggaagcgg cccatcatcg cggtcagggt cttgttgctg gtgaaggtca gcgggatgcc    22740
gcggtgctcc tcgttcacat acaggtggca gatgcggcgg tacacctcgc cctgctcggg    22800
catcagctgg aaggcggact tcaggtcgct ctccacgcgg taccgctcca tcagcagcgt    22860
catgacttcc atgcccttct cccaggccga aacgatcggc aggctcaggg ggttcttcac    22920
cgttgtcatc ttagtcgccg ccgccgaggt caggggggtcg ttctcgtcca gggtctcaaa    22980
cactcgcttg ccgtccttct cggtgatgcg cacgggggga agctgaagc ccacggccgc     23040
cagctcctcc tcggcctgcc tttcgtcctc gctgtcctgg ctgatgtctt gcaaaggcac    23100
atgcttggtc ttgcggggtt tcttttggg cggcagaggc ggcggcggag acgtgctggg    23160
cgagcgcgag ttctcgctca ccacgactat ttcttcttct tggccgtcgt ccgagaccac    23220
gcggcggtag gcatgcctct tctggggcag aggcggaggc gacgggctct cgcggttcgg    23280
cgggcggctg gcagagcccc ttccgcgttc gggggtgcgc tcctggcggc gctgctctga    23340
ctgacttcct ccgcggccgg ccattgtgtt ctcctaggga gcaagcatgg agactcagcc    23400
```

-continued

```
atcgtcgcca acatcgccat ctgccccgc cgccgccgac gagaaccagc agcagcagaa    23460
tgaaagctta accgccccgc cgcccagccc cacctccgac gccgcggccc cagacatgca    23520
agagatggag gaatccatcg agattgacct gggctacgtg acgcccgcgg agcacgagga    23580
ggagctggca gcgcgctttt cagccccgga agagaaccac caagagcagc cagagcagga    23640
agcagagagc gagcagagcc aggctgggct cgagcatggc gactacctga gcggggcaga    23700
ggacgtgctc atcaagcatc tggcccgcca atgcatcatc gtcaaggatg cgctgctcga    23760
ccgcgccgag gtgcccctca gcgtggcgga gctcagccgc gcctacgagc gcaacctctt    23820
ctcgccgcgc gtgccccca agcgccagcc caacggcacc tgcgagccca cccgcgcct    23880
caacttctac ccggtcttcg cggtgcccga ggccctggcc acctaccacc tcttttcaa     23940
gaaccaaagg atcccccgtct cctgccgcgc caacccgcacc cgcgccgacg ccctgctcaa    24000
cctgggcccc ggcgcccgcc tacctgatat cgcctccttg gaagaggttc ccaagatctt    24060
cgagggtctg ggcagcgacg agactcgggc cgcgaacgct ctgcaaggaa gcggagagga    24120
gcatgagcac cacagcgccc tggtggagtt ggaaggcgca aacgcgcgcc tggcggtcct    24180
caagcgcacg gtcgagctga cccacttcgc ctacccggcg ctcaacctgc cccccaaggt    24240
catgagcgcc gtcatggacc aggtgctcat caagcgcgcc tcgcccctct cggaggagga    24300
gatgcaggac cccgagagct cggacgaggg caagcccgtg gtcagcgacg agcagctggc    24360
gcgctggctg ggagcgagta gcacccccca gagcctggaa gagcggcgca agctcatgat    24420
ggccgtggtc ctggtgaccg tggagctgga gtgtctgcgc cgcttcttcg ccgacgcgga    24480
gaccctgcgc aaggtcgagg agaacctgca ctacctcttc aggcacgggt tcgtgcgcca    24540
ggcctgcaag atctccaacg tggagctgac caacctggtc tcctacatgg catcctgca    24600
cgagaaccgc tggggcaga acgtgctgca caccaccctg cgcggggagg cccgccgcga    24660
ctacatccgc gactgcgtct acctgtacct ctgccacacc tggcagacgg gcatgggcgt    24720
gtggcagcag tgcctggagg agcagaacct gaaagagctc tgcaagctcc tgcagaagaa    24780
cctgaaggcc ctgtggaccg ggttcgacga gcgcaccacc gcctcggacc tggccgacct    24840
catcttcccc gagcgcctgc ggctgacgct gcgcaacggg ctgccgact ttatgagcca      24900
aagcatgttg caaaactttc gctctttcat cctcgaacgc tccgggatcc tgcccgccac    24960
ctgctccgcg ctgccctcgg acttcgtgcc gctgaccttc gcgagtgcc cccgccgct    25020
ctggagccac tgctacctgc tgcgtctggc caactacctg gcctaccact cggacgtgat    25080
cgaggacgtc agcggcgagg gtctgctcga gtgccactgc cgctgcaacc tctgcacgcc    25140
gcaccgctcc ctggcctgca accccagct gctgagcgag acccagatca tcggcacctt    25200
cgagttgcaa ggccccggcg aggagggcaa gggggtctg aaactcacc cggggctgtg      25260
gacctcggcc tacttgcgca agttcgtgcc cgaggactac catcccttcg agatcaggtt    25320
ctacgaggac caatcccagc cgcccaaggc cgagctgtcg gcctgcgtca tcacccaggg    25380
ggccatcctg gcccaattgc aagccatcca gaaatcccgc caagaatttc tgctgaaaaa    25440
gggccacggg gtctacttgg acccccagac cggagaggag ctcaaccccca gcttccccca    25500
ggatgcccag aggaagcagc aagaagctga aagtggagct gccgctgccg ccggaggatt    25560
tggaggaaga ctgggagagc agtcaggcag aggaggagga gatggaagac tgggacagca    25620
ctcaggcaga ggaggacagc ctgcaagaca gtctggaaga cgaggtggag gaggaggcag    25680
aggaagaagc agccgccgcc agaccgtcgt cctcggcgga gaaagcaagc agcacgata    25740
ccatctccgc tccgggtcgg ggtctcggcg gccgggccca cagtaggtgg gacgagaccg    25800
```

-continued

```
ggcgcttccc gaaccccacc acccagaccg gtaagaagga gcggcaggga tacaagtcct    25860
ggcgggggca caaaaacgcc atcgtctcct gcttgcaagc ctgcggggc  aacatctcct    25920 tcacccggcg ctacctgctc ttccaccgcg gggtgaactt cccccgcaac atcttgcatt    25980
actaccgtca cctccacagc ccctactact gtttccaaga agaggcagaa acccagcagc    26040
agcagaaaac cagcagcagc tagaaaatcc acagcggcgg cggcggcagg tggactgagg    26100
atcgcggcga acgagccggc gcagaccegg gagctgagga accggatctt tcccaccctc    26160
tatgccatct tccagcagag tcggggcag  gagcaggaac tgaaagtcaa gaaccgttct    26220
ctgcgctcgc tcacccgcag ttgtctgtat cacaagagcg aagaccaact tcagcgcact    26280
ctcgaggacg ccgaggctct cttcaacaag tactgcgcgc tcactcttaa agagtagccc    26340
gcgcccgccc acacacggaa aaaggcggga attacgtcac cacctgcgcc cttcgcccga    26400
ccatcatcat gagcaaagag attcccacgc cttacatgtg gagctaccag ccccagatgg    26460
gcctggccgc cggcgccgcc caggactact ccacccgcat gaactggctc agtgccgggc    26520
ccgcgatgat ctcacgggtg aatgacatcc gcgcccgccg aaaccagata tcctagaac    26580 agtcagcgat caccgccacg ccccgccatc accttaatcc gcgtaattgg cccgccgccc    26640
tggtgtacca ggaaattccc cagcccacga ccgtactact tccgcgagac gcccaggccg    26700
aagtccagct gactaactca ggtgtccagc tggccggcgg cgccgccctg tgtcgtcacc    26760
gccccgctca gggtataaag cggctggtga tccgaggcag aggcacacag ctcaacgacg    26820
aggtggtgag ctcttcgctg ggtctgcgac ctgacggagt cttccaactc gccggatcgg    26880
ggagatcttc cttcacgcct cgtcaggccg tcctgacttt ggagagttcg tcctcgcagc    26940
cccgctcggg tggcatcggc actctccagt tcgtggagga gttcactccc tcggtctact    27000
tcaaccccct ctccggctcc cccggccact acccggacga gttcatcccg aacttcgacg    27060
ccatcagcga gtcggtggac ggctacgatt gaatgtccca tggtggcgcg gctgacctag    27120
ctcggcttcg acacctggac cactgccgcc gcttccgctg cttcgctcgg atctcgccg    27180 agtttgccta ctttgagctg cccgaggagc accctcaggg cccggccac  ggagtgcgga    27240 tcatcgtcga aggggcctc  gactcccacc tgcttcggat cttcagccag cgtccgatcc    27300
tggtcgagcg cgagcaagga cagacccgtc tgaccctgta ctgcatctgc aaccaccccg    27360
gcctgcatga aagtctttgt tgtctgctgt gtactgagta taataaaagc tgagatcagc    27420
gactactccg gacttccgtg tgttcctgaa tccatcaacc agtccctgtt cttcaccggg    27480
aacgagaccg agctccagct ccagtgtaag ccccacaaga agtacctcac ctggctgttc    27540
cagggctccc cgatcgccgt tgtcaaccac tgcgacaacg acggagtcct gctgagcggc    27600
cctgccaacc ttactttttc cacccgcaga agcaagctcc agctcttcca acccttcctc    27660
cccgggacct atcagtgcgt ctcgggaccc tgccatcaca ccttccacct gatcccgaat    27720
accacagcgt cgctccccgc tactaacaac caaactaccc accaacgcca ccgtcgcgac    27780 cttttcctctg aatctaatac cactaccgga ggtgagctcc gaggtcgacc aacctctggg    27840
atttactacg gccccctggga ggtggtgggg ttaatagcgc taggcctagt tgtgggtggg    27900
cttttggctc tctgctacct atacctccct tgctgttcgt acttagtggt gctgtgttgc    27960
tggtttaaga aatggggcag atcaccctag tgagctgcgg tgtgctggtg gcggtggtgc    28020
tttcgattgt gggactgggc ggcgcggctg tagtgaagga gaaggccgat ccctgcttgc    28080
atttcaatcc cgacaaatgc cagctgagtt ttcagcccga tggcaatcgg tgcgcggtgc    28140
```

```
tgatcaagtg cggatgggaa tgcgagaacg tgagaatcga gtacaataac aagactcgga   28200
acaatactct cgcgtccgtg tggcagcccg gggaccccga gtggtacacc gtctctgtcc   28260
ccggtgctga cggctccccg cgcaccgtga ataatacttt cattttttgcg cacatgtgcg   28320
acacggtcat gtggatgagc aagcagtacg atatgtggcc ccccacgaag gagaacatcg   28380
tggtcttctc catcgcttac agcctgtgca cggtgctaat caccgctatc gtgtgcctga   28440
gcattcacat gctcatcgct attcgcccca gaaataatgc cgaaaaagag aaacagccat   28500
aacacgtttt ttcacacacc ttgtttttac agacaatgcg tctgttaaat ttttttaaaca   28560
ttgtgctcag tattgcttat gcctctggct atgcaaacat acagaaaacc ctctatgtag   28620
gatctgatga tacactagag ggtacccaat cacaagctag ggtttcatgg tatttttata   28680
aaagctcaga taatcctatt actctttgca aaggtgatca ggggcggaca acaaagccgc   28740
ctatcacatt tagctgtacc agaacaaatc tcacgctttt ctcaattaca aaacaatatg   28800
ctggtatttta ttacagtaca aactttcata gtgggcaaga taaatattat actgttaagg   28860
tagaaaatcc taccactcct agaactacca ccaccaccac caccaccacc actactgcga   28920
agcccactaa acctaaaact accaagaaaa ccactgtgaa aactacaact agaaccacca   28980
caactacaga accaccacc agcacaacac ttgctgcaac tacacacaca cacactgagc   29040
taaccttaca gaccactaat gatttgatag ccctgttgca aaaggggggat aacagcacca   29100
cttccaatga ggagatcccc aaatccatga ttggcattat tgttgctgta gtggtgtgca   29160
tgttgatcat cgccttgtgc atggtgtact atgccttctg ctacagaaag cacagactga   29220
acgacaagct ggaacactta ctaagtgttg aattttaatt ttttagaacc atgaagatcc   29280
taggcctttt agttttttct atcattacct ctgctctatg caattctgac aatgaggacg   29340
ttactgtcgt tgtcggatca aattatacac tgaaaggtcc agcgaagggt atgctttcgt   29400
ggtattgctg gtttggaact gacactgatc aaactgagct ttgcaatgca atgaaaggtc   29460
aaataccaac ctcaaaaatt aaacataaat gcaatggtac tgacttagta ctactcaata   29520
tcacgaaatc atatgctggc agctattcat gccctggaga tgatgctgag aacatgattt   29580
tttacaaagt aactgttgtt gatcccacta ctccaccacc caccaccaca actactcaca   29640
ccacacacac agaacaaaca ccagaggcag cagaagcaga gttggccttc caggttcacg   29700
gagattcctt tgctgtcaat acccctacac ccgatcatcg gtgtccgggg ctgctagtca   29760
gcggcattgt cggtgtgctt tcgggattag cagtcataat catctgcatg ttcatttttg   29820
cttgctgcta tagaaggctt taccgacaaa aatcagaccc actgctgaac ctctatgttt   29880
aatttttttcc agagccatga aggcagttag cgctctagtt ttttgttctt tgattggcat   29940
tgttttttgc aatcctatta ctagagttag ctttattaaa gatgtgaatg ttactgaggg   30000
gggcaatgtg acactggtag gtgtagaggg tgctaaaaac accacctgga caaaatacca   30060
ccttgggtgg aaagatattt gcaattggag tgtcactgtg tacacatgtg agggagttaa   30120
tcttaccatt gtcaatgcca cctcagctca aaatggtaga attcaaggac aaagtgttag   30180
tgtgaccagt gatgggtatt ttacccaaca tacttttatc tatgacgtta aagtcatacc   30240
actgcctacg cctagcccac ctagcaccac tacacaaaca acccacacta cacagacaac   30300
cacatacagt acatcaaatc agcctaccac cactacagca gcagaggttg ccagctcgtc   30360
tggagttcaa gtggcatttt tgttgttgcc cccatctagc agtccactg ctattaccaa   30420
tgagcagact actgcatttt tgtccactgt cgagagccac accacagcta cctccagtgc   30480
cttctctagc accgccaatc tctcctcgct ttcctctaca ccaatcagtc ccgctactac   30540
```

```
tactaccccc gctattcttc ccactcccct gaagcaaaca gacggcggca tgcaatggca    30600
gatcaccctg ctcattgtga tcgggttggt catcctagcc gtgttgctct actacatctt    30660
ctgccgccgc attcccaacg cgcaccgcaa gccggtctac aagcccatca ttgtcgggca    30720
gccggagccg cttcaggtgg aaggggtct aaggaatctt ctcttctctt ttacagtatg     30780
gtgattgaac tatgattcct agacaattct tgatcactat tcttatctgc ctcctccaag    30840
tctgtgccac cctcgctctg gtggccaacg ccagtccaga ctgtattggg cccttcgcct    30900
cctacgtgct ctttgccttc atcacctgca tctgctgctg tagcatagtc tgcctgctta    30960
tcaccttctt ccagttcatt gactggatct ttgtgcgcat cgcctacctg cgccaccacc    31020
cccagtaccg cgaccagcga gtggcgcagc tgctcaggct cctctgataa gcatgcgggc    31080
tctgctactt ctcgcgcttc tgctgttagt gctccccgt cccgttgacc ccggcccccc     31140
cactcagtcc cccgaggagg tccgcaaatg caaattccaa gaaccctgga attcctcaa     31200 atgctaccgc caaaaatcag acatgcatcc cagctggatc atgatcattg ggatcgtgaa    31260
cattctggcc tgcaccctca tctcctttgt gatttacccc tgctttgact ttggttggaa    31320
ctcgccagag gcgctctatc tcccgcctga acctgacaca ccaccacagc aacctcaggc    31380
acacgcacta ccaccaccac agcctaggcc acaatacatg cccatattag actatgaggc    31440
cgagccacag cgacccatgc tccccgctat tagttacttc aatctaaccg gcggagatga    31500
ctgacccact ggcaacaac aacgtcaacg accttctcct ggacatggac ggccgcgcct     31560
cggagcagcg actcgcccaa cttcgcattc gccagcagca ggagagagcc gtcaaggagc    31620
tgcaggacgg catagccatc caccagtgca agaaaggcat cttctgcctg gtgaaacagg    31680
ccaagatctc ctacgaggtc acccagaccg accatcgcct ctcctacgag ctcctgcagc    31740
agcgccagaa gttcacctgc ctggtcggag tcaaccccat cgtcatcacc cagcagtcgg    31800
gcgataccaa ggggtgcatc cactgctcct gcgactcccc cgactgcgtc cacactctga    31860
tcaagaccct ctgcggcctc cgcgacctcc tccccatgaa ctaatcaccc acttatccag    31920
tgaaataaaa aaataatcat ttgatttgaa ataaagatac aatcatattg atgatttgag    31980
tttaacaaaa ataaagaatc acttacttga aatctgatac caggtctctg tccatatttt    32040
ctgccaacac cacctcactc ccctcttccc agctctggta ctgcaggccc cggcgggctg    32100
caaacttcct ccacacgctg aagggatgt caaattcctc ctgcccctca atcttcattt     32160
tatcttctat cagatgtcca aaaagcgcgt ccgggtggat gatgacttcg accccgtcta    32220
cccctacgat gcagacaacg caccgaccgt gcccttcatc aacccccct tcgtctcttc     32280 agatggattc caagagaagc ccctgggggt gttgtccctg cgactggccg accccgtcac    32340
caccaagaac ggggaaatca ccctcaagct gggagagggg gtggacctcg actcctcggg    32400
aaaactcatc tccaacacgg ccaccaaggc cgctgcccct ctcagttttt ccaacaacac    32460
catttccctt aacatggatc ccccttttta cactaaagat ggaaaattag ccttacaagt    32520
ttctccacca ttaaatatac tgagaacaag cattctaaac acactagctt taggttttgg    32580
atcaggttta ggactccgtg gctctgcctt ggcagtacag ttagtctctc cacttacatt    32640
tgatactgat ggaaacataa agcttacctt agacagaggt tgcatgttaa caacaggaga    32700
tgcaattgaa agcaacataa gctgggctaa aggtttaaaa tttgaagatg gagccatagc    32760
aaccaacatt ggaaatgggt tagagttttgg aagcagtagt acagaaacag gtgtcgatga    32820
tgcttaccca atccaagtta aacttggatc tggccttagc tttgacagta caggagccat    32880
```

```
aatggctggt aacaaagaag acgataaact cactttgtgg acaacacctg atccatcacc    32940
aaactgtcaa atactcgcag aaaatgatgc aaaactaaca ctttgcttga ctaaatgtgg    33000
tagtcaaata ctggccactg tgtcagtctt agttgtagga agtggaaacc taaacccat    33060 tactggcacc gtaagcagtg ctcaggtgtt tctacgtttt gatgcaaacg gtgttctttt    33120
aacagaacat tctacactaa aaaatactg ggggtatagg cagggagata gcatagatgg     33180
cactccatat gtcaatgctg taggattcat gcccaattta aaagcttatc caaagtcaca    33240
aagttctact actaaaaata atatagtagg gcaagtatac atgaatggag atgtttcaaa    33300
acctatgctt ctcactataa ccctcaatgg tactgatgac agcaacagta catattcaat    33360 gtcatttca tacacctgga ctaatggaag ctatgttgga gcaacatttg gagctaactc     33420
ttataccttc tcctcatcg cccaagaatg aatactgtat cccaccctgc atgcccaacc     33480
ctcccccacc tctgtctata tggaaaactc tgaaacacaa aataaaataa agttcaagtg    33540
ttttattgat tcaacagttt tacaggattc gagcagttat ttttcctcca ccctcccagg    33600
acatggaata caccaccctc tccccccgca cagccttgaa catctgaatg ccattggtga    33660
tggacatgct tttggtctcc acgttccaca cagtttcaga gcgagccagt ctcgggtcgg    33720
tcagggagat gaaaccctcc gggcactccc gcatctgcac ctcacagctc aacagctgag    33780
gattgtcctc ggtggtcggg atcacggtta tctggaagaa gcagaagagc ggcggtggga    33840
atcatagtcc gcgaacggga tcggccggtg gtgtcgcatc aggccccgca gcagtcgctg    33900
ccgccgccgc tccgtcaagc tgctgctcag ggggtccggg tccagggact ccctcagcat    33960
gatgcccacg gccctcagca tcagtcgtct ggtgcggcgg gcgcagcagc gcatgcggat    34020
ctcgctcagg tcgctgcagt acgtgcaaca caggaccacc aggttgttca acagtccata    34080
gttcaacacg ctccagccga aactcatcgc gggaaggatg ctacccacgt ggccgtcgta    34140
ccagatcctc aggtaaatca agtggcgccc cctccagaac acgctgccca tgtacatgat    34200
ctccttgggc atgtggcggt tcaccactc ccggtaccac atcaccctct ggttgaacat     34260
gcagccccgg atgatcctgc ggaaccacag ggccagcacc gccccgcccg ccatgcagcg    34320
aagagacccc gggtcccggc aatggcaatg gaggacccac cgctcgtacc cgtggatcat    34380
ctgggagctg aacaagtcta tgttggcaca gcacaggcac acgctcatgc atctcttcag    34440
cactctcagc cctcgggggg tcaaaaccat atcccagggc acgggaaact cttgcaggac    34500
agcgaagccc gcagaacagg gcaatcctcg cacataactt acattgtgca tggacagggt    34560
atcgcaatca ggcagcaccg ggtgatcctc caccagagaa gcgcgggtct cggtctcctc    34620
acagcgtggt aaggggccg gccgatacgg gtgatggcgg gacgcggctg atcgtgttcg    34680
cgaccgtgtc atgatgcagt tgcttttcgga cattttcgta cttgctgaag cagaacctgg    34740
tccgggcgct gcacaccgat cgccggcggc ggtctcggcg cttggaacgc tcggtgttga    34800
agttgtaaaa cagccactct ctcagaccgt gcagcagatc tagggcctca ggagtgatga    34860
agatcccatc atgcctgatg gctctgatca catcgaccac cgtggaatgg gccagaccca    34920
gccagatgat gcaattttgt tgggtttcgg tgacggcggg ggaggaaga acaggaagaa     34980 ccatgattaa cttttaatcc aaacggtctc ggagcacttc aaaatgaagg tcgcggagat    35040
ggcacctctc gccccgctg tgttggtgga aaataacagc caggtcaaag gtgatacggt     35100
tctcgagatg ttccacggtg gcttccagca aagcctccac gcgcacatcc agaaacaaga    35160
caatagcgaa agcgggaggg ttctctaatt cctcaatcat catgttacac tcctgcacca    35220
tccccagata attttcattt ttccagcctt gaatgattcg aactagttcc tgaggtaaat    35280
```

```
ccaagccagc catgataaag agctcgcgca gagcgccctc caccggcatt cttaagcaca    35340
ccctcataat tccaagatat tctgctcctg gttcacctgc agcagattga caagcgggat    35400
atcaaaatct ctgccgcgat ccctgagctc ctccctcagc aataactgta agtactcttt    35460
catatcctct ccgaaatttt tagccatagg accccagga ataagagaag ggcaagccac    35520
attacagata aaccgaagtc cccccagtg agcattgcca aatgtaagat tgaaataagc    35580
atgctggcta gacccggtga tatcttccag ataactggac agaaaatcgg gcaagcaatt    35640
tttaagaaaa tcaacaaaag aaaaatcttc caggtgcacg tttagggcct cgggaacaac    35700
gatggagtaa gtgcaagggg tgcgttccag catggttagt tagctgatct gtaaaaaaac    35760
aaaaaataaa acattaaacc atgctagcct ggcgaacagg tgggtaaatc gttctctcca    35820
gcaccaggca ggccacgggg tctccggcgc gaccctcgta aaaattgtcg ctatgattga    35880
aaaccatcac agagagacgt tcccggtggc cggcgtgaat gattcgagaa gaagcataca    35940
cccccggaac attggagtcc gtgagtgaaa aaaagcggcc gaggaagcaa tgaggcacta    36000
caacgctcac tctcaagtcc agcaaagcga tgccatgcgg atgaagcaca aaattttcag    36060
gtgcgtaaaa aatgtaatta ctcccctcct gcacaggcag cgaagctccc gatccctcca    36120
gatacacata caaagcctca gcgtccatag cttaccgagc ggcagcagca gcggcacaca    36180
acaggcgcaa gagtcagaga aaagactgag ctctaacctg tccgcccgct ctctgctcaa    36240
tatatagccc cagatctaca ctgacgtaaa ggccaaagtc taaaaatacc cgccaaataa    36300
tcacacacgc ccagcacacg cccagaaacc ggtgacacac tcaaaaaaat acgcgcactt    36360
cctcaaacgc ccaaactgcc gtcatttccg ggttccacg ctacgtcatc aaaacacgac    36420
tttcaaattc cgtcgaccgt taaaaacgtc acccgccccg cccctaacgg tcgccgctcc    36480
cgcagccaat cagcgccccg catcccaaa ttcaaacagc tcatttgcat attaacgcgc    36540
accaaaagtt tgaggtatat tattgatgat g                                  36571
```

CHIMPANZEE CLADE E ADENOVIRUS NUCLEIC ACID-AND AMINO ACID-SEQUENCES, VECTORS CONTAINING SAME, AND USES THEREOF

CROSS-REFERENCE TO RELATED APPLICATIONS

This application is a Divisional of application Ser. No. 13/147,193, filed Sep. 30, 2011, which is an U.S. National Phase of PCT/EP2010/000616, entitled "SIMIAN ADENOVIRUS NUCLEIC ACID-AND AMINO ACID-SEQUENCES, VECTORS CONTAINING SAME, AND USES THEREOF," filed on Feb. 2, 2010 and issued as U.S. Pat. No. 9,718,863, which claims the benefit of PCT patent application PCT/EP2009/000672, filed Feb. 2, 2009, U.S. provisional patent application Ser. No. 61/266,342, filed on Dec. 3, 2009, U.S. provisional patent application Ser. No. 61/174,852, filed on May 1, 2009, and U.S. provisional application Ser. No. 61/172,624, filed on Apr. 24, 2009, the disclosures of which are incorporated herein by reference in their entirety for all purposes.

FIELD OF INVENTION

The present invention relates to novel adenovirus strains with an improved seroprevalence. In one aspect, the present invention relates to isolated polypeptides of adenoviral capsid proteins such as hexon, penton and fiber protein and fragments thereof and polynucleotides encoding the same. Also provided is a vector comprising the isolated polynucleotide according to the invention and adenoviruses comprising the isolated polynucleotides or polypeptides according to the invention and a pharmaceutical composition comprising said vector, adenovirus, polypeptide and/or polynucleotide. The invention also relates to the use of the isolated polynucleotides, the isolated polypeptides, the vector, the adenoviruses and/or the pharmaceutical composition for the therapy or prophylaxis of a disease.

BACKGROUND OF THE INVENTION

The adenoviruses (Ads) comprise a large family of double-stranded DNA viruses found in amphibians, avians, and mammals which have a nonenveloped icosahedral capsid structure (Straus, Adenovirus infections in humans; *The Adenoviruses*, 451-498, 1984; Hierholzer et al., J. Infect. Dis., 158: 804-813,1988; Schnurr and Dondero, *Intervirology.*, 36: 79-83,1993; Jong et al., *J. Clin. Microbiol.*, 37: 3940-3945: 1999). In contrast to retroviruses, adenoviruses can transduce numerous cell types of several mammalian species, including both dividing and nondividing cells, without integrating into the genome of the host cell.

Generally speaking, adenoviral DNA is typically very stable and remains episomal (e. g., extrachromosomal), unless transformation or tumorigenesis has occurred. In addition, adenoviral vectors can be propagated to high yields in well-defined production systems which are readily amenable to pharmaceutical scale production of clinical grade compositions. These characteristics and their well-characterized molecular genetics make recombinant adenoviral vectors good candidates for use as vaccine carriers. The production of recombinant adenoviral vectors may rely on the use of a packaging cell line which is capable of complementing the functions of adenoviral gene products that have been either deleted or engineered to be nonfunctional.

Presently, two well-characterized human subgroup C adenovirus serotypes (i. e., hAd2 and hAd5) are widely used as the sources of the viral backbone for most of the adenoviral vectors that are used for gene therapy. Replication-defective human adenoviral vectors have also been tested as vaccine carriers for the delivery of a variety of immunogens derived from a variety of infectious agents. Studies conducted in experimental animals (e. g. rodents, canines and nonhuman primates) indicate that recombinant replication-defective human adenoviral vectors carrying transgenes encoding immunogens as well as other antigens elicit both humoral and cell-mediated immune responses against the transgene product. Generally speaking, investigators have reported success using human adenoviral vectors as vaccine carriers in nonhuman experimental systems by either using immunization protocols that utilizes high doses of recombinant adenoviral vectors that are predicted to elicit immune responses; or by using immunization protocols which employ the sequential administration of adenoviral vectors that are derived from different serotypes but which carry the same transgene product as boosting immunizations (Mastrangeli, et. al., Human Gene Therapy, 7: 79-87 (1996).

Viral vectors based on human adenovirus type 5 (Ad5) have been developed for different gene therapy and vaccine applications. Although Ad5-based vectors are extremely efficient in animal models, the presence of a pre-existing immunity in humans against Ad5 wild type virus has been demonstrated in clinical trials to reduce the efficiency of gene transduction. In particular, a clear reduction of the immunization efficiency was demonstrated in subjects with titers of neutralizing antibodies over 200 enrolled in vaccine clinical trial based on Ad5 vectors. The most extensive characterization of an Ad5 vectored vaccine was obtained in the HIV vaccine STEP trial conducted by Merck (Moore J P et al. Science. 2008 May 9; 320(5877):753-5). The vaccine study was based on the co-injection of 3 Ad5 vectors expressing different HIV antigens as proof of concept study in subjects with high risk of HIV infection. Surprisingly, the data revealed an increase of HIV infection rate in vaccinated subjects with anti-Ad5 pre-existing immunity rather then a protective effect. Although the mechanism of this paradoxical observation is not clear yet, the results raised additional questions on the safety and efficiency of vectors based on adenovirus of human origin for vaccine application in healthy subjects. Taken together all results obtained so far in different vaccine and gene therapy clinical trials such as the trials with Ad5 vectors increased the need for an adenovirus characterized in a very low or absent pre-existing immunity in humans.

SUMMARY OF THE INVENTION

In a first aspect the present invention provides an isolated polynucleotide that encodes an adenoviral fiber protein or a functional derivative thereof and that is selected from the group consisting of:
(a) a polynucleotide encoding a polypeptide having the amino acid sequence according to any of SEQ ID NOs: 14-19, 50 and 53;
(b) a polynucleotide encoding the functional derivative of a polypeptide according to any of SEQ ID NOs: 14-19, 50 and 53, wherein said functional derivative comprises the deletion, insertion and/or substitution of one or more amino acid residues; and
(c) a polynucleotide encoding a functional derivative having an amino acid sequence which is at least 85% identical over its entire length to the amino acid sequence of any of SEQ ID NOs: 14-19, 50 and 53.

In a further aspect the present invention relates to an isolated polynucleotide that encodes an adenoviral hexon protein or a functional derivative thereof and that is selected from the group consisting of:
(a) a polynucleotide encoding a polypeptide having the amino acid sequence according to any of SEQ ID NOs: 20-25, 51 and 54;
(b) a polynucleotide encoding the functional derivative of a polypeptide according to any of SEQ NOs: 20-25, 51 and 54, wherein said functional derivative comprises the deletion, insertion and/or substitution of one or more amino acid residues; and
(c) a polynucleotide encoding a functional derivative having an amino acid sequence which is at least 95% identical over its entire length to the amino acid sequence of any of SEQ NOs: 20-25, 51 and 54.

Also provided is an isolated polynucleotide that encodes an adenoviral penton protein or a functional derivative thereof and that is selected from the group consisting of:
(a) a polynucleotide encoding a polypeptide having the amino acid sequence according to any of SEQ ID NOs: 26-31, 52 and 55;
(b) a polynucleotide encoding the functional derivative of a polypeptide according to any of SEQ NOs: 26-31, 52 and 55, wherein said functional derivative comprises the deletion, insertion and/or substitution of one or more amino acid residues; and
(c) a polynucleotide encoding a functional derivative having an amino acid sequence which is at least 85% identical over its entire length to the amino acid sequence of any of SEQ ID NOs: 26-31, 52 and 55.

The invention also relates to a polynucleotide comprising at least one of the isolated polynucleotide according to the invention as outlined above. The invention further provides an isolated adenoviral capsid polypeptide encoded by the isolated polynucleotide according to the invention or a functional derivative thereof.

In a further aspect the invention provides a vector comprising the isolated polynucleotide according to the invention.

Also provided is a recombinant adenovirus, preferably a replication-incompetent adenovirus, comprising an isolated polynucleotide according to the invention and/or at least one isolated adenoviral capsid polypeptide according to the invention.

A further aspect of the invention is a composition comprising an adjuvant and at least one of the following (i) through (iv):
(i) one or more isolated adenoviral capsid polypeptides according to the invention;
(ii) an isolated polynucleotide according to the invention;
(iii) a vector according to the invention;
(iv) a recombinant adenovirus according to the invention;
and, optionally, a pharmaceutically acceptable excipient.

The invention further relates to a cell comprising at least one of the following:
(i) one or more isolated adenoviral capsid polypeptides according to the invention;
(ii) an isolated polynucleotide according to the invention;
(iii) a vector according to the invention;
(iv) a recombinant adenovirus according to the invention.

A further aspect of the invention relates to the use of an isolated adenoviral capsid polypeptide according to the invention; an isolated polynucleotide according to the invention; a vector according to the invention; a recombinant adenovirus according to the invention; and/or the composition according to the invention for the therapy or prophylaxis of a disease.

DETAILED DESCRIPTION OF THE INVENTION

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

Preferably, the terms used herein are defined as described in "A multilingual glossary of biotechnological terms: (IUPAC Recommendations)", Leuenberger, H. G. W, Nagel, B. and Klbl, H. eds. (1995), Helvetica Chimica Acta, CH-4010 Basel, Switzerland) and as described in "Pharmaceutical Substances: Syntheses, Patents, Applications" by Axel Kleemann and Jurgen Engel, Thieme Medical Publishing, 1999; the "Merck Index: An Encyclopedia of Chemicals, Drugs, and Biologicals", edited by Susan Budavari et al., CRC Press, 1996, and the United States Pharmacopeia-25/National Formulary-20, published by the United States Pharmcopeial Convention, Inc., Rockville Md., 2001.

Throughout this specification and the claims which follow, unless the context requires otherwise, the word "comprise", and variations such as "comprises" and "comprising", will be understood to imply the inclusion of a stated feature, integer or step or group of features, integers or steps but not the exclusion of any other feature, integer or step or group of integers or steps. In the following passages different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

In the following, some definitions of terms frequently used in this specification are provided. These terms will, in each instance of its use, in the remainder of the specification have the respectively defined meaning and preferred meanings.

Generally speaking, the adenoviral genome is well characterized. There is general conservation in the overall organization of the adenoviral genome with respect to specific open reading frames being similarly positioned, e.g. the location of the E1A, E1B, E2A, E2B, E3, E4, L1, L2, L3, L4 and L5 genes of each virus. Each extremity of the adenoviral genome comprises a sequence known as an inverted terminal repeat (ITRs), which is necessary for viral replication. The virus also comprises a virus-encoded protease, which is necessary for processing some of the structural proteins required to produce infectious virions. The structure of the adenoviral genome is described on the basis of the order in which the viral genes are expressed following host cell transduction. More specifically, the viral genes are referred to as early (E) or late (L) genes according to whether transcription occurs prior to or after onset of DNA replication. In the early phase of transduction, the E1A, E1B, E2A, E2B, E3 and E4 genes of adenovirus are expressed to prepare the host cell for viral replication. During the late phase of infection, expression of the late genes L1-L5, which encode the structural components of the virus particles are activated.

The following Table 1 provides an overview over the sequences referred to herein:

TABLE 1

| Designation/Strain | SEQ ID NO: Protein | Polynucleotide |
|---|---|---|
| HIV gag | 1 | HIV gag |
| TLR9 agonist | 2 | TLR9 agonist |
| HVR7 primer1 | 3 | HVR7 primer1 |
| HVR7 primer2 | 4 | HVR7 primer2 |
| HVR1-6fd | 5 | HVR1-6fd |
| HVR1-6rev | 6 | HVR1-6rev |
| PanAd1 left end P1 | 7 | PanAd1 left end P1 |
| PanAd1 left end P2 | 8 | PanAd1 left end P2 |
| PanAd1 right end P1 | 9 | PanAd1 right end P1 |
| PanAd1 right end P2 | 10 | PanAd1 right end P2 |
| pIX P1 | 11 | pIX P1 |
| pIX P2 | 12 | pIX P2 |
| Bonobo Adenovirus type 1 (PanAd1). Complete genome | 13 | Bonobo Adenovirus type 1 (PanAd1). Complete genome |
| ChAd55 | 14 | Fiber |
| ChAd73 | 15 | Fiber |
| ChAd83 | 16 | Fiber |
| ChAd146 | 17 | Fiber |
| ChAd147 | 18 | Fiber |
| PanAd1 | 19 | Fiber |
| ChAd55 | 20 | Hexon |
| ChAd73 | 21 | Hexon |
| ChAd83 | 22 | Hexon |
| ChAd146 | 23 | Hexon |
| ChAd147 | 24 | Hexon |
| PanAd1 | 25 | Hexon |
| ChAd55 | 26 | Penton |
| ChAd73 | 27 | Penton |
| ChAd83 | 28 | Penton |
| ChAd146 | 29 | Penton |
| ChAd147 | 30 | Penton |
| PanAd1 | 31 | Penton |
| ChAd55 | 32 | | Fiber |
| ChAd73 | 33 | | Fiber |
| ChAd83 | 34 | | Fiber |
| ChAd146 | 35 | | Fiber |
| ChAd147 | 36 | | Fiber |
| PanAd1 | 37 | | Fiber |
| ChAd55 | 38 | | Hexon |
| ChAd73 | 39 | | Hexon |
| ChAd83 | 40 | | Hexon |
| ChAd146 | 41 | | Hexon |
| ChAd147 | 42 | | Hexon |
| PanAd1 | 43 | | Hexon |
| ChAd55 | 44 | | Penton |
| ChAd73 | 45 | | Penton |
| ChAd83 | 46 | | Penton |
| ChAd146 | 47 | | Penton |
| ChAd147 | 48 | | Penton |
| PanAd1 | 49 | | Penton |
| PanAd2 | 50 | Fiber | |
| PanAd2 | 51 | Hexon | |
| PanAd2 | 52 | Penton | |
| PanAd3 | 53 | Fiber | |
| PanAd3 | 54 | Hexon | |
| PanAd3 | 55 | Penton | |
| PanAd2 | 56 | | Fiber |
| PanAd2 | 57 | | Hexon |
| PanAd2 | 58 | | Penton |
| PanAd3 | 59 | | Fiber |
| PanAd3 | 60 | | Hexon |

TABLE 1-continued

| Designation/Strain | SEQ ID NO: Protein | Polynucleotide |
|---|---|---|
| PanAd3 | 61 | | Penton |
| Bonobo Adenovirus type 2 (PanAd2). Complete genome | 62 | | Bonobo Adenovirus type 2 (PanAd2). Complete genome |
| Bonobo Adenovirus type 3 (PanAd3). Complete genome | 63 | | Bonobo Adenovirus type 3 (PanAd3). Complete genome |
| Ad5 E4 ORF6 coding sequence | 64 | | Ad5 E4 ORF6 coding sequence |
| ChAd83 Complete genome | 65 | | ChAd83 Complete genome |

As used herein, the term "isolated" refers to a molecule which is substantially free of other molecules with which it is naturally associated with. An isolated molecule is thus free of other molecules that it would encounter or contact in a living animal in nature, i.e. outside an experimental setting.

As used herein, the term "protein", "peptide", "polypeptide", "peptides" and "polypeptides" are used interchangeably throughout. These terms refers to both naturally occurring peptides, e.g. naturally occurring proteins and synthesized peptides that may include naturally or non-naturally occurring amino acids. Peptides can be also chemically modified by modifying a side chain or a free amino or carboxy-terminus of a natural or non-naturally occurring amino acid. This chemical modification includes the addition of further chemical moieties as well as the modification of functional groups in side chains of the amino acids, such as a glycosylation. A peptide is a polymer preferably having at least 3, 4, 5, 6, 7, 8, 9, 10, 15, 20, 25, 30, 35, 40, 45, 50, 55, 60, 65, 70, 75, 80, 85, 90, 95, or at least 100 amino acids, most preferably at least 8 or at least 30 amino acids. As the polypeptides and proteins disclosed herein are derived from adenovirus, it is preferred that the molecular mass of an isolated polypeptide or protein as used herein does not exceed 200 kDa.

The term "vector" as used herein includes any vectors known to the skilled person including plasmid vectors, cosmid vectors, phage vectors such as lambda phage, viral vectors such as adenovirus (Ad) vectors (e.g., non-replicating Ad5, Ad11, Ad26, Ad35, Ad49, ChAd3, ChAd4, ChAd5, ChAd7, ChAd8, ChAd9, ChAd10, ChAd11, ChAd16, ChAd17, ChAd19, ChAd20, ChAd22, ChAd24, ChAd26, ChAd30, ChAd31, ChAd37, ChAd38, ChAd44, ChAd63 and ChAd82 vectors or replication-competent Ad4 and Ad7 vectors known from the prior art, e.g. WO 2005/071093 A2), adeno-associated virus (AAV) vectors (e.g., AAV type 5), alphavirus vectors (e.g., Venezuelan equine encephalitis virus (VEE), sindbis virus (SIN), semliki forest virus (SFV), and VEE-SIN chimeras), herpes virus vectors, measles virus vectors, pox virus vectors (e.g., vaccinia virus, modified vaccinia virus Ankara (MVA), NYVAC (derived from the Copenhagen strain of vaccinia), and avipox vectors: canary-pox (ALVAC) and fowlpox (FPV) vectors), and vesicular stomatitis virus vectors, viral like particles, or bacterial spores. A vector also includes expression vectors, cloning vectors and vectors that are useful to generate recombinant adenoviruses in host cells.

The term "expression cassette" refers to a nucleic acid molecule which comprises at least one nucleic acid sequence that is to be expressed, along with its transcription and translation control sequences. Changing the expression cassette will cause the vector in which it is incorporated to direct the expression of a different sequence or combination of sequences. Because of the restriction sites being preferably engineered to be present at the 5' and 3' ends, the cassette can be easily inserted, removed, or replaced with another cassette. Preferably, an expression cassette includes cis-regulating elements for efficient expression of a given gene, such as promoter, initiation-site and/or polyadenylation-site, as further described below.

The term "antibody" refers to both monoclonal and polyclonal antibodies, i.e., any immunoglobulin protein or portion thereof which is capable of binding an antigen or hapten. Antigen-binding portions may be produced by recombinant DNA techniques or by enzymatic or chemical cleavage of intact antibodies. In some embodiments, antigen-binding portions include Fab, Fab', F(ab')$_2$, Fd, Fv, dAb, and complementarity determining region (CDR) variants, single-chain antibodies (scFv), chimeric antibodies, humanized antibodies, diabodies, and polypeptides that contain at least a portion of an antibody that is sufficient to confer specific antigen binding to the polypeptide.

The administration of an immunogen/antigen for inducing/generating an immune response in a mammal in the context of the present invention is termed "priming", and the administration of an immunogen/antigen for enhancing an immune response against said immunogen/antigen, e.g. a particular pathogen (such as a virion or a virus pathogen, an antigen of a pathogenic bacterium or a tumorantigen) in a mammal is termed "boosting". The phrase "heterologous prime-boost" means that the vector for inducing/generating an immune response (priming) in a mammal and the vector for enhancing the immune response (boosting) in a mammal are different. "Heterologous prime-boost" is useful if a subject, e.g. patient has developed antibodies against a first vector and a boosting is required. Thus, in a preferred embodiment of heterologous prime-boost two different adenoviruses may be used, e.g. for vaccination and/or gene therapy. In this context, a first and a second adenovirus are sufficiently different, if the antibody response induced during priming by the first adenovirus does not prevent more than 70% or preferably more than 80% of the second adenovirus particles administered for boosting from entering the nucleus of cells of the animal that has been subjected to priming and boosting.

The term "replication-competent" recombinant adenovirus (AdV) refers to an adenovirus which can replicate in a host cell in the absence of any recombinant helper proteins comprised in the cell. Preferably, a "replication-competent" adenovirus comprises the following intact or functional essential early genes: E1A, E1B, E2A, E2B, E3 and E4. Wild type adenoviruses isolated from a particular animal will be replication competent in that animal.

The term "replication-defective" recombinant AdV refers to an adenovirus that has been rendered to be incapable of replication because it has been engineered to comprise at least a functional deletion, i.e. a deletion which impairs the function of a gene without removing it entirely, e.g. introduction of artificial stop codons, deletion or mutation of active sites or interaction domains, mutation or deletion of a regulatory sequence of a gene etc, or a complete removal of a gene encoding a gene product that is essential for viral replication, such as one or more of the adenoviral genes selected from E1, E2, E3 and E4. The recombinant chimpanzee adenoviral vectors of the invention are preferably replication-defective.

The term "identity" or "identical" in the context of polynucleotide, polypeptide or protein sequences refers to the number of residues in the two sequences that are identical when aligned for maximum correspondence. Specifically, the percent sequence identity of two sequences, whether nucleic acid or amino acid sequences, is the number of exact matches between two aligned sequences divided by the length of the shorter sequence and multiplied by 100. Alignment tools that can be used to align two sequences are well known to the person skilled in the art and can, for example, be obtained on the World Wide Web, e.g., ClustalW (www.ebi.ac.uk/clustalw) or Align (http://www.ebi.ac.uk/emboss/align/index.html). The alignments between two sequences may be carried out using standard settings, for Align EMBOSS::needle preferably: Matrix: Blosum62, Gap Open 10.0, Gap Extend 0.5. Those skilled in the art understand that it may be necessary to introduce gaps in either sequence to produce a satisfactory alignment. The "best sequence alignment" between two polypeptides is defined as the alignment that produces the largest number of aligned identical residues.

Adenoviruses

An adenovirus (Ad) is a non-enveloped, icosahedral virus that has been identified in several avian and mammalian hosts. Human adenoviruses (hAds) belong to the *Mastadenovirus* genus which includes all known human and many Ads of animal (e. g., bovine, porcine, canine, marine, equine, simian and ovine) origin. Human adenoviruses are generally divided into six subgroups (A-F) based on a number of biological, chemical, immunological and structural criteria which include hemagglutination properties of rat and rhesus monkey erythrocytes, DNA homology, restriction enzyme cleavage patterns, percentage G+C content and oncogenicity (Straus, 1984, in *The Adenoviruses*, ed. H. Ginsberg, pps. 451-498, New York Plenus Press, and Horwitz, 1990; in *Virology*, eds. B. N. Fields and D. M. Knipe, pps. 1679-1721).

The adenoviral virion has an icosahedral symmetry and, depending on the serotype, a diameter of 60-90 nm. The icosahedral capsid comprises three major proteins, hexon (II), penton base (III) and a knobbed fiber (IV) protein (W. C. Russel, J. Gen. Virol., 81: 2573-2604 (2000)). One aspect of the preexisting immunity that is observed in humans is humoral immunity, which can result in the production and persistence of antibodies that are specific for adenoviral proteins. The humoral response elicited by adenovirus is mainly directed against the three major structural proteins: hexon, penton and fiber.

To date, 51 distinct human adenovirus serotypes have been recognized and grouped into subgroups on the basis of their hemagglutination properties and biophysical and biochemical criteria. Published reports have established that titers comprising antibodies against multiple serotypes are common (Dambrosio, E. (1982) J. Hyg. (London) 89: 209-219) and that a substantial portion of the titers have neutralizing activity.

As mentioned, recombinant adenoviruses are useful in gene-therapy and as vaccines. Viral vectors based on chimpanzee adenovirus represent an alternative to the use of human derived Ad vectors for the development of genetic vaccines (Farina S F, J Virol. 2001 December; 75(23): 11603-13; Fattori E, Gene Ther. 2006 July; 13(14):1088-96). Adenoviruses isolated from chimpanzees are closely related to adenoviruses isolated from humans as demonstrated by their efficient propagation in cells of human origin. However, since human and chimp adenoviruses are close relatives, a serologic cross reactivity between the two virus species can be expected.

This presumption has been confirmed when chimpanzee adenoviruses were isolated and characterized. Nevertheless, adenovirus isolates from chimpanzees showed a reduced cross reactivity with the common serotypes of human adenovirus epitopes. Thus, a chimpanzee adenovirus (also abbreviated herein as "ChAd" for common chimpanzee adenovirus and "PanAd" for bonobo chimpanzee adenovirus) provides a basis for reducing the adverse effects associated with the preexisting immunity in humans to common serotypes of human adenoviruses. However, a low to intermediate neutralizing titer against chimp adenoviruses isolated so far is detected in subsets of human sera and, thus, all known serotypes of chimpanzee adenoviruses are still neutralized by human blood sera to some degree.

The present invention comprises the unexpected finding that novel chimpanzee adenovirus strains could be isolated, namely ChAd55, ChAd73, ChAd83, ChAd146, ChAd147 isolated from the Common Chimpanzee (*Pan troglodytes*) and PanAd1, PanAd2 and PanAd3 isolated from bonobos (*Pan paniscus*). All these novel strains show no measurable seroprevalence in humans, i.e. these adenovirus strains represent an exception among chimpanzee adenoviruses described so far in that all human sera tested completely negative for the presence of neutralizing antibodies. In this context, a neutralizing antibody refers to an antibody that binds to an epitope of the adenovirus and prevents it from producing a productive infection in a host cell or prevents the transduction of a target cell with a replication incompentent vector expressing a transgene, e.g. the adenovirus DNA is capable of entering a host cell. While neutralizing antibodies were observed for all prior-art chimpanzee-derived adenoviruses, the novel adenovirus types ChAd55, ChAd73, ChAd83, ChAd146, ChAd147 PanAd1, PanAd2 and PanAd3 are characterized by a complete absence of preexisting neutralizing antibody in humans directed against these adenovirus types. Thus, these adenoviruses provide a valuable medical tool that can e.g. be used for immunization and/or gene therapy.

As detailed further below, the invention provides, in one aspect, novel sequences of adenovirus capsid proteins that represent the most surface exposed adenovirus epitopes, namely hexon, penton and fiber protein. As already mentioned, no neutralizing antibodies specific for the viruses according to the invention are comprised in human blood sera. Thus, one advantage of the aforementioned novel chimpanzee hexon, penton and fiber protein sequences is that the sequences of these proteins can be used to enhance prior art adenoviruses, which have been engineered for e.g. medical purposes. For example, the capsid proteins or functional fragments thereof of the present invention can be used to e.g. replace/substitute one or more of the major structural capsid proteins or functional fragments thereof, respectively, of a different adenovirus, e.g. a prior art adenovirus, to obtain improved recombinant adenoviruses with a reduced seroprevalence in humans. As the novel adenoviruses of the invention but also adenoviruses which have been re-engineered as described will not encounter any significant inhibitory immune response in humans when administered, their overall transduction efficiency and infectivity will be enhanced. Thus, such improved adenoviruses are expected to be, e.g., more effective vaccines as the entry into host cells and the expression of the antigen cassette will not be hampered by any significant titer of neutralizing antibodies. In addition, as shown in the examples, a potent immune response against HIV gag was elicited even in naïve mice vaccinated with a recombinant HIV-gag encoding adenovirus that comprises hexon, penton and fiber proteins of the ChAd55, ChAd73, ChAd83, ChAd146, ChAd147, PanAd1, PanAd2 or PanAd3 isolate. The immune response elicited by ChAd55-gag, ChAd73-gag, ChAd83-gag, ChAd146-gag, ChAd147-gag, PanAd1-gag, PanAd2-gag and PanAd3-gag adenoviruses is comparable with the response observed with the most potent vectors developed so far based on recombinant human Ad5 vector of the prior art expressing HIV gag protein (see data of an ELIspot assay in FIG. 5A, 5B, 5C).

As mentioned before, the humoral response elicited by an adenovirus is mainly directed against the three major adenoviral structural proteins: hexon, penton and fiber, all of which comprise polypeptide sequences that are part of the adenoviral capsid and that are exposed to the outside of the virus particle (see also: Madisch I, et al., J. Virol 2005 December; 79(24):15265-76; and also: Madisch I, et al., J Virol. 2007 August; 81(15):8270-81; and Pichla-Gollon S L, et al, J. Virol. 2007 February; 81(4):1680-9).

As depicted in the multiple sequence alignment shown in FIG. 1, the novel adenovirus isolates of the group of PanAd1, PanAd2, PanAd3, ChAd55, ChAd73, ChAd83, ChAd146 and ChAd147 of the present invention share a very similar hexon protein sequence. In the alignment also the hypervariable regions (HVRs) are labeled which occur in loops at the top of the hexon molecule that lie on the exterior of the virion and cover a large amount of its surface (see Jophn J. Rux et. Al, J. of Virology, September 2003, vol. 77, no. 17). The sequence relatedness of the further capsid proteins fiber and penton of the novel chimpanzee adenoviruses is provided in FIGS. 2 and 3, respectively. All three structural capsid proteins are expected to contribute to the low seroprevalence and can, thus, be used independently from each other or in combination to suppress the affinity of an adenovirus to preexisting neutralizing antibodies, e.g. to manufacture a recombinant chimeric adenovirus with a reduced seroprevalence.

Thus, in a first aspect the invention provides an isolated polynucleotide that encodes an adenoviral fiber protein or a functional derivative thereof and that is selected from the group consisting of:

(a) a polynucleotide encoding a polypeptide having the amino acid sequence according to any of SEQ ID NOs: 14-19, 50 and 53; i.e. SEQ ID NO: 14, 15, 16, 17, 18, 19, 50 or 53;

(b) a polynucleotide encoding the functional derivative of a polypeptide according to any of SEQ ID NOs: 14-19, 50 and 53, i.e. SEQ ID NO: 14, 15, 16, 17, 18, 19, 50 o 53; wherein said functional derivative comprises the deletion, insertion and/or substitution of one or more amino acid residues; and (c) a polynucleotide encoding a functional derivative having an amino acid sequence which is at least 85%, 86%, 87%, 88%, 89%, 90%, 91%, 92%, 93%, 94%, 95%, 96%, 97%, 98% or at least 99%, more preferably at least 85% and most preferable at least 99% identical over its entire length to the amino acid sequence of any of SEQ ID NOs: 14-19, 50 and 53, i.e. SEQ ID NO: 14, 15, 16, 17, 18, 19, 50 or 53.

By "adenoviral fiber protein" is meant the knobbed fiber (IV) protein comprised in an adenovirus. In a preferred embodiment, the isolated polynucleotide comprised in the first aspect of the invention and preferred embodiments thereof described below encodes a fiber protein or a functional derivative thereof that has the same function as a fiber protein or a fragment thereof in an infectious adenovirus virion. Thus, a recombinant adenovirus comprising said fiber or functional fiber derivative preferably as a capsid protein is capable of entering a host cell. It can be easily determined if a recombinant adenovirus can enter a host cell. For example, after contacting a host cell with the adenovirus, the recombinant host cell can be washed and lysed and it can be determined whether adenoviral RNA and/or DNA is found in the host cell using, e.g. an appropriate hybridization probe specific for adenoviral RNA and/or DNA. Alternatively or additionally, the host cell after having been brought into contact with the recombinant adenovirus may be washed, lysed and probed with adenovirus specific antibodies, e.g. using a Western blot. In yet another alternative, it is observed, e.g. in vivo, whether the host cell expresses a gene product, for example a fluorescent protein upon infection with a recombinant adenovirus that comprises a suitable expression cassette to express the gene product in the host cell.

It is further preferred that the fiber protein and functional derivative thereof has an affinity to an adenoviral penton protein, such as to SEQ ID NOs: 26-31, 52 and/or 55. The average skilled person is well aware of how to test protein-protein affinities. To determine if a first protein is capable of binding a second protein, such as a penton protein of a chimpanzee derived adenovirus, he may use, for example, a genetic yeast two-hybrid assay or a biochemical assay such as a pull-down, an enzyme-linked immunosorbent assay (ELISA), a fluorescence-activated cell sorting (FACS)-based assay or a Plasmon resonance assay. When using pull-down or Plasmon resonance assays, it is useful to fuse at least one of the proteins to an affinity tag such as HIS-tag, GST-tag or other, as is well known in the art of biochemistry. An adenoviral fiber protein in its glycosylated form is further capable of trimerizing. Thus, it is also preferred that the fiber protein or a fragment thereof encoded by the polynucleotide according to the first aspect of the invention is capable of being glycosylated and/or of forming a trimer.

As used throughout this application, the phrase "functional derivative" of a protein or polypeptide generally refers to a modified version of the protein or polypeptide, e.g. one or more amino acids of the protein or polypeptide may be deleted, inserted, modified and/or substituted. The derivative is functional, if, as mentioned also above, a chimeric adenovirus comprising the functional derivative in its capsid is capable of infecting a host cell. Furthermore, in the context of a "functional derivative", an insertion refers to the insertion of one or more amino acids into the original polypeptide or protein. It is preferred that a functional derivative does not comprise more than 1, 2, 3, 4, 5, 6, 7, 8, 9, 10, 15, 20, 25, 30, 35, 40, 45, 50, 60, 70, 80, 90 or more than 100 amino acid changes (i.e. deleted, inserted, modified and/or substituted amino acids). In another embodiment, it is preferred that not more than 1%, 2%, 3%, 4%, 5%, 6%, 7%, 8%, 9%, 10%, 15%, or more than 20% (most preferably not more than 5%) of all amino acids of the protein or polypeptide are changed (i.e. are deleted, inserted, modified and/or substituted amino acids). Amino acids of the protein or polypeptide may also be modified, e.g. chemically modified. For example, the side chain or a free amino or carboxy-terminus of an amino acid of the protein or polypeptide may be modified by e.g. glycosylation, amidation, phosphorylation, ubiquitination, e.t.c. The chemical modification can also take place in vivo, e.g. in a host-cell, as is well known in the art. For examples, a suitable chemical modification motif, e.g. glycosylation sequence motif present in the amino acid sequence of the protein will cause the protein to be glycosylated. A substitution in a derivative may be a conservative or a non-conservative substitution, preferably a conservative substitution. In some embodiments, a substitution also includes the exchange of a naturally occurring amino acid with a not naturally occurring amino acid. A conservative substitution comprises the substitution of an amino acid with another amino acid having a chemical property similar to the amino acid that is substituted. Preferably, the conservative substitution is a substitution selected from the group consisting of:
(i) a substitution of a basic amino acid with another, different basic amino acid;
(ii) a substitution of an acidic amino acid with another, different acidic amino acid;
(iii) a substitution of an aromatic amino acid with another, different aromatic amino acid;
(iv) a substitution of a non-polar, aliphatic amino acid with another, different non-polar, aliphatic amino acid; and
(v) a substitution of a polar, uncharged amino acid with another, different polar, uncharged amino acid.

A basic amino acid is preferably selected from the group consisting of arginine, histidine, and lysine. An acidic amino acid is preferably aspartate or glutamate. An aromatic amino acid is preferably selected from the group consisting of phenylalanine, tyrosine and tryptophane. A non-polar, aliphatic amino acid is preferably selected from the group consisting of glycine, alanine, valine, leucine, methionine and isoleucine. A polar, uncharged amino acid is preferably selected from the group consisting of serine, threonine, cysteine, proline, asparagine and glutamine. In contrast to a conservative amino acid substitution, a non-conservative amino acid substitution is the exchange of one amino acid with any amino acid that does not fall under the above-outlined conservative substitutions (i) through (v).

If a functional derivative comprises a deletion, then in the derivative one or several amino acids that are present in the reference polypeptide or protein sequence have been removed. The deletion may, however, not be so extensive that the derivative comprises less than 200 amino acids in total.

Means for determining sequence identity have been described already above. In addition, the determination of percent identity between two sequences can also be determined using the mathematical algorithm of Karlin and Altschul (1993) Proc. Natl. Acad. Sci. USA 90: 5873-5877. Such an algorithm is also incorporated into the BLASTN and BLASTP programs of Altschul et al. (1990) J. Mol. Biol. 215: 403-410. When utilizing BLASTN and BLASTP it is preferred that the default parameters of these programs are used.

As mentioned before, the hyper variable domains of an adenoviral hexon protein are exposed to the outside of the adenovirus. Thus, these regions of the adenoviral capsid can be recognized and bound by neutralizing antibodies. Thus, an adenovirus with a capsid comprising a hexon protein derived from one of the novel adenovirus isolates of the present invention will exhibit an improved, i.e. smaller seroprevalence in humans. Thus, in a second aspect the invention provides an isolated polynucleotide that encodes an adenoviral hexon protein or a functional derivative thereof and that is selected from the group consisting of:
(a) a polynucleotide encoding a polypeptide having the amino acid sequence according to any of SEQ ID NOs: 20-25, 51 and 54, i.e. SEQ ID NO: 20, 21, 22, 23, 24, 25, 51 or 54;
(b) a polynucleotide encoding the functional derivative of a polypeptide according to any of SEQ ID NOs: 20-25, 51 and 54, i.e. SEQ ID NO: 20, 21, 22, 23, 24, 25, 51 or 54 wherein said functional derivative comprises the deletion, insertion and/or substitution of one or more amino acid residues; and
(c) a polynucleotide encoding a functional derivative having an amino acid sequence which is at least 95%, 98%, 99%, 99.5%, 99.9% or at least 99.95%, more preferably at least 98% and most preferable at least 99.95% identical over its entire length to the amino acid sequence of any of SEQ ID NOs: 20-25, 51 and 54, i.e. SEQ ID NO: 20, 22, 23, 24, 25, 51 or 54.

In a preferred embodiment, the isolated polynucleotide comprised in the second aspect of the invention and preferred embodiments thereof described below encodes a hexon protein or a functional derivative thereof that has the same function as a hexon protein or a functional fragment thereof in an infectious adenovirus virion. Thus, a recombinant adenovirus comprising said hexon or functional derivative thereof preferably as a capsid protein is capable of entering a host cell. One suitable method for generating functional derivatives of a hexon protein is described in U.S. Pat. No. 5,922,315, which is incorporated by reference. In this method, at least one loop region of the adenovirus hexon is changed with at least one loop region of another adenovirus serotype. For example, a loop region of a hexon protein of the invention can be used to substitute the corresponding hexon loop of an adenovirus of the prior art to generate an improved hybrid adenovirus. Analogously also derivatives of penton and fiber proteins of the invention can be generated.

In a third aspect, the invention provides an isolated polynucleotide that encodes an adenoviral penton protein or a functional derivative thereof and that is selected from the group consisting of:
(a) a polynucleotide encoding a polypeptide having the amino acid sequence according to any of SEQ ID NOs: 26-31, 52 and 55, i.e. SEQ ID NO: 26, 27, 28, 29, 30, 31, 52 or 55;
(b) a polynucleotide encoding the functional derivative of a polypeptide according to any of SEQ ID NOs: 26-31, 52 and 55, i.e. SEQ ID NO: 26, 27, 28, 29, 30, 31, 52 or 55; wherein said functional derivative comprises the deletion, insertion and/or substitution of one or more amino acid residues; and
(c) a polynucleotide encoding a functional derivative having an amino acid sequence which is at least 85%, 86%, 87%, 88%, 89%, 90%, 91%, 92%, 93%, 94%, 95%, 96%, 97%, 98% or at least 99%, more preferably at least 85% and most preferable at least 99% identical over its entire length to the amino acid sequence of any of SEQ ID NOs: 26-31, 52 and 55, i.e. SEQ ID NO: 26, 27, 28, 29, 30, 31, 52 or 55.

It is preferred that the penton protein and functional derivative thereof has an affinity to an adenoviral fiber protein, such as to SEQ NOs: 14-19, 50 and/or 53. The average skilled person is well aware of how to test protein-protein affinities as described above. By "adenoviral penton protein" is meant the penton base (III) protein comprised in an adenovirus. An adenoviral penton protein is characterized in that it localizes to the corners of the icosahedral symmetry of the capsid. As mentioned, in a preferred embodiment of the polynucleotide of the first, second and/or third aspect of the invention and preferred embodiments thereof described herein below, the polynucleotide encodes one or more polypeptides, wherein a recombinant adenovirus comprising said one or more polypeptides preferably as a capsid protein(s) is capable to infect, i.e. enter a host cell.

In the following, preferred embodiments of the first, second and third aspect of the invention will be specified for each of the novel chimpanzee adenovirus isolates disclosed herein.

Adenovirus ChAd55

In a preferred embodiment of the first aspect of the invention, the isolated polynucleotide encodes an adenoviral fiber protein with an amino acid sequence according to SEQ ID NO: 14 or a functional derivative thereof, wherein the functional derivative (i) does not comprise more than 1, 2, 3, 4, 5, 6, 7, 8, 9, 10, 15, 20, 25, 30, 35, 40, 45, 50, 60, 70, 80, 90 or more than 100, preferably not more than 10 deleted, inserted, modified and/or substituted amino acids or (ii) has an amino acid sequence which is at least 85%, 86%, 87%, 88%, 89%, 90%, 91%, 92%, 93%, 94%, 95%, 96%, 97%, 98% or at least 99%, more preferably at least 85% and most preferable at least 99% identical over its entire length to the amino acid sequence of SEQ ID NO: 14.

In a preferred embodiment of the second aspect of the invention, the isolated polynucleotide encodes an adenoviral hexon protein with an amino acid sequence according to SEQ ID NO: 20 or a functional derivative thereof, wherein the functional derivative (i) does not comprise more than 1, 2, 3, 4, 5, 6, 7, 8, 9, 10, 15, 20, 25, 30, 35, 40, 45, 50, 60, 70, 80, 90 or more than 100, preferably not more than 10 deleted, inserted, modified and/or substituted amino acids or (ii) has an amino acid sequence which is at least 95%, 98%, 99%, 99.5%, 99.9% or at least 99.95%, more preferably at least 98% identical over its entire length to the amino acid sequence of SEQ ID NO: 20.

In a preferred embodiment of the third aspect of the invention, the isolated polynucleotide encodes an adenoviral penton protein with an amino acid sequence according to SEQ ID NO: 26 or a functional derivative thereof, wherein the functional derivative (i) does not comprise more than 1, 2, 3, 4, 5, 6, 7, 8, 9, 10, 15, 20, 25, 30, 35, 40, 45, 50, 60, 70, 80, 90 or more than 100, preferably not more than 10 deleted, inserted, modified and/or substituted amino acids or (ii) has an amino acid sequence which is at least 98%, 99%, 99.5%, 99.9% or at least 99.95%, more preferably at least 98% and most preferable at least 99.9% identical over its entire length to the amino acid sequence of SEQ ID NO: 26.

In a further aspect the invention relates to a polynucleotide comprising the first, the second, the third, the first and second, the first and third, the second and third or the first, second and third aspect. It is preferred that the polynucleotide comprising this or these polynucleotide(s) comprises other adenoviral genes and nucleotide segments, which are adjacent to the hexon, penton and/or fiber gene in the adenovirus genome, e.g. using the Ad5 genome as a reference. It is preferred that the polynucleotide also comprises sequences required for packaging of the polynucleotide into an adenoviral particle.

Adenovirus ChAd73

In a preferred embodiment of the first aspect of the invention, the isolated polynucleotide encodes an adenoviral fiber protein with an amino acid sequence according to SEQ ID NO: 15 or a functional derivative thereof, wherein the functional derivative (i) does not comprise more than 1, 2, 3, 4, 5, 6, 7, 8, 9, 10, 15, 20, 25, 30, 35, 40, 45, 50, 60, 70, 80, 90 or more than 100, preferably not more than 10 deleted, inserted, modified and/or substituted amino acids or (ii) has an amino acid sequence which is at least 98%, 99% or at least 99.9% more preferably at least 99% and most preferable at least 99.9% identical over its entire length to the amino acid sequence of SEQ ID NO: 15.

In a preferred embodiment of the second aspect of the invention, the isolated polynucleotide encodes an adenoviral hexon protein with an amino acid sequence according to SEQ ID NO: 21 or a functional derivative thereof, wherein the functional derivative (i) does not comprise more than 1, 2, 3, 4, 5, 6, 7, 8, 9, 10, 15, 20, 25, 30, 35, 40, 45, 50, 60, 70, 80, 90 or more than 100, preferably not more than 10 deleted, inserted, modified and/or substituted amino acids or (ii) has an amino acid sequence which is at least 95%, 98%, 99%, 99.5%, 99.9% or at least 99.95%, more preferably at least 98% identical over its entire length to the amino acid sequence of SEQ ID NO: 21.

In a preferred embodiment of the third aspect of the invention, the isolated polynucleotide encodes an adenoviral penton protein with an amino acid sequence according to SEQ ID NO: 27 or a functional derivative thereof, wherein the functional derivative (i) does not comprise more than 1, 2, 3, 4, 5, 6, 7, 8, 9, 10, 15, 20, 25, 30, 35, 40, 45, 50, 60, 70, 80, 90 or more than 100, preferably not more than 10 deleted, inserted, modified and/or substituted amino acids or (ii) has an amino acid sequence which is at least 98%, 99%, 99.5%, 99.9% or at least 99.95%, more preferably at least 98% and most preferable at least 99% identical over its entire length to the amino acid sequence of SEQ ID NO: 27.

In a further aspect the invention relates to a polynucleotide comprising the first, the second, the third, the first and second, the first and third, the second and third or the first, second and third aspect. It is preferred that the polynucleotide comprising this or these polynucleotide(s) comprises other adenoviral genes and nucleotide segments, which are adjacent to the hexon, penton and/or fiber gene in the adenovirus genome, e.g. using the Ad5 genome as a reference. It is preferred that the polynucleotide also comprises sequences required for packaging of the polynucleotide into an adenoviral particle.

Adenovirus ChAd83

In a preferred embodiment of the first aspect of the invention, the isolated polynucleotide encodes an adenoviral fiber protein with an amino acid sequence according to SEQ ID NO: 16 or a functional derivative thereof, wherein the functional derivative (i) does not comprise more than 1, 2, 3, 4, 5, 6, 7, 8, 9, 10, 15, 20, 25, 30, 35, 40, 45, 50, 60, 70, 80, 90 or more than 100, preferably not more than 10 deleted, inserted, modified and/or substituted amino acids or (ii) has the amino acid sequence of SEQ ID NO: 16.

In a preferred embodiment of the second aspect of the invention, the isolated polynucleotide encodes an adenoviral hexon protein with an amino acid sequence according to SEQ ID NO: 22 or a functional derivative thereof, wherein the functional derivative (i) does not comprise more than 1, 2, 3, 4, 5, 6, 7, 8, 9, 10, 15, 20, 25, 30, 35, 40, 45, 50, 60, 70, 80, 90 or more than 100, preferably not more than 10 deleted, inserted, modified and/or substituted amino acids or (ii) has an amino acid sequence which is at least 95%, 98%, 99%, 99.5%, 99.9% or at least 99.95%, more preferably at least 98% identical over its entire length to the amino acid sequence of SEQ ID NO: 22.

In a preferred embodiment of the third aspect of the invention, the isolated polynucleotide encodes an adenoviral penton protein with an amino acid sequence according to SEQ ID NO: 28 or a functional derivative thereof, wherein the functional derivative (i) does not comprise more than 1, 2, 3, 4, 5, 6, 7, 8, 9, 10, 15, 20, 25, 30, 35, 40, 45, 50, 60, 70, 80, 90 or more than 100, preferably not more than 10 deleted, inserted, modified and/or substituted amino acids or (ii) has an amino acid sequence which is at least 98%, 99%, 99.5%, 99.9% or at least 99.95%, more preferably at least 98% and most preferable at least 99% identical over its entire length to the amino acid sequence of SEQ ID NO: 28.

In a most preferred embodiment, the polynucleotide of the invention consists of or comprises a polynucleotide which is at least 90%, 91%, 92%, 93%, 94%, 95%, 96%, 97%, 98% identical and most preferably at least 99% or 100% identical over its entire length to a sequence that consists of SEQ ID NO: 65 or to a sequence that consists of SEQ ID NO: 65 but lacks any of the genomic regions E1A, E1B, E2A, E2B, E3 and/or E4 of SEQ ID NO: 65, most preferably that lacks the genomic regions E1, E3 and E4 of SEQ ID NO: 65.

In a further aspect the invention relates to a polynucleotide comprising the first, the second, the third, the first and second, the first and third, the second and third or the first, second and third aspect. It is preferred that the polynucleotide comprising this or these polynucleotide(s) comprises other adenoviral genes and nucleotide segments, which are adjacent to the hexon, penton and/or fiber gene in the adenovirus genome, e.g. using the ChAd83 genome as set out in SEQ ID NO: 65. It is preferred that the polynucleotide also comprises sequences required for packaging of the polynucleotide into an adenoviral particle.

Adenovirus ChAd146

In a preferred embodiment of the first aspect of the invention, the isolated polynucleotide encodes an adenoviral fiber protein with an amino acid sequence according to SEQ ID NO: 17 or a functional derivative thereof, wherein the functional derivative (i) does not comprise more than 1, 2, 3, 4, 5, 6, 7, 8, 9, 10, 15, 20, 25, 30, 35, 40, 45, 50, 60, 70, 80, 90 or more than 100, preferably not more than 10 deleted, inserted, modified and/or substituted amino acids or (ii) has the amino acid sequence of SEQ ID NO: 17.

In a preferred embodiment of the second aspect of the invention, the isolated polynucleotide encodes an adenoviral hexon protein with an amino acid sequence according to SEQ ID NO: 23 or a functional derivative thereof, wherein the functional derivative (i) does not comprise more than 1, 2, 3, 4, 5, 6, 7, 8, 9, 10, 15, 20, 25, 30, 35, 40, 45, 50, 60, 70, 80, 90 or more than 100, preferably not more than 10 deleted, inserted, modified and/or substituted amino acids or (ii) has an amino acid sequence which is at least 95%, 98%, 99%, 99.5%, 99.9% or at least 99.95%, more preferably at least 98% identical over its entire length to the amino acid sequence of SEQ ID NO: 23.

In a preferred embodiment of the third aspect of the invention, the isolated polynucleotide encodes an adenoviral penton protein with an amino acid sequence according to SEQ ID NO: 29 or a functional derivative thereof, wherein the functional derivative (i) does not comprise more than 1, 2, 3, 4, 5, 6, 7, 8, 9, 10, 15, 20, 25, 30, 35, 40, 45, 50, 60, 70, 80, 90 or more than 100, preferably not more than 10 deleted, inserted, modified and/or substituted amino acids or (ii) has an amino acid sequence which is at least 98%, 99%, 99.5%, 99.9% or at least 99.95%, more preferably at least 98% and most preferable at least 99% identical over its entire length to the amino acid sequence of SEQ ID NO: 29.

In a further aspect the invention relates to a polynucleotide comprising the first, the second, the third, the first and second, the first and third, the second and third or the first, second and third aspect. It is preferred that the polynucleotide comprising this or these polynucleotide(s) comprises other adenoviral genes and nucleotide segments, which are adjacent to the hexon, penton and/or fiber gene in the adenovirus genome e.g. using the Ad5 genome as a reference. It is preferred that the polynucleotide also comprises sequences required for packaging of the polynucleotide into an adenoviral particle.

Adenovirus ChAd147

In a preferred embodiment of the first aspect of the invention, the isolated polynucleotide encodes an adenoviral fiber protein with an amino acid sequence according to SEQ ID NO: 18 or a functional derivative thereof, wherein the functional derivative (i) does not comprise more than 1, 2, 3, 4, 5, 6, 7, 8, 9, 10, 15, 20, 25, 30, 35, 40, 45, 50, 60, 70, 80, 90 or more than 100, preferably not more than 10 deleted, inserted, modified and/or substituted amino acids or (ii) has an amino acid sequence which is at least 85%, 86%, 87%, 88%, 89%, 90%, 91%, 92%, 93%, 94%, 95%, 96%, 97%, 98% or at least 99%, more preferably at least 85% and most preferable at least 90% identical over its entire length to the amino acid sequence of SEQ ID NO: 18.

In a preferred embodiment of the second aspect of the invention, the isolated polynucleotide encodes an adenoviral hexon protein with an amino acid sequence according to SEQ ID NO: 24 or a functional derivative thereof, wherein the functional derivative (i) does not comprise more than 1, 2, 3, 4, 5, 6, 7, 8, 9, 10, 15, 20, 25, 30, 35, 40, 45, 50, 60, 70, 80, 90 or more than 100, preferably not more than 10 deleted, inserted, modified and/or substituted amino acids or (ii) has an amino acid sequence which is at least 95%, 98%, 99%, 99.5%, 99.9% or at least 99.95%, more preferably at least 98% identical over its entire length to the amino acid sequence of SEQ ID NO: 24.

In a preferred embodiment of the third aspect of the invention, the isolated polynucleotide encodes an adenoviral penton protein with an amino acid sequence according to SEQ ID NO: 30 or a functional derivative thereof, wherein the functional derivative (i) does not comprise more than 1, 2, 3, 4, 5, 6, 7, 9, 10, 15, 20, 25, 30, 35, 40, 45, 50, 60, 70, 80, 90 or more than 100, preferably not more than 10 deleted, inserted, modified and/or substituted amino acids or (ii) has an amino acid sequence which is at least 98%, 99%, 99.5%, 99.9% or at least 99.95%, more preferably at least 98% and most preferable at least 99% identical over its entire length to the amino acid sequence of SEQ ID NO: 30.

In a further aspect the invention relates to a polynucleotide comprising the first, the second, the third, the first and second, the first and third, the second and third or the first, second and third aspect. It is preferred that the polynucleotide comprising this or these polynucleotide(s) comprises other adenoviral genes and nucleotide segments, which are adjacent to the hexon, penton and/or fiber gene in the adenovirus genome e.g. using the Ad5 genome as a reference. It is preferred that the polynucleatide also comprises sequences required for packaging of the polynucleotide into an adenoviral particle.

Adenovirus PanAd1

In a preferred embodiment of the first aspect of the invention, the isolated polynucleotide encodes an adenoviral fiber protein with an amino acid sequence according to SEQ ID NO: 19 or a functional derivative thereof, wherein the functional derivative (i) does not comprise more than 1, 2, 3, 4, 5, 6, 7, 8, 9, 10, 15, 20, 25, 30, 35, 40, 45, 50, 60, 70, 80, 90 or more than 100, preferably not more than 10 deleted, inserted, modified and/or substituted amino acids or (ii) has an amino acid sequence which is at least 85%, 86%, 87%, 88%, 89%, 90%, 91%, 92%, 93%, 94%, 95%, 96%, 97%, 98% or at least 99%, more preferably at least 85% and most preferable at least 99% identical over its entire length to the amino acid sequence of SEQ ID NO: 19.

In a preferred embodiment of the second aspect of the invention, the isolated polynucleotide encodes an adenoviral hexon protein with an amino acid sequence according to SEQ ID NO: 25 or a functional derivative thereof, wherein the functional derivative (i) does not comprise more than 1, 2, 3, 4, 5, 6, 7, 8, 9, 10, 15, 20, 25, 30, 35, 40, 45, 50, 60, 70, 80, 90 or more than 100, preferably not more than 10 deleted, inserted, modified and/or substituted amino acids or (ii) has an amino acid sequence which is at least 95%, 98%, 99%, 99.5%, 99.9% or at least 99.95%, more preferably at least 98% and most preferably at least 99% identical over its entire length to the amino acid sequence of SEQ ID NO: 25.

In a preferred embodiment of the third aspect of the invention, the isolated polynucleotide encodes an adenoviral penton protein with an amino acid sequence according to SEQ ID NO: 31 or a functional derivative thereof, wherein the functional derivative (i) does not comprise more than 1, 2, 3, 4, 5, 6, 7, 8, 9, 10, 15, 20, 25, 30, 35, 40, 45, 50, 60, 70, 80, 90 or more than 100, preferably not more than 10 deleted, inserted, modified and/or substituted amino acids or (ii) has an amino acid sequence which is at least 85%, 86%, 87%, 88%, 89%, 90%, 91%, 92%, 93%, 94%, 95%, 96%, 97%, 98% or at least 99%, more preferably at least 85% and most preferable at least 90% identical over its entire length to the amino acid sequence of SEQ ID NO: 31.

In a most preferred embodiment, the polynucleotide of the invention consists of or comprises a polynucleotide which is at least 90%, 91%, 92%, 93%, 94%, 95%, 96%, 97%, 98% identical and most preferably at least 99% or 100% identical over its entire length to a sequence that consists of SEQ ID NO: 13 or to a sequence that consists of SEQ ID NO: 13 but lacks any of the genomic regions E1A, E1B, E2A, E2B, E3 and/or E4 of SEQ ID NO: 13, most preferably that lacks the genomic regions E1, E3 and E4 of SEQ ID NO: 13.

In a further aspect the invention relates to a polynucleotide comprising the first, the second, the third, the first and second, the first and third, the second and third or the first, second and third aspect, it is preferred that the polynucleotide comprising this or these polynucleotide(s) comprises other adenoviral genes and nucleotide segments, which are adjacent to the hexon, penton and/or fiber gene in the adenovirus genome, e.g. using the PanAd1 genome as set out in SEQ ID NO: 13. It is preferred that the polynucleotide also comprises sequences required for packaging of the polynucleotide into an adenoviral particle.

Adenovirus PanAd2

In a preferred embodiment of the first aspect of the invention, the isolated polynucleotide encodes an adenoviral fiber protein with an amino acid sequence according to SEQ ID NO: 50 or a functional derivative thereof, wherein the functional derivative (i) does not comprise more than 1, 2, 3, 4, 5, 6, 7, 8, 9, 10, 15, 20, 25, 30, 35, 40, 45, 50, 60, 70, 80, 90 or more than 100, preferably not more than 10 deleted, inserted, modified and/or substituted amino acids or (ii) has an amino acid sequence which is at least 85%, 86%, 87%, 88%, 89%, 90%, 91%, 92%, 93%, 94%, 95%, 96%, 97%, 98% or at least 99%, more preferably at least 85% and most preferable at least 99% identical over its entire length to the amino acid sequence of SEQ ID NO: 50.

In a preferred embodiment of the second aspect of the invention, the isolated polynucleotide encodes an adenoviral hexon protein with an amino acid sequence according to SEQ ID NO: 51 or a functional derivative thereof, wherein the functional derivative (i) does not comprise more than 1, 2, 3, 4, 5, 6, 7, 8, 9, 10, 15, 20, 25, 30, 35, 40, 45, 50, 60, 70, 80, 90 or more than 100, preferably not more than 10 deleted, inserted, modified and/or substituted amino acids or (ii) has an amino acid sequence which is at least 95%, 98%, 99%, 99.5%, 99.9% or at least 99.95%, more preferably at least 98% and most preferably at least 99% identical over its entire length to the amino acid sequence of SEQ ID NO: 51.

In a preferred embodiment of the third aspect of the invention, the isolated polynucleotide encodes an adenoviral penton protein with an amino acid sequence according to SEQ ID NO: 52 or a functional derivative thereof, wherein the functional derivative (i) does not comprise more than 1, 2, 3, 4, 5, 6, 7, 8, 9, 10, 15, 20, 25, 30, 35, 40, 45, 50, 60, 70, 80, 90 or more than 100, preferably not more than 10 deleted, inserted, modified and/or substituted amino acids or (ii) has an amino acid sequence which is at least 85%, 86%, 87%, 88%, 89%, 90%, 91%, 92%, 93%, 94%, 95%, 96%, 97%, 98% or at least 99%, more preferably at least 85% and most preferable at least 90% identical over its entire length to the amino acid sequence of SEQ ID NO: 52.

In a most preferred embodiment, the polynucleotide of the invention consists of or comprises a polynucleotide which is at least 90%, 91%, 92%, 93%, 94%, 95%, 96%, 97%, 98% identical and most preferably at least 99% or 100% identical over its entire length to a sequence that consists of SEQ ID NO: 62 or to a sequence that consists of SEQ ID NO: 62 but lacks any of the genomic regions E1A, E1B, E2A, E2B, E3 and/or E4 of SEQ ID NO: 62, most preferably that lacks the genomic regions E1, E3 and E4 of SEQ ID NO: 62.

In a further aspect the invention relates to a polynucleotide comprising the first, the second, the third, the first and second, the first and third, the second and third or the first, second and third aspect. It is preferred that the polynucleotide comprising this or these polynucleotide(s) comprises other adenoviral genes and nucleotide segments, which are adjacent to the hexon, penton and/or fiber gene in the adenovirus genome, e.g. using the PanAd1 genome as set out in SEQ ID NO: 62. It is preferred that the polynucleotide also comprises sequences required for packaging of the polynucleotide into an adenoviral particle.

Adenovirus PanAd3

In a preferred embodiment of the first aspect of the invention, the isolated polynucleotide encodes an adenoviral fiber protein with an amino acid sequence according to SEQ ID NO: 53 or a functional derivative thereof, wherein the functional derivative (i) does not comprise more than 1, 2, 3, 4, 5, 6, 7, 8, 9, 10, 15, 20, 25, 30, 35, 40, 45, 50, 60, 70, 80, 90 or more than 100, preferably not more than 10 deleted, inserted, modified and/or substituted amino acids or (ii) has an amino acid sequence which is at least 85%, 86%, 87%, 88%, 89%, 90%, 91%, 92%, 93%, 94%, 95%, 96%, 97%, 98% or at least 99%, more preferably at least 85% and most preferable at least 99% identical over its entire length to the amino acid sequence of SEQ ID NO: 53.

In a preferred embodiment of the second aspect of the invention, the isolated polynucleotide encodes an adenoviral hexon protein with an amino acid sequence according to SEQ ID NO: 54 or a functional derivative thereof, wherein the functional derivative (i) does not comprise more than 1, 2, 3, 4, 5, 6, 7, 8, 9, 10, 15, 20, 25, 30, 35, 40, 45, 50, 60, 70, 80, 90 or more than 100, preferably not more than 10 deleted, inserted, modified and/or substituted amino acids or (ii) has an amino acid sequence which is at least 95%, 98%, 99%, 99.5%, 99.9% or at least 99.95%, more preferably at least 98% and most preferably at least 99% identical over its entire length to the amino acid sequence of SEQ ID NO: 54.

In a preferred embodiment of the third aspect of the invention, the isolated polynucleotide encodes an adenoviral penton protein with an amino acid sequence according to SEQ ID NO: 55 or a functional derivative thereof, wherein the functional derivative (i) does not comprise more than 1, 2, 3, 4, 5, 6, 7, 8, 9, 10, 15, 20, 25, 30, 35, 40, 45, 50, 60, 70, 80, 90 or more than 100, preferably not more than 10 deleted, inserted, modified and/or substituted amino acids or (ii) has an amino acid sequence which is at least 85%, 86%, 87%, 88%, 89%, 90%, 91%, 92%, 93%, 94%, 95%, 96%, 97%, 98% or at least 99%, more preferably at least 85% and most preferable at least 90% identical over its entire length to the amino acid sequence of SEQ ID NO: 55.

In a most preferred embodiment, the polynucleotide of the invention consists of or comprises a polynucleotide which is at least 90%, 91%, 92%, 93%, 94%, 95%, 96%, 97%, 98% identical and most preferably at least 99% or 100% identical over its entire length to a sequence that consists of SEQ ID NO: 63 or to a sequence that consists of SEQ ID NO: 63 but lacks any of the genomic regions E1A, E1B, E2A, E2B, E3 and/or E4 of SEQ ID NO: 63, most preferably that lacks the genomic regions E1, E3 and E4 of SEQ ID NO: 63.

In a further aspect the invention relates to a polynucleotide comprising the first, the second, the third, the first and second, the first and third, the second and third or the first, second and third aspect and most preferably the first, second and third aspect of the invention. It is preferred that the polynucleotide comprising this or these polynucleotide(s) comprises other adenoviral genes and nucleotide segments, which are adjacent to the hexon, penton and/or fiber gene in the adenovirus genome, e.g. using the PanAd1 genome as set out in SEQ ID NO: 63. It is preferred that the polynucleotide also comprises sequences required for packaging of the polynucleotide into an adenoviral particle.

In a recombinant adenovirus, a fiber, hexon and penton protein according to the first, second and third aspect of the invention, and according to the respective preferred embodiments disclosed herein, contributes each individually to reduce the interaction of said recombinant adenovirus with human and/or rodent neutralizing antibodies. Accordingly, polynucleotides which encode said fiber, hexon and/or penton protein of the present invention are useful to construct enhanced recombinant adenoviruses. Thus, in a further, fourth aspect the invention provides a polynucleotide comprising at least one, preferably at least two and most preferably three isolated polynucleotides selected from the group of polynucleotides consisting of a polynucleotide according to the first aspect of the invention, the second aspect of the invention and the third aspect of the invention. Thus, most preferably, the fourth aspect is an isolated polynucleotide comprising the first, second and third aspect of the invention. In a preferred embodiment, the polynucleotide according to the fourth aspect of the invention is a polynucleotide selected from the group consisting of:

(i) a polynucleotide comprising one polynucleotide according to the first, second or third aspect of the invention;
(ii) a polynucleotide comprising a polynucleotide according to the first aspect of the invention and a polynucleotide according to the second aspect of the invention;
(iii) a polynucleotide comprising a polynucleotide according to the first aspect of the invention and a polynucleotide according to the third aspect of the invention;
(iv) a polynucleotide comprising a polynucleotide according to the second aspect of the invention and a polynucleotide according to the third aspect of the invention; and
(v) a polynucleotide comprising a polynucleotide according to the first, second and third aspect of the invention;

wherein it is preferred that said polynucleotides comprised in the polynucleotide according to (i) through (v) are selected from the same adenovirus isolate, e.g. all three polynucleotides encoding fiber, hexon and penton protein or functional derivative thereof, respectively, are from only one of the following adenoviruses: ChAd55, ChAd73, ChAd83, ChAd146, ChAd147 PanAd1, PanAd2 or PanAd3. Furthermore, it is preferred that in the fourth aspect of the invention or in a preferred embodiment thereof, e.g. as outlined above, each "functional derivative" does not comprise more than 10, more than 5 or more than 3 amino acid changes (i.e. deleted, inserted, modified and/or substituted amino acids).

Table 2 below lists a number of particularly preferred embodiments of the polynucleotide of the fourth aspect of invention outlined above. Preferred is a polynucleotide selected from polynucleotides A1 through AF1 shown in Table 2, wherein the polynucleotide comprises three polynucleotides according to alternative (c) of the first, second and third aspect of the invention, each of which respectively encodes an adenoviral fiber, hexon and penton protein or a functional derivative thereof. Table 2 below shows the minimal sequence identity (i.e. at least the indicated sequence identity) which each of said three encoded proteins has to have over its entire length to the amino acid sequence according to the SEQ ID NO which is also shown in Table 2:

TABLE 2

| Preferred embodiment | Fiber Protein | | Hexon Protein | | Penton Protein | |
|---|---|---|---|---|---|---|
| | Minimal %-Identity | to SEQ ID NO: | Minimal %-Identity | to SEQ ID NO: | Minimal %-Identity | to SEQ ID NO: |
| A1 - ChAd55 | 85% | 14 | 95% | 20 | 98% | 26 |
| B1 - ChAd73 | 98% | 15 | 95% | 21 | 98% | 27 |
| C1 - ChAd83 | 100% | 16 | 95% | 22 | 98% | 28 |
| D1 - ChAd146 | 100% | 17 | 95% | 23 | 98% | 29 |
| E1 - ChAd147 | 85% | 18 | 95% | 24 | 98% | 30 |
| F1 - PanAd1 | 85% | 19 | 95% | 25 | 98% | 31 |
| G1 - ChAd55 | 90% | 14 | 95% | 20 | 100% | 26 |
| H1 - ChAd73 | 90% | 15 | 95% | 21 | 98% | 27 |
| I1 - ChAd83 | 90% | 16 | 95% | 22 | 98% | 28 |
| J1 - ChAd146 | 90% | 17 | 95% | 23 | 98% | 29 |
| K1 - ChAd147 | 90% | 18 | 95% | 24 | 98% | 30 |
| L1 - PanAd1 | 90% | 19 | 95% | 25 | 90% | 31 |
| M1 - ChAd55 | 98% | 14 | 98% | 20 | 98% | 26 |
| N1 - ChAd73 | 98% | 15 | 98% | 21 | 98% | 27 |
| O1 - ChAd83 | 98% | 16 | 98% | 22 | 98% | 28 |
| P1 - ChAd146 | 98% | 17 | 98% | 23 | 98% | 29 |
| Q1 - ChAd147 | 98% | 18 | 98% | 24 | 98% | 30 |
| R1 - PanAd1 | 98% | 19 | 98% | 25 | 98% | 31 |
| S1 - ChAd55 | 99% | 14 | 99% | 20 | 99% | 26 |
| T1 - ChAd73 | 99% | 15 | 99% | 21 | 99% | 27 |
| U1 - ChAd83 | 99% | 16 | 99% | 22 | 99% | 28 |
| V1 - ChAd146 | 99% | 17 | 99% | 23 | 99% | 29 |
| W1 - ChAd147 | 99% | 18 | 99% | 24 | 99% | 30 |

TABLE 2-continued

| Preferred embodiment | Fiber Protein | | Hexon Protein | | Penton Protein | |
|---|---|---|---|---|---|---|
| | Minimal %-Identity | to SEQ ID NO: | Minimal %-Identity | to SEQ ID NO: | Minimal %-Identity | to SEQ ID NO: |
| X1 - PanAd1 | 99% | 19 | 99% | 25 | 99% | 31 |
| Y1 - PanAd2 | 80% | 50 | 95% | 51 | 85% | 52 |
| Z1 - PanAd2 | 90% | 50 | 95% | 51 | 90% | 52 |
| AA1 - PanAd2 | 98% | 50 | 98% | 51 | 98% | 52 |
| AB1 - PanAd2 | 99% | 50 | 99% | 51 | 99% | 52 |
| AC1 - PanAd3 | 75% | 53 | 95% | 54 | 85% | 55 |
| AD1 - PanAd3 | 90% | 53 | 95% | 54 | 90% | 55 |
| AE1 - PanAd3 | 98% | 53 | 98% | 54 | 98% | 55 |
| AF1 - PanAd3 | 99% | 53 | 99% | 54 | 99% | 55 |

For example, preferred polynucleotide A1 as shown in Table 1 above comprises:
(i) a polynucleotide encoding a polypeptide having an amino acid sequence which is at least 85% identical over its entire length to SEQ ID NO: 14;
(ii) a polynucleotide encoding a polypeptide having an amino acid sequence which is at least 95% identical over its entire length to SEQ ID NO: 20; and
(iii) a polynucleotide encoding a polypeptide having an amino acid sequence which is at least 98% identical over its entire length to SEQ ID NO: 26;

As mentioned above it is most preferred that said "functional derivative" of a polynucleotide listen in table 2 does not comprise more than 10 amino acid changes (i.e. deleted, inserted, modified and/or substituted amino acids).

Table 3 below lists further preferred embodiments of the polynucleotide of the fourth aspect of the invention. Preferred is a polynucleotide selected from polynucleotides A2 through J2 selected from Table 3, wherein the polynucleotide comprises three polynucleotides designated, "Polynucleotide 1", "Polynucleotide 2" and "Polynucleotide 3", wherein each respective polynucleotide has at least the indicated sequence identity over its entire length to the corresponding polynucleotide according to the SEQ ID NO shown in Table 3:

TABLE 3

| Preferred embodiment | Polynucleotide 1 | | Polynucleotide 2 | | Polynucleotide 3 | |
|---|---|---|---|---|---|---|
| | Minimal %-Identity | to SEQ ID NO: (polynucleotide encoding Fiber protein) | Minimal %-Identity | to SEQ ID NO: (polynucleotide encoding Hexon protein) | Minimal %-Identity | to SEQ ID NO: (polynucleotide encoding Penton protein) |
| A2 - ChAd55 | 98% | 32 | 98% | 38 | 98% | 44 |
| B2 - ChAd73 | 98% | 33 | 98% | 39 | 98% | 45 |
| C2 - ChAd83 | 98% | 34 | 98% | 40 | 98% | 46 |
| D2 - ChAd146 | 98% | 35 | 98% | 41 | 98% | 47 |
| E2 - ChAd147 | 98% | 36 | 98% | 42 | 98% | 48 |
| F2 - PanAd1 | 98% | 37 | 98% | 43 | 98% | 49 |
| G2 - ChAd55 | 99% | 32 | 99% | 38 | 99% | 44 |
| H2 - ChAd73 | 99% | 33 | 99% | 39 | 99% | 45 |
| I2 - ChAd83 | 99% | 34 | 99% | 40 | 99% | 46 |
| J2 - ChAd146 | 99% | 35 | 99% | 41 | 99% | 47 |
| K2 - ChAd147 | 99% | 36 | 99% | 42 | 99% | 48 |
| L2 - PanAd1 | 99% | 37 | 99% | 43 | 99% | 49 |
| G2 - PanAd2 | 98% | 56 | 98% | 57 | 98% | 58 |
| H2 - PanAd2 | 99% | 56 | 99% | 57 | 99% | 58 |
| I2 - PanAd3 | 98% | 59 | 98% | 60 | 98% | 61 |
| J2 - PanAd3 | 99% | 59 | 99% | 60 | 99% | 61 |

Thus, as an example, preferred embodiment A2 ("A2—ChAd55") of Table 3 above is a polynucleotide comprising:
(i) a polynucleotide that is at least 98% identical to SEQ ID NO: 32 over its entire length;
(ii) a polynucleotide that is at least 98% identical to SEQ ID NO: 38 over its entire length; and
(iii) a polynucleotide that is at least 98% identical to SEQ ID NO: 44 over its entire length.

Table 4 below lists a number of further particularly preferred embodiments of the polynucleotide of the fourth aspect of invention outlined above. Preferred is a polynucleotide selected from polynucleotides A3 through H3 shown in Table 4, wherein the polynucleotide encodes an adenoviral fiber, hexon and penton protein according to the indicated SEQ ID NO or a functional derivative thereof, wherein all three proteins and/or encoded functional derivatives in total comprises equal or less than 1, 2, 3, 4, 5, 6, 7, 8, 9, 10, 15, 20, 25, 30, 35, 40, 45, 50, 60, 70, 80, 90 or more than 100, preferably not more than 20 deleted, inserted, modified and/or substituted amino acids:

TABLE 4

| Preferred embodiment | Fiber Protein according to SEQ ID NO: | Hexon Protein according to SEQ ID NO: | Penton Protein according to SEQ ID NO: |
| --- | --- | --- | --- |
| A3 - ChAd55 | 14 | 20 | 26 |
| B3 - ChAd73 | 15 | 21 | 27 |
| C3 - ChAd83 | 16 | 22 | 28 |
| D3 - ChAd146 | 17 | 23 | 29 |
| E3 - ChAd147 | 18 | 24 | 30 |
| F3 - PanAd1 | 19 | 25 | 31 |
| G3 - PanAd2 | 50 | 51 | 52 |
| H3 - PanAd3 | 53 | 54 | 55 |

In another embodiment of the polynucleotide of the fourth aspect of invention, the polynucleotide encodes an adenoviral fiber and hexon protein of the same strain according to the respective SEQ ID NO as shown in Table 4 or functional derivatives thereof. In a further embodiment of the polynucleotide of the fourth aspect of invention, the polynucleotide encodes an adenoviral fiber and penton protein of the same strain according to the respective SEQ ID NO as shown in Table 4 or functional derivatives thereof. In a further embodiment of the polynucleotide of the fourth aspect of invention, the polynucleotide encodes an adenoviral hexon and penton protein of the same strain according to the respective SEQ ID NO as shown in Table 4 or functional derivatives thereof. In this context, said functional derivative comprises in each instance less than 1, 2, 3, 4, 5, 6, 7, 8, 9 or less than 10, most preferably less than 3 deleted, inserted, modified and/or substituted amino acids.

In a further preferred embodiment of the fourth aspect of the invention, the polynucleotide consists of or comprises a polynucleotide which is at least 90%, 91%, 92%, 94%, 95%, 96%, 97%, 98%, 99%, 99.9% or 100%, preferably 98% identical over its entire length to a sequence that (i) consists of any one of SEQ ID NO: 13, 62, 63 or 65 or to (ii) a sequence that consists of any one of SEQ ID NO: 13, 62 63 or 65 that lacks one or more of the genomic regions E1A, E1B, E2A, E2B, E3 ORF1, E3 ORF2, E3 ORF3, E3 ORF4, E3 ORF5, E3 ORF6, E3 ORF7, E3 ORF8, E3 ORF9, E4 ORF7, E4 ORF6, E4 ORF5, E4 ORF4, E4 ORF3, E4 ORF2 and/or E4 ORF1. Thus, the aforementioned one or more genomic regions will preferably not be considered in the alignment when determining the percent identity. In another preferred embodiment of the isolated polynucleotide of the invention, the polynucleotide comprises or consists of SEQ ID NO: 13, 62, 63 or 65, wherein one or more of the genomic regions E1A, E1B, E2A, E2B, E3 ORF1, E3 ORF2, E3 ORF3, E3 ORF4, E3 ORF5, E3 ORF6, E3 ORF7, E3 ORF8, E3 ORF9, E4 ORF7, E4 ORF6, E4 ORF5, E4 ORF4, E4 ORF3, E4 ORF2 and E4 ORF1 are deleted from SEQ ID NO: 13, 62, 63 or 65, respectively, or substituted with a transgene or an expression cassette encoding a heterologous protein as described herein. In a most preferred embodiment adenoviral regions E1, E3 and/or E4 are deleted as also exemplified in example 2. The aforementioned preferred polynucleotides, which lack one or more of the indicated genomic regions may further comprise a polynucleotide sequence encoding for a heterologous protein or an expression cassette comprising such a polynucleotide sequence encoding for a heterologous protein. Said polynucleotide sequence encoding for a heterologous protein and said expression cassette comprising such a polynucleotide sequence encoding for a heterologous protein may be inserted into e.g. the deleted regions of the polynucleotide of the invention as is well known in the art and also described in the examples below. Said heterologous protein may be a molecule for delivery into a target cell such as described herein, e.g. a polynucleotide encoding an antigenic protein or a fragment thereof, preferably an antigenic protein or a fragment of a pathogen such as HIV gag protein, a tumour antigen or a protein of the herpes simplex virus as described in the examples. Thus, in a preferred embodiment, the isolated polynucleotide according to the invention further comprises a polynucleotide encoding an antigen selected from the group consisting of a virus antigen, an antigen of a pathogenic bacterium and a tumorantigen. In one embodiment, said heterologous protein can thus be an antigen selected from the group consisting of an RNA virus antigen, an antigen of a pathogenic bacterium and a tumorantigen. An antigen refers to any protein or peptide capable of eliciting an immune response in a mammal. An antigen comprises preferably at least 8 amino acids and most preferably comprises between 8 and 12 amino acids. Thus, when determining the sequence identity, the genomic regions E1A, E1B, E2A, E2B, E3 and/or E4 are preferably not considered in the alignment, i.e. the alignment is done using a sequence that consists of the entire sequence SEQ ID NO: 13, 62 63 or 65 but excluding the genomic regions E1A, E1B, E2A, E2B, E3, E4 and/or any polynucleotide encoding a heterologous polypeptide or expression cassette comprising such polynucleotide. As also mentioned above, it is preferred that the polynucleotide according to the fourth aspect of the invention and all its preferred embodiments encodes functional hexon, penton and/or fiber capsid proteins or functional derivatives thereof, e.g. the encoded proteins have the same function as the respective capsid proteins or fragments thereof in an infectious adenovirus virion. Thus, a recombinant adenovirus comprising in its capsid said encoded recombinant penton, hexon and/or fiber proteins or functional derivatives thereof is capable of entering a host cell. It is further preferred that the capsid proteins or functional derivatives thereof according to the invention or encoded by polynucleotides of the invention have no seroprevalence in human.

The invention further provides an isolated protein encoded by the isolated polynucleotide according to the invention, i.e. an isolated adenoviral capsid polypeptide encoded by the isolated polynucleotide according to the first, second and/or third aspect of the invention or a functional derivative thereof. In this context, the "functional derivative" in one embodiment does not comprise more than 5, 10 or not more than 25 amino acid changes (i.e. deleted, inserted, modified and/or substituted amino acids).

The invention further relates to a vector comprising an isolated polynucleotide according to the invention.

Preferably, the vector does not comprise a gene in a genomic region selected from the group of genomic regions consisting of E1A, E1B, E2A, E2B, E3 and E4, and/or comprises at least one gene of a genomic region selected from the group of E1A, E1B, E2A, E2B, E3 and E4, wherein said at least one gene comprises a deletion and/or mutation which renders the at least one gene non-functional. One possibility to render one of these gene products non-functional is to introduce one or more artificial stop-codons (e.g. TAA) into the open reading frame of these genes. Methods of rendering the virus replication-defective are well known in the art (see e.g. Brody et al, 1994 Ann NY Acad Sci., 716: 90-101).

In some embodiments the polynucleotide of the invention comprises a polynucleotide encoding a hexon protein; penton protein; fiber protein; hexon protein and penton protein; hexon protein and fibre protein; penton protein and fibre protein; or hexon protein, penton protein and fibre protein of the invention and further comprises additional adenoviral polynucleotides. Thus, in one preferred embodiment, the isolated polynucleotide according to the invention comprises at least one of the following:
(a) an adenoviral 5'-inverted terminal repeat (ITR);
(b) an adenoviral E1a region, or a fragment thereof selected from among the 13S, 12S and 9S regions;
(c) an adenoviral E1b region, or a fragment thereof selected from among the group consisting of the small T, large T and IX regions;
(d) an adenoviral E2b region; or a fragment thereof selected from among the group consisting of the small pTP, Polymerase and IVa2 regions;
(e) an adenoviral L1 region, or a fragment thereof, said fragment encoding an adenoviral protein selected from the group consisting of the 28.1 kD protein, polymerase, agnoprotein, 52/55 kDa protein, and IIIa protein;
(f) an adenoviral L2 region or a L2 region comprising a polynucleotide encoding the penton protein of the invention, or a fragment thereof, said fragment encoding an adenoviral protein selected from the group consisting of a penton protein or the penton protein of the invention, VII, V, and Mu protein;
(g) an adenoviral L3 region or a L3 region comprising a polynucleotide encoding the hexon protein of the invention, or a fragment thereof, said fragment encoding an adenoviral protein selected from the group consisting of the VI protein, hexon protein or the hexon protein of the invention and endoprotease;
(h) an adenoviral E2a region;
(i) an adenoviral L4 region, or a fragment thereof said fragment encoding an adenoviral protein selected from the group consisting of the 100 kD protein, the 33 kD homolog, and protein VIII;
(j) an adenoviral E3 region, or a fragment thereof selected from the group consisting of E3 ORF1, E3 ORF2, E3 ORF3, E3 ORF4, E3 ORF5, E3 ORF6, E3 ORF7, E3 ORF8, and E3 ORF9;
(k) an adenoviral L5 region or a L5 region comprising a polynucleotide encoding the fibre protein of the invention, or a fragment thereof said fragment encoding the fiber protein or the fiber protein of the invention;
(l) an adenoviral E4 region, or a fragment thereof selected from the group consisting of E4 ORF7, E4 ORF6, E4 ORF5, E4 ORF4, E4 ORF3, E4 ORF2, and E4 ORF1; in particular ORF6 of said E4 region; and/or
(m) an adenoviral 3'-ITR.

In some embodiments of the aforementioned polynucleotide it may be desirable as also described above that preferably, the polynucleotide does not comprise an ORF of a genomic region as outlined above (such as e.g. region E3 and/or E4 as defined in example 2) and/or comprises an adenoviral gene which comprises a deletion and/or mutation which renders the at least one gene non-functional. In these preferred embodiments the suitable adenoviral regions will be modified to not include the aforementioned gene(s) or to render the selected gene(s) non-functional. Any adenoviral gene deletions will make space to insert transgenes such as a minigene cassette as described herein. Furthermore, gene deletions can be used to generate adenoviral vectors which are incapable to replicate without the use of a packaging cell line or a helper virus as is well known in the art. Thus, the final recombinant adenovirus comprising a polynucleotide as outlined above which comprises one or more of the specified gene/region deletions or loss-of-function mutations can provide a safer recombinant adenovirus for e.g. gene therapy or vaccination.

In a particularly preferred embodiment, the polynucleotide of the invention comprises at least one of the following:
(a) the 5'-inverted terminal repeat (ITR) region of any one of SEQ ID NO: 13, 62, 63 or 65;
(b) the adenovirus E1a region of any one of SEQ ID NO: 13, 62, 63 or 65, or a fragment thereof selected from among the 13S, 12S and 9S regions;
(c) the adenovirus E1b region of any one of SEQ ID NO: 13, 62, 63 or 65, or a fragment thereof selected from among the group consisting of the small T, large T and IX regions;
(d) the adenovirus E2b region of any one of SEQ ID NO: 13, 62, 63 or 65; or a fragment thereof selected from among the group consisting of the small pTP, Polymerase and IVa2 regions;
(e) the adenovirus L1 region of any one of SEQ ID NO: 13, 62, 63 or 65, or a fragment thereof, said fragment encoding an adenoviral protein selected from the group consisting of the 28.1 kD protein, polymerase, agnoprotein, 52/55 kDa protein, and IIIa protein;
(f) the adenovirus L2 region of any one of SEQ ID NO: 13, 62, 63 or 65, or a fragment thereof, said fragment encoding an adenoviral protein selected from the group consisting of the penton protein with the amino acid sequence of SEQ ID NO: 31, 52 or 55, VII, V, and Mu protein;
(g) the adenovirus L3 region of any one of SEQ ID NO: 13, 62, 63 or 65, or a fragment thereof, said fragment encoding an adenoviral protein selected from the group consisting of the VI protein, hexon protein with the amino acid sequence of SEQ ID NO: 25, 51 or 54 and endoprotease;
(h) the adenovirus E2a region of any one of SEQ ID NO: 13, 62, 63 or 65;
(i) the adenovirus L4 region of any one of SEQ ID NO: 13, 62, 63 or 65, or a fragment thereof said fragment encoding an adenoviral protein selected from the group consisting of the 100 kD protein, the 33 kD homolog, and protein VIII;
(j) the adenovirus E3 region of any one of SEQ ID NO: 13, 62, 63 or 65, or a fragment thereof selected from the group consisting of E3 ORF1, E3 ORF2, E3 ORF3, E3 ORF4, E3 ORF5, E3 ORF6, E3 ORF7, E3 ORF8, and E3 ORF9;

(k) the adenovirus L5 region of any one of SEQ ID NO: 13, 62, 63 or 65, or a fragment thereof said fragment encoding the fiber protein with the amino acid sequence of SEQ ID NO:19, 50 or 53;

(l) the adenovirus E4 region of any one of SEQ ID NO: 13, 62, 63 or 65, or a fragment thereof selected from the group consisting of E4 ORF7, E4 ORF6, E4 ORF5, E4 ORF4, E4 ORF3, E4 ORF2, and E4 ORF1; or ORF6 of Ad5 E4 region (SEQ ID NO: 64); and (m) the 3'-ITR of any one of SEQ ID NO: 13, 62, 63 or 65.

In one embodiment the isolated polynucleotide of the invention further encodes one or more, preferably all of the following adenoviral proteins: protein VI, protein VIII, protein IX, protein IIIa and protein IVa2. Preferably these proteins are encoded by from the respective open reading frames of the PanAd1, PanAd2 or PanAd3 genomic sequence disclosed herein. An average person skilled in the art of recombinant adenoviruses is well aware of how to determine the open reading frames that encode for the above specified adenoviral proteins. He is also aware of the structure of adenoviral genomes and can map, without undue burden, the individual adenoviral regions and ORFs outlined herein to e.g. any of the novel adenoviral genomes PanAd1, PanAd2 or PanAd3 of the invention.

In order to express a polynucleotide, preferably a cDNA, encoding one or more adenoviral proteins of the invention, one can subclone said polynucleotide into an expression vector that contains a strong promoter to direct transcription, a transcription/translation terminator, and a ribosome-binding site for translational initiation. Suitable bacterial promoters are well known in the art, e.g., *E. coli, Bacillus* sp., and *Salmonella*, and kits for such expression systems are commercially available. Similarly eukaryotic expression systems for mammalian cells, yeast, and insect cells are well known in the art and are also commercially available.

In addition to the promoter, the expression vector typically contains a transcription unit or expression cassette that contains all the additional elements required for the expression of the adenoviral protein-encoding nucleic acid in host cells. A typical expression cassette thus contains a promoter operatively linked to the nucleic acid sequence encoding the adenoviral protein/polypeptide and signals required for efficient polyadenylation of the transcript, ribosome binding sites, and translation termination. Additional elements of the cassette may include, for example enhancers. An expression cassette should also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23D, and fusion expression systems such as GST and LacZ, but there are many more known in the art to the skilled person that can be usefully employed.

Expression vectors containing regulatory elements from eukaryotic viruses are typically used in eukaryotic expression vectors, e.g. SV40 vectors, papilloma virus vectors, and vectors derived from Epstein-Barr virus. Other exemplary eukaryotic vectors include pMSG, pAV009/A.sup.+, pMTO10/A.sup.+, pMAMneo-5, baculovirus pDSVE, pcDNA3.1, pIRES and any other vector allowing expression of proteins under the direction of e.g. the HCMV immediate-early promoter, SV40 early promoter, SV40 late promoter, metallothionein promoter, murine mammary tumor virus promoter. Rous sarcoma virus promoter, polyhedrin promoter, or other promoters shown effective for expression in eukaryotic cells.

Some expression systems have markers that provide gene amplification such as thymidine kinase, hygromycin B phosphotransferase, and dihydrofolate reductase. Alternatively, high yield expression systems not involving gene amplification are also suitable.

The elements that may also be included in expression vectors include a replicon that functions in *E. coli*, a gene encoding drug resistance to permit selection of bacteria that harbor recombinant plasmids, and unique restriction sites in nonessential regions of the plasmid to allow insertion of eukaryotic sequences. The particular drug resistance gene chosen is not critical—any of the many drug resistance genes known in the art are suitable. The prokaryotic sequences are optionally chosen such that they do not interfere with the replication of the DNA in eukaryotic cells, if necessary.

Standard transfection methods can be used to produce bacterial, mammalian, yeast or insect cell lines. Any of the well-known procedures for introducing foreign polynucleotide sequences into host cells may be used. For example, commercially available liposome-based transfection kits such as Lipofectamine™ (Invitrogen), commercially available lipid-based transfection kits such as Fugene (Roche Diagnostics), polyethylene glycol-based transfection, calcium phosphate precipitation, gene gun (biolistic), electroporation, or viral infection and any of the other well known methods for introducing cloned genomic DNA, cDNA, synthetic DNA or other foreign genetic material into a host cell may be used. It is only necessary that the particular genetic engineering procedure used be capable of successfully introducing at least one gene into the host cell capable of expressing the receptor.

An expressed adenoviral protein can be optionally purified using standard techniques. For example, the cells may be lysed either mechanically or by osmotic shock before being subject to precipitation and chromatography steps, the nature and sequence of which will depend on the particular recombinant material to be recovered. Alternatively, the recombinant protein may be secreted and recovered from the culture medium in which the recombinant cells had been cultured as is known in the art of protein expression.

In one preferred embodiment the vector of the invention is a plasmid vector, e.g. an expression vector. A plasmid vector according to the invention can also be used to generate a recombinant adenovirus.

Thus, a further aspect of the present invention is a recombinant adenovirus, preferably a replication-incompetent adenovirus, comprising an isolated polynucleotide according to the invention and/or at least one isolated adenoviral capsid polypeptide according to the invention. Preferably the recombinant adenovirus of the invention comprises a hexon a fiber and a penton protein of the present invention, e.g. a combination as outlined in Table 2 above. In a preferred embodiment, the recombinant adenovirus is characterized in that it is capable of infecting a human cell—preferably capable of infecting a human cell after said adenovirus was incubated for one hour in a human blood serum derived from a human that has not previously been exposed to a chimpanzee adenovirus.

As the sequence information of the novel hexon, penton and fiber proteins of the invention are provided, said recombinant adenovirus is obtainable e.g. by constructing a recombinant adenovirus which is composed of the usual adenoviral proteins but which has a capsid that comprises at least one isolated adenoviral capsid polypeptide according to the invention or a functional derivative thereof. In this regard it is preferred that the recombinant adenovirus comprises an L2 region which comprises a polynucleotide sequence encoding the penton protein of the invention, an L3 region which comprises a polynucleotide sequence encoding the hexon protein of the invention and/or an L5 region which comprises a polynucleotide sequence encoding the fiber protein of the invention. Most preferably said recombinant adenovirus comprises an L2 region, an L3 region and an L5 region encoding, respectively, at least for the penton, hexon and fiber protein of the invention.

Methods for the construction of recombinant adenoviruses are well known in the art. Useful techniques for the preparation of recombinant adenoviruses are, for example, reviewed in Graham & Prevec, 1991 In Methods in Molecular Biology: Gene Transfer and Expression Protocols, (Ed. Murray, p. 109; and Hitt et al., 1997 "Human Adenovirus Vectors for Gene Transfer into Mammalian Cells" Advances in Pharmacology 40:137-206. Further methods are described in WO 2006/086284. For the preparation of replication deficient adenoviruses, one or several of the E1A, E1B, E2A, E2B, E3 and E4 gene products may be expressed in a complementing cell line that can be used for the propagation and rescue of recombinant adenoviruses that are replication-incompetent, because they lack e.g. one of the aforementioned gene products. The use of such cell-lines is also described in the references outlined above.

In one embodiment, the polynucleotides of the invention (or vectors comprising said polynucleotides of the invention as described herein) are used to produce recombinant adenoviral particles. The recombinant adenoviruses are preferably functionally deleted as mentioned above in one or more adenoviral regions such as e.g. the E1a or E1b regions, and optionally bearing other mutations, e. g., temperature-sensitive mutations or deletions in other adenoviral genes. In other embodiments, it is desirable to retain an intact E1a and/or E1b region in the recombinant adenoviruses. Such an intact E1 region may be located in its native location in the adenoviral genome or placed in the site of a deletion in the native adenoviral genome (e.g., in the E3 region).

In the construction of adenovirus vectors for delivery of a gene to a host, e.g. human (or other mammalian) cell, a range of adenovirus nucleic acid sequences can be employed in the vectors of the invention. For example, all or a portion of the adenovirus delayed early gene E3 may be eliminated from the adenovirus sequence which forms a part of the recombinant virus. The function of simian E3 is believed to be irrelevant to the function and production of the recombinant virus particle. In some embodiments, adenovirus vectors may also be constructed having a deletion of at least the ORF6 region of the E4 gene, and more desirably because of the redundancy in the function of this region, the entire E4 region. Still another vector of this invention contains a deletion in the delayed early gene E2a. Deletions may also be made in any of the late genes L1 through L5 of the simian adenovirus genome. Similarly, deletions in the intermediate genes IX and IVa2 may be useful for some purposes. Other deletions may be made in the other structural or non-structural adenovirus genes. The above discussed deletions may be used individually, i. e., an adenovirus sequence for use in the present invention may contain deletions in only a single region. Alternatively, deletions of entire genes or portions thereof effective to destroy their biological activity may be used in any combination. For example, in one exemplary vector according to the invention, the adenovirus sequence may have deletions of the E1 and the E4 region, or of the E1, E2a and E3 region, or of the E1 and E3 regions, or of E1, E2a and E4 regions, with or without deletion of E3, and so on. As discussed above, such deletions may be used in combination with other adenoviral gene mutations, such as temperature-sensitive mutations, to achieve a desired result.

An adenoviral vector lacking any essential adenoviral sequences (e. g., a region selected from E1a, E1b, E2a, E2b, E4 ORF6, L1 or L4) may be cultured in the presence of the missing adenoviral gene products which are required for viral infectivity and propagation of an adenoviral particle. These helper functions may be provided by culturing the adenoviral vector in the presence of one or more helper constructs (e. g., a plasmid or virus) or a packaging host cell (complementing cell line as also described above). See, for example, the examples included herein and the techniques described for preparation of a "minimal" human adenovirus vector in International Patent Application WO96/13597 published May 9, 1996, and incorporated herein by reference.

Useful helper viruses contain selected adenovirus gene sequences that complement the respective genes that are deleted in preferred embodiments of the adenovirus vector of the invention and/or that are not expressed by the packaging cell line in which the vector is transfected. In one embodiment, the helper virus is replication-defective and contains a variety of adenovirus genes in addition to the sequences described above.

Helper viruses may also be formed into poly-cation conjugates as described in Wu et al, J. Biol. Chem., 264: 16985-16987 (1989); K. J. Fisher and J. M. Wilson, Biochem, J., 299: 49 (Apr. 1, 1994). A helper virus may optionally contain a second reporter minigene. A number of such reporter genes are known to the art. The presence of a reporter gene on the helper virus which is different from the transgene on the adenovirus vector allows both the Ad vector and the helper virus to be independently monitored. This second reporter may be used to facilitate separation between the resulting recombinant virus and the helper virus upon purification.

To generate recombinant adenoviruses (Ad) deleted in any of the genes described in the context of preferred embodiments herein, the function of the deleted gene region, if essential to the replication and infectivity of the virus, is preferably supplied to the recombinant virus by a helper virus or cell line, i. e., a complementation or packaging cell line. In many circumstances, a cell line expressing the human E1 can be used to transcomplement the vector used to generate recombinant adenoviruses. This is particularly advantageous because, due to the diversity between the polynucleotide sequences of the invention and the human adenoviral E1 sequences found in currently available packaging cells, the use of the current human E1-containing cells will prevent the generation of replication-competent adenoviruses during the replication and production process. However, in certain circumstances, it will be desirable to utilize a cell line which expresses the E1 gene products for the production of an E1-deleted recombinant adenovirus.

If desired, one may utilize the sequences provided herein to generate a packaging cell or cell line that expresses, at a minimum, the adenovirus E1 gene from a ChAd55, ChAd73, ChAd83, ChAd146, ChAd147, PanAd1, PanAd2 or PanAd3 adenovirus under the transcriptional control of a promoter for expression in a selected parent cell line, such as e.g. a HeLa cell. Inducible or constitutive promoters may be employed for this purpose. Examples of promoters are provided e.g. in the examples described herein. Such E1-expressing cell lines are useful in the generation of recombinant adenovirus E1 deleted vectors. Additionally, or alternatively, the invention provides cell lines that express one or more adenoviral gene products, e. g., E1a, E1b, E2a, and/or E4 ORF6, preferably Ad5 E4 ORF6 (see also the examples below), which can be constructed using essentially the same procedures for use in the generation of recombinant adenoviral vectors. Such cell lines can be utilized to transcomplement adenovirus vectors deleted in essential genes that encode those products, or to provide helper functions necessary for packaging of a helper-dependent virus (e. g., adeno-associated virus).

Generally, when delivering a vector of the invention comprising e.g. a minigene by transfection, the vector is delivered in an amount from about 0.1 µg to about 100 µg DNA, and preferably about 10 to about 50 µg DNA to about $1 \times 10^4$ cells to about $1 \times 10^3$ cells, and preferably about $10^5$ cells. However, the relative amounts of vector DNA to host cells may be adjusted, taking into consideration such factors as the selected vector, the delivery method and the host cells selected. Introduction of the vector into a host cell may be achieved by any means known in the art or as disclosed herein, including transfection, and infection, e. g. using $CaPO_4$ transfection or electroporation.

For the construction and assembly of the desired minigene-containing recombinant adenovirus, the vector can in one example be transfected in-vitro in the presence of a helper virus into the packaging cell line, allowing homologous recombination to occur between the helper and the vector sequences, which permits the adenovirus-transgene sequences in the vector to be replicated and packaged into virion capsids, resulting in the recombinant viral vector particles as is well known in the art. A recombinant adenoviruses of the invention is useful e.g. in transferring a selected transgene into a selected host cell.

In a preferred embodiment of the adenovirus of the invention, the adenovirus has a seroprevalence of less than 5% in human subjects and preferably no seroprevalence in human subjects, most preferably no seroprevalence in human subjects that have not previously been in contact with a chimpanzee adenovirus. In this context it is preferred that the human subjects belong to an ethnic group selected from Europeans, indigenous people of Africa, Asians, indigenous people of America and indigenous people of Oceania. Methods for the identification of the ethnic origin of a human subject are comprised in the art (see e.g. WO2003/102236).

In a further preferred embodiment of the recombinant adenovirus according to the invention, the adenovirus DNA is capable of entering a mammalian target cell, i.e. it is infectious. An infectious recombinant adenoviruses of the invention can be used as a vaccine and for gene therapy as also described below. Thus, in another embodiment it is preferred that the recombinant adenovirus comprises a molecule for delivery into a target cell. Preferably, the target cell is a mammalian cell, e.g. a chimpanzee cell, a rodent cell or a human cell. For example, the molecule for delivery into a target cell can be an expression cassette as defined herein. Methods to introduce an expression cassette into the genome of an adenovirus are well known in the art (see for example the literature citations provided above). In one example a recombinant adenovirus of the present invention that comprises an expression cassette, encoding e.g. a minigene or an antigene, can be generated by replacing a genomic region of the adenovirus selected from E1A, E1B, E2A, E2B, E3 and E4 with said expression cassette. The genomic regions E1A, E1B, E2A, E2B, E3 and E4 of the adenoviruses of the invention can easily be identified by an alignment with known and annotated adenoviral genomes such as from human Ad5 (see: Birgitt Tauber and Thomas Dobner, Oncogene (2001) 20, p. 7847-7854; and also: Andrew J. Davison, et al., "Genetic content and evolution of adenoviruses", Journal of General Virology (2003), 84, p. 2895-2908). Non-limiting examples of how to generate modified adenoviruses comprising a molecule for delivery into a target cell are also provided in examples 1 and 2 and FIG. 4 below.

The molecule for delivery into a target cell is preferably a polynucleotide but may also be a polypeptide or a small chemical compound, preferably having a therapeutic or diagnostic activity. In one particularly preferred embodiment, the molecule for delivery into a target cell is a polynucleotide that comprises an adenovirus 5' inverted terminal repeat sequence (ITR), a gene, e.g. SEQ ID NO: 1 and a 3' ITR. It will be evident to the skilled person that the molecular size of the molecule has to be chosen such that the capsid can form around and package the molecule, when the recombinant adenovirus is produced, e.g. in a packaging cell line. Thus, preferably the gene is a minigene which can have e.g. up to 7000 and maximally up to 8000 base pairs.

In a preferred embodiment, the molecule for delivery into a target cell comprised in the recombinant adenovirus according to the invention is a polynucleotide encoding an antigenic protein or a fragment thereof. An antigenic protein or fragment thereof is capable of eliciting an immune response in a mammal and may be in a particularly preferred embodiment the gag protein of HIV as shown in the examples and being encoded by a polynucleotide according to SEQ ID NO: 1.

In a particularly preferred embodiment, the recombinant adenovirus of the invention is an adenovirus that has been deposited at ECACC (European Collection of Cell Culture, Porton Down, Salisbury, SP4 OJG, UK) and has a deposit number selected from the group consisting of 08110601 (ChAd83), 08110602 (ChAd73), 08110603 (ChAd55), 08110604 (ChAd147) and 08110605 (ChAd146). The deposits of the aforementioned adenoviral strains (Latin name: *Mastadenovirus*, Adenoviridae) have been made on Nov. 6, 2008 by Okairos A G, Elisabethenstr. 3, 4051 Basel, Switzerland.

These deposits will be maintained under the terms of the Budapest Treaty on the International Recognition of the Deposit of Microorganisms for the Purposes of Patent Procedure. These deposits were made merely as a convenience for those of skill in the art and are not an admission that a deposit is required under 35 U. S. C. 112. All restrictions on the availability to the public of the deposited material will be irrevocably removed, except for the requirements specified in 37 C. F. R. 1.808 (b), upon the granting of a patent.

Another preferred embodiment of the recombinant adenovirus of the invention is an adenovirus derived from an adenovirus selected from the group consisting of 08110601 (ChAd83), 08110602 (ChAd73), 08110603 (ChAd55), 08110604 (ChAd147) and 08110605 (ChAd146). Preferably the adenovirus derived of one of the aforementioned deposited adenoviruses has been altered by introducing a functional deletion, deletion or modification in its genome, e.g. to obtain a replication incompetent adenovirus and/or an adenovirus that is capable of expressing a transgene in a host cell. For example, one or more genes selected from the group consisting of E1A, E1B, E2A, E2B, E3 and E4 gene can be deleted, rendered non-functional, and/or can be replaced by an expression cassette as outlined above. Additionally, one or more genes of another adenovirus may be introduced, preferably for a deleted gene. A skilled person is well aware of how to introduce these genomic alterations in the deposited strains. In this respect, methods of generating modified adenoviruses comprising a molecule for delivery into a target cell, which is a preferred modification of the deposited strains, have been described above.

In a further aspect a composition is provided that comprises an immunological adjuvant and at least one of the following (i) through (iv):
(i) an isolated protein according to the invention;
(ii) an isolated polynucleotide according to the invention;
(iii) a vector according to the invention;
(iv) a recombinant adenovirus according to the invention; and, optionally, a pharmaceutically acceptable excipient.

A composition according to the invention that comprises an adjuvant can be used as a vaccine, e.g. for human subjects. The immunological adjuvant also referred to herein in short as "adjuvant"; accelerates, prolongs and/or enhances the quality and/or strength of an immune response to an antigen/immunogen, in comparison to the administration of the antigen alone, thus, reducing the quantity of antigen/immunogen necessary in any given vaccine, and/or the frequency of injection necessary in order to generate an adequate immune response to the antigen/immunogen of interest.

Examples of adjuvants that may be used in the context of the composition according to the present invention are gel-like precipitates of aluminum hydroxide (alum); $AlPO_4$; alhydrogel; bacterial products from the outer membrane of Gram-negative bacteria, in particular monophosphoryl lipid A (MPLA), lipopolysaccharides (LPS), muramyl dipeptides and derivatives thereof; Freund's incomplete adjuvant; liposomes, in particular neutral liposomes, liposomes containing the composition and optionally cytokines; non-ionic block copolymers; ISCOMATRIX adjuvant (Drane et al., 2007); unmethylated DNA comprising CpG dinucleotides (CpG motif), in particular CpG ODN with a phosphorothioate (PTO) backbone (CpG PTO ODN) or phosphodiester (PO) backbone (CpG PO ODN); synthetic lipopeptide derivatives, in particular $Pam_3Cys$; lipoarabinomannan; peptidoglycan; zymosan; heat shock proteins (HSP), in particular HSP 70; dsRNA and synthetic derivatives thereof, in particular Poly I:poly C; polycationic peptides, in particular poly-L-arginine; taxol; fibronectin; flagellin; imidazoquinoline; cytokines with adjuvant activity, in particular GM-CSF, interleukin-(IL-)2, IL-6, IL-7, IL-18, type I and II interferons, in particular interferon-gamma, TNF-alpha; 25-dihydroxyvitamin D3 (calcitriol); and synthetic oligopeptides, in particular MHCII-presented peptides. Non-ionic block polymers containing polyoxyethylene (POE) and polyoxypropylene (POP), such as POE-POP-POE block copolymers may be used as an adjuvant (Newman et al., 1998). This type of adjuvant is particularly useful for compositions comprising nucleic acids as active ingredient.

Optionally, various pharmaceutically acceptable excipients may be used. Preferred pharmaceutically acceptable excipients are mentioned below when discussing the uses according to the invention.

Activation of specific receptors can stimulate an immune response. Such receptors are known to the skilled artisan and comprise, for example, cytokine receptors, in particular type I cytokine receptors, type II cytokine receptors, TNF receptors; and vitamin D receptor acting as transcription factor; and the Toll-like receptors 1 (TLR1), TLR-2, TLR 3, TLR4, TLR5, TLR-6, TLR7, and TLR9. Agonists to such receptors have adjuvant activity, i.e., are immunostimulatory. In a preferred embodiment, the adjuvant of the composition of the present invention may be one or more Toll-like receptor agonists. In a more preferred embodiment, the adjuvant is a Toll-like receptor 4 agonist. In a particular preferred embodiment, the adjuvant is a Toll-like receptor 9 agonist, preferably being encoded by the nucleotide tccatgacgttcctgacgtt (SEQ ID NO: 2).

In a further aspect the invention provides a cell, preferably a non-simian cell, comprising at least one of the following:
(i) an isolated protein according to the invention;
(ii) an isolated polynucleotide according to the invention;
(iii) a vector according to the invention;
(iv) a recombinant adenovirus according to the invention;

The cell may be selected of a bacterial cell such as an *E. coli* cell, a yeast cell such as *Saccharomyces cerevisiae* or *Pichia pastoris*, a plant cell, an insect cell such as SF9 or Hi5 cells, or a mammalian cell. Preferred examples of mammalian cells are Chinese hamster ovary (CHO) cells, human embryonic kidney (HEK 293) cells, HELA cells, human hepatoma cells (e.g. Huh7.5), Hep G2 human hepatoma cells, Hep 3B human hepatoma cells and the like.

If the cell comprises an isolated polyucleotide according to (ii), this polynucleotide may be present in the cell either (i) freely dispersed as such, or (ii) integrated into the host cell genome or mitochondrial DNA.

In a further preferred embodiment, the cell is a host cell, preferably a 293 cell or a PER.C6™ cell, that expresses at least one adenoviral gene selected from the group consisting of E1a, E1b, E2a, E2b, E4, L1, L2, L3, L4 and L5.

Also provided is the use of the isolated polynucleotide according to the invention, the isolated protein according to the invention, the vector according to the invention, the recombinant adenovirus according to the invention and/or the pharmaceutical composition according to the invention for the therapy or prophylaxis of a disease.

Adenoviral vectors have demonstrated great potential as vaccine vectors. Preclinical and clinical studies have demonstrated the feasibility of vector design, robust antigen expression and protective immunity using this system. Thus, a preferred embodiment is the use according to the invention, wherein the therapy or prophylaxis is a vaccination, e.g. for human subjects. Detailed instructions of how adenoviruses are used and prepared for vaccination are provided as ample literature comprised in the art and known to the skilled person.

If the use is a vaccination, a recombinant adenovirus of the invention can be administered in an immunologically and/or prophylactically effective dose which is preferably $1 \times 10^8$ to $1 \times 10^{11}$ viral particles (i.e., $1 \times 10^8$, $5 \times 10^8$, $1 \times 10^9$, $5 \times 10^9$, $1 \times 10^{10}$, $2.5 \times 10^{10}$ or $5 \times 10^{10}$ particles). Furthermore, for a vaccination which requires a boosting, it is preferred to apply a "heterologous prime-boost" methodology, as defined above. Furthermore, when using the isolated polynucleotide according to the invention, the isolated protein according to the invention, the vector according to the invention, the recombinant adenovirus according to the invention and/or the pharmaceutical composition according to the invention in a vaccine, it is preferred that the vaccine comprises an adjuvant. Preferred immunological adjutants have been mentioned herein and can be used in such vaccine.

A recombinant adenovirus prepared using a polynucleotide or recombinant adenoviral protein or fragment thereof according to the invention can be used to transduce a host cell with a polynucleotide, e.g. DNA. Thus, a preferably replication deficient, albeit infectious, i.e. capable of entering a host cell, adenovirus can be prepared to express any custom protein or polypeptide in a host cell. Thus, in a preferred embodiment, the therapy recited in the use according to the invention is gene therapy. If an isolated polynucleotide, an isolated protein, a vector, a recombinant adenovirus and/or a pharmaceutical composition according to the invention is used for gene therapy and is administered to a subject to be treated, it is preferred that it is administered in a sufficiently large dose such that the treatment results in one or more cells of the patient being transfected, i.e. transduced. If a recombinant adenovirus and/or a pharmaceutical composition according to the invention is administered by any of the preferred means of administrations disclosed herein, it is preferred that an effective dose which is preferably $1\times10^8$ to $5\times10^{11}$ viral particles (i.e., $1\times10^8$, $5\times10^8$, $1\times10^9$, $5\times10^9$, $1\times10^{10}$, $2.5\times10^{10}$, $5\times10^{10}$, $1\times10^{11}$ or, most preferably, $5\times10^{11}$ particles) is administered. In preferred embodiments, the preferably heterologous polynucleotide that is comprised in the recombinant adenovirus of the invention is capable of expressing a protein or polypeptide in a host cell of the subject, wherein the protein or polypeptide comprises a signal peptide which effects secretion of the protein or polypeptide from said host cell. For example, a patient in need of a certain protein can be treated using an adenovirus of the present invention which comprises a cDNA that encodes a secretable form of that protein.

In a further embodiment of the use of the present invention, the isolated polynucleotide, isolated protein, vector, adenovirus and/or pharmaceutical composition according to the invention (in the following referred to as pharmaceutical according to the invention) is formulated to further comprise one or more pharmaceutically acceptable diluents; carriers; excipients, including fillers, binders, lubricants, glidants, disintegrants, and adsorbents; and/or preservatives.

The pharmaceutical according to the invention can be administered by various well known routes, including oral, rectal, intragastrical and parenteral administration, e.g. intravenous, intramuscular, intranasal, intradermal, subcutaneous and similar administration routes. Parenteral-, intramuscular- and intravenous administration is preferred. Preferably the pharmaceutical according to the invention is formulated, as syrup, an infusion or injection solution, a tablet, a capsule, a capslet, lozenge, a liposome, a suppository, a plaster, a band-aid, a retard capsule, a powder, or a slow release formulation. Preferably the diluent is water, a buffer, a buffered salt solution or a salt solution and the carrier preferably is selected from the group consisting of cocoa butter and vitebesole.

Particular preferred pharmaceutical forms for the administration of the pharmaceutical according to the invention during the use of the present invention are forms suitable for injectable use and include sterile aqueous solutions or dispersions and sterile powders for the extemporaneous preparation of sterile injectable solutions or dispersion. Typically, such a solution or dispersion will include a solvent or dispersion medium, containing, for example, water-buffered aqueous solutions, e.g. biocompatible buffers, ethanol, polyol, such as glycerol, propylene glycol, polyethylene glycol, suitable mixtures thereof, surfactants or vegetable oils.

Infusion or injection solutions can be accomplished by any number of art recognized techniques including but not limited to addition of preservatives like anti-bacterial or anti-fungal agents, e.g. parabene, chlorobutanol, phenol, sorbic acid or thimersal. Further, isotonic agents, such as sugars or salts, in particular sodium chloride may be incorporated in infusion or injection solutions.

Preferred diluents of the present invention are water, physiological acceptable buffers, physiological acceptable buffer salt solutions or salt solutions. Preferred carriers are cocoa butter and vitebesole. Excipients which can be used with the various pharmaceutical forms of the pharmaceutical according to the invention can be chosen from the following non-limiting list:
a) binders such as lactose, mannitol, crystalline sorbitol, dibasic phosphates, calcium phosphates, sugars, microcrystalline cellulose, carboxymethyl cellulose, hydroxyethyl cellulose, polyvinyl pyrrolidone and the like;
b) lubricants such as magnesium stearate, talc, calcium stearate, zinc stearate, stearic acid, hydrogenated vegetable oil, leucine, glycerids and sodium stearyl fumarates,
c) disintegrants such as starches, croscaramellose, sodium methyl cellulose, agar, bentonite, alginic acid, carboxymethyl cellulose, polyvinyl pyrrolidone and the like.

Other suitable excipients can be found in the Handbook of Pharmaceutical Excipients, published by the American Pharmaceutical Association, which is herein incorporated by reference.

Certain amounts of the pharmaceutical according to the invention are preferred for the therapy or prophylaxis of a disease. It is, however, understood that depending on the severity of the disease, the type of the disease, as well as on the respective patient to be treated, e.g. the general health status of the patient, etc., different doses of the pharmaceutical according to the invention are required to elicit a therapeutic or prophylactic effect. The determination of the appropriate dose lies within the discretion of the attending physician.

If the pharmaceutical according to the invention is to be used prophylactically, it may be formulated as a vaccine. In this case the pharmaceutical according to the invention is preferably administered in above outlined preferred and particular preferred doses. Preferably, the administration of the vaccine is repeated at least two, three, four, five, six, seven, eight nine or at least 10 times over the course of a defined period of time, until the vaccinated subject has generated sufficient antibodies against the pharmaceutical according to the invention so that the risk of developing the respective disease has lessened. The period of time in this case is usually variable depending on the antigenicity of the vaccine. Preferably the period of time is not more than four weeks, three months, six months or three years. In one embodiment, if an adenovirus according to the invention is used for vaccination purposes, at least one of the hyper variable domains of the hexon protein can be replaced by an immunogenic epitope of the respective disease agent that the vaccination is directed against. Vaccines typically contain one or more adjuvants as outlined above. A detailed summary of the use of adenoviruses for vaccination and methods pertaining thereto is provided in: Bangari D S and Mittal S K (2006) Vaccine, 24(7), p. 849-862; see also: Thou D, et al., Expert Opin Biol Ther. 2006 January; 6(1):63-72; and: Folgori A, et al., Nat Med. 2006 February; 12(2):190-7; see also: Draper S J, et al., Nat Med. 2008 August; 14(8):819-21, Epub 2008 Jul. 27.

Various modifications and variations of the invention will be apparent to those skilled in the art without departing from the scope of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the relevant fields are intended to be covered by the present invention.

The following figures are merely illustrative of the present invention and should not be construed to limit the scope of the invention as indicated by the appended claims in any way.

BRIEF DESCRIPTION OF THE FIGURES

FIGS. 1A-1D Multiple sequence alignment between hexon proteins of various adenovirus isolates of the invention, using Clustal-W with default settings. Hexon proteins of said novel chimpanzee adenovirus isolates are shown (designated as PanAd1, PanAd2, PanAd3, ChAd55, ChAd73, ChAd83, ChAd146 and ChAd147). The hypervariable domains 1 through 7 are designated as "HVR 1-6" and "HVR 7", respectively.

FIGS. 2A-2C Multiple sequence alignment between fiber proteins of adenovirus ChAd55 and of further novel chimpanzee adenovirus isolates (designated as PanAd1, PanAd2, PanAd3, ChAd73, ChAd83, ChAd146 and ChAd147), using Clustal-W with default settings.

FIGS. 3A-3C Multiple sequence alignment between penton proteins of adenovirus ChAd55 and of further novel chimpanzee adenovirus isolates (designated as PanAd1, PanAd2, PanAd3, ChAd73, ChAd83, ChAd146 and ChAd147), using Clustal-W with default settings.

FIGS. 5A-5C Cell-mediated immune response in mice vaccinated with recombinant adenoviruses comprising an expression cassette for the expression of HIV gag protein (SEQ ID NO:1). The vaccination potency of recombinant human Ad5 and chimpanzee ChAd55 (FIG. 5A), of recombinant human Ad5 and bonobo PanAd1. PanAd2 and PanAd3 adenovirus (FIG. 5B) and of recombinant ChAd55, ChAd73, ChAd83, ChAd146 and ChAd147 was compared (FIG. 5C). The immune response was measured by Interferon-γ ELIspot assay by incubating the cells with a CD8 HIV gag epitope mapped in Balb/C mice. The results are reported as spot forming cells per $10^6$ splenocytes.

FIGS. 7A-7B PanAd HSV immunization of BALB/c mice is shown in FIG. 7A and PanAd cancer Ag immunization of BALB/c mice is shown in FIG. 7B.

FIG. 8 PanAd HIV gag immunization of *Macaca fascicularis* is shown in a priming/boosting vaccination experiment.

EXAMPLES

Example 1

Adenovirus Isolation and Characterization

Figure 4:
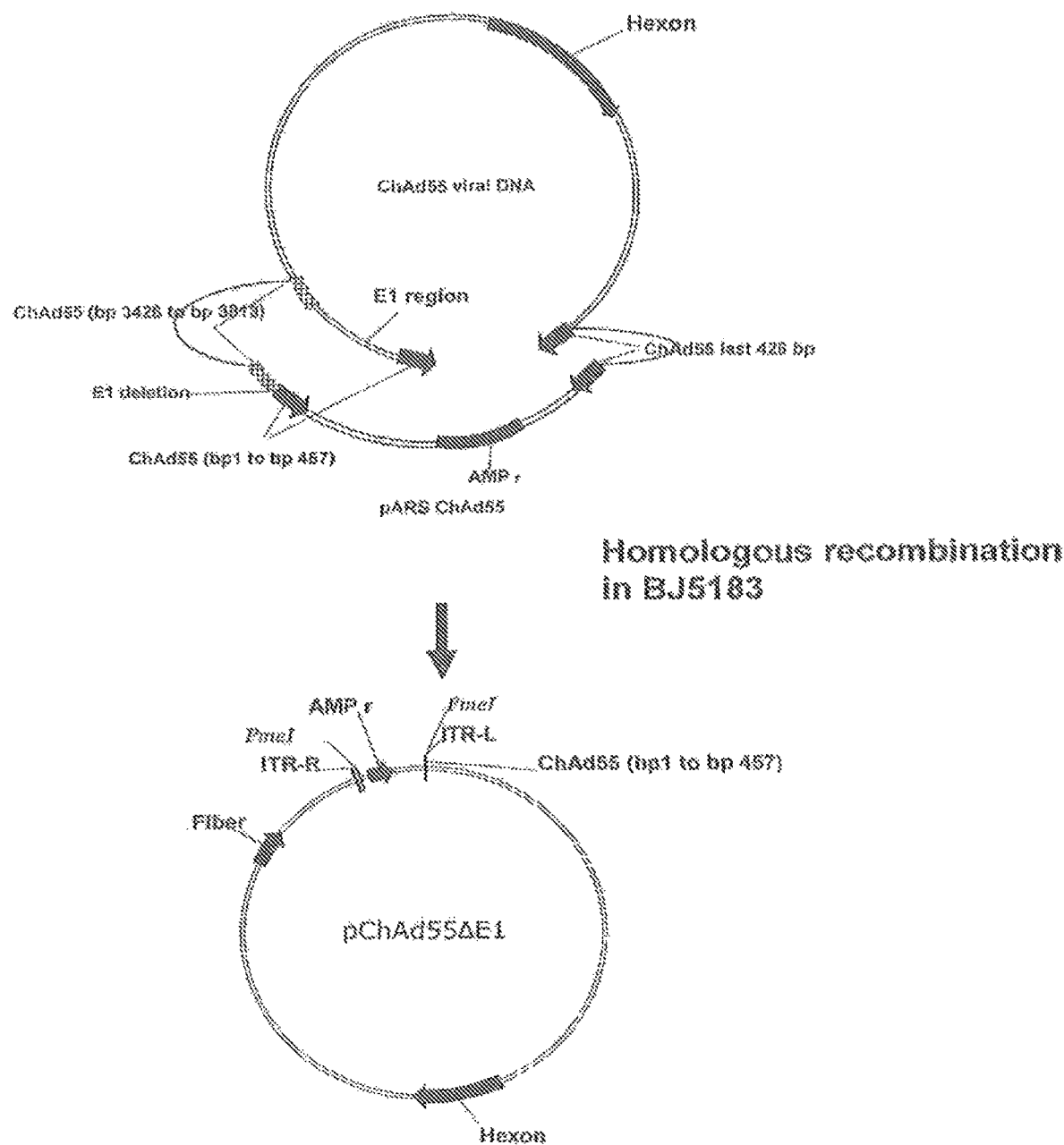
FIG. 4 Diagram of construction of a replication-defective adenovirus vector by homologous recombination with wild type viral genome and the corresponding shuttle plasmid. See also example 2.

ChAd55, ChAd73, ChAd83, ChAd146, ChAd147 are a group of chimpanzee adenoviruses obtained from healthy animals housed in different European and US facilities. ChAd55, ChAd73, ChAd83, ChAd146, ChAd147 have the property of no detectable reactivity with human sera. PanAd1, PanAd2 and PanAd3 are new adenovirus isolated from healthy bonobos (*Pan Paniscus*) housed in different European and US facilities. PanAd1, PanAd2 and PanAd3 have the property of no detectable reactivity with human sera.

The common chimpanzee and bonobo adenovirus stocks were cloned by infecting 293 cells seeded in 96-well plates, after the first passage of amplification. The virus cloning was performed by limiting dilution of the cell lysate obtained at the first passage of the virus amplification. 5 isolated clones were picked up and serially propagated. After 3-4 serial passages of amplification, a large-scale preparation of adenovirus was performed on cells planted on 5 two-layer cell-factories (NUNC) (200 millions of cells/cell factory). Purified viral particles were obtained from cell lysate by two ultra-centrifugation steps on cesium chloride density gradients.

Genomic DNA was isolated from $3 \times 10^{12}$ pp of purified virus preparation by digestion with Proteinase K (0.5 mg/ml) in 1% SDS-TEN (2 hrs at 55° C.). After a Phenol-Chloroform extraction and Ethanol precipitation, the genomic DNA was resuspended in water and submitted for genomic sequencing.

An initial classification of the new isolates was obtained by sequence analysis of the hypervariable region 7 (HVR7) of the hexon gene. To this end two primers were designed on the highly conserved regions flanking HVR7: TGTCCTAC-CARCTCTTGCTTGA (SEQ ID NO. 3) and GTGGAARG-GCACGTAGCG (SEQ ID NO. 4). The HVR7 was amplified by PCR using purified viral DNA or crude 293 lysate as template and then sequenced. More detailed information about the isolate was obtained by sequencing the hypervariable regions 1 to 6. The DNA region containing HVR1-6 was amplified by PCR using oligonucleotides HVR1-6fd, CAYGATGTGACCACCGACCG (SEQ ID NO. 5) and HVR1-6rev, GTGTTYCTGTCYTGCAAGTC (SEQ ID NO. 6). Based on HVRs sequence analysis the new isolated viruses were classified into subgroup E (ChAd55, ChAd73, ChAd83, ChAd146, ChAd147) and subgroup C (PanAd1, PanAd2 and PanAd3) of human Ad virus classification (Horowitz, M S (1990), Adenoviridae and their replication. In Virology B. N. Fields and D. M. Knipe, eds (raven Press, New York) pp. 1679-1740).

A phylogenetic tree was obtained by alignment of human and chimp adenovirus hexon amino acid sequences. The results are consistent with the initial classification based on nucleotide sequence alignment limited to hexon HVR1-6 and 7 by using Align X program (Informax, Inc) demonstrating a close phylogenetic relationship of ChAd55, ChAd73, ChAd83, ChAd146, ChAd147 isolates with human Ad4 (subgroup E) while bonobo adenovirus isolate PanAd1, PanAd2 and PanAd3 are related to human Ad1, 2, 5, 6 (subgroup C).

Example 2

Vector Construction

The PanAd1, PanAd2 and PanAd3 and ChAd55, ChAd73, ChAd83, ChAd146, ChAd147 virus genomes were cloned in a plasmid vector following the strategy detailed below. All manipulations of the vector genome were performed in *E. coli* following standard techniques. Vector systems were developed by deleting E1 and E3 regions from ChAd and PanAd backbones. The E1 region was substituted with expression cassettes based on human CMV IE promoter and BGHpA signal containing HCV non structural region (HCV NS) and HIV gag (SEQ ID NO: 1) genes for the evaluation of the immunological potency in animal models. In addition, ChAd and PanAd vectors expressing the secreted alkaline phosphatase gene (SEAP) were constructed for the neutralization assay. The vectors were propagated in 293 cells and purified by CsCl gradients following standard protocols.

The construction of PanAd1, PanAd2 and PanAd3 ΔE1 vectors proceeded through the steps provided below.

I. Construction of PanAd Shuttle Vector

PanAd1 genome was used to construct a shuttle vector for cloning by homologous recombination the entire genome of PanAd1, PanAd2 and PanAd3. Briefly, the shuttle vector used to clone bonobo adenovirus 1 referred to herein as pBAd1RLD_EGFP was constructed as follows:

PanAd1 left end (nt 1-450) was amplified by PCR with oligonucleotides 5'-ATCTGGAATTCGTTTAAACCAT-CATCAATAATATACCTTATTTTG-3' (SEQ ID NO: 7) and 5'-TCAGGAACTAGTTCCGTATACCTATAATAAT AAAACGGAGACTTTG-3' (SEQ ID NO): 8) digested with SpeI and EcoRI then ligated into a plasmid vector already containing HCMV-EGFP-bgh polyA cassette by generating pBAd1-L. PanAd1 right end (nt 37362-37772) was then amplified by PCR with oligonucleotides 5'-TC-CAGCGGCGCGCCAGACCCGAGTCTTACCAGGA-3' (SEQ ID NO: 9) and 5'-ATTCAGGATCCGAAT-TCGTTTAAACCATCATCAATAATATACCTTATTTG-3' (SEQ ID NO: 10), and cloned in pBAd1-L thus generating plasmid pBAd1-RL.

A PanAd1 DNA fragment (nt 3498-4039) containing pIX coding region was subsequently amplified by PCR with the oligonucleotides 5'-TATTCTGCGATCGCTGAGGTGGGT-GAGTGGGCG-3' (SEQ ID NO: 11) and 5'-ITACTG-GCGCGCCTGCCTCGAGTAAACGGCATTTGCAGGA-GAAG-3' (SEQ ID NO: 12) then cloned into pBAd1-RL obtaining the plasmid pBAd1RLD EGFP shuttle. Shuttle plasmids containing the expression cassettes for secreted alkaline phosphatase (SEAP), HIV gag, HCV non structural region (NS) genes were also constructed by substituting the EGFP gene in pBAd1RLD EGFP shuttle.

The HIV gag HCV NS region, SEAP and EGFP expression cassette based on human cytomegalovirus (HCMV) promoter and bovine growth hormone polyadenylation signal (Bgh polyA) were constructed as described in Emini et al., International Publication Number WO 03/031588. The viral DNA cassette was designed to contain restriction enzyme sites (PmeI) that are present only at the end of both ITRs to allow the release of viral DNA from plasmid DNA.

II. Construction of ΔE1 PanAd1, PanAd2 and PanAd3 Vector

PanAd1, PanAd2 and PanAd3 vectors were constructed by homologous recombination in *E. coli* strain BJ5183, BJ5183 cells were co-transformed with PanAd1, 2 and 3 purified viral DNAs and pBAd1RLD-EGFP or pBAd1RLD-Gag. Homologous recombination between pIX genes, right ITR DNA sequences present at the ends of linearized pBAd1RLD-EGFP or pBAd1RLD-Gag and viral genomic DNAs allowed its insertion in the plasmid vector, by deleting at the same time the E1 region that was substituted by the expression cassette. This strategy allowed for the construction of the preadeno plasmids pPanAd1, pPanAd2 and pPanAd3 expressing EGFP or HIV gag transgenes. SEAP or HCV-NS expression cassettes were then cloned into pPanAd 1, 2 and 3 vectors by replacing either EGFP or Gag expression cassettes.

III. E3 Region Deletion

A deletion of the E3 region was introduced in PanAd1, PanAd2 and PanAd3 vector backbones by using a strategy involving several steps of cloning and homologous recombination in *E. coli*, PanAd1 E3 deletion spans from nucleotide 28636 to nucleotide 32596 of genomic PanAd1 sequence (SEQ ID NO.: 13); PanAd2 E3 deletion spans from nucleotide 28653 to nucleotide 32599 of genomic PanAd2 sequence (SEQ ID NO.: 62); PanAd3 E3 deletion spans from nucleotide 28684 to nucleotide 32640 of genomic PanAd3 sequence (SEQ ID NO.: 63).

IV. E4 Region Deletion

The native E4 region of PanAd1, PanAd2 and PanAd3 was deleted and replaced with Ad5 E4 ORF6 coding sequence (SEQ ID NO.: 64). The coordinates of the E4 deletion introduced in the PanAd 1, 2 and 3 backbones are the following:

PanAd1 E4 deletion spans from nucleotide 34690 to 37369 (SEQ ID NO.: 13);
PanAd2 E4 deletion spans from nucleotide 34696 to 37400. (SEQ ID NO.: 62);
PanAd3 E4 deletion spans from nucleotide 34690-37369 (SEQ ID NO.: 63).

The deleted region contains all PanAd E4 orfs while the E4 native promoter and polyadenylation signal were not deleted The HIV gag and HCV NS region expression cassette based on human cytomegalovirus (HCMV) promoter and bovine growth hormone polyadenylation signal (Bgh polyA) was constructed as described in Emini et al., International Publication Number WO 03/031588 and inserted into PanAd1, 2 and 3 ΔE1 EGFP vector by homologous recombination in *E. coli* strain BJ5183 exploiting the homologies between HCMV and Bgh polyA DNA sequences.

V. ChAd55 DE1 Expression Vector Construction and Rescue Construction of Shuttle Vector for ChAd55 Cloning ChAd55 shuttle was constructed by following the same strategy described above for PanAd vectors then used for the cloning of the ChAd55 viral genomes. To this end, the shuttle vector pARS ChAd55 containing the right end as well as the left end of viral genome (left end from the ITR to the pIX gene with the E1 region deleted and substituted with the expression cassette) was linearized with AscI restriction enzyme and co-transformed into *E. coli* strain BJ5183 with ChAd55 purified viral DNA. Homologous recombination between DNA sequences from pIX genes and right ITR present at the ends of linearized pARS ChAd55 and ChAd55, ChAd73, ChAd83, ChAd146 and ChAd147 purified viral genomic DNAs allowed their insertion into the plasmid vector by deleting at the same time the E1 region. A diagram of the chimp adenovirus 55 (ChAd55) genome cloning strategy is provided in FIG. 4.

Expression cassettes based on human cytomegalovirus (HCMV) promoter and bovine growth hormone poly-adenylation signal (Bgh polyA) were constructed to express secreted alkaline phosphatase (SEAP), EGFP, HIV gag, HCV NS genes. All expression cassettes were inserted into the single SnaBI site of pARS ChAd55 vector to be transferred by homologous recombination into the ΔE1 adenovirus pre-plasmids.

Example 3

Immunization Experiments

Figure 5B:
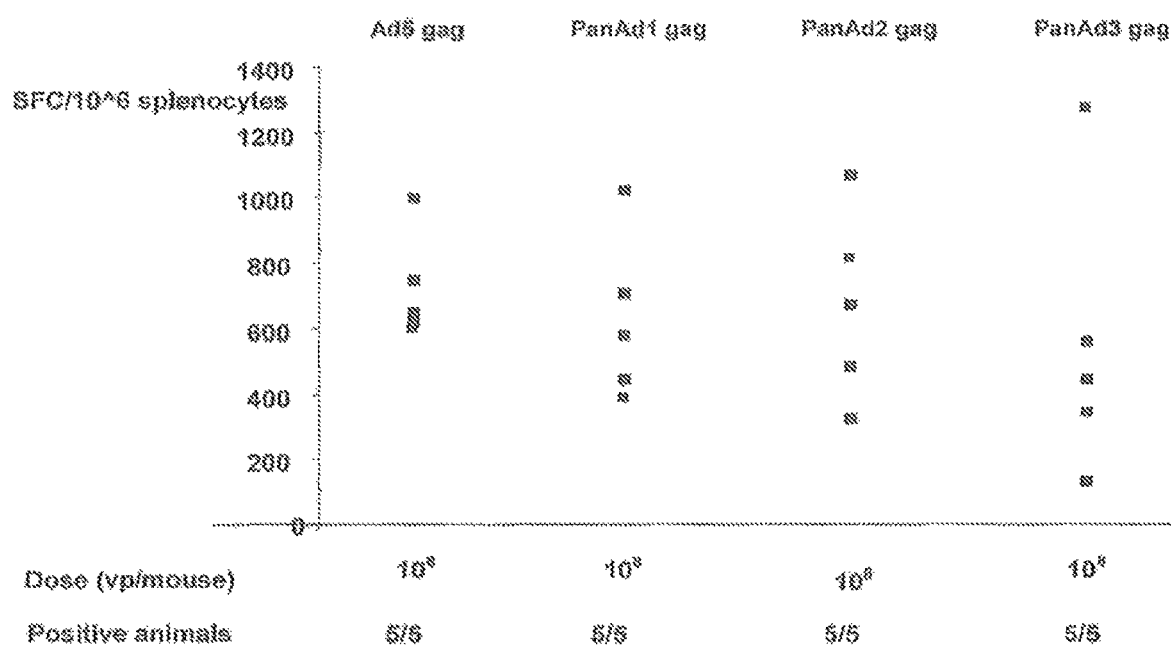
Figure 5C:
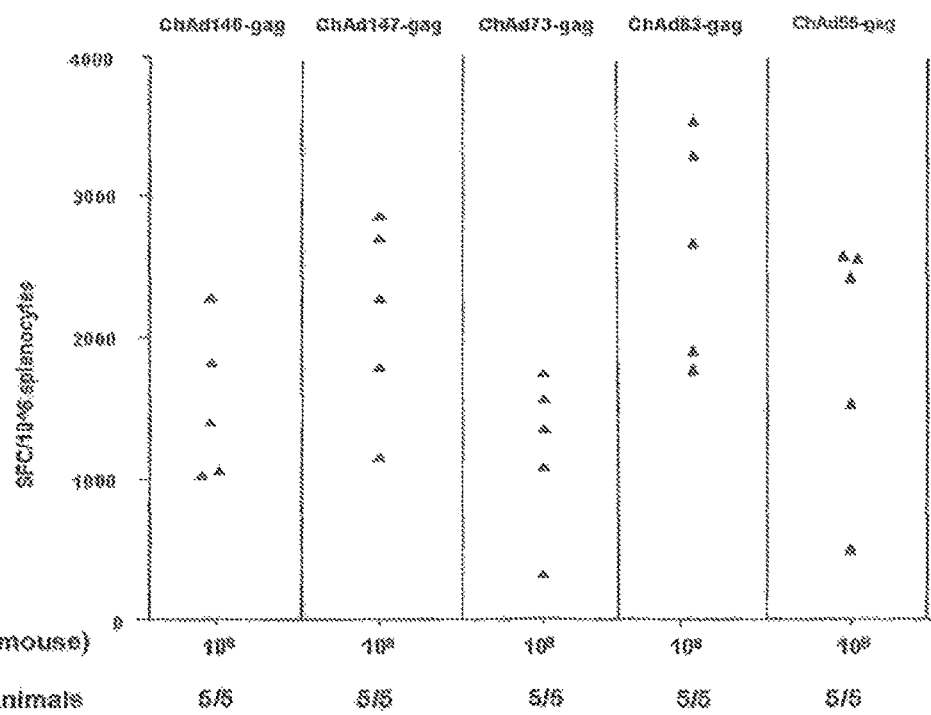

The efficiency of ChAd55, ChAd73, ChAd83, ChAd146, ChAd147, PanAd1, PanAd2 and PanAd3 vectors as potential recombinant vaccine was evaluated in mice with vectors expressing HIV gag transgene. The vector potency of ChAd55 gag was compared with human Ad5 gag in immunization experiments performed in parallel. Groups of 10 animals were injected in the quadriceps with a dose of the vector of $10^8$ vp/mouse for Ad5gag or ChAd55gag (FIG. 5A). In a separate experiment a group of 5 animals were injected with a dose of the vector of $10^8$ vp/mouse for Ad5gag or PanAd1gag, PanAd2gag and PanAd3gag (FIG. 5B). The potency of ChAd73 gag, ChAd83 gag, ChAd146 gag and Chad147gag was also determined by immunizing groups of 5 mice with a dose of vector of $10^8$ vp/mouse in parallel with ChAd55 gag (FIG. 5C). The immune response elicited against HIV gag was measured by Interferon-γ Elispot assay on splenocytes. The results of immunization experiments with ChAd55, ChAd73, ChAd83, ChAd146, ChAd147 and PanAd1, PanAd2 and PanAd3 in comparison with human Ad5 gag vector show that the novel adenoviruses of the invention are at least as effective in eliciting a specific immune response as the prior art recombinant adenovirus Ad5.

Example 4

Neutralization Studies

Figure 6:
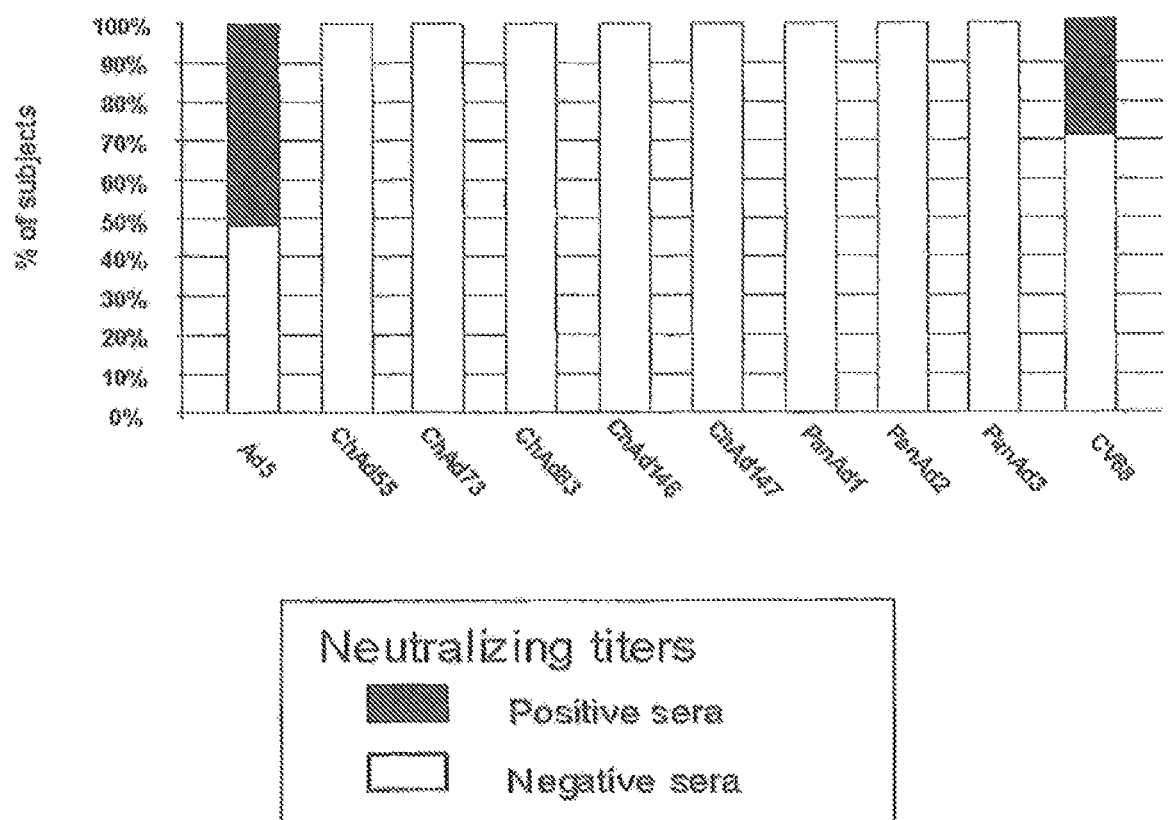
FIG. 6 The seroprevalence of novel adenovirus vectors was evaluated on a panel of human sera of European origin. The seroprevalence of human adenovirus type 5 (Ad5) and of chimpanzee adenoviruses ChAd55, ChAd73, ChAd83, ChAd146, ChAd147, PanAd1, PanAd2, PanAd3 and CV-68 were evaluated in parallel on the same panel. The data are expressed as % of subjects showing an immunoprevalence. Neutralizing antibodies were only detected against Ad5 and CV-68 adenoviruses but not for any of the novel adenoviruses of the present invention.

Neutralization assays were carried out in order to evaluate the prevalence in human sera of neutralizing antibodies against the common chimpanzee adenovirus 55, 73, 83, 146, 147 and the Bonobo adenovirus type 1, 2 and 3. The assay evaluated the effects of serum preincubation on the ability of ChAd55, ChAd73, ChAd83, ChAd146, ChAd147, PanAd1, PanAd2 and PanAd3 carrying the gene for secreted alkaline phosphatase (SEAP) to transduce human 293 cells. The neutralization titer is defined as the dilution of serum giving a 50% reduction of the SEAP activity observed in the positive control with the virus in absence of serum. Each serum sample was tested at various dilutions (five 4-fold increments starting from 1/18 dilution through 1:4608). Samples were pre-incubated for one hour at 37° C. and then added to 293 cells seeded into 96-well plates ($3 \times 10^4$ cells/well). A panel of human sera was tested for neutralization activity. In parallel the same panel was tested on Ad5 and on chimp and bonobo Ad SEAP vectors. The results are provided in FIG. 6. The results indicate that the seroprevalence on chimpanzee adenoviruses is lower than human adenovirus Ad5. However, in general the presence of neutralizing antibodies against already described ChAds (CV-68) can be detected in a subset of subjects. On the contrary, all human sera tested so far failed to neutralize ChAd55 and PanAd1, PanAd2 and PanAd3 even at very low titer. The same was observed for ChAd73, ChAd83, ChAd146 and ChAd147. Therefore, the novel adenovirus isolates ChAd55, ChAd73, ChAd83, ChAd146, ChAd147 and PanAd1, PanAd2 and PanAd3 represent the ideal solution to the problem of the pre-existing anti-human Ad immunity that limits the administration of viral vectors based on common human Ad serotypes such as Ad5.

Example 5

Immunization Efficiency of PanAd1 and 3 Vectors in Comparison with Ad5 Vectors

The efficiency of PanAd1 and PanAd3 vectors as potential recombinant vaccines was evaluated in BALB/c mice with vectors expressing herpes simplex virus (HSV) antigen and with vectors expressing a cancer antigen. The vector potency of PanAd1 and 3 expressing HSV Ag and the cancer Ag was compared with the corresponding vectors based on human Ad5.

To evaluate the antiviral potency, 9 groups of BALB/c mice were injected in the quadriceps with increasing doses of the vectors starting from $10^7$ vp/mouse up to $10^9$ vp/mouse in parallel with PanAd1-HSV, PanAd3-HSV and Ad5-HSV (see FIG. 7A). The immune response elicited against the HSV antigen was measured by Interferon-γ Elispot assay on mouse splenocytes incubated with a peptide pool covering the entire amino acid sequence of the antigen. The results of immunization experiments with PanAd1, PanAd2 and PanAd3 in comparison with human Ad5 vector reported in FIG. 7 showed that the novel adenoviruses of the invention are more effective in eliciting a specific immune response than the prior art recombinant adenovirus Ad5 at each concentration tested. This is clearly demonstrated by the higher frequency of antigen-specific T-cell observed in mice immunized with PanAd1 and PanAd3 vectors.

The efficiency in eliciting anti-tumoral T-cell response by PanAd vectors was evaluated by immunizing groups of BALB/c mice by injecting in the quadriceps increasing doses of the vectors starting from $10^7$ vp/mouse up to $10^9$ vp/mouse. Two groups of BALB/C mice were injected with Ad5 vector expressing the tumor antigen at $10^7$ vp/mouse and $10^9$ vp/mouse. In parallel 3 groups of BALB/c mice were immunized with $10^7$, $10^8$, $10^9$ vp of PanAd1 or PanAd3 vectors carrying the same tumor antigen. The T cell response was measured by Interferon-γ Elispot assay on splenocytes using a single peptide representing a mapped CD8 epitope. The results shown in FIG. 7B demonstrated a higher frequency of responding animals at the lowest dose of the vaccine as well as a higher frequency of antigen-specific T-cell in the groups of animals immunized with the PanAd vectors in comparison with those immunized with Ad5 vector.

Example 6

Immunization of *Macaca fascicularis* with PanAd Vectors

Two groups of 3 macaques were immunized by intramuscular injection of CsCl-purified PanAd1 and PanAd3 in a heterologous prime/boost regimen. Each animal in the group 1 received a dose of $10^8$ vp while the animals in the group 2 received a dose of $10^{10}$ vp of PanAd3 Gag vector in the deltoid muscle at week 0. All animals in both groups were than boosted with a single dose of PanAd1 Gag of $10^{10}$ vp at week 13.

CMI was measured at different time points by IFN-γ ELISPOT assay. This assays measure HIV antigen-specific CD8+ and CD4+ T lymphocyte responses. Peptides based on the amino acid sequence of HIV Gag protein were prepared for use in these assays to measure immune responses in adenovirus vector vaccinated monkeys. The individual peptides are overlapping 20-mers, offset by 10 amino acids.

The IFNγ-ELISPOT assay provides a quantitative determination of antigen-specific T lymphocyte responses. PBMC are serially diluted and placed in microplate wells coated with anti-rhesus IFN-γ antibody (MD-1 U-Cytech). They are cultured with a HIV Gag peptide pool for 20 hours, resulting in the restimulation of the precursor cells and secretion of IFN-γ. The cells are washed away, leaving the secreted IFN bound to the antibody-coated wells in concentrated areas where the cells were sitting. The captured IFN is detected with biotinylated anti-rhesus IFN antibody (detector Ab U-Cytech) followed by alkaline phosphatase-conjugated streptavidin (Pharmingen 13043E). The addition of insoluble alkaline phosphatase substrate results in dark spots in the wells at the sites where the cells were located, leaving one spot for each T cell that secreted IFN-γ.

The number of spots per well is directly related to the precursor frequency of antigen-specific T cells. Gamma interferon was selected as the cytokine visualized in this assay (using specific anti-gamma interferon monoclonal antibodies) because it is the most common, and one of the most abundant cytokines synthesized and secreted by activated T lymphocytes. For this assay, the number of spot forming cells (SFC) per million PBMCs is determined for samples in the presence and absence (media control) of peptide antigens. Data from macaques on PBMC obtained at different time points post dose 1 and post dose 2 are shown in FIG. 8. All animals primed with PanAd3 at both doses showed a T cell response against HIV Gag, efficiently boosted by the second injection of PanAd1 demonstrating that, as already suggested by the hexon, penton and fiber sequence alignment, PanAd1 and PanAd3 are distinct serotypes that can be combined in a heterologous prime-boost immunization regimen. Thus, in another aspect the invention provides the use of two recombinant adenoviruses of the invention for a heterologous prime-boost immunization wherein the two recombinant adenoviruses of the invention are of distinct adenoviral serotypes, most preferably of PanAd1 and PanAd3 as described herein.

The invention claimed is:

1. A recombinant adenoviral vector encoding a heterologous hexon protein comprising a polynucleotide that encodes an adenoviral hexon protein, wherein the polynucleotide is selected from the group consisting of:
    (a) a polynucleotide encoding a polypeptide having the amino acid sequence of SEQ ID NO: 16;
    (b) a polynucleotide encoding a polypeptide having the amino acid sequence of SEQ ID NO: 16, wherein the polypeptide comprises a deletion, insertion or substitution of not more than 35 amino acid residues; and
    (c) a polynucleotide encoding a polypeptide having an amino acid sequence which is at least 90% identical over its entire length to the amino acid sequence of SEQ ID NO: 16;
    further comprising at least one of a polynucleotide encoding a polypeptide having the amino acid sequence of SEQ ID NO: 22 and a polynucleotide encoding a polypeptide having the amino acid sequence of SEQ ID NO: 28.

2. The recombinant adenoviral vector of claim 1 wherein the vector comprises a polynucleotide encoding a polypeptide having the amino acid sequence of SEQ ID NO: 16, polynucleotide encoding a polypeptide having the amino acid sequence of SEQ ID NO: 22 and a polynucleotide encoding a polypeptide having the amino acid sequence of SEQ ID NO: 28.

3. The recombinant adenoviral vector of claim 2, wherein the E4 region of the vector comprises ORF6 from human adenovirus.

* * * * *